(12) United States Patent
Steitz et al.

(10) Patent No.: US 8,470,990 B2
(45) Date of Patent: *Jun. 25, 2013

(54) RIBOSOME STRUCTURE AND PROTEIN SYNTHESIS INHIBITORS

(75) Inventors: Thomas A. Steitz, Branford, CT (US); Peter B. Moore, North Haven, CT (US); Joyce A. Sutcliffe, Clinton, CT (US); Adegboyega K. Oyelere, New Haven, CT (US); Joseph A. Ippolito, Guilford, CT (US)

(73) Assignees: Rib-X Pharmaceuticals, Inc., New Haven, CT (US); Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/645,877

(22) Filed: Dec. 23, 2009

(65) Prior Publication Data
US 2010/0204253 A1 Aug. 12, 2010

Related U.S. Application Data

(63) Continuation of application No. 11/067,522, filed on Feb. 25, 2005, now Pat. No. 7,666,849, which is a continuation of application No. 10/211,931, filed on Aug. 2, 2002, now Pat. No. 6,947,845, which is a continuation-in-part of application No. 10/072,634, filed on Feb. 8, 2002, now Pat. No. 6,952,650, which is a continuation-in-part of application No. 09/922,251, filed on Aug. 3, 2001, now Pat. No. 6,947,844.

(60) Provisional application No. 60/348,731, filed on Jan. 14, 2002, provisional application No. 60/352,024, filed on Jan. 25, 2002.

(51) Int. Cl.
*C07H 21/04* (2006.01)
*C12N 15/11* (2006.01)

(52) U.S. Cl.
USPC .......................................... 536/23.2; 514/44

(58) Field of Classification Search
USPC .......................................... 514/44; 536/23.2
See application file for complete search history.

(56) References Cited

U.S. PATENT DOCUMENTS

| | | | |
|---|---|---|---|
| 5,180,719 A | 1/1993 | White et al. |
| 5,281,703 A | 1/1994 | White et al. |
| 5,336,768 A | 8/1994 | Albrecht et al. |
| 5,466,681 A | 11/1995 | Krivan et al. |
| 5,693,791 A | 12/1997 | Truett |
| 5,866,549 A | 2/1999 | Or et al. |
| 5,905,144 A | 5/1999 | Truett |
| 6,380,356 B1 | 4/2002 | Griffin et al. |
| 6,437,119 B1 | 8/2002 | Truett |
| 6,446,032 B1 | 9/2002 | Schimmel |
| 6,468,979 B1 | 10/2002 | Pellacini et al. |
| 6,638,908 B1 | 10/2003 | Steitz et al. |
| 6,939,848 B2 | 9/2005 | Steitz et al. |
| 6,947,844 B2 | 9/2005 | Steitz et al. |
| 6,947,845 B2 | 9/2005 | Steitz et al. |
| 6,952,650 B2 | 10/2005 | Steitz et al. |
| 7,666,849 B2 * | 2/2010 | Steitz et al. ................. 514/44 R |
| 2002/0022257 A1 | 2/2002 | Suh et al. |
| 2002/0086308 A1 | 7/2002 | Steitz et al. |
| 2002/0188108 A1 | 12/2002 | Noller et al. |
| 2003/0027315 A1 | 2/2003 | Yonath et al. |
| 2003/0232779 A1 | 12/2003 | Steitz et al. |
| 2004/0137518 A1 | 7/2004 | Lambert et al. |
| 2005/0234227 A1 | 10/2005 | Steitz et al. |
| 2006/0136146 A1 | 6/2006 | Steitz et al. |

FOREIGN PATENT DOCUMENTS

| | | |
|---|---|---|
| EP | 1172374 | 1/2002 |
| EP | 1186614 | 3/2002 |
| EP | 1188769 | 3/2002 |
| WO | WO-9507271 | 3/1995 |
| WO | WO-9618633 | 6/1996 |
| WO | WO-9735195 | 9/1997 |
| WO | WO-9963937 | 12/1999 |
| WO | WO-0032619 | 6/2000 |
| WO | WO-0180863 | 11/2001 |

OTHER PUBLICATIONS

Agalarov, S et al., (2000) "Structure of the S15, S6, S18-rRNA Complex: Assembly of the 30S Ribosome Central Domain," Science vol. 288, pp. 107-112.

Agrawal, R., et al., (1998) "Visualization of Elongation Factor G on the *Escherichia coli* 70S Ribosome: The Mechanism of Translocations," Proc. Natl. Acad. Sci. USA vol. 95, pp. 6134-6138.

Ban, N., et al., (1998) "A 9 .ANG. Resolution X-Ray Crystallographic Map of the Large Ribosomal Subunit," Cell vol. 93, pp. 1105-1115.

Ban, N., et al., (1999) "Placement of Protein and RNA Structures into a 5 .ANG.-Resolution Map of the 50S Ribosomal Subunit," Nature vol. 400, pp. 841-847.

Ban, N., et al., (2000) "The Complete Atomic Structure of the Large Ribosomal Subunit at 2.4 .ANG. Resolution," Science vol. 289, No. 5481, pp. 821-1096.

Baranov, P., et al., (1998) "The Database of Ribosomal Cross Links (DRC)," Nucleic Acids Research vol. 26, No. 1, pp. 187-189.

Brodersen, D., et al., (2000) "The Structural Basis for the Action of the Antibiotics Tetracycline, Pactamycin, and Hygromycin B on the 30S Ribosomal Subunit," Cell vol. 103, pp. 1143-1154.

(Continued)

*Primary Examiner* — Nizal Chandrakumar
(74) *Attorney, Agent, or Firm* — Goodwin Procter LLP

(57) ABSTRACT

The invention provides methods for producing high resolution crystals of ribosomes and ribosomal subunits as well as crystals produced by such methods. The invention also provides high resolution structures of ribosomal subunits either alone or in combination with protein synthesis inhibitors. The invention provides methods for identifying ribosome-related ligands and methods for designing ligands with specific ribosome-binding properties as well as ligands that may act as protein synthesis inhibitors. Thus, the methods and compositions of the invention may be used to produce ligands that are designed to specifically kill or inhibit the growth of any target organism.

3 Claims, 43 Drawing Sheets
(33 of 43 Drawing Sheet(s) Filed in Color)

OTHER PUBLICATIONS

Brunger, A., (1997) "Patterson Correlation Searches and Refinement," Methods in Enzymology, vol. 276, pp. 558-580.
Brunger, A., et al., (1998) "Crystallography & NMR System: A New Software Suite for Macromolecular Structure Determination," Acta Cryst. vol. D54, pp. 905-921.
Carter, A., et al., (2000) "Functional Insights from the Structure of the 30S Ribosomal Subunit and It's Interactions with Antibiotics," Nature vol. 407, pp. 340-348.
Carter, A., et al., (2001) "Crystal Structure of an Initiation Factor Bound to the 30S Ribosomal Subunit," Science vol. 291, pp. 498-501.
Cate, J., et al., (1999) "X-Ray Crystal Structures of 70S Ribosome Functional Complexes," Science vol. 285, No. 5, pp. 2095-2104.
Clemons, W. Jr., et al., (1999) "Structure of a Bacterial 30S Ribosomal Subunit at 5.5 .ANG. Resolution," Nature vol. 400, pp. 833-840.
Cudney B. (1999) "Protein Crystallization and Dumb Luck," The Rikagu Journal 16(1): 1-7.
Culver, G., et al., (1999) "Identification of an RNA-Protein Bridge Spanning the Ribosomal Subunit Interface," Science vol. 285, pp. 2133-2135.
Dahlberg, A., et al., (2001) "The Ribosome in Action," Science vol. 292, pp. 868-869.
Davies, C. et al., (1998) "Ribosomal Proteins S5 and L6: High-Resolution Crystal Structures and Roles in Protein Synthesis and Antibiotic Resistance," Journal of Molecular Biology, vol. 279, pp. 873-888.
Di Giambattista, M., et al., (1990) "Affinity Labeling of the Virginiamycin S. Binding Site on Bacterial Ribosome," Biochemistry vol. 29, pp. 9203-9211.
Douthwaite, (1992) "Functional Interactions within 23S rRNA Involving the Peptidyltransferase Center,"0 Journal of Bacteriology vol. 174, No. 4, pp. 1333-1338.
Douthwaite, S., et al., (1993) "Erythromycin Binding is Reduced in Ribosomes with Conformational Alterations in the 23 S rRNA Peptidyl Transferase Loop," Journal Mol. Biol. vol. 232, pp. 725-731.
Douthwaite, S., et al., (1995) "Recognition Determinants for Proteins and Antibiotics within 23S rRNA," Biochem. Cell Biol. vol. 73, pp. 1179-1185.
Drenth, *Principles of Protein X-Ray Crystallography* (2nd ed.), Chap. 1, pp. 1-21 (1999 Springer-Verlag New York, Inc.).
Drenth, "Principles of Protein X-ray Crystallography," 1994, Springer-Verlag, pp. 1-18.
Fitzhugh, A., et al., (1998) "Antibiotic Inhibitors of the Peptidyl Transferase Center. 1. Clindamycin as a Composite Analogue of the Transfer RNA Fragments L-Pro-Met and the D-Ribosyl Ring of Adenosine," Bioorganic and Medicinal Chemistry Letters, vol. 8, pp. 87-92.
Dube et al., Structure (1998) 6:389-399.
Flower, "Drug Design Cutting Edge Approaches," The Royal Society of Chemistry (2002), pp. 21-27.
Fourmy et al. (1996) "Structure of the A Site of *Escherichia coli* 16S Ribosomal RNA Complexed with an Aminoglycoside Antibiotic" Science 274(5291):1367-1371.
Franceshi et al. (1993) "Towards Atomic Resolution of Prokaryotic Ribosomes: Crystallographic, Genetic and Biochemical Studies" in The Translational Apparatus 397-410.
Gabashvili, I., et al., (2000) "Solution Structure of the *E coli* 70S Ribosome at 11.5 .ANG. Resolution," Cell, vol. 100, pp. 537-549.
Garrett, R., et al., (1996) "The Peptidyl Transferase Center," Ribosomal RNA pp. 327-355.
Garza-Ramos, G. et al., (2001) "Binding Site of Macrolide Antibiotics on the Ribosome: New Resistance Mutation Identifies a Specific Interaction of Ketolides with rRNA," Journal of Bacteriology, vol. 183, No. 23, pp. 6898-6907.
Gonzales, R., et al., (2001) "Infections Due to Vancomycin-Resistant *Enterococcus faecium* Resistant to linezolid," The Lancet vol. 357, p. 1179.
Green, R., et al., (1997) "Ribosomes and Translation," Annu. Rev. Biochemistry vol. 66, pp. 679-716.
Gregory, S., et al., (1999) "Erythromycin Resistance Mutations in Ribosomal Proteins L22 and L4 Perturb the Higher Order Structure of 23 S Ribosomal RNA," J. Mol. Biol. vol. 289, pp. 827-834.
Gschwend, D. et al., (1996) "Molecular Docking Towards Drug Discovery," Journal of Molecular Recognition, vol. 9, pp. 175-186.
Giege et al., "Crystallogenesis of Biological Macromolecules: Facts and Perspectives," Acta Cryst. (1994) D50: 339-350.
Glotz et al. (1987) "Three-Dimensional Crystals of Ribosomes and Their Subunits from Eu- and Archaebacteria" Biochemistry International 15 (5):953-960.
Guettell, R. (1996) "Comparative Sequence Analysis and the Structure of 16S and 23S rRNA," Ribosomal RNA pp. 111-128.
Hanessian et al. (1984) "Quantamycin": A Computer-Stimulated New-Generation Inhibitor of Bacterial Ribosomal Binding Journal American Chemical Society 106:6114-6115.
Hansen et al., "Structural Insights into Peptide Bond Formation," Proc. Natl. Acad. Sci. USA, 99(18):11670-11675 (2002).
Hansen et al., "The Structures of Four Marcolide Antibiotics Bound to the Large Ribosomal Subunit," Molecular Cell, 10:117-128 (2002).
Hansen et al. (2003) "Structures of Five Antibiotics Bound at the Peptidyl Transferase Center of the Large Ribosomal Subunit," J. Mol. Biol. 330, 1061-1075.
Hansen, H.A.S., et al., (1990) "Crystals of Complexes Mimicking Protein Biosynthesis are Suitable Crystallographic Studies," Bioclumica et Biophysica Acta, vol. 1050, pp. 1-7.
Hansen, L., et al., (1999) "The Macrolide-Ketolide Antibiotic Binding Site is Formed by Structures in Domains II and V of 23S Ribosomal RNA," Molecular Microbiology, vol. 31, No. 2, pp. 623-631.
Harms, J., et al., (1999) "Elucidating the Medium-Resolution Structure of Ribosomal Parti cles: an Interplay between Electron Cryo-Microscopy and X-ray Crystallography," Structure vol. 7, No. 8, pp. 931-941.
Harms, J., et al., (2001) "High Resolution Structure of the Large Ribosomal Subunit from a Mesophilic eubacterium," Cell, vol. 107, pp. 679-688.
Hecker et al. (1993) "Application of Hygromycin A Structure Activity Relationships to the Antibiotic A201A" Bioorganic & Medicinal Chemistry Letters 3(2):295-298.
Hegyi et al., J. Mol. Biol. (1999) 288:147-164.
Hermann et al. (1999) "Docking of Cationic Antibiotics to Negatively Charged Pockets on RNA Folds" J. Med. Chem. 42(7):1250-1261.
Holmes et al. (1993) "Novel Dimeric Penicillin Derived Inhibitors of HIV-1 Proteinase: interaction woth the Catalytic Aspartates" Bioorganic & Medicinal Chemistry Letters 3(4):503-508.
Hope et al. (1989) "Cryocrystallography of Ribosomal Particles" Acta. Cryst. B45: 190-199.
Ioannou et al. (1998) "Kinetics of Inhibition of Rabbit Reticulocyte Peptidyltransferase by Anisomycin and Sparsomycin" Molecular Pharmacology 53(6):1089-1096.
Kirillov et al. (1999) "Peptidyl Transferase Antibiotics Perurb the Relative Positioning of the 3'-Terminal Adenosine of P/P'-Site-Bound tRNA and 23S rRNA in the Ribosome" RNA 5(8):1003-1013.
Klein et al., "The Kink-Turn: A New RNA Secondary Structure Motif," EMBO J., 20(15):4214-4221 (2001).
Kloss, P., et al., (1999) "Resistance Mutations in 23 S rRNA Idenitfy the Site of Action of the Protein Syntesis Inhibitor Linezolid in the Ribosomal Peptidyl Transferase Center," J. Mol. Biol, vol. 294, No. 1, pp. 93-101.
Kundrot, C.E. (2004) "Which Srategy for a Protein Crystallization Project?" Cellular Molecular Life Sciences 61:525-536.
Lazaro, E., et al., (1991) "Chemical, Biochemical and Genetic Endeavors Characterizing the Interaction of Sparsomycin with the Ribosome," Biochimie vol. 73, pp. 1137-1143.
Lazaro, E., et al., (1996) "A Sparomycin-Resistant Mutant *Halobacterium salinarium* Lacks a Modification at Nucleotide U2603 in the Peptidyl Transferase Centre of 23 S rRNA," J. Mol. Biol, vol. 261, No. 2, pp. 231-238.

Lipinski, C., et al., (1997) "Experimental and Computational Approaches to Estimate Solubility and Permeability in Drug Discovery and Development Settings," Adv. Drug Delivery Rev. vol. 23, No. 3-25.

Malhotra et al., J. Mol. Biol. (1998), 280:103-116.

Maskowski et al., (1987) "Single Crystals of Large Ribosomal Particles from *Halobacterium* marismortui Diffract to 6 .ANG., " Journal Molecular Biology vol. 193 pp. 818-822.

Matadeen, R., et al., (1999) "The *Escherichia coli* Large Ribosomal Subunit at 7.5 .ANG. Resolution," Structure, vol. 7, No. 12, pp. 1575-1583.

Moazed et al., (1989) "Interaction of +RNA with 23S rRNA in the Ribosomal A, P, and E Sites," Cell vol. 57, pp. 585-597.

Moazed, D., et al., (1987) "Chloramphenicol, Erythromycin, Carbomycin and Vernamycin B Protect Overlapping Sites in the Peptidyl Transferase Region of 23S Ribosomal RNA," Biochimie , vol. 69, pp. 879-884.

Moore, P.B. (1998) "The Three-Dimensional Structure of the Ribosome and its Components," Annu. Rev. Biophys. vol. 27, pp. 35-58.

Moore, P.B. (1999) "Structural Motifs in RNA," Annu. Rev. Biochemistry vol. 67, pp. 287-300.

Mueller, F., et al., (2000) "The 3D Arrangement of the 23 S and 5 S rRNA in the *Escherichia coli* 50 S Ribosomal Subunit Based on a Cryo-Electron Microscopic Reconstruction at 7.5 .ANG. Resolution," Journal Molecular Biology vol. 298, pp. 35-59.

Mussig, J., et al., (1989) "Crystals of Wild-type, Mutated, Derivatized and Complexed 50 S Ribosomal Subunits from *Bacillus stearothermophilus* Suitable for X-ray Analysis," J. Mol. Biol. vol. 205, pp. 619-621.

Nakatogawa, H., et al., (2002) "The Ribosomal Exit Tunnel Functions as a Discriminating Gate," Cell vol. 108, pp. 629-636.

Navaza, J., et al., (1997) "AMoRe: An Automated Molecular Replacement Program Package," Methods in Enzymology vol. 276, pp. 581-595.

Nissen et al., "RNA Tertiary Interactions in the Large Ribosomal Subunit: The A-Minor Motif," Proc. Natl. Acad. Sci. USA, 98(9):4899-4903 (2001).

Nissen, P., et al., (2000) "The Structural Basis of Ribosome Activity in Peptide Bond Synthesis," Science vol. 289, pp. 920-930.

Nitta, I., et al., (1998) "Reconstitution of Peptide Bond Formation with *Escherichia coli* 23S Ribosomal RNA Domains," Science vol. 281, pp. 666-669.

Noller, H., (1991) "Ribosomal RNA and Translation," Ann. Rev. Biochemistry vol. 60, pp. 191-227.

Ogle, J., et al., (2001) "Recognition of Cognate Transfer RNA by the 30S Ribosomal Subunit," Science vol. 292, pp. 897-902.

Pestka, S., (1974) "Antibiotics as Probes of Ribosome Structure: Binding of Chloramphenicol and Erythromycin to Polyribosomes; Effect of Other Antibiotics," Antimicrobial Agents and Chemotherapy vol. 5, No. 3, pp. 255-267.

Porse, B., et al., (1999) "Ribosomal Mechanics, Antibiotics, and GTP Hydrolysis," Cell vol. 97, pp. 423-426.

Porse, B., et al., (1999) "Sites of Interaction of Streptogramin A and B Antibiotics in the Peptidyl Transferase Loop of 23 S rRNA and the Synergism of Their Inhibitory Mechanisms," J. Mol. Biol. vol. 286, No. 2, pp. 375-387.

Ramakrishnan, V., (2002) "Ribosome Structure and the Mechanism of Translation," Cell vol. 108, pp. 557-572.

Ramakrishnan, V., et al., (1995) "Structures of Prokaryotic Ribosomal Proteins: Implications of RNA Binding and Evolution," Biochem. Cell Biol. vol. 73, pp. 979-986.

Rao et al. (1997) "Tight Binding of a Dimeric Derivative of Vancomycin with Dimeric L-Lys-D-Ala-D-Ala" J. Am. Chem. Soc. 119:10286-10290.

Rodriguez-Fonseca, C., et al., (1995) "Fine Structure of the Peptidyl Transderase Centre on 23 S-like rRNAs Deuced from Chemical Probing of Antibiotic-Ribosome Complexes," J. Mol. Biol, vol. 247, pp. 224-235.

Schlunzen, F., et al., (1995) "A Milestone in Ribosomal Crystallography: The Construction of Preliminary Electron Density Maps at Intermediate Resolution," Biochemistry Cell Biology vol. 73, pp. 739-749.

Schlunzen, F., et al., (2000) "Structure of Functionally Activated Small Ribosomal Subunit at 3.3 .ANG. Resolution," Cell vol. 102, pp. 615-623.

Schluzen, F., et al., (2001) "Structural Basis for the Interaction of Antibiotics with the Peptidyl Transferase Centre in Eubacteria," Nature vol. 413, pp. 814-821.

Schmeing et al., "A Pre-Translocational Intermediate in Protein Synthesis Observed in Crystals of Enzymatically Active 50S Subunits," Nature Struct. Biol., 9(3):225-230 (2002).

Shevack et al. (1985) "Characterization and Crystallization of Ribosomal Particles from *Halobacterium* Marismortui" FEBS Letters 184(1):68-71.

Shinabarger, D., et al., (1997) "Mechanism of Action of Oxazolidinones: Effects of Linezolid and Eperezolid on Translation Reactions," Antimicrobial Agents and Chemotherapy vol. 41, No. 10, pp. 2132-2136.

Shuker et al. (1996) "Discovering High-Affinity Ligands for Proteins: SAR by NMR" Science 274(5292):1531-1541.

Spahn, C.M.T., et al., "Throwing a Spanner in the Works: Antibiotics and the Translation Apparatus," Journal of Molecular Medicine vol. 74, No. 8. pp. 423-439, 1996.

Spickler et al. (1997) "Streptomycin Binds to the Decoding Center of 16 S Ribosomal RNA" J. Mol. Biol. 273(3):586-599.

Swaney, S., et al., (1998) "The Oxazolidinone Linezolid Inhibits Initiation of Protein Synthesis in Bacteria," Antimicrobial Agents and Chemotherapy vol. 42, No. 12, pp. 3251-3255.

Szymanski et al. (2003) "5S rRNA: Structure and Interactions," Biochemical Journal 371:641-651.

Tanihara et al. (1998) "Thrombin-Sensitive Peptide Linkers for Biological Signal-Responsive Drug Release Systems" Peptides 19(3):421-425.

Tenson, T., et al., (2002) "Regulatory Nascent Peptides in the Ribosomal Tunnel," Cell vol. 108, pp. 591-594.

Timmermans, P., et al., (1982) "Sparsophenicol: A New Synthetic Hybrid Antibiotic Inhibiting Ribosomal Peptide Synthesis" J. Med. Chem. vol. 25, pp. 1123-1125.

Tocilj, A., et al., (1999) "The Small Ribosomal Subunit from *Thermus thermophilius* at 4.5 .ANG. Resolution: Pattern Fittings and the Identification of a Functional Site," Proc. Natl. Acad. Sci. USA vol. 96, pp. 14252-14257.

Trakhanov, S.D., et al., (1987) "Crystallization of 70 S Ribosomes and 30 S Ribosomal Subunits from *Thermaus thermophilus*, " Febs Letters, vol. 220, No. 2, pp. 319-322.

Tronrud, D., (1997) "TNT Refinement Package," Macromolecular Crystallography, Part B, Methods in Enzymology, vol. 277, pp. 306-319.

Tsiodras, S., et al., (2001) "Linezolid Resistance in a Clinical Isolate of *Staphylococcus aureus*," The Lancet vol. 358, pp. 207-208.

Vannuffel et al., (1992) "Identification of a Single Base Change in Ribosomal RNA Leading to Erythromycin Resistance," The Journal of Biological Chemistry vol. 267(12), pp. 8377-8382.

Vannuffel et al., (1996) "Mechanism of Action of Streptogramins and Macrolides," Drugs vol. 51, Suppl 1, pp. 20-30.

Vester et al., (1988) "The Importance of Highly Conserved Nucleotides in the Binding Region of Chloramphenicol at the Peptidyl transfer Centre of *Escherichia coli* 23S Ribosomal RNA," The EMBO Journal vol. 7, No. 11, pp. 3577-3587.

Vester et al., (2001) "Macrolide Resistance Conferred by Base Substitutions," Antimicrobial Agents and Chemotherapy vol. 45, No. 1, pp. 1-12.

Vince et al. (1975) "Chloramphenicol Binding Site with Analogues of Chloramphenico I and Puromycin" Antimicrobial Agents and Chemotherapy 8(4):439-443.

Volkmann et al., (1990) "Characterization and Preliminary Crystallographic Studies on Large Ribosomal Subunits from *Thermus thermophilus*," J. Mol. Biol. vol. 216, pp. 239-241.

Von Bohlen, (1991) "Characterization and Preliminary Attempts for Derivatization of Crystals of Large Ribosomal Subunits from *Haloarcula marismortui* Diffracting to 3 .ANG. Resolution," Journal Molecular Biology vol. 222, pp. 11-15.

Wang et al. (1997) "Dimeric Aminoglycosides: Design, Synthesis and RNA Binding" Bioorganic & Medicinal Chemistry Letters 7(14):1951-1956.

Weber, "Overview of Crystallization Methods," Methods in Enzymology (1997) vol. 276, pp. 13-22.

Welch, M., et al., (1995) "An Inhibitor of Ribosomal Peptidyl Transferase Using Transition-State Analogy," Biochemistry vol. 34, pp. 385-390.

Welch, M., et al., (1997) "23S rRNA Similarity from Selection for Peptidyl Transferase Mimicry," Biochemistry vol. 36, pp. 6614-6623.

Wimberly, B., et al., (2000) "Structure of the 30S Ribosomal Subunit," Nature vol. 407, pp. 327-339.

Wittmann et al., (1982) "Crystallization of *Escherichia coli* Ribosomes," Febs Letters vol. 146, No. 1, pp. 217-220.

Wong et al. (1998) "Specificity of Aminoglycoside Antibiotics for the A-Site of the Decoding Region of Ribosomal RNA" Chemistry & Biology 5(7):397-406.

Wool, I., et al., (1995) "Structure and Evolution of Mammalian Ribosomal Proteins," Biochemistry Cell Biology vol. 73, pp. 933-947.

Xiong, L., et al., (2000) "Oxazolidinone Resistance Mutations in 23S rRNA of *Escherichia coli* Reveal the Central Region of Domain V as the Primary Site of Drug Action," Journal of Bacteriology vol. 182, No. 19, pp. 5325-5331.

Yonath et al. (1980) "Crystallization of the Large Ribosomal Subunits from *Bacillus stearothermophilus*" Biochem. Intern'l. 1(5): 428-435.

Yonath et al. (1984) "Some X-ray Diffraction Patterns from Single Crystals of the Large Ribosomal Subunit from *Bacillus stearothermophilus*" J. Mol. Biol. 177:201-206.

Yonath et al. (1988) "Crystallography of Ribosomal Particles" J. Cryst. Growth 90: 231-244.

Yonath, A., et al., (1998) "Crystallographic Studies on the Ribosome, a Large Macromolecular Assembly Exhibiting Severe Nonisomorphism, Extreme Beam Sensitivity and No Internal Symmetry," Acta Cryst, vol. A54, pp. 945-955.

Yonath et al. (1988) "Crystallographic and Image Reconstruction Studies on Ribosomal Particles from Bacterial Sources," Methods in Enzymology 164:95-117.

Yonath, A., et al., (1986) "Characterization of Single Crystals of the Large Ribosomal Particles from *Bacillus stearothermophilus*," J. Mol. Biol. vol. 187, pp. 633-636.

Yusupov, M., et al., (1991) "*Thermus thermophilus* Ribosomes for Crystallographic Studies," Biochimie , vol. 73, pp. 887-897.

Yusupov, M.,et al., (2001) "Crystal Structure of the Ribosome 5.5 .ANG. Resolution," Science vol. 292, pp. 883-896.

Yusupova, G., et al., (2001) "The Path of Messenger RNA through the Ribosome," Cell vol. 106, pp. 233-241.

Zemlicka, J., et al., (1993) "Hybrids of Antibiotics Inhibitin Protein Synthesis, Synthesis and Biological Activity," J. Med. Chem. vol. 36, pp. 1239-1244.

European Search Report for Application No. 02255442.2 dated Mar. 6, 2003.

European Search Report for EP Patent Application 01306825.8 dated May 24, 2002.

\* cited by examiner

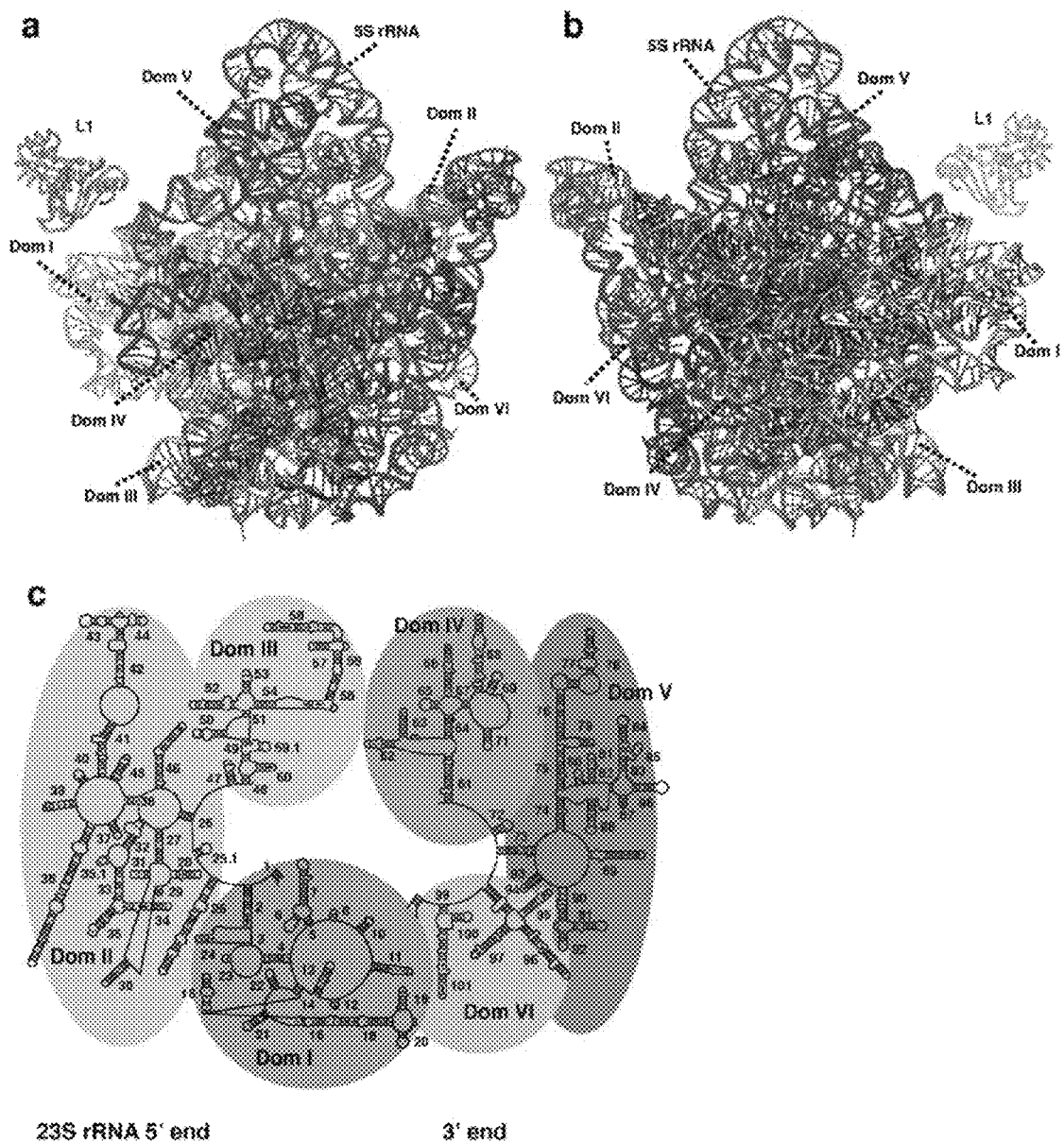

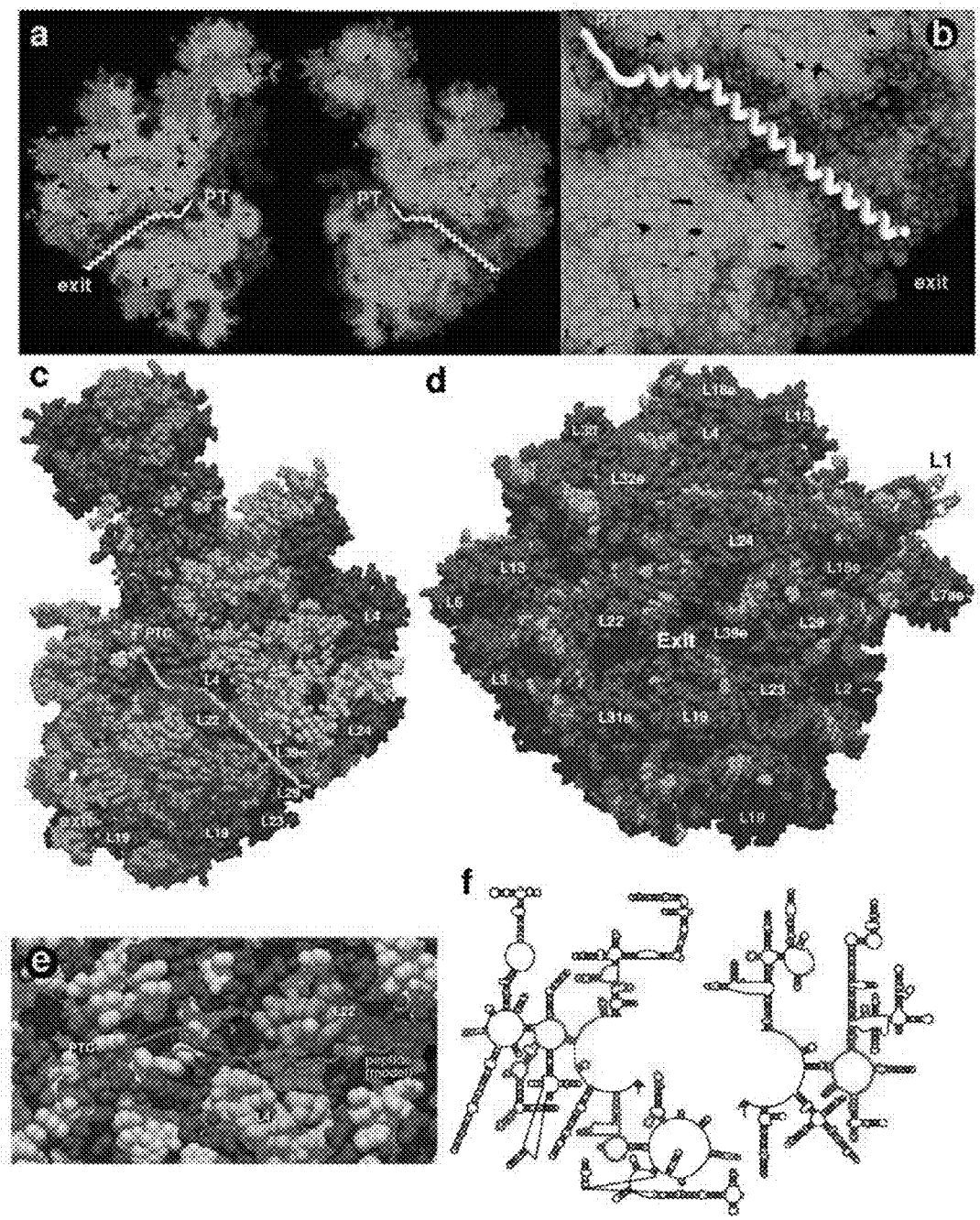

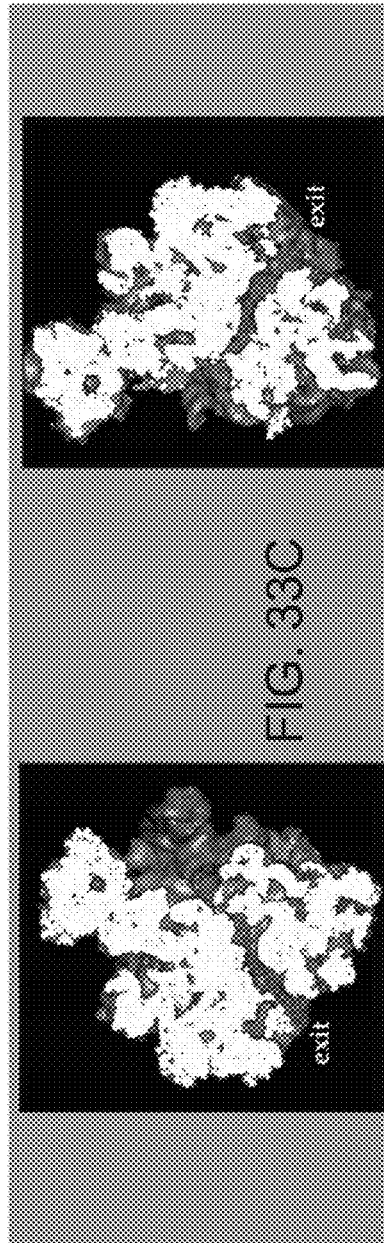
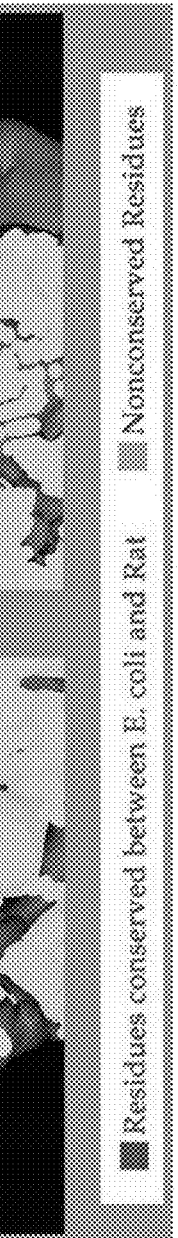
FIG. 33A
FIG. 33B
FIG. 33C
FIG. 33D 1 n = 1, Sparsochloramphenicol Hybrid A
2 n = 2, Sparsochloramphenicol Hybrid B

RIBOSOME STRUCTURE AND PROTEIN SYNTHESIS INHIBITORS

REFERENCE TO RELATED APPLICATIONS

This application is a continuation of co-pending U.S. application Ser. No. 11/067,522, filed Feb. 25, 2005, which is a continuation of U.S. application Ser. No. 10/211,931, filed Aug. 2, 2002, which is a continuation-in-part of U.S. application Ser. No. 10/072,634, filed Feb. 8, 2002, which is a continuation-in-part of U.S. application Ser. No. 09/922,251, filed Aug. 3, 2001, and claims the benefit of (i) U.S. Provisional Application No. 60/348,731, filed Jan. 14, 2002, and (ii) U.S. Provisional Application No. 60/352,024, filed Jan. 25, 2002, the disclosures of each of which are incorporated by reference herein in their entireties.

GOVERNMENT LICENSE RIGHTS

Certain work described herein was supported, in part, by Federal Grant Nos. NIH-GM22778 and NIH-GM54216, awarded by the National Institutes of Health. The Government may have certain rights in the invention.

FIELD OF THE INVENTION

The present invention relates generally to the field of protein biosynthesis and to modulators, for example, inhibitors, of protein biosynthesis. More particularly, the invention relates to: methods and compositions for elucidating the three-dimensional structure of the large ribosomal subunit, either alone or in combination with a protein synthesis inhibitor; the three-dimensional structure of the large ribosomal subunit, either alone or in combination with a protein synthesis inhibitor; the use of such structures in the design and testing of novel protein synthesis inhibitors; and novel protein synthesis inhibitors.

BACKGROUND

I. Ribosomes: Structure, Function, and Composition

Ribosomes are ribonucleoproteins which are present in both prokaryotes and eukaryotes. They comprise about two-thirds RNA and one-third protein. Ribosomes are the cellular organelles responsible for protein synthesis. During gene expression, ribosomes translate the genetic information encoded in a messenger RNA into protein (Garrett et al. (2000) "*The Ribosome: Structure, Function, Antibiotics and Cellular Interactions,*" American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation—the peptidyl-transferase reaction of protein synthesis—and includes (at least) two different tRNA binding sites: the A-site which accommodates the incoming aminoacyl-tRNA, which is to contribute its amino acid to the growing peptide chain, and the P-site which accommodates the peptidyl-tRNA complex, i.e., the tRNA linked to all the amino acids that have so far been added to the peptide chain. The large ribosomal subunit also includes one or more binding sites for G-protein factors that assist in the initiation, elongation, and termination phases of protein synthesis. The large and small ribosomal subunits behave independently during the initiation phase of protein synthesis; however, they assemble into complete ribosomes when elongation is about to begin.

The molecular weight of the prokaryotic ribosome is about $2.6 \times 10^6$ daltons. In prokaryotes, the small ribosomal subunit contains a 16S (Svedberg units) ribosomal RNA (rRNA) having a molecular weight of about $5.0 \times 10^5$ daltons. The large ribosomal subunit contains a 23S rRNA having a molecular weight of about $1.0 \times 10^6$ daltons and a 5S rRNA having a molecular weight of about $4.0 \times 10^5$ daltons. The prokaryotic small subunit contains about 20 different proteins and its large subunit contains about 35 proteins. The large and small ribosomal subunits together constitute a 70S ribosome in prokaryotes.

Eukaryotic ribosomes generally are bigger than their prokaryotic counterparts. In eukaryotes, the large and small subunits together make an 80S ribosome. The small subunit of a eukaryotic ribosome includes a single 18S rRNA, while the large subunit includes a 5S rRNA, a 5.8S rRNA, and a 28S rRNA. The 5.8S rRNA is structurally related to the 5' end of the prokaryotic 23S rRNA, and the 28S rRNA is structurally related to the remainder of the prokaryotic 23S rRNA (Moore (1998) *Annu. Rev. Biophys.* 27: 35-58). Eukaryotic ribosomal proteins are qualitatively similar to the prokaryotic ribosomal proteins; however, the eukaryotic proteins are bigger and more numerous (Moore (1998) supra).

II. Structural Conservation of the Large Ribosomal Subunit

While the chemical composition of large ribosomal subunits vary from species to species, the sequences of their components provide unambiguous evidence that they are similar in three-dimensional structure, function in a similar manner, and are related evolutionarily. The evolutionary implications of rRNA sequence data available are reviewed in the articles of Woese and others in part II of *Ribosomal RNA. Structure, Evolution, Processing and Function in Protein Biosynthesis*, (Zimmermann and Dahlberg, eds., CRC Press, Boca Raton, Fla., 1996). The article by Garret and Rodriguez-Fonseca in part IV of the same volume discusses the unusually high level of sequence conservation observed in the peptidyl transferase region of the large ribosomal subunit. The ribosomes of archeal species like *Haloarcula marismortui* resemble those obtained from eubacterial species like *E. coli* in size and complexity. However, the proteins in *H. marismortui* ribosomes are more closely related to the ribosomal proteins found in eukaryotes (Wool et al. (1995) *Biochem. Cell Biol.* 73: 933-947).

III. Determination of the Structure of Ribosomes

Much of what is known about ribosome structure is derived from physical and chemical methods that produce relatively low-resolution information. Electron microscopy (EM) has contributed to an understanding of ribosome structure ever since the ribosome was discovered. In the 1970s, low resolution EM revealed the shape and quaternary organization of the ribosome. By the end of 1980s, the positions of the surface epitopes of all the proteins in the *E. coli* small subunit, as well as many in the large subunit, had been mapped using immunoelectron microscopy techniques (Oakes et al. (1986), *Structure, Function and Genetics of Ribosomes*, (Hardesty, B. and Kramer, G., eds.) Springer-Verlag, New York, N.Y., pp.

47-67; Stoeffler et al. (1986), *Structure, Function and Genetics of Ribosomes*, (Hardesty, B. and Kramer, G., eds.) Springer-Verlag, New York, N.Y., pp. 28-46). In the last few years, advances in single-particle cryo-EM and image reconstruction have led to three-dimensional reconstructions of the *E. coli* 70S ribosome and its complexes with tRNAs and elongation factors to resolutions of between 15 Å and 25 Å (Stark et al. (1995) *Structure* 3: 815-821; Stark et al. (1997) *Nature* 3898: 403-406; Agrawal et al. (1996) *Science* 271: 1000-1002; Stark et al. (1997) *Cell* 28: 19-28). Additionally, three-dimensional EM images of the ribosome have been produced at resolutions sufficiently high so that many of the proteins and nucleic acids that assist in protein synthesis can be visualized bound to the ribosome. An approximate model of the RNA structure in the large subunit has been constructed to fit a 7.5 Å resolution electron microscopic map of the 50S subunit from *E. coli* and available biochemical data (Mueller et al. (2000) *J. Mol. Biol.* 298: 35-59).

While the insights provided by EM have been useful, it has long been recognized that a full understanding of ribosome structure would derive only from X-ray crystallography. In 1979, Yonath and Wittman obtained the first potentially useful crystals of ribosomes and ribosomal subunits (Yonath et al. (1980) *Biochem. Internat.* 1: 428-435). By the mid 1980s, scientists were preparing ribosome crystals for X-ray crystallography (Maskowski et al. (1987) *J. Mol. Biol.* 193: 818-822). The first crystals of 50S ribosomal subunit from *H. marismortui* were obtained in 1987. In 1991, improvements were reported in the resolution of the diffraction data obtainable from the crystals of the 50S ribosomal subunit of *H. marismortui* (van Bohlen, K. (1991) *J. Mol. Biol.* 222: 11).

In 1995, low resolution electron density maps for the large and small ribosomal subunits from halophilic and thermophilic sources were reported (Schlunzen et al. (1995) *Biochem. Cell Biol.* 73: 739-749). However, these low resolution electron density maps proved to be spurious (Ban et al. (1998) *Cell* 93: 1105-1115).

The first electron density map of the ribosome that showed features recognizable as duplex RNA was a 9 Å resolution X-ray crystallographic map of the large subunit from *Haloarcula marismortui* (Ban et al. (1998) supra). Extension of the phasing of that map to 5 Å resolution made it possible to locate several proteins and nucleic acid sequences, the structures of which had been determined independently (Ban et al. (1999) *Nature* 400: 841-847).

At about the same time, using similar crystallographic strategies, a 7.8 Å resolution map was generated of the entire *Thermus thermophilus* ribosome showing the positions of tRNA molecules bound to its A-, P-, and E- (protein exit site) sites (Cate et al. (1999) *Science* 285: 2095-2104), and a 5.5 Å resolution map of the 30S subunit from *T. thermophilus* was obtained that allowed the fitting of solved protein structures and the interpretation of some of its RNA features (Clemons, Jr. et al. (1999) *Nature* 400: 833-840). Subsequently, a 4.5 Å resolution map of the *T. thermophilus* 30S subunit was published, which was based in part on phases calculated from a model corresponding to 28% of the subunit mass that had been obtained using a 6 Å resolution experimental map (Tocilj et al. (1999) *Proc. Natl. Acad. Sci. USA* 96: 14252-14257).

IV. Location of the Peptidyl Transferase Site in the Large Ribosomal Subunit

It has been known for about 35 years that the peptidyl transferase activity responsible for the peptide bond formation that occurs during messenger RNA-directed protein synthesis is intrinsic to the large ribosomal subunit (Traut et al. (1964) *J. Mol. Biol.* 10: 63; Rychlik (1966) *Biochim. Biophys. Acta* 114: 425; Monro (1967) *J. Mol. Biol.* 26: 147-151; Maden et al. (1968) *J. Mol. Biol.* 35: 333-345) and it has been understood for even longer that the ribosome contains proteins as well as RNA. In certain species of bacteria, for example, the large ribosomal subunit contains about 35 different proteins and two RNAs (Noller (1984) *Ann. Rev. Biochem.* 53: 119-162; Wittmann-Liebold et al. (1990) *The Ribosome: Structure, Function, and Evolution*, (W. E. Hill et al., eds.) American Society for Microbiology, Washington, D.C. (1990), pp. 598-616). These findings posed three related questions. Which of the almost 40 macromolecular components of the large ribosomal subunit contribute to its peptidyl transferase site, where is that site located in the large subunit, and how does it work?

By 1980, the list of components that might be part of the ribosome's peptidyl transferase had been reduced to about half a dozen proteins and 23S rRNA (see Cooperman (1980) *Ribosomes: Structure, Function and Genetics*, (G. Chambliss et al., eds.) University Park Press, Baltimore, Md. (1980), 531-554), and following the discovery of catalytic RNAs (Guerrier-Takada et al. (1983) *Cell* 35: 849-857; Kruger et al. (1982) *Cell* 31: 147-157), the hypothesis that 23S rRNA might be its sole constituent, which had been proposed years earlier, began to gain favor. In 1984, Noller and colleagues published affinity labeling results which showed that U2619 and U2620 (in *E. coli*: U2584, U2585) are adjacent to the CCA-end of P-site-bound tRNA (Barta et al. (1984) *Proc. Nat. Acad. Sci. USA* 81: 3607-3611; Vester et al. (1988) *EMBO J.* 7: 3577-3587). These nucleotides appear to be part of a highly conserved internal loop in the center of domain V of 23S rRNA. The hypothesis that this loop is intimately involved in the peptidyl transferase activity was supported by the observation that mutations in that loop render cells resistant to many inhibitors of peptidyl transferase, and evidence implicating it in this activity has continued to mount (see, Noller (1991) *Ann. Rev. Biochem.* 60: 191-227; Garrett et al. (1996) *Ribosomal RNA: Structure, Evolution, Processing and Function in Protein Biosynthesis*, (R. A. Zimmerman and A. E. Dahlberg, eds.) CRC Press, Boca Raton, Fla. (1996), pp. 327-355).

Definitive proof that the central loop in domain V is the sole component of the ribosome involved in the peptidyl transferase activity has remained elusive, however. Studies have shown that it was possible to prepare particles that retained peptidyl transferase activity by increasingly vigorous proteinizations of large ribosomal subunits, however, it was not possible to produce active particles that were completely protein-free. Nevertheless, combined with earlier reconstitution results (Franceschi et al. (1990) *J. Biol. Chem.* 265: 6676-6682), this work reduced the number of proteins that might be involved to just two: L2 and L3 (see, Green et al. (1997) *Annu. Rev. Biochem.* 66: 679-716). More recently, Watanabe and coworkers reported success in eliciting peptidyl transferase activity from in vitro synthesized, protein-free 23S rRNA (Nitta et al. (1998) *RNA* 4: 257-267), however, their observations appear not to have withstood further scrutiny. Thus the question still remained: is the ribosome a ribozyme or is it not?

Over the years, the location of the peptidyl transferase site in the ribosome has been approached almost exclusively by electron microscopy. In the mid-1980s evidence that there is a tunnel running through the large ribosomal subunit from the middle of its subunit interface side to its back (Milligan et al. (1986) *Nature* 319: 693-695; Yonath et al. (1987) *Science* 236: 813-816) began to accumulate, and there has been strong reason to believe that polypeptides pass through it as they are synthesized (Bernabeu et al. (1982) *Proc. Nat. Acad. Sci. USA* 79: 3111-3115; Ryabova et al. (1988) *FEBS Letters* 226: 255-260; Beckmann et al. (1997) *Science* 278: 2123-2126). More recent cryo-EM investigations (Frank et al. (1995) *Nature* 376: 441-444; Frank et al. (1995) *Biochem. Cell Biol.* 73: 757-765; Stark et al. (1995) supra) confirmed the existence of the tunnel and demonstrated that the CCA-ends of ribosome-bound tRNAs bound to the A- and P-sites are found in the subunit interface end of the tunnel. Consequently, the peptidyl transferase site must be located at that same position, which is at the bottom of a deep cleft in the center of the subunit interface surface of the large subunit, immediately below its central protuberance.

The substrates of the reaction catalyzed at the peptidyl transferase site of the large subunit are an aminoacyl-tRNA (aa-tRNA) and a peptidyl-tRNA. The former binds in the ribosome's A-site and the latter in its P-site. The α-amino group of the aa-tRNA attacks the carbon of the carbonyl acylating the 3' hydroxyl group of the peptidyl-tRNA, and a tetrahedral intermediate is formed at the carbonyl carbon. The tetrahedral intermediate resolves to yield a peptide extended by one amino acid esterified to the A-site bound tRNA and a deacylated tRNA in the P-site.

This reaction scheme is supported by the observations of Yarus and colleagues who synthesized an analogue of the tetrahedral intermediate by joining an oligonucleotide having the sequence CCdA to puromycin via a phosphoramide group (Welch et al. (1995) *Biochemistry* 34: 385-390). The sequence CCA, which is the 3' terminal sequence of all tRNAs, binds to the large subunit by itself, consistent with the biochemical data showing that the interactions between tRNAs and the large subunit largely depend on their CCA sequences (Moazed et al. (1991) *Proc. Natl. Acad. Sci. USA* 88: 3725-3728). Puromycin is an aa-tRNA analogue that interacts with the ribosomal A-site, and the phosphoramide group of the compound mimics the tetrahedral carbon intermediate. This transition state analogue, CCdA-phosphate-puromycin (CCdA-p-Puro), binds tightly to the ribosome, and inhibits its peptidyl transferase activity (Welch et al. (1995) supra).

V. Structure Determination of Macromolecules Using X-ray Crystallography

In order to better describe the efforts undertaken to determine the structure of ribosomes, a general overview of X-ray crystallography is provided below.

Each atom in a crystal scatters X-rays in all directions, but crystalline diffraction is observed only when a crystal is oriented relative to the X-ray beam so that the atomic scattering interferes constructively. The orientations that lead to diffraction may be computed if the wavelength of the X-rays used and the symmetry and dimensions of the crystal's unit cell are known (Blundell et al. (1976) *Protein Crystallography (Molecular Biology Series)*, Academic Press, London). The result is that if a detector is placed behind a crystal that is being irradiated with monochromatic X-rays of an appropriate wavelength, the diffraction pattern recorded will consist of spots, each spot representing one of the orientations that gives rise to constructive interference.

Each spot in such a pattern, however it is recorded, is characterized by (i) an intensity (its blackness); (ii) a location, which encodes the information about diffraction orientation; and (iii) a phase. If all of those things are known about each spot in a crystal diffraction pattern, the distribution of electrons in the unit cell of the crystal may be computed by Fourier transformation (Blundell et al. (1976) supra), and from that distribution or electron density map, atomic positions can be determined.

Unfortunately, the phase information essential for computing electron distributions cannot be measured directly from diffraction patterns. One of the methods routinely used to determine the phases of macromolecules, such as proteins and nucleic acids, is called multiple isomorphous replacement (MIR) which involves the introduction of new X-ray scatterers into the unit cell of the crystal. Typically, these additions are heavy atoms, which make a significant contribution to the diffraction pattern. It is important that the additions be sufficiently low in number so that their positions can be located and that they leave the structure of the molecule or of the crystal cell unaltered, i.e., the crystals should be isomorphous. Isomorphous replacement usually is performed by diffusing different heavy-metal complexes into the channels of the preformed protein crystals. Macromolecules expose side chains (such as SH groups) in these solvent channels that are able to bind heavy metals. It is also possible to replace endogenous light metals in metalloproteins with heavier ones, e.g., zinc by mercury, or calcium by samarium. Alternatively, the isomorphous derivative can be obtained by covalently attaching a heavy metal to the macromolecule in solution and then subjecting it to crystallization conditions.

Heavy metal atoms routinely used for isomorphous replacement include but are not limited to mercury, uranium, platinum, gold, lead, and selenium. Specific examples include mercury chloride, ethyl-mercury phosphate, and osmium pentamine, iridium pentamine. Since such heavy metals contain many more electrons than the light atoms (H, N, C, O, and S) of the protein, the heavy metals scatter x-rays more strongly. All diffracted beams would therefore increase in intensity after heavy-metal substitution if all interference were positive. In fact, however, some interference is negative; consequently, following heavy-metal substitution, some spots increase in intensity, others decrease, and many show no detectable difference.

Phase differences between diffracted spots can be determined from intensity changes following heavy-metal substitution. First, the intensity differences are used to deduce the positions of the heavy atoms in the crystal unit cell. Fourier summations of these intensity differences give maps, of the vectors between the heavy atoms, the so-called Patterson maps. From these vector maps, the atomic arrangement of the heavy atoms is deduced. From the positions of the heavy metals in the unit cell, the amplitudes and phases of their contribution to the diffracted beams of protein crystals containing heavy metals is calculated.

This knowledge then is used to find the phase of the contribution from the protein in the absence of the heavy-metal atoms. As both the phase and amplitude of the heavy metals and the amplitude of the protein alone is known, as well as the amplitude of the protein plus heavy metals (i.e., protein heavy-metal complex), one phase and three amplitudes are known. From this, the interference of the X-rays scattered by the heavy metals and protein can be calculated to determine if the interference is constructive or destructive. The extent of positive or negative interference, with knowledge of the phase of the heavy metal, give an estimate of the phase of the protein. Because two different phase angles are determined and are equally good solutions, a second heavy-metal complex can be used which also gives two possible phase angles. Only one of these will have the same value as one of the two previous phase angles; it therefore represents the correct phase angle. In practice, more than two different heavy-metal complexes are usually made in order to give a reasonably good estimate of the phase for all reflections. Each individual phase estimate contains experimental errors arising from errors in the measured amplitudes. Furthermore, for many reflections, the intensity differences are too small to measure after one particular isomorphous replacement, and others can be tried.

The amplitudes and the phases of the diffraction data from the protein crystals are used to calculate an electron-density map of the repeating unit of the crystal. This map then is interpreted to accommodate the residues of the molecule of interest. That interpretation is made more complex by several limitations in the data. First, the map itself contains errors, mainly due to errors in the phase angles. In addition, the quality of the map depends on the resolution of the diffraction data, which, in turn, depends on how well-ordered the crystals are. This directly influences the quality of the map that can be produced. The resolution is measured in angstrom units (Å); the smaller this number is, the higher the resolution and, therefore, the greater the amount of detail that can be seen.

Building the initial model is a trial-and-error process. First, one has to decide how a polypeptide chain or nucleic acid weaves its way through the electron-density map. The resulting chain trace constitutes a hypothesis by which one tries to match the density of side chains to the known sequence of the polypeptide or nucleic acid. When a reasonable chain trace has finally been obtained, an initial model is built that fits the atoms of the molecule into the electron density. Computer graphics are used both for chain tracing and for model building to present the data and manipulated the models.

The initial model will contain some errors. Provided the crystals diffract to high enough resolution (e.g., better than 3.5 Å), most or substantially all of the errors can be removed by crystallographic refinement of the model using computer algorithms. In this process, the model is changed to minimize the difference between the experimentally observed diffraction amplitudes and those calculated for a hypothetical crystal containing the model (instead of the real molecule). This difference is expressed as an R factor (residual disagreement) which is 0.0 for exact agreement and about 0.59 for total disagreement.

In general, the R factor for a well-determined macromolecular structure preferably lies between 0.15 and 0.35 (such as less than about 0.24-0.28). The residual difference is a consequence of errors and imperfections in the data. These derive from various sources, including slight variations in the conformation of the protein molecules, as well as inaccurate corrections both for the presence of solvent and for differences in the orientation of the microcrystals from which the crystal is built. This means that the final model represents an average of molecules that are slightly different both in conformation and orientation.

In refined structures at high resolution, there are usually no major errors in the orientation of individual residues, and the estimated errors in atomic positions are usually around 0.1-0.2 Å, provided the sequence of the protein or nucleic acid is known. Hydrogen bonds, both within the molecule of interest and to bound ligands, can be identified with a high degree of confidence.

Typically, X-ray structures can be determined provided the resolution is better than 3.5 Å. Electron-density maps are interpreted by fitting the known amino acid and/or nucleic acid sequences into regions of electron density.

VI. The Need for Higher Resolution for the 50S Ribosomal Subunit

Although the art provides crystals of the 50S ribosomal subunit, and 9 Å and 5 Å resolution X-ray crystallographic maps of the structure of the 50S ribosome, the prior art crystals and X-ray diffraction data are not sufficient to establish the three-dimensional structures of all 31 proteins and 3,043 nucleotides of the 50S ribosomal subunit. Thus, the prior art crystals and maps are inadequate for the structure-based design of active agents, such as herbicides, drugs, insecticides, and animal poisons.

More detailed, higher resolution X-ray crystallographic maps are necessary in order to determine the location and three-dimensional structure of the proteins and nucleotides in ribosomes and ribosomal subunits, particularly for the 50S ribosomal subunit. An accurate molecular structure of the 50S ribosomal subunit will not only enable further investigation and understanding of the mechanism of protein synthesis, but also the development of effective therapeutic agents and drugs that modulate (e.g., induce or inhibit) protein synthesis.

SUMMARY OF THE INVENTION

The present invention is based, in part, upon the determination of a high resolution atomic structure of a ribosomal subunit, more particularly, a large subunit of a ribosome. In addition, the invention is based, in part, upon the determination of high resolution atomic structures of certain protein synthesis inhibitors, namely antibiotics, when they are interacting with the large subunit of the ribosome.

The invention provides the structure of the large subunit of a ribosome isolated from the organism, *Haloarcula marismortui*. However, in view of the high level of sequence and structural homology between ribosomes of organisms in different kingdoms, the structural information disclosed herein can be used to produce, using routine techniques, high resolution structural models of large ribosomal units for any organism of interest.

Although there is significant homology between ribosomes of different organisms, for example, between ribosomes of humans and certain human pathogens, there still are differences that can be exploited therapeutically. For example, many clinically and commercially significant protein synthesis inhibitors, for example, antibiotics such as streptomycin, tetracycline, chloramphenicol and erythromycin, selectively target bacterial ribosomes and disrupt bacterial protein synthesis but at the same time do not target or otherwise significantly affect human ribosome function. As a result, over the years antibiotics have proven to be invaluable in the treatment of microbial infections in humans. However, there is still an ongoing need for new protein synthesis inhibitors, particularly because of the development of strains of pathogens that are resistant to known antibiotics. The information provided herein provides insights into the design of new protein synthesis inhibitors.

The invention provides computer systems containing atomic co-ordinates that define at least a portion of the three-dimensional structure of a ribosome, more specifically, a large ribosomal subunit. In addition, the invention provides methods of using the atomic co-ordinates to identify new molecules that can selectively bind ribosomes, and that preferably act as selective inhibitors of protein synthesis. In addition, the invention provides computer systems containing atomic co-ordinates that define at least a portion of certain antibiotics when interacting with their binding sites in the large ribosomal subunit. In addition, the invention provides methods of using the atomic co-ordinates of the antibiotics to identify new molecules that selectively bind ribosomes, and that preferably act as selective inhibitors of protein synthesis. In addition, the invention provides new families of protein synthesis inhibitors. Each of these aspects of the invention is discussed in more detail below.

In one aspect, the invention provides a computer system comprising: (a) a memory having stored therein data indicative of atomic co-ordinates derived from an electron density map having a resolution of at least about 4.5 Å, more preferably of at least about 3.0 Å, and most preferably of about 2.4 Å and defining a ribofunctional locus of a large subunit of a ribosome; and (b) a processor in electrical communication with the memory, the processor comprising a program for generating a three-dimensional model representative of the ribofunctional locus. In a preferred embodiment, the computer system further comprises a device, for example, a computer monitor, or terminal for providing a visual representation of the molecular model. In another preferred embodiment, the processor further comprises one or more programs to facilitate rational drug design.

In a preferred embodiment, the computer system further comprises at least a portion of the atomic co-ordinates deposited at the Protein Data Bank under accession number PDB ID: 1FFK (large ribosomal subunit), 1FFZ (large ribosomal subunit complexed with CCdA-p-Puro), 1 FG0 (large ribosomal subunit complexed with a mini-helix analogue of aminoacyl-tRNA), 1JJ2 (large ribosomal structure), 1K73 (large ribosomal subunit complexed with anisomycin), 1KC8 (large ribosomal subunit complexed with blasticidin), 1K8A (large ribosomal subunit complexed with carbomycin), 1 KD1 (large ribosomal subunit complexed with spiramycin); or 1K9M (large ribosomal subunit complexed with tylosin) or recorded on compact disk, Disk No. 1 of 1.

In a preferred embodiment, the atomic co-ordinates further define at least a portion of a protein synthesis inhibitor, for example, an antibiotic, more specifically an antibiotic selected from the group consisting of anisomycin, blasticidin, carbomycin A, sparsomycin, spiramycin, tylosin, virginiamycin M, azithromycin, linezolid, chloramphenicol and erythromycin, complexed with a ribofunctional locus. More specifically, the invention provides atomic co-ordinates of the large ribosomal subunit together the atomic co-ordinates of antibiotics interacting with the large ribosomal subunit. These atomic co-ordinates are recorded on compact disk, Disk No. 1, and correspond to: large ribosomal subunit complexed with anisomycin (file name: anisomysin.pdb or ANISOMYC.PDB); large ribosomal subunit complexed with blasticidin (file name: blasticidin.pdb or BLASTICI.PDB); large ribosomal subunit complexed with carbomycin (file name: carbomycin.pdb or CARBOMYC.PDB); large ribosomal subunit complexed with tylosin (file name: tylosin.pdb or TYLOSIN.PDB); large ribosomal subunit complexed with sparsomycin (file name: sparsomycin.pdb or SPARSOMY.PDB); large ribosomal subunit complexed with virginiamycin M (file name: virginiamycin.pdb or VIRGINIA.PDB); large ribosomal subunit complexed with spiramycin (file name: spiramycin.pdb or SPIRAMYC.PDB); large ribosomal subunit complexed with azithromycin (file name: AZITHROM.PDB or azithromycin.pdb); or large ribosomal subunit complexed with linezolid (file name: LINEZOLI.PDB or linezolid.pdb); or large ribosomal subunit complexed with erythromycin (file name: erythromycin.pdb).

In a preferred embodiment, the ribofunctional locus comprises at least a portion of an active site in the ribosomal subunit, for example, at least a portion of one or more of: a peptidyl transferase site (a portion of which may be defined by a plurality of residues set forth in Table 5A or 5B); an A-site (a portion of which may be defined by a plurality of residues set forth in Table 6A or 6B); a P-site (a portion of which may be defined by a plurality of residues set forth in Table 7A or 7B); a polypeptide exit tunnel (a portion of which may be defined by a plurality of residues set forth in Table 8A or 8B, Table 9, or Table 10); or an antibiotic binding domain (a portion of which may be defined by a plurality of residues set forth in Table 11A or 11B, Table 12A or 12B, Table 13A or 13B, Table 14A or 14B, Table 15A or 15B, Table 16A or 16B, Table 17A or 17B, Table 18A or 18B, Table 19A or 19B, or Table 20A or 20B). A plurality of residues shall be considered to include at least 3 residues, preferably at least 5 residues, and more preferably at least 10 residues. The ribofunctional locus may be defined by atoms of ribosomal RNA, one or more ribosomal proteins, or a combination of ribosomal RNA and one or more ribosomal proteins.

In another preferred embodiment, the atomic co-ordinates are produced by molecular modeling. Using the atomic co-ordinates provided herein, the skilled artisan may generate models of any ribosome of interest using conventional techniques, for example, conventional homology modeling, and or molecular replacement techniques. In another embodiment, the atomic co-ordinates are produced by homology modeling using at least a portion of the atomic co-ordinates deposited at the Protein Data Bank under accession number PDB ID: 1FFK, 1FFZ, 1FG0, 1JJ2, 1K73, 1KC8, 1K8A, 1KD1, or 1K9M, or any of the atomic co-ordinates included in compact disk, Disk No. 1. In another embodiment, the atomic co-ordinates are produced by molecular replacement using at least a portion of the atomic co-ordinates deposited at the Protein Data Bank under accession number PDB ID: 1FFK, 1FFZ, 1FG0, 1 JJ2, 1K73, 1KC8, 1K8A, 1KD1 or 1K9M, or any of the atomic co-ordinates recorded on compact disk, Disk No. 1.

In a preferred embodiment, the atomic co-ordinates define residues that are conserved between ribosomes or ribosomal subunits of pathogens, for example, prokaryotic organisms, and, optionally but more preferably, are also absent from ribosomes or ribosomal subunits of a host organism, for example, a human. In another preferred embodiment, the atomic co-ordinates may define residues that are conserved between ribosomes or ribosomal subunits of prokaryotic organisms, for example, bacteria, and, optionally but more preferably, are also absent from ribosomal subunits of eukaryotes, for example, a mammal, more preferably, a human. This information can be used, for example, via the use of one or more molecular models, to identify targets for rational drug design that may be exploited to develop new molecules, for example, protein synthesis inhibitors, that disrupt protein synthesis in a pathogen, for example, a bacteria, but do not disrupt or otherwise substantially affect protein synthesis in a host organism, for example, a human.

In another aspect, the invention provides a variety of methods for designing, testing and refining new molecules via rational drug design. For example, the invention provides a method that comprises the steps of (a) providing a model, for example, a molecular model, having a ribofunctional locus of a large subunit of a ribosome, wherein the model is defined by the spatial arrangement of atoms derived from an electron density map having a resolution of at least about 4.5 Å, more preferably to at least about 3.0 Å, and most preferably to about 2.4 Å; and (b) using the model to identify a candidate molecule having a surface complementary to the ribofunctional locus. Preferably, the candidate molecule stereochemically interfits and more preferably binds with the ribofunctional locus of the large subunit of the ribosome.

In a preferred embodiment, the method comprises one or more additional steps of: producing the candidate molecule identified in such a method; determining whether the candidate molecule, when produced, modulates (for example, induces or reduces) ribosomal activity; identifying a modified molecule; producing the modified molecule; determining whether the modified molecule, when produced, modulates ribosomal activity; and producing the modified molecule for use either alone or in combination with a pharmaceutically acceptable carrier. The candidate molecule and/or the modified molecule may be an antibiotic or antibiotic analogue, for example, a macrolide antibiotic or a macrolide analogue.

In a preferred embodiment, the ribofunctional locus used in such a method comprises at least a portion of an active site in the ribosomal subunit. In another preferred embodiment, the ribofunctional locus is defined by at least a portion of one or more of: a peptidyl transferase site (a portion of which may be defined by a plurality of residues set forth in Table 5A or Table 5B); an A-site (a portion of which may be defined by a plurality of residues set forth in Table 6A or Table 6B); a P-site (a portion of which may be defined by a plurality of residues set forth in Table 7A or Table 7B); a polypeptide exit tunnel (a portion of which may be defined by a plurality of residues set forth in Table 8A, Table 8B, Table 9, Table 10); or an antibiotic binding domain (a portion of which may be defined by a plurality of residues set forth in Table 11A, Table 11B, Table 12A, Table 12B, Table 13A, Table 13B, Table 14A, Table 14B, Table 15A, Table 15B, Table 16A, Table 16B, Table 17A, Table 17B, Table 18A, Table 18B, Table 19A, Table 19B, Table 20A or Table 20B). The ribofunctional locus may be defined by atoms of ribosomal RNA, one or more ribosomal proteins, or a combination of ribosomal RNA and one or more ribosomal proteins.

In another preferred embodiment, the atomic co-ordinates are used to produce a molecular model in an electronic form. The atomic co-ordinates preferably are produced by molecular modeling. In another embodiment, the atomic co-ordinates are produced by homology modeling using at least a portion of the atomic co-ordinates deposited at the Protein Data Bank under accession number PDB ID: 1FFK, 1FFZ, 1FG0, 1JJ2, 1K73, 1KC8, 1K8A, 1KD, or 1K9M, or the atomic co-ordinates recorded on compact disk, Disk No. 1. In another embodiment, the atomic co-ordinates are produced by molecular replacement using at least a portion of the atomic co-ordinates deposited at the Protein Data Bank under accession number PDB ID: 1FFK, 1FFZ, 1FG0, 1JJ2, 1K73, 1KC8, 1K8A, 1 KD1, or 1K9M or any of the atomic co-ordinates included on compact disk, Disk No. 1.

In a preferred embodiment, the atomic co-ordinates may define residues that are conserved among ribosomes or ribosomal subunits of pathogens, for example, prokaryotic organisms, and, optionally but more preferably, are also absent in ribosomes or ribosomal subunits of a host organism, for example, a human. In another preferred embodiment, the atomic co-ordinates may define residues that are conserved between ribosomes or ribosomal subunits of prokaryotic organisms, for example, bacteria, and, optionally but more preferably, are also absent from ribosomes or ribosomal subunits of eukaryotes, for example, a mammal, more preferably a human. This information can be used, for example, via the use of one or more molecular models, to identify targets for rational drug design that may be exploited to develop new molecules, for example, protein synthesis inhibitors, that disrupt protein synthesis in a pathogen, for example, a bacteria but do not disrupt or otherwise substantially affect protein synthesis in a host organism, for example, a human.

In a preferred embodiment, the computer system further comprises at least a portion of the atomic co-ordinates deposited at the Protein Data Bank under accession number PDB ID: 1FFK (large ribosomal subunit), 1FFZ (large ribosomal subunit complexed with CCdA-p-Puro), 1FG0 (large ribosomal subunit complexed with a mini-helix analogue of aminoacyl-tRNA), 1JJ2 (large ribosomal subunit), 1K73 (large ribosomal subunit complexed with anisomycin), 1KC8 (large ribosomal subunit complexed with blasticidin), 1K8A (large ribosomal subunit complexed with carbomycin), 1KD1 (large ribosomal subunit complexed with spiramycin); or 1K9M (large ribosomal subunit complexed with tylosin), or recorded on compact disk, Disk No. 1.

In another aspect, the invention provides a computer system comprising: (a) a memory having stored therein data indicative of atomic co-ordinates derived from an electron density map defining at least a portion of a protein synthesis inhibitor when the protein synthesis inhibitor is interacting with a ribofunctional locus of a large subunit of a ribosome; and (b) a processor in electrical communication with the memory, the processor comprising a program for generating a three-dimensional model representative of at least a portion of the protein synthesis inhibitor. In a preferred embodiment, the computer system further comprises a device, for example, a computer monitor, or terminal for providing a visual representation of the molecular model. In another preferred embodiment, the processor further comprises one or more programs to facilitate rational drug design.

In a preferred embodiment, the atomic co-ordinates further define at least a portion of a protein synthesis inhibitor, for example, an antibiotic, more specifically an antibiotic selected from the group consisting of anisomycin, blasticidin, carbomycin A, sparsomycin, spiramycin, tylosin, virginiamycin M, azithromycin, linezolid and erythromycin, complexed with a ribofunctional locus. In a preferred embodiment, the ribofunctional locus comprises at least a portion of an active site of a ribosome, for example, at least a portion of one or more of (i) a peptidyl transferase site, (ii) an A-site, (iii) a P-site, (iv) a polypeptide exit tunnel.

More specifically, the invention provides atomic co-ordinates of antibiotics interacting with the large ribosomal subunit. These atomic co-ordinates are recorded on compact disk, Disk No. 1, and correspond to: large ribosomal subunit complexed with anisomycin (file name: anisomysin.pdb or ANISOMYC.PDB); large ribosomal subunit complexed with blasticidin (file name: blasticidin.pdb or BLASTICI.PDB); large ribosomal subunit complexed with carbomycin A (file name: carbomycin.pdb or CARBOMYC.PDB); large ribosomal subunit complexed with tylosin (file name: tylosin.pdb or TYLOSIN.PDB); large ribosomal subunit complexed with sparsomycin (file name: sparsomycin.pdb or SPARSOMY.PDB); large ribosomal subunit complexed with virginiamycin M (file name: virginiamycin.pdb or VIRGINIA.PDB); large ribosomal subunit complexed with spiramycin (file name: spiramycin.pdb or SPIRAMYC.PDB); large ribosomal subunit complexed with azithromycin (file name: AZITHROM.PDB or azithromycin.pdb); or large ribosomal subunit complexed with linezolid (file name: LINEZOLI.PDB or linezolid.pdb); or large ribosomal subunit complexed with erythromycin (file name: erythromycin.pdb).

In another aspect, the invention provides a method of identifying a lead candidate for a new protein synthesis inhibitor. The method comprises the steps of (a) providing a molecular model of at least a portion of a protein synthesis inhibitor when the protein synthesis inhibitor is interacting with a ribofunctional locus of a large subunit of a ribosome; and (b) using the model to identify the lead candidate. In a preferred embodiment, the lead candidate is capable of interacting, and still more preferably binding a ribofunctional locus.

In another preferred embodiment, the method comprises the additional step of producing the lead compound. After synthesis, the lead compound can be tested for biological activity, for example, modulation of ribosome activity in an in vitro assay or growth inhibition of micro-organisms of interest. Based on the results of such studies, it is possible to determine structure-activity relationships, which may then be used to design further modifications of the lead compound in order to improve a particular feature of interest. The modified lead compounds then can be produced and assessed for biological activity, as before. Once a compound of interest has been designed, synthesized and tested for activity, it may then be produced in commercially feasible quantities for use as a pharmaceutical.

In a preferred embodiment, the starting molecule (i.e., the protein synthesis inhibitor), the lead compound and the penultimate compound is an antibiotic or antibiotic analogue. In another embodiment, the lead compound and also the penultimate compound is a hybrid antibiotic (i.e., comprises a portion of a first antibiotic and a portion of a second, different antibiotic).

In another preferred embodiment, the model used in the practice of the invention is a model of an antibiotic selected from the group consisting of anisomycin, blasticidin, carbomycin A, sparsomycin, spiramycin, tylosin, virginiamycin M, azithromycin, linezolid, or erythromycin. The model preferably comprises a portion of the atomic co-ordinates recorded on compact disk, Disk No. 1 of 1 under file name: anisomycin.pdb, blasticidin.pdb, carbomycin.pdb, sparsomycin.pdb, spiramycin.pdb, tylosin.pdb, virginiamycin.pdb, ANISOMYC.PDB, BLASTICI.PDB, CARBOMYC.PDB, SPARSOMY.PDB, SPIRAMYC.PDB, TYLOSIN.PDB, VIRGINIA.PDB, AZITHROM.PDB, LINEZOLI.PDB, azithromycin.pdb, linezolid.pdb, or erythromycin.pdb. In another preferred embodiment, the penultimate compound is an analogue of an antibiotic selected from the group consisting of anisomycin, blasticidin, carbomycin A, sparsomycin, spiramycin, tylosin, virginiamycin M, azithromycin, linezolid, or erythromycin.

In a preferred embodiment, the ribofunctional locus comprises at least a portion of an active site of a ribosome, for example, at least a portion of one or more of (i) a peptidyl transferase site, (ii) an A-site, (iii) a P-site, and (iv) a polypeptide exit tunnel. In another embodiment, the molecular model useful in the practice of the invention is in an electronic form, in which case the molecular model preferably is generated by molecular modeling.

In another aspect, the invention provides new protein synthesis inhibitors that disrupt the function of a target ribosome. These inhibitors can be readily designed and tested as disclosed herein.

One type of protein synthesis inhibitor of the invention comprises: a first binding domain having a surface, for example, a solvent accessible surface, that mimics or duplicates a surface of a known first molecule, for example, a first antibiotic, that binds with a first contact site, for example, a first ribofunctional locus, in or on a large ribosomal subunit; and a second binding domain having a surface, for example, a solvent accessible surface, that mimics or duplicates a surface of a known second molecule, for example, a second antibiotic, that binds with a second contact site, for example, a second ribofunctional locus, in or on the ribosomal subunit. The first domain is attached to the second domain so as to permit both the first domain and the second domain to bind simultaneously with their respective contact sites within or on the ribosomal subunit so as to disrupt protein synthesis in a ribosomal subunit. In a preferred embodiment, the protein synthesis inhibitor has a molecular weight of less than about 1,500 and an $IC_{50}$ of lower than about 50 µM, more preferably less than about 10 µM.

Another type of protein synthesis inhibitor is a synthetic, engineered molecule that comprises: (i) a binding domain having a surface, for example, a solvent accessible surface, that mimics or duplicates a solvent accessible surface of a known molecule, for example, a first known antibiotic, which binds with a contact site, for example, a ribofunctional locus in or on a ribosomal subunit; and (ii) a novel effector domain attached to the binding domain which, upon binding of the binding domain with the contact site, occupies a space within or adjacent to the ribosomal subunit thereby disrupting protein synthesis in the ribosomal subunit. In a preferred embodiment, the protein synthesis inhibitor has a molecular weight of less than about 1,500 and an $IC_{50}$ of lower than about 50 µM, more preferably less than about 10 µM.

In another aspect, the invention provides new protein synthesis inhibitors, for example, a molecule capable of contacting at least three residues but less than thirteen contact residues in Table 11A that together define an anisomycin binding pocket of a large ribosomal subunit, a molecule capable of contacting at least three residues but less than ten contact residues in Table 12A that together define a blasticidin binding pocket of a large ribosomal subunit, a molecule capable of contacting at least three residues but less than sixteen contact residues in Table 13A that together define a carbomycin A binding pocket of a large ribosomal subunit, a molecule capable of contacting at least three residues but less than twenty contact residues in Table 14A that together define a tylosin binding pocket of a large ribosomal subunit, a molecule capable of contacting at least three residues but less than nine contact residues in Table 15A that together define a sparsomycin binding pocket of a large ribosomal subunit, a molecule capable of contacting at least three residues but less than thirteen contact residues in Table 16A that together define a virginiamycin M binding pocket of a large ribosomal subunit, a molecule capable of contacting at least three residues but less than fifteen contact residues in Table 17A that together define a spiramycin binding pocket of a large ribosomal subunit, a molecule capable of contacting at least three residues but less than thirteen contact residues in Table 18A that together define an erythromycin binding pocket of a large ribosomal subunit, a molecule capable of contacting at least three but less than eleven contact residues in Table 19A that together define an azithromycin binding pocket of a large ribosomal subunit, or a molecule capable of contacting at least three residues but less than fifteen contact residues in Table 20A that together define a linezolid binding pocket of a large ribosomal subunit. The contact residues are those residues in the large ribosomal subunit that are in van der Waals contact with the antibiotic of interest.

In yet another aspect, the invention provides a protein synthesis inhibitor comprising, for example, a molecule capable of contacting a plurality of residues in Table 11A that together define an anisomycin binding pocket of a large ribosomal subunit, but lacking one or more atoms present in the anisomycin molecule, the atomic co-ordinates of which are recorded on Disk No. 1 under file name ANISOMYC.PDB; a molecule capable of contacting a plurality of residues in Table 12A that together define a blasticidin binding pocket of a large ribosomal subunit, but lacking one or more atoms present in the blasticidin molecule, the atomic co-ordinates of which are recorded on Disk No. 1 under file name BLASTICI.PDB; a molecule capable of contacting a plurality of residues in Table 13A that together define a carbomycin A binding pocket of a large ribosomal subunit, but lacking one or more atoms present in carbomycin A, the atomic co-ordinates of which are recorded on Disk No. 1 under file name CARBOMYC.PDB; a molecule capable of contacting a plurality of residues in Table 14A that together define a tylosin binding pocket of a large ribosomal subunit, but lacking one or more atoms present in tylosin, the atomic co-ordinates of which are recorded on Disk No. 1 under file name TYLOSIN.PDB; a molecule capable of contacting a plurality of residues in Table 15A that together define a sparsomycin binding pocket of a large ribosomal subunit, but lacking one or more atoms present in sparsomycin, the atomic co-ordinates of which are recorded on Disk No. 1 under file name SPARSOMY.PDB; a molecule capable of contacting a plurality of residues in Table 16A that together define a virginiamycin M binding pocket of a large ribosomal subunit, but lacking one or more atoms present in virginiamycin M, the atomic co-ordinates of which are recorded on Disk No. 1 under file name VIRGINIA.PDB; a molecule capable of contacting a plurality of residues in Table 17A that together define a spiramycin binding pocket of a large ribosomal subunit, but lacking one or more atoms present in spiramycin, the atomic co-ordinates of which are recorded on Disk No. 1 under file name SPIRAMYC.PDB; a molecule capable of contacting a plurality of residues in Table 18A that together define an erythromycin binding pocket of a large ribosomal subunit, but lacking one or more atoms present in erythromycin, the atomic co-ordinates of which are recorded on Disk No. 1 under file name erythromycin.pdb; a molecule capable of contacting a plurality of residues in Table 19A that together define an azithromycin binding pocket of a large ribosomal subunit, but lacking one or more atoms present in azithromycin, the atomic co-ordinates of which are recorded on Disk No. 1 under file name azithromycin.pdb; or a molecule capable of contacting a plurality of residues in Table 20A that together define a linezolid binding pocket of a large ribosomal subunit, but lacking one or more atoms present in linezolid, the atomic co-ordinates of which are recorded on Disk No. 1 under file name linezolid.pdb.

The foregoing aspects and embodiments of the invention may be more fully understood by reference to the following figures, detailed description and claims. Further advantages are evident from the drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Color renditions similar to some of the following figures can be found, for example, in Ban et al. (2000) *Science* 289: 905-920; or Nissen et al. (2000) *Science* 289: 920-930.

The objects and features of the invention may be more fully understood by reference to the drawings described below:

FIGS. 1(A)-(E) show the electron density from a 2.4 Å resolution electron density map. Specifically, FIG. 1(A) shows a stereo view of a junction between 23S rRNA domains II, III, and IV. FIG. 1(B) shows the extended region of protein L2 interacting with surrounding RNA. FIG. 1(C) shows in detail the L2 region with a bound $Mg^{2+}$ ion. FIG. 1(D) shows in detail L2 with amino acid side chains. FIG. 1(E) shows helices 94-97 from domain 6.

Figure 2:
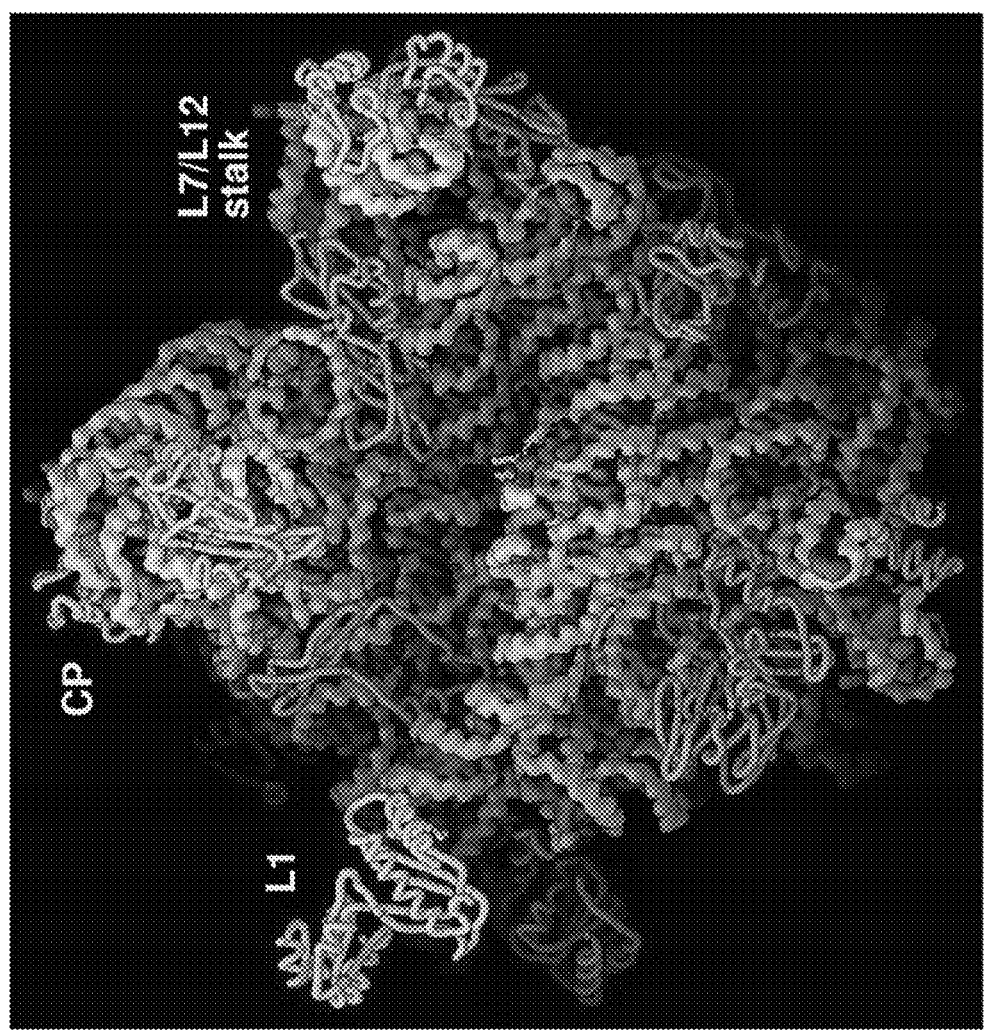

FIG. 2 shows the *H. marismortui* large ribosomal subunit in the crown view. The subunit is shown in the crown view, with its L7/L12 stalk to the right, its L1 stalk to the left, and its central protuberance (CP) up. In this view, the surface of the subunit that interacts with the small ribosomal subunit faces the reader. RNA is shown in gray in a space-filling rendering. The backbones of the proteins visible are rendered in gold. A transition state analogue bound to the peptidyl transferase site of the subunit is indicated in green. The particle is approximately 250 Å across.

Figure 3A:
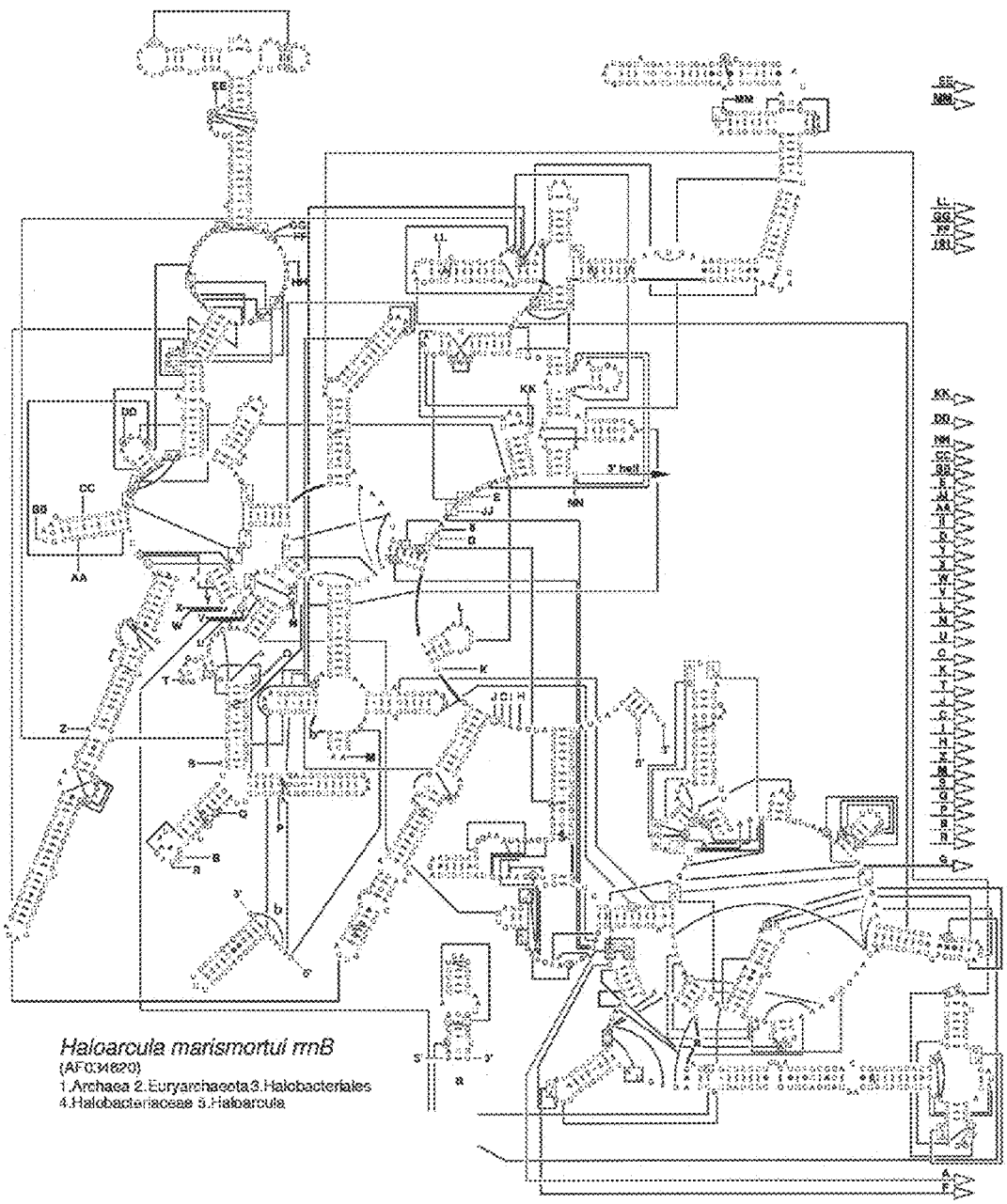
Figure 3B:
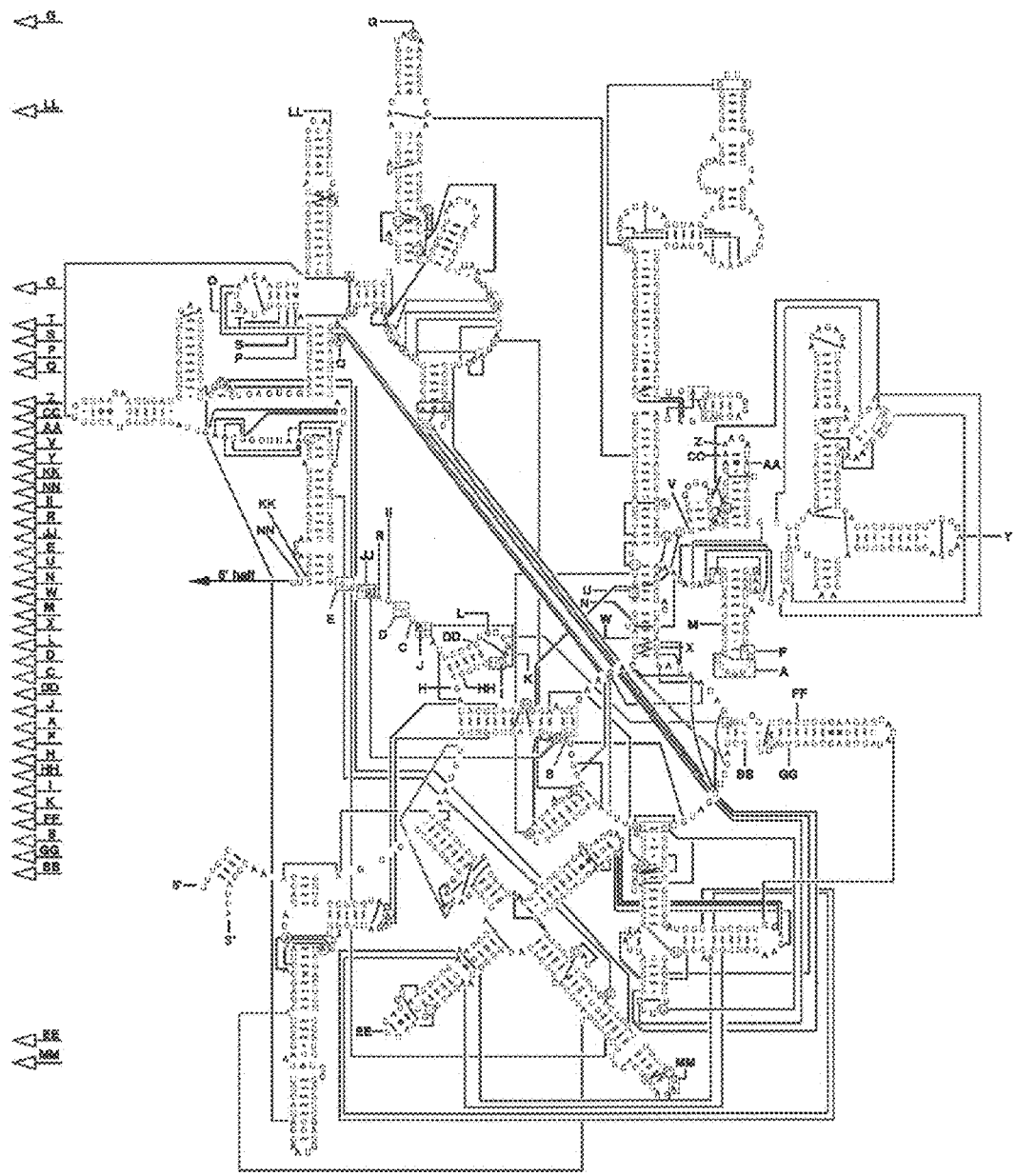

FIGS. 3(A)-(B) show the secondary structure of the 23S rRNA from *H. marismortui*. The secondary structure of this 23S rRNA is shown in a standardized format. FIG. 3(A) shows the 5' half of the large subunit rRNA. FIG. 3(B) show the 3' half of the large subunit rRNA. This diagram shows all the base pairings seen in the crystal structure of the large subunit that are stabilized by at least two hydrogen bonds. Pairings shown in red were predicted and are observed. Those shown in green were predicted, but are not observed. Interactions shown in blue are observed, but were not predicted. Bases shown in black do not appear to be involved in pairing interactions. Sequences that cannot be visualized in the 2.4 Å resolution electron density map are depicted in gray with the secondary structures predicted for them.

Figure 4D:
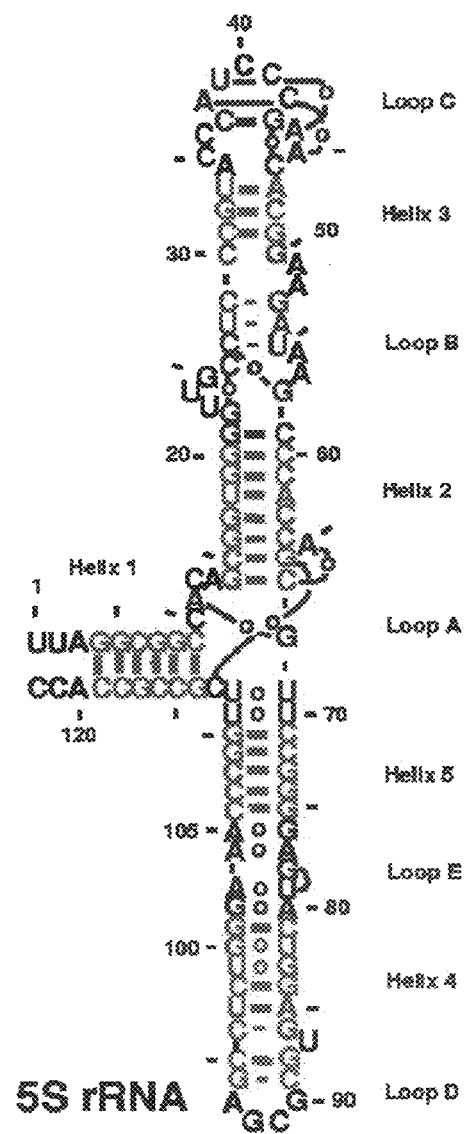

FIGS. 4(A)-(L) show the tertiary structures of the RNA domains in the *H. marismortui* large ribosomal subunit, its RNA as a whole, and schematics of its RNAs. Specifically, FIGS. 4(A) and 4(B) show the RNA structure of the entire subunit. Domains are color coded as shown in the schematic of FIG. 5(C). FIG. 4(A) shows the particle in the crown view. FIG. 4(B) shows the image in FIG. 4(A) rotated 180° about an axis running vertically in the plane of the image. FIGS. 4(C) and 4(D) show a schematic diagram of 23S rRNA and the secondary structure of 5S rRNA. FIG. 4(C) shows a schematic diagram of 23S rRNA secondary structure of FIG. 3 with helices numbered according to Leffers et al. ((1987) *J. Mol. Biol.* 195: 43-61), and the domains of the molecule are indicated by color shading. FIG. 4(D) shows the secondary structure of 5S rRNA from *H. marismortui*. Thick lines joining bases represent Watson-Crick pairing. Bases joined by a lower case "o" indicate non-Watson-Crick pairing. Bases joined by thin lines interact via a single hydrogen bond. Bases shown in black are not paired. Bases shown in red are phylogenetically predicted pairing that have now been confirmed (Symanski et al. (1998) *Nucl. Acids Res.* 26: 156-159). Pairs shown in blue are observed, but were not predicted, and pairs shown in green were predicted but are not observed. FIGS. 4(E) through 4(L) show stereo views of the RNA domains in the 23S rRNA and of 5S rRNA. Each domain is color-coded from its 5' end to its 3' end to facilitate the viewer following its trajectory in three-dimensions. The surfaces where the most important inter-domain interactions occur are shown in mono to the right of the stereo views. FIG. 4(E) shows domain I; FIG. 4(F) shows domain II; FIG. 4(G) shows domain III; FIG. 4(H) shows domain IV; FIG. 4(I) shows domain V, crown view; FIG. 4(J) shows domain V, back view; FIG. 4(K) shows domain VI; and FIG. 4(L) shows 5S rRNA.

FIGS. 5(A)-(C) show conservations and expansions in the 23S rRNA of *H. marismortui*. The generality of the RNA in these images is gray. Sequences that are found to be >95% conserved across the three phylogenetic kingdoms are shown in red. Sequences where expansion in the basic 23S structure is permitted are shown in green (Gutell et al. (2000) supra), Specifically, FIG. 5(A) shows the particle rotated with respect to the crown view so that its active site cleft can be seen. FIG. 5(B) shows the crown view. FIG. 5(C) shows the back view of the particle, i.e., the crown view rotated 180° about its vertical axis.

Figure 6:
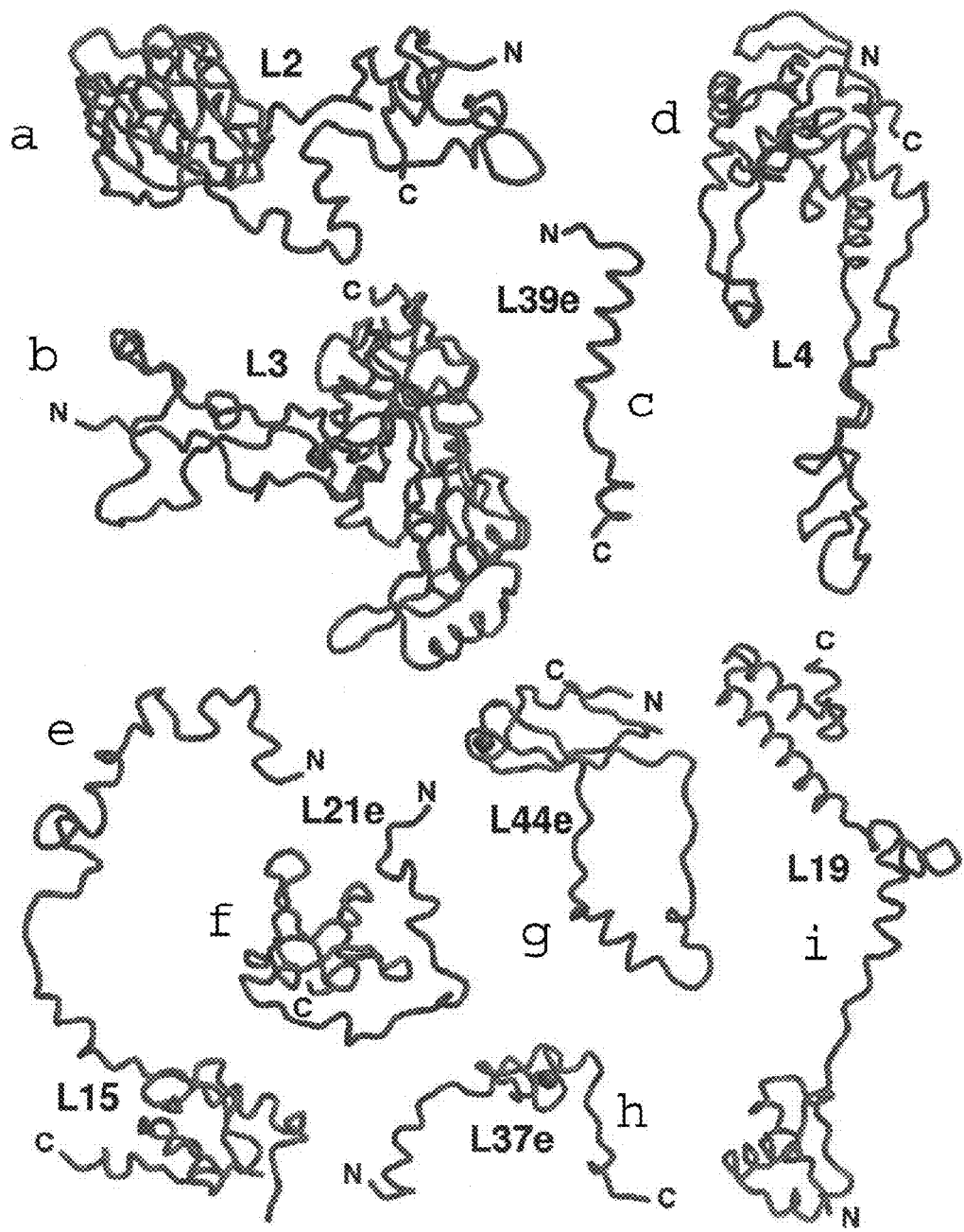

FIGS. 6(A)-(I) show structures of some large subunit ribosomal proteins that have non-globular extensions. Only the backbones of the proteins are shown. The globular domains of these proteins are shown in green, and their non-globular extensions are depicted in red. The positions of the zinc ions in L44e and L37e are also indicated. FIG. 6(A) shows L2; FIG. 6(B) shows L3; FIG. 6(C) shows L39; FIG. 6(D) shows L4; FIG. 6(E) shows L15; FIG. 6(F) shows L21e; FIG. 6(G) shows L44e; FIG. 6(H) shows L37e; FIG. 6(I) shows L19;

FIGS. 7(A)-(C) show proteins that appear on the surface of the large ribosomal subunit. The RNA of the subunit is shown in gray, as in FIG. 2, and protein backbones are shown in gold. Specifically, FIG. 7(A) shows the subunit in the crown view of the subunit. FIG. 7(B) shows the back side of the subunit in the crown view orientation. FIG. 7(C) shows the bottom view; the end of the peptide tunnel appears in the center of this image. The proteins visible in each image are identified in the small images at the lower left corner of the Figure.

Figure 8:
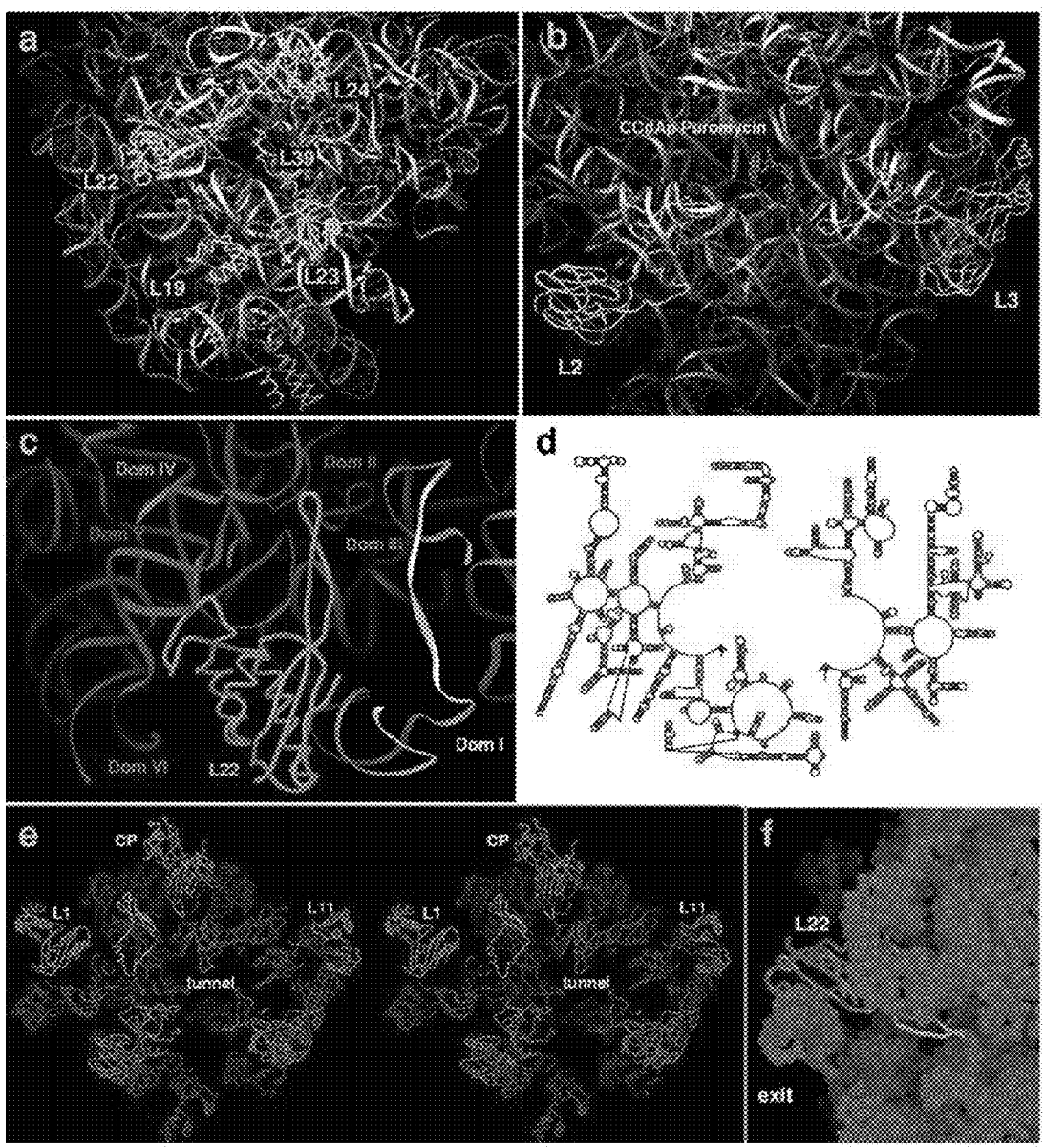

FIGS. 8(A)-(F) show the protein distribution and protein-RNA interactions in the large ribosomal subunit. Specifically, FIG. 8(A) shows the structures of proteins in the neighborhood of the end of the peptide tunnel and how they relate to the RNA sequences with which they interact. Protein L22 extends a long β hairpin extension inside the 23S rRNA. L24 has a similar extension but the entire protein is on the surface of the particle. L39 is the only protein in the subunit that lacks tertiary structure, while L37e has both $NH_2$ and COOH terminal extensions. L19 is unique in having two globular domains on the surface of the subunit connected by an extended sequence that weaves through the RNA. The end of L39 (green) actually enters the tunnel, while L37e (red) is entirely surrounded by RNA. FIG. 8(B) shows the non-globular extensions of L2 and L3 reaching through the mass of 23S rRNA towards the peptidyl transferase site, which is marked by a CCdA-p-puromycin molecule. FIG. 8(C) shows L22 interacting with portions of all six of the domains of 23S rRNA. FIG. 8(D) shows a schematic of 23S rRNA showing the locations of the sequences that make at least van der Waals contact with protein (red). FIG. 8(E) shows a stereo view of the proteins of the large ribosomal subunit with all the RNA stripped away. Proteins are color red as an aid to visualization only. FIG. 8(F) shows a cross section of the subunit in the area of the tunnel exit. Protein L22 is shown as ribbons in red, and the β hairpin loop where mutations confer erythromycin resistance is shown in orange. Atoms on the surface are shown in gray, protein atoms are shown in green, and atoms at the slice interface are shown in blue.

Figure 9:
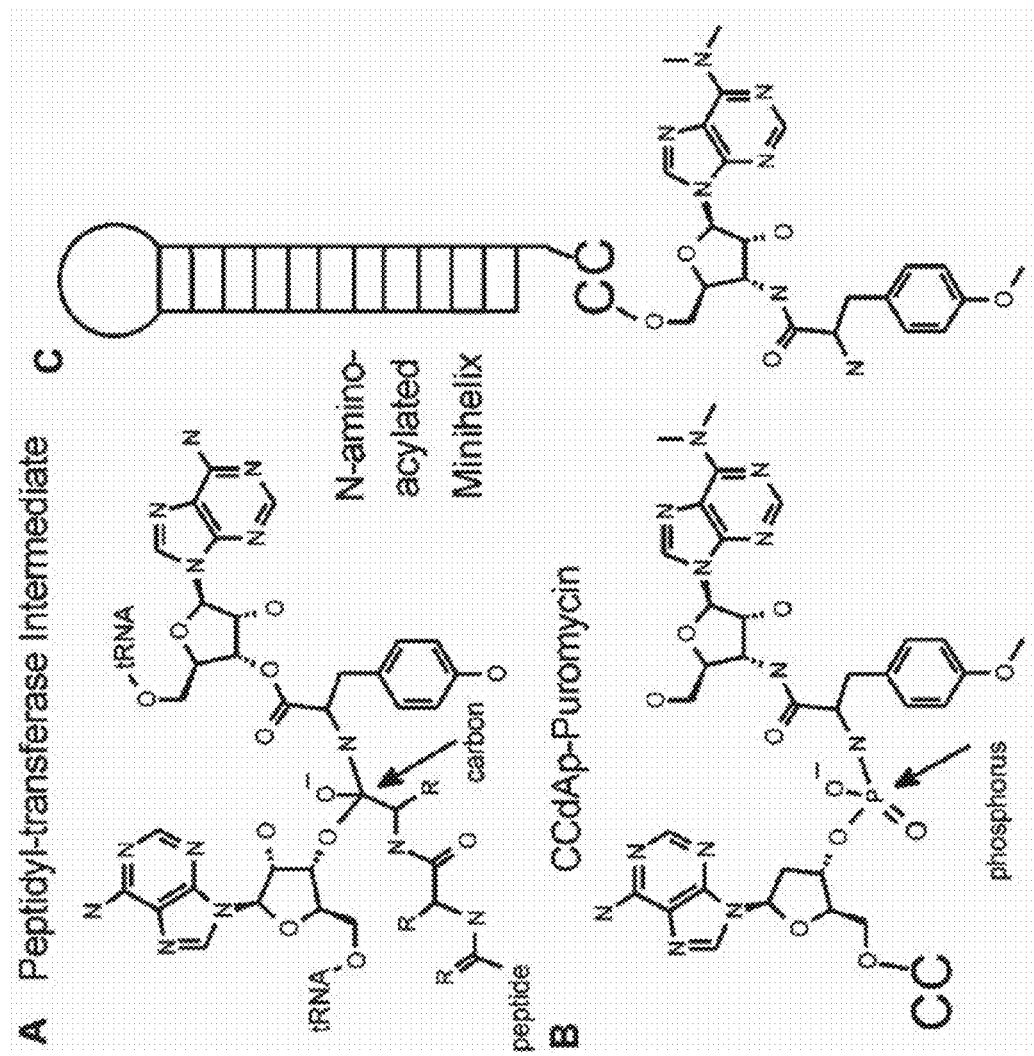

FIGS. 9(A)-(C) show chemical structures of ribosome peptidyl transferase substrates and analogues. Specifically, FIG. 9(A) shows the tetrahedral carbon intermediate produced during peptide bond formation; the tetrahedral carbon is indicated by an arrow. FIG. 9(B) shows the transition state analogue formed by coupling the 3' OH of CCdA to the amino group of the O-methyl tyrosine residue of puromycin via a phosphate group, CCdA-p-Puro (Welch et al. (1995) supra). FIG. 9(C) shows an amino-N-acylated mini helix constructed to target the A-site. The oligonucleotide sequence 5' phosphate CCGGCGGGCUGGUUCAAACCGGCCCGC-CGGACC 3' (SEQ ID NO: 1) puromycin should form 12 base pairs. The construct was based on a mini helix which is a suitable substrate for amino-acylation by Tyr-tRNA synthetase. The 3' OH of its terminal C is coupled to the 5' OH of the N6-dimethyl A moiety of puromycin by a phosphodiester bond.

Figure 10:
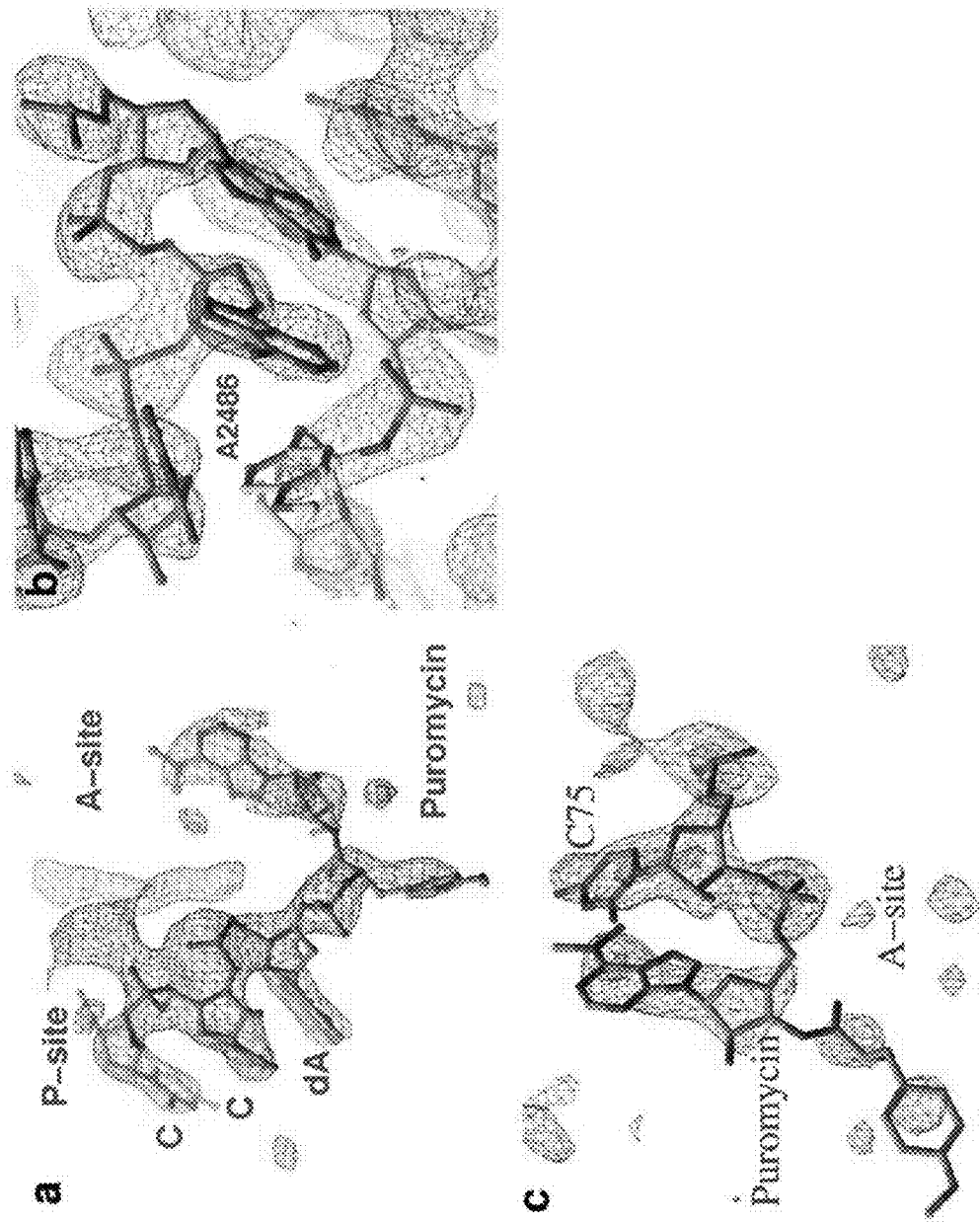

FIGS. 10(A)-(C) show experimentally phased electron density maps of the substrate analogue complexes at 3.2 Å resolution, with models superimposed (oxygen, red; phosphorus, purple; nitrogen, blue; and carbon, green for rRNA and yellow for substrate). Specifically, FIG. 10(A) shows an $F_o$(complex)-$F_o$(parent) difference electron density map with a skeletal model of CCdA-p-Puro superimposed. FIG. 10(B) shows a 2$F_o$(complex)-$F_o$(parent) electron density map of the CCdA-p-Puro in the active site region with the structures of the ribosome and inhibitor superimposed showing the proximity of the N3 of A2486 (2451) to the phosphate, non-bridging oxygen in this complex. FIG. 10(C) shows an $F_o$(complex)-$F_o$(parent) differences electron density map of the tRNA acceptor stem analogue with a skeletal model of CCpuro superimposed. There is density only for the ribose and phosphate of C74 and none for the rest of the RNA hairpin.

Figure 11:
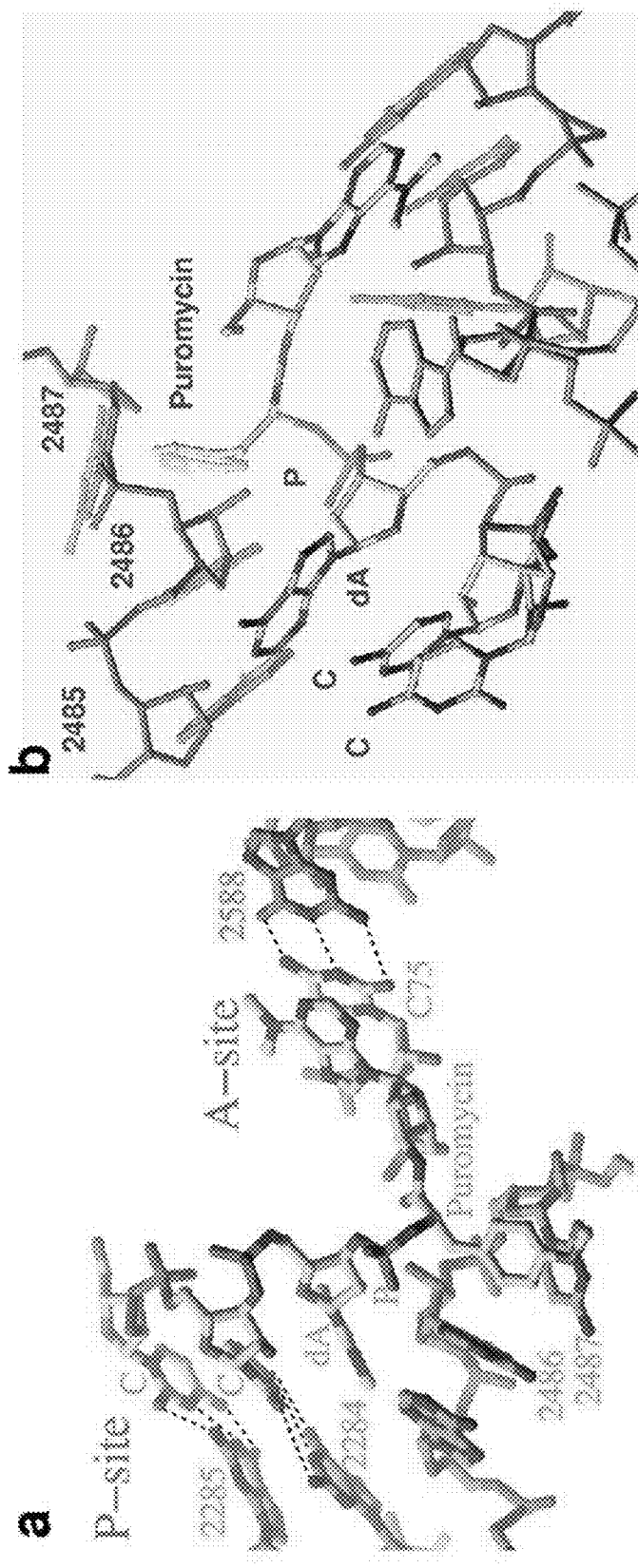

FIGS. 11(A) and (B) show a combined model of the CCA portion of the mini helix bound to the A-site and CCdA-p-Puro bound to the A- and P-sites, color coded as in FIG. 2. Specifically, FIG. 11(A) shows the base-pairing interactions between the P-site C74 and C75 and the P loop of 23S rRNA on the left and the A-site C75 with the A loop of 23S rRNA on the right. The catalytic A2486 is near the phosphate oxygen (P) that is the analogue of the tetrahedral intermediate oxyanion. FIG. 11(B) shows A2637 (in all blue) lying between the two CCA's and A2486 (green) whose N3 approaches a non-bridging phosphate oxygen. The N1 atoms of the A76 bases from the A- and P-site tRNAs are making nearly identical interactions with a ribose 2' OH in both the A- and P-loops, respectively, and an approximate 2-fold axis relates these residues.

Figure 12:
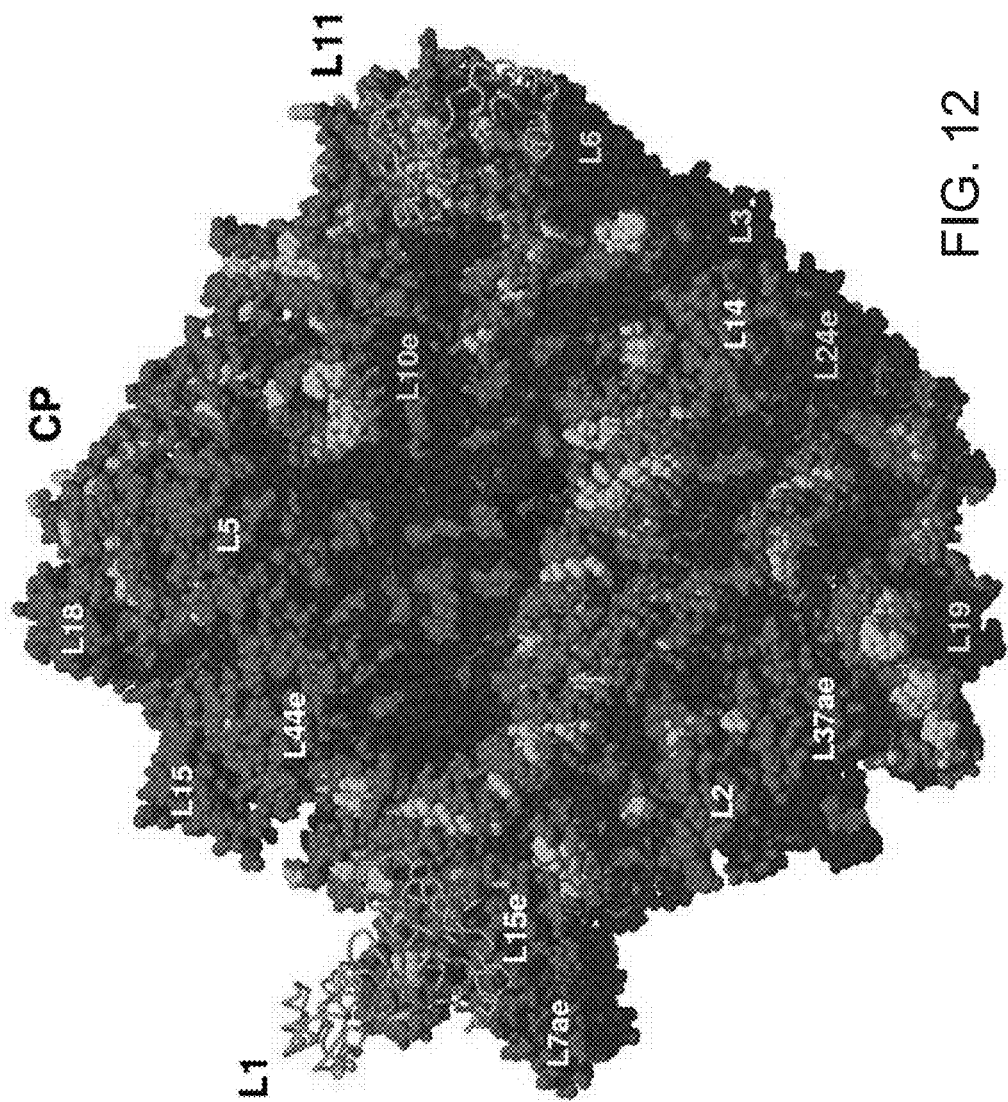

FIG. 12 shows a space filling model of the 23S and 5S rRNA, the proteins and the CCdA-p-Puro inhibitor viewed down the active site cleft in a rotated "crown view." The bases are white and the sugar phosphate backbones are yellow. The inhibitor is shown in red and the numbered proteins are shown in blue. The L1 and L11 proteins positioned at lower resolution are in blue backbone. The central protuberance is labeled CP.

Figure 13:
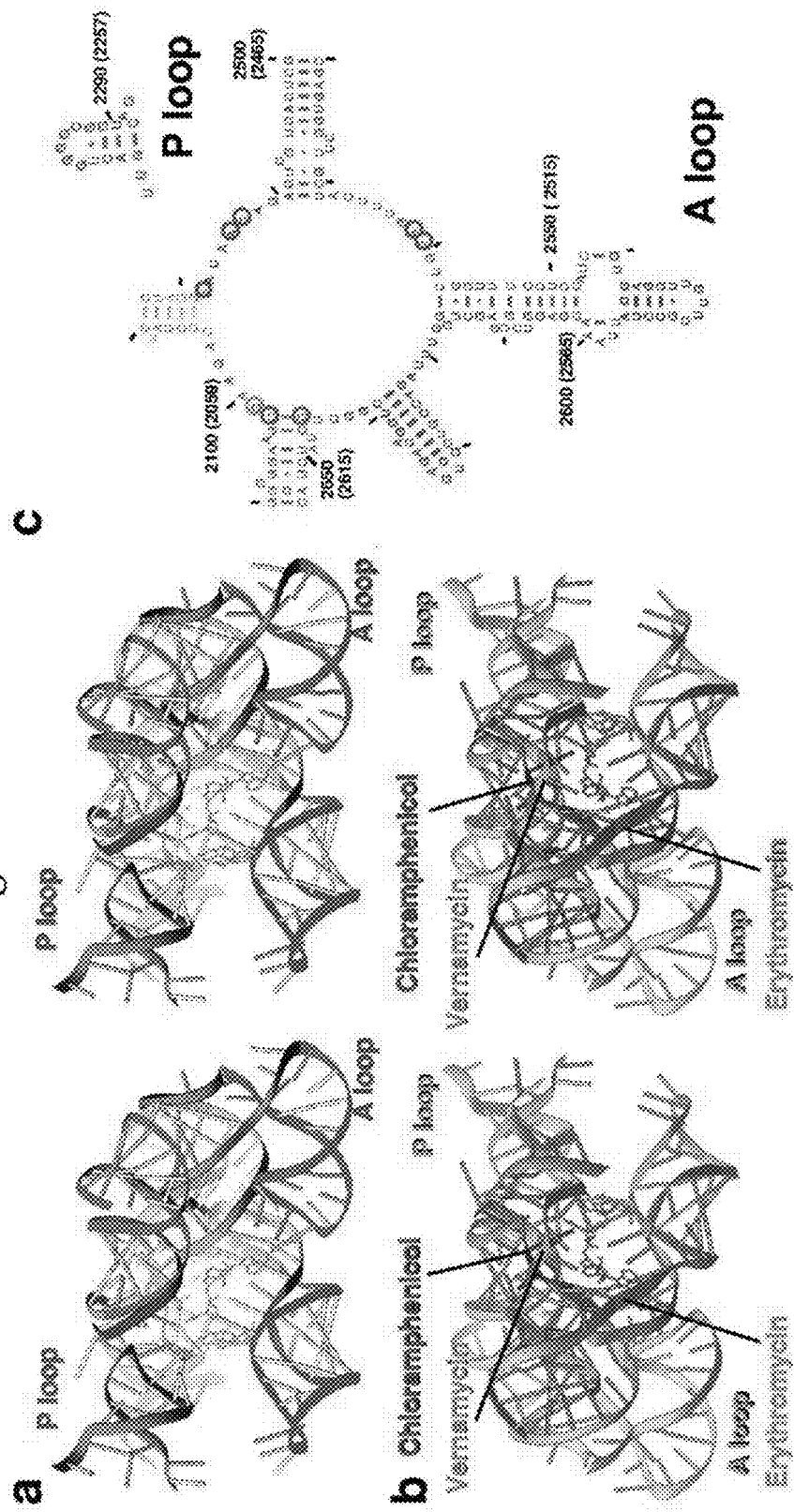

FIG. 13(A) shows a stereo view diagram of the three-dimensional distribution of the residues comprising the loops A and P and the peptidyl transferase loop. FIG. 13(B) shows a stereo view of the central loop in domain V from the direction of the tunnel. The residues are color coded based on mutations which confer antibiotic resistance. FIG. 13(C) shows domain V active site with its central loop shown as the secondary structure.

Figure 14:
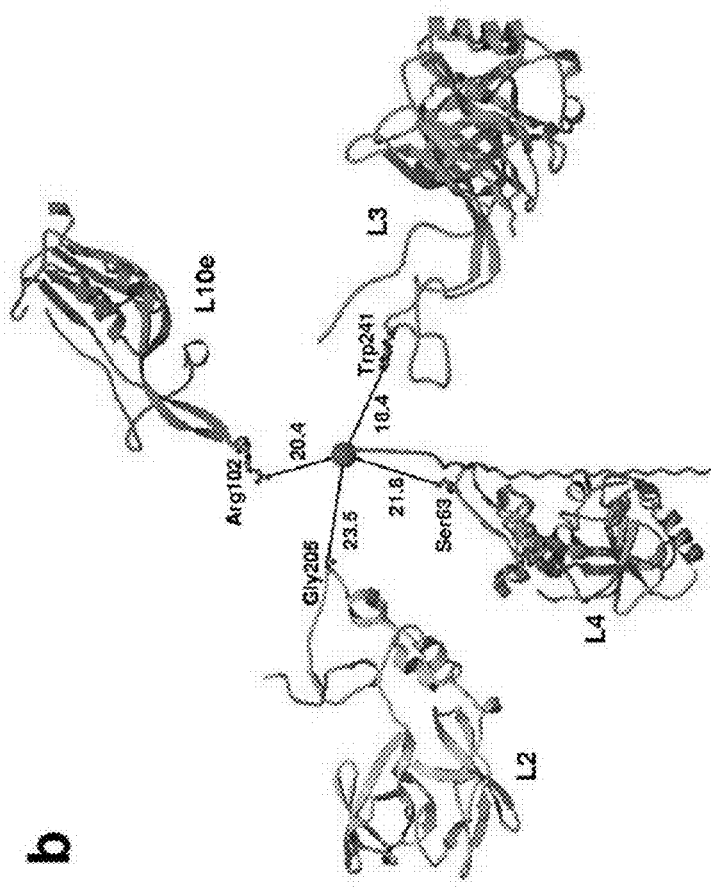

FIGS. 14(A) and (B) show the closest approach of polypeptides to the peptidyl transferase active site marked by a ball and stick representation of the Yarus inhibitor, CCdA-p-Puro. Specifically, FIG. 14(A) shows a coil representation of domain V RNA backbone in red and bases in gray and a ribbon backbone representation of all thirteen proteins that interact with it. FIG. 14(B) shows a close-up view of the active site with the RNA removed. The phosphate of the Yarus analogue and the proteins whose extensions are closest to the inhibitor are shown in ribbon with their closest side-chains in all atom representation. The distances in Å between the closest protein atoms and the phosphorous analogue of the tetrahedral carbon (pink) are shown, as is a modeled peptide (pink).

Figure 15:
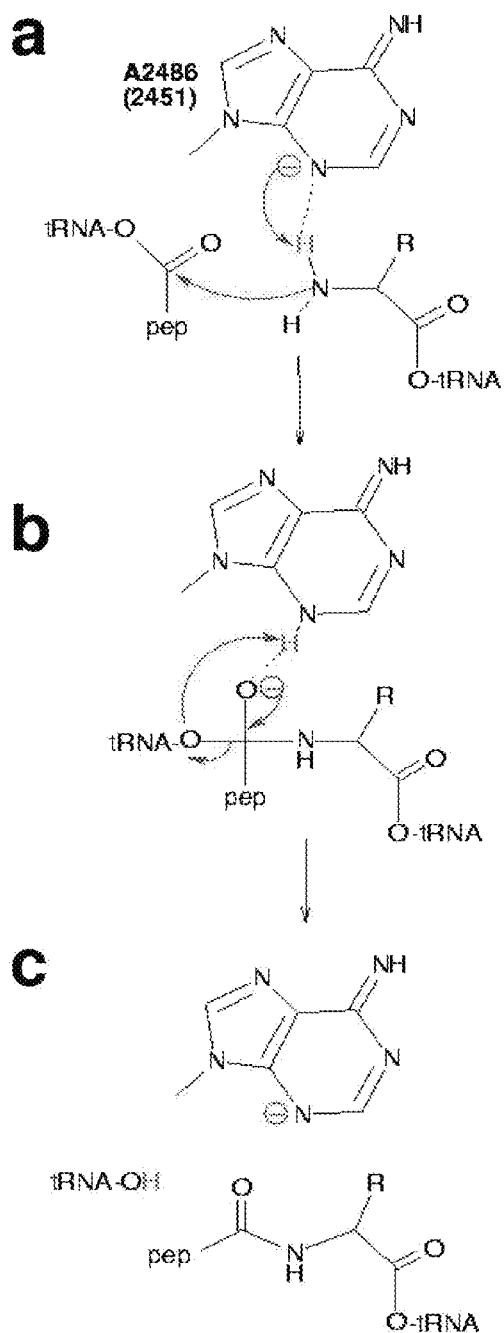

FIG. 15 shows conserved nucleotides in the peptidyl transferase region that binds CCdA-p-Puro A space filling representation of the active site region with the Yarus inhibitor viewed down the active site cleft. All atoms belonging to 23S rRNA nucleotides that are 95% conserved in all three kingdoms (Gutell et al. (2000) supra) are colored red and all other nucleotides are white; the inhibitor is colored blue.

Figure 16:
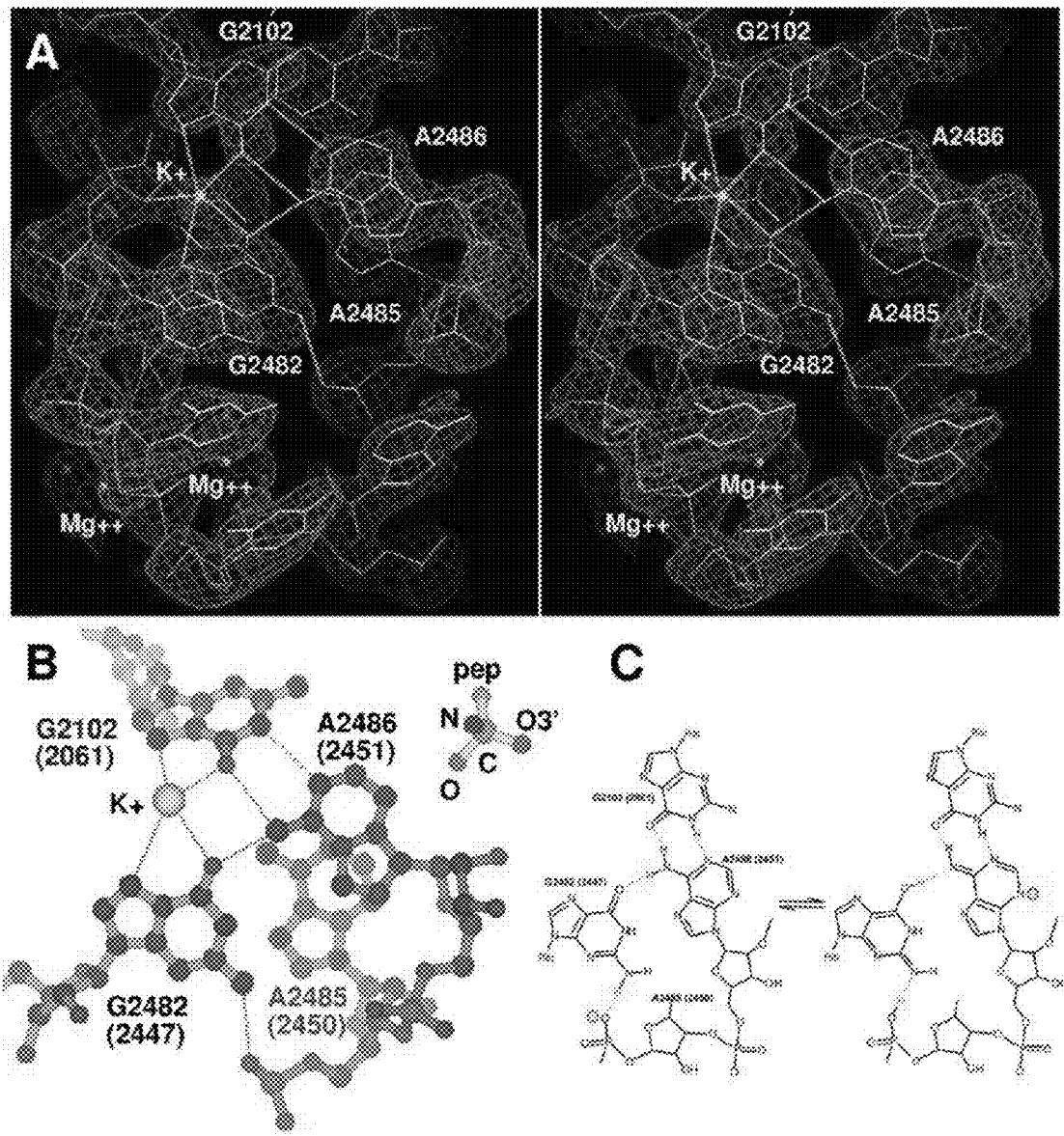

FIGS. 16(A)-(C) show the catalytic apparatus of the peptidyl transferase active site. Specifically, FIG. 16(A) shows stereo view of a portion of the experimental 2.4 Å resolution electron density map (Ban et al. (2000) *Science* 289: 905-920) of the large subunit in the region of the catalytic site in stereo.

The structure the RNA involved in interactions with A2486 is superimposed. Residues G2102 (2061) and G2482 (2447) are hydrogen bonded to the N6 of A2486 (2451) and G2482 which interacts with a neighboring phosphate group. FIG. 16(B) shows a skeletal representation with dashed hydrogen-bonds showing G2482, G2102, A2486 and the buried phosphate that is proposed to result in a charge relay through G2482 to the N3 of A2486. FIG. 16(C) shows the normal and rarer imine tautomeric forms of G2482 and A2486 that are proposed to be stabilized by the buried phosphate of residue 2485.

Figure 17:
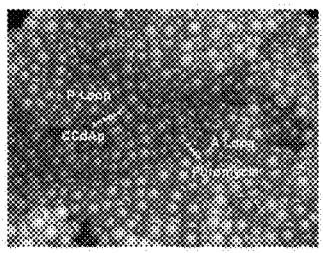

FIGS. 17(A)-(C) show the proposed mechanism of peptide synthesis catalyzed by the ribosome. Specifically, FIG. 17(A) shows the N3 of A2486 abstracting a proton from the $NH_2$ group as the latter attacks the carbonyl carbon of the peptidyl-tRNA. FIG. 17(B) shows a protonated N3 stabilizing the tetrahedral carbon intermediate by hydrogen bonding to the oxyanion. FIG. 17(C) shows the proton transferred from the N3 to the peptidyl tRNA 3' OH as the newly formed peptide deacylates.

Figures 18A, 18B:
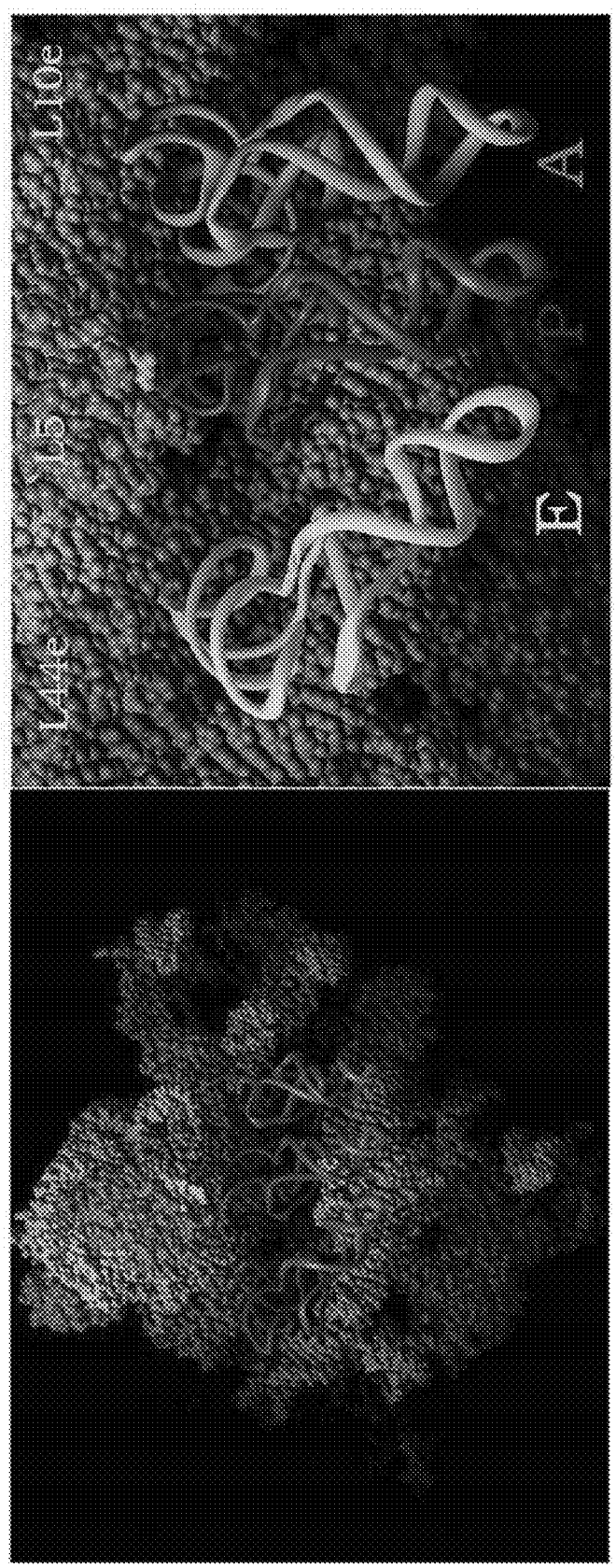

FIGS. 18(A) and (B) show space filling representations of the 50S ribosomal subunit with the 3 tRNA molecules, in the same relative orientation that they are found in the 70S ribosome structure by Noller and colleagues docked onto the CCA's bound in the A-Site and P-Site. Specifically, FIG. 18(A), shown on the left-hand side, shows the whole subunit in rotated crown view with the rRNA in yellow, proteins in pink and tRNAs in orange. FIG. 18(B), shown on the right-hand side, shows a close-up view showing the numbered proteins are in pink and the rRNA in blue. A backbone ribbon representation of the A-, P-, and E-sites are shown in yellow, red and white, respectively.

FIGS. 19(A)-(F) show the polypeptide exit tunnel. Specifically, FIG. 19(A) shows the subunit cut in half, roughly bisecting its central protuberance and its peptide tunnel along the entire length. The two halves have been opened like the pages of a book. All ribosome atoms are shown in CPK representation, with all RNA atoms that do not contact solvent shown in white and all protein atoms that do not contact solvent shown in green. Surface atoms of both protein and RNA are color-coded with carbon in yellow, oxygen in red, and nitrogen in blue. A possible trajectory for a polypeptide passing through the tunnel is shown as a white ribbon. The peptidyl transferase site (PT) is also shown. FIG. 19(B) shows detail of the polypeptide exit tunnel with the distribution of polar and non-polar groups, with atoms colored as in FIG. 19(A), the constriction in the tunnel formed by proteins L22 and L4 (green patches close to PT), and the relatively wide exit of the tunnel. A modeled polypeptide is in white. FIG. 19(C) shows the tunnel surface with backbone atoms of the RNA color coded by domain: domain I (white), II (light blue), III (gold), IV (green), V (orange), 5S (pink) and proteins are blue. The peptidyl transferase center (PTC) is shown. FIG. 19(D) is a space filling representation of the large subunit surface at the tunnel exit showing the arrangement of proteins, some of which might play roles in protein secretion. The RNA is in white (bases) and yellow (backbone) and the numbered proteins are blue. A modeled polypeptide is exiting the tunnel in red. FIG. 19(E) shows a close-up view of the half of the exit tunnel showing the relationship of the peptidyl transferase center (PTC) to proteins L4 (yellow) and L22 (blue). The Yarus inhibitor and a modeled peptide are purple and the 23S rRNA is in red and white. FIG. 19(F) shows a secondary structure schematic of 23S rRNA identifying the sequences that contact the tunnel in red.

Figure 20:
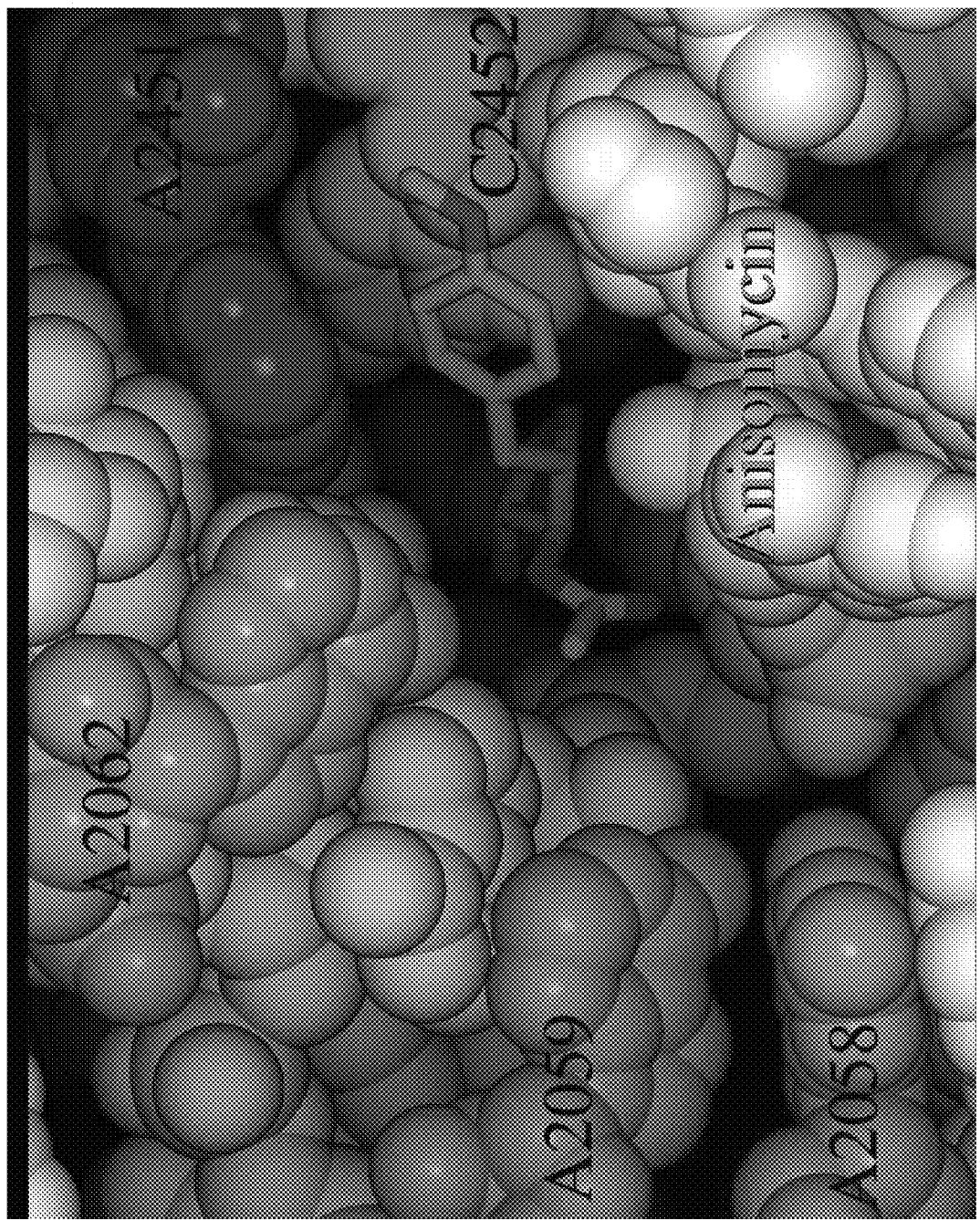

FIG. 20 is a pictorial representation showing the spatial relationship between the antibiotic anisomycin bound to a large ribosomal subunit.

Figure 21:
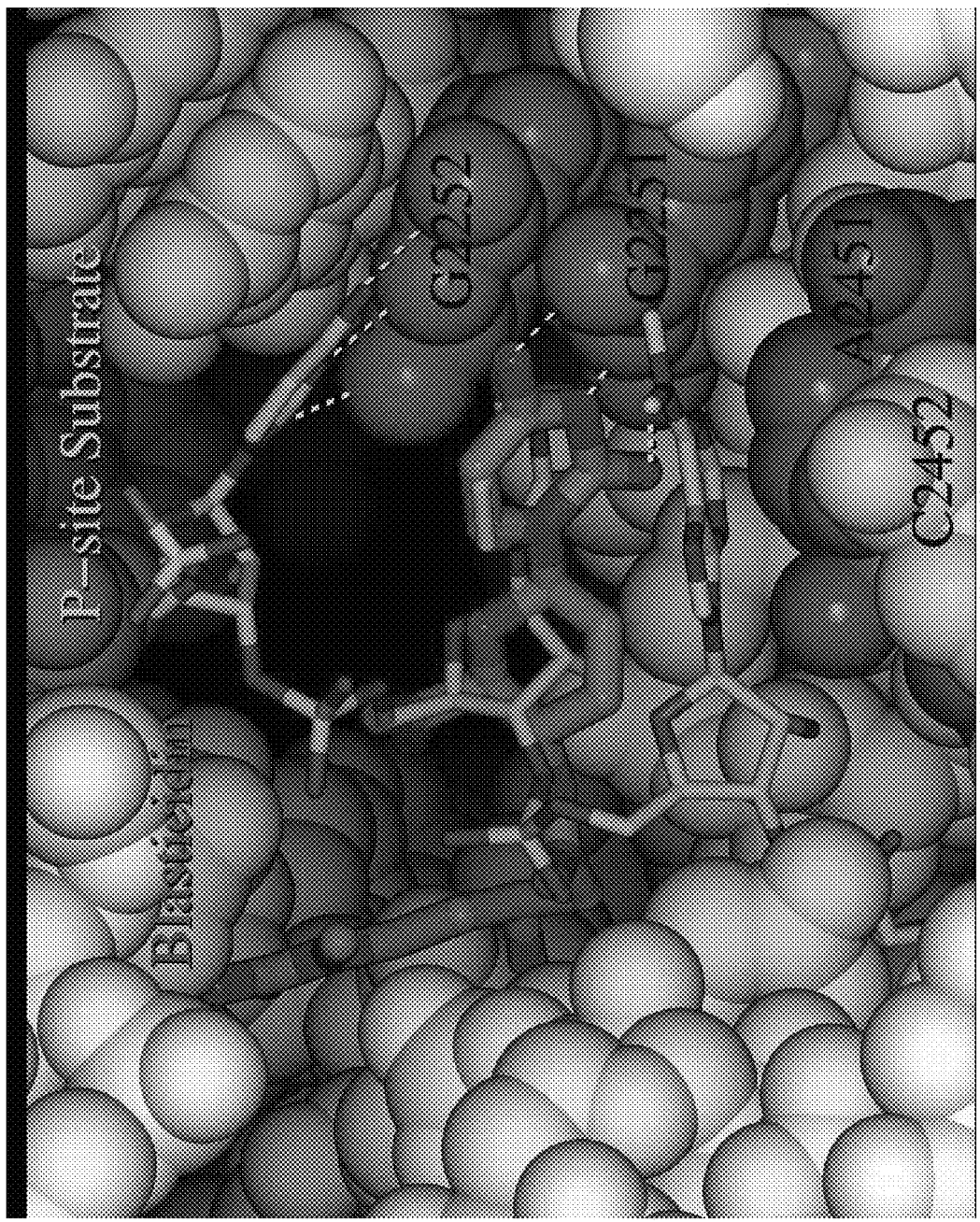

FIG. 21 is a pictorial representation showing the spatial relationship between the antibiotic blasticidin bound to a large ribosomal subunit.

Figure 22:
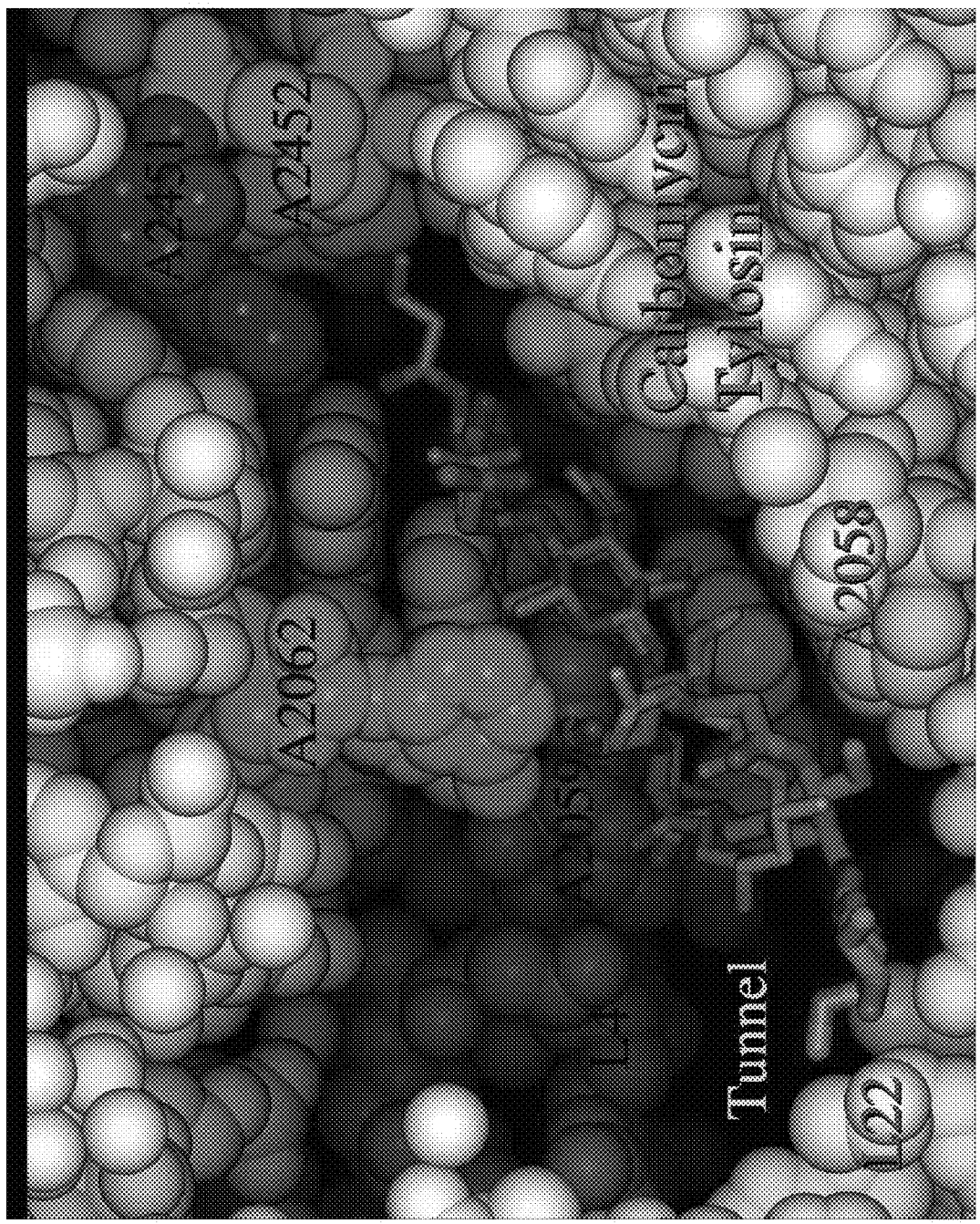

FIG. 22 is a pictorial representation showing the spatial relationship between the antibiotics carbomycin and tylosin bound to a large ribosomal subunit.

Figure 23:
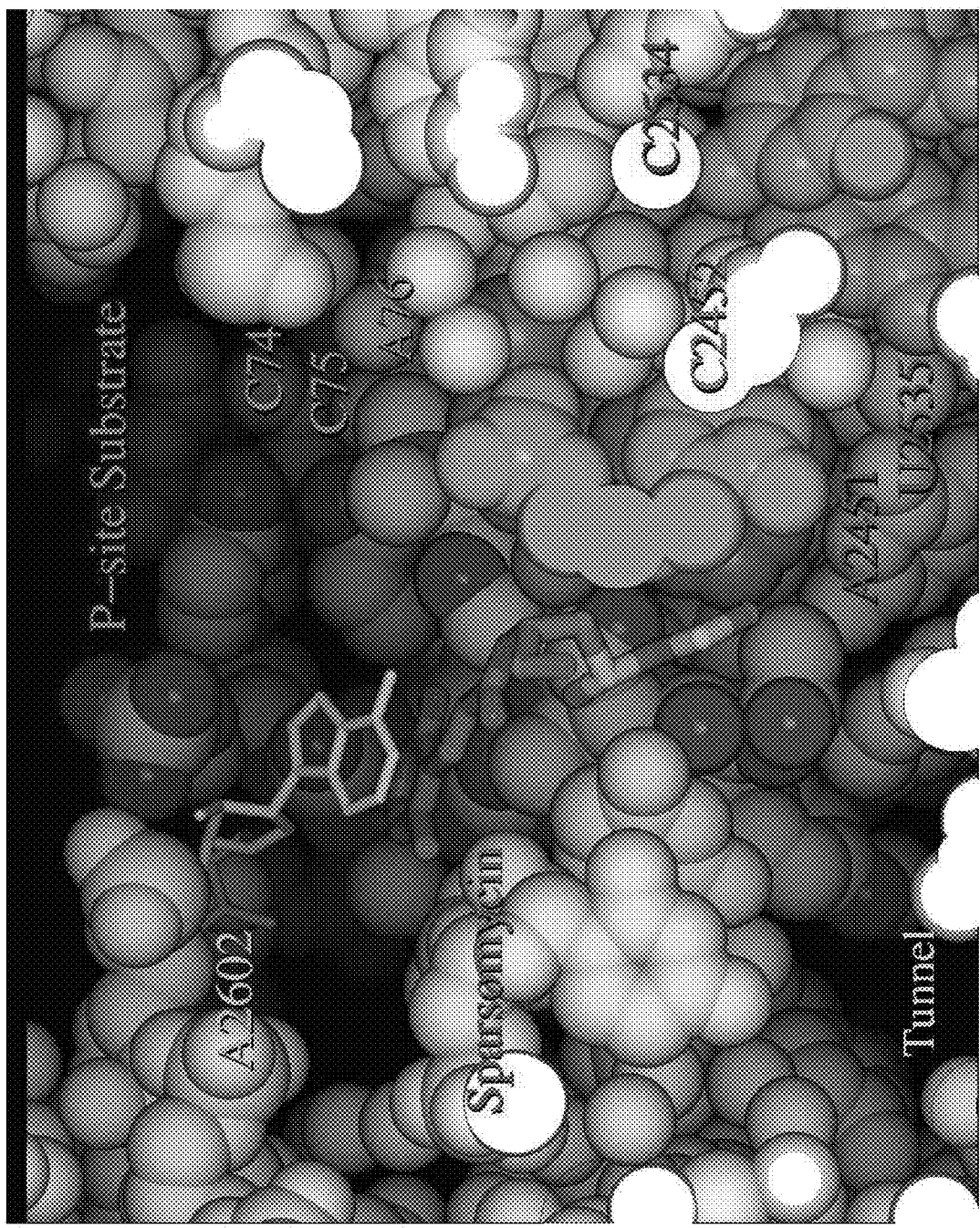

FIG. 23 is a pictorial representation showing the spatial relationship between the antibiotic sparsomycin bound to a large ribosomal subunit.

Figure 24:
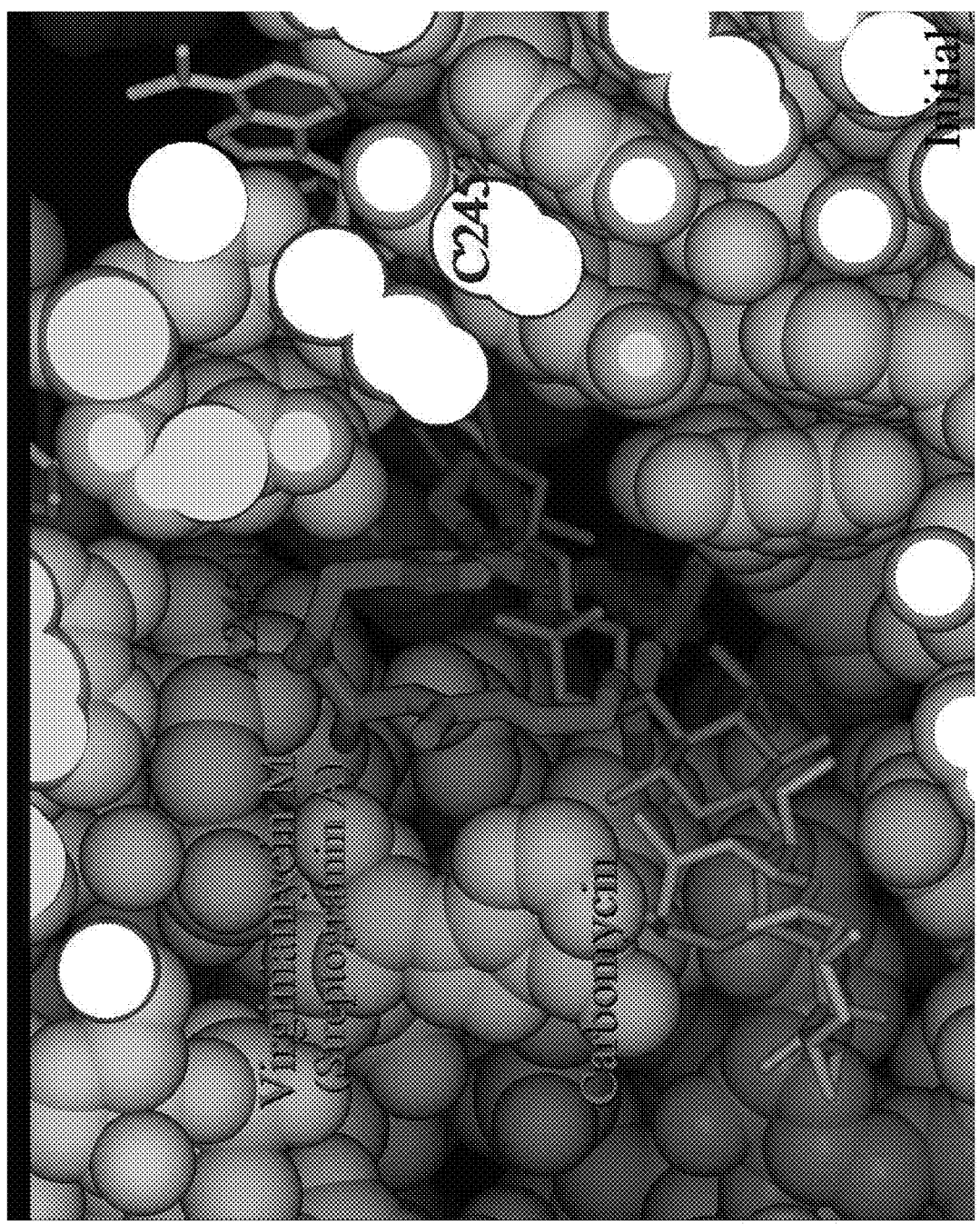

FIG. 24 is a pictorial representation showing the spatial relationship between the antibiotics virginiamycin M (streptogramin A) and carbomycin A bound to a large ribosomal subunit.

Figure 25:
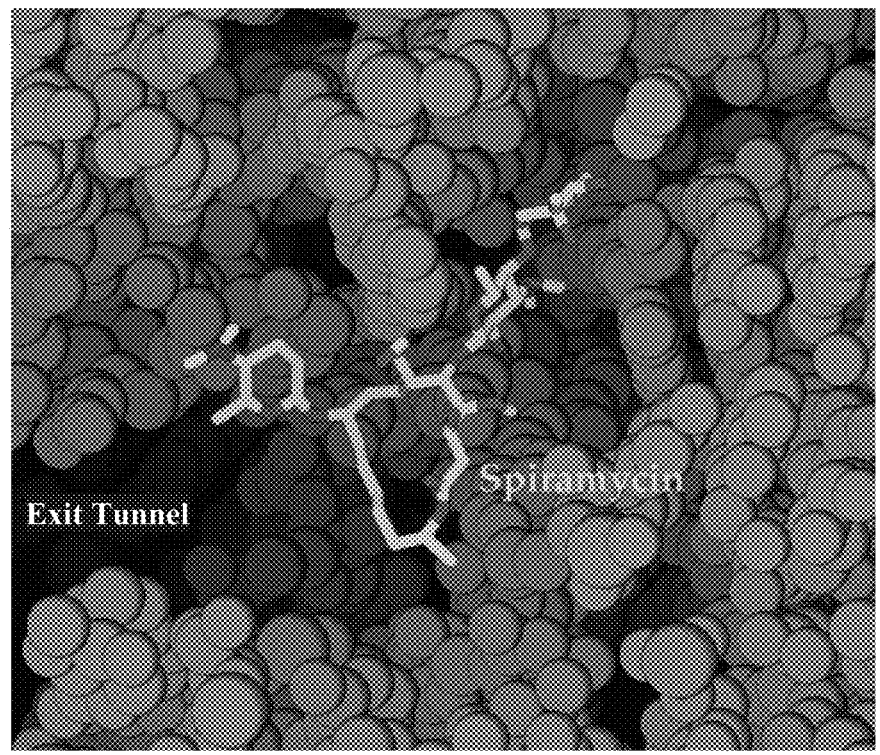

FIG. 25 is a pictorial representation showing the spatial relationship between the antibiotic spiramycin bound to a large ribosomal subunit.

Figure 26:
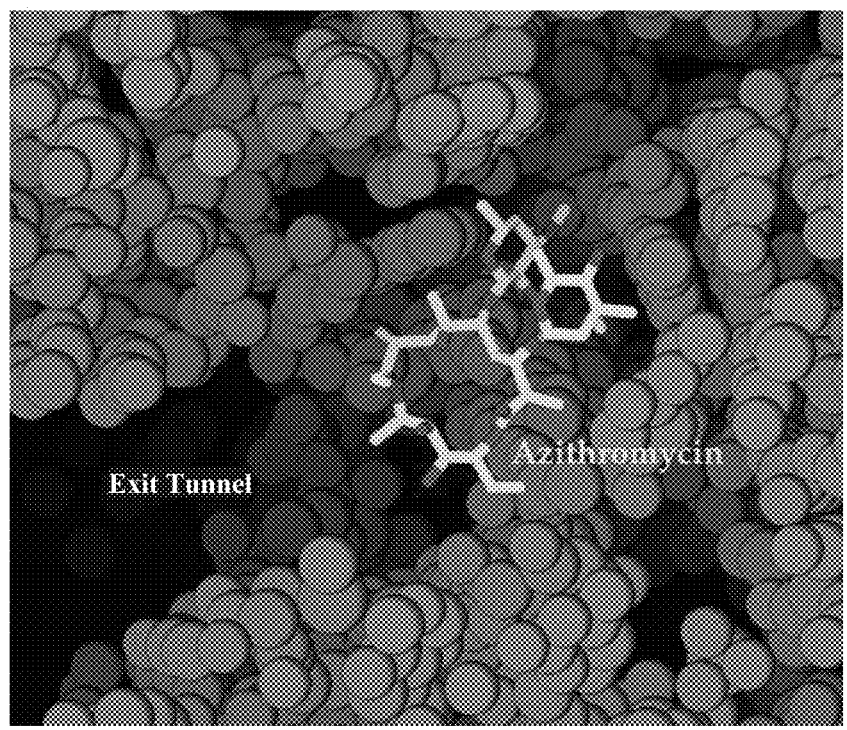

FIG. 26 is a pictorial representation showing the spatial relationship between the antibiotic azithromycin bound to a large ribosomal subunit.

Figure 27:

FIG. 27 is a pictorial representation showing the spatial relationship between the antibiotic linezolid bound to a large ribosomal subunit.

Figure 28:
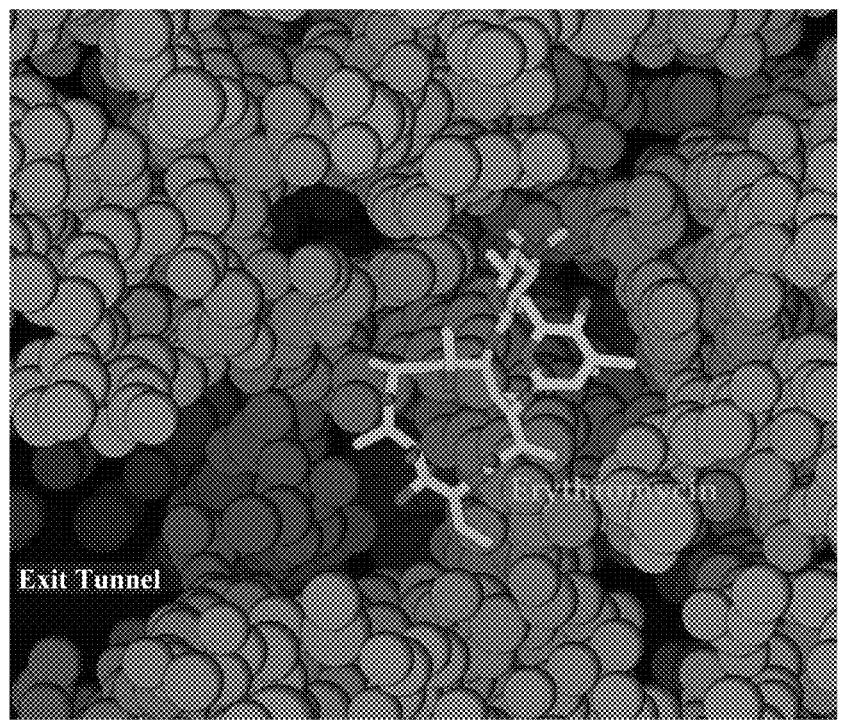

FIG. 28 is a pictorial representation showing the spatial relationship between the antibiotic erythromycin bound to a large ribosomal subunit.

Figure 29:
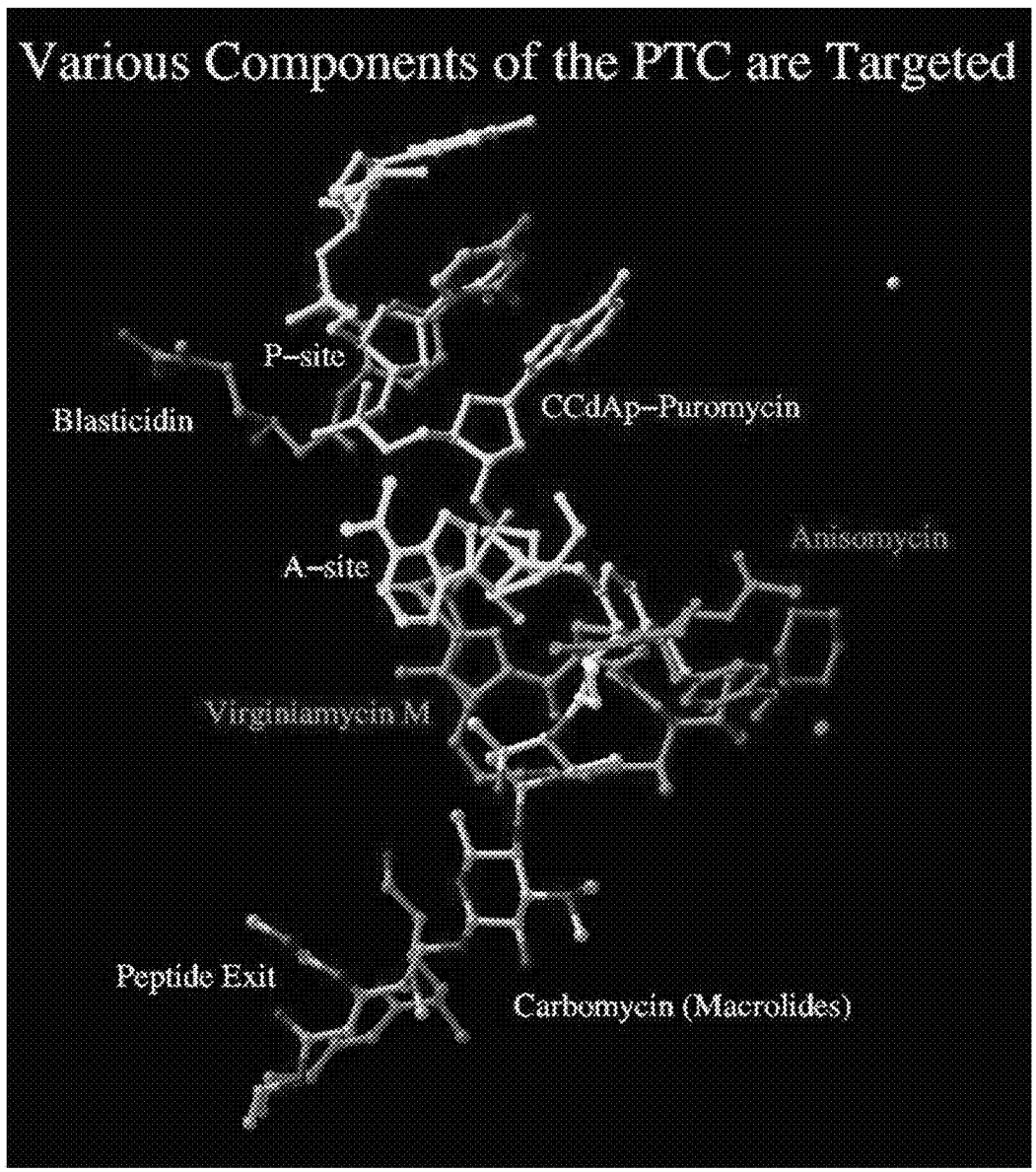

FIG. 29 is a pictorial representation showing the spatial relationship of certain antibiotics, namely, anisomycin, blasticidin, carbomycin A, and virginiamycin M, bound to a large ribosomal subunit. The locations of the bound antibiotics are shown relative to the ribosomal A-site, P-site, and polypeptide exit tunnel.

Figures 30A, 30B, 30C:
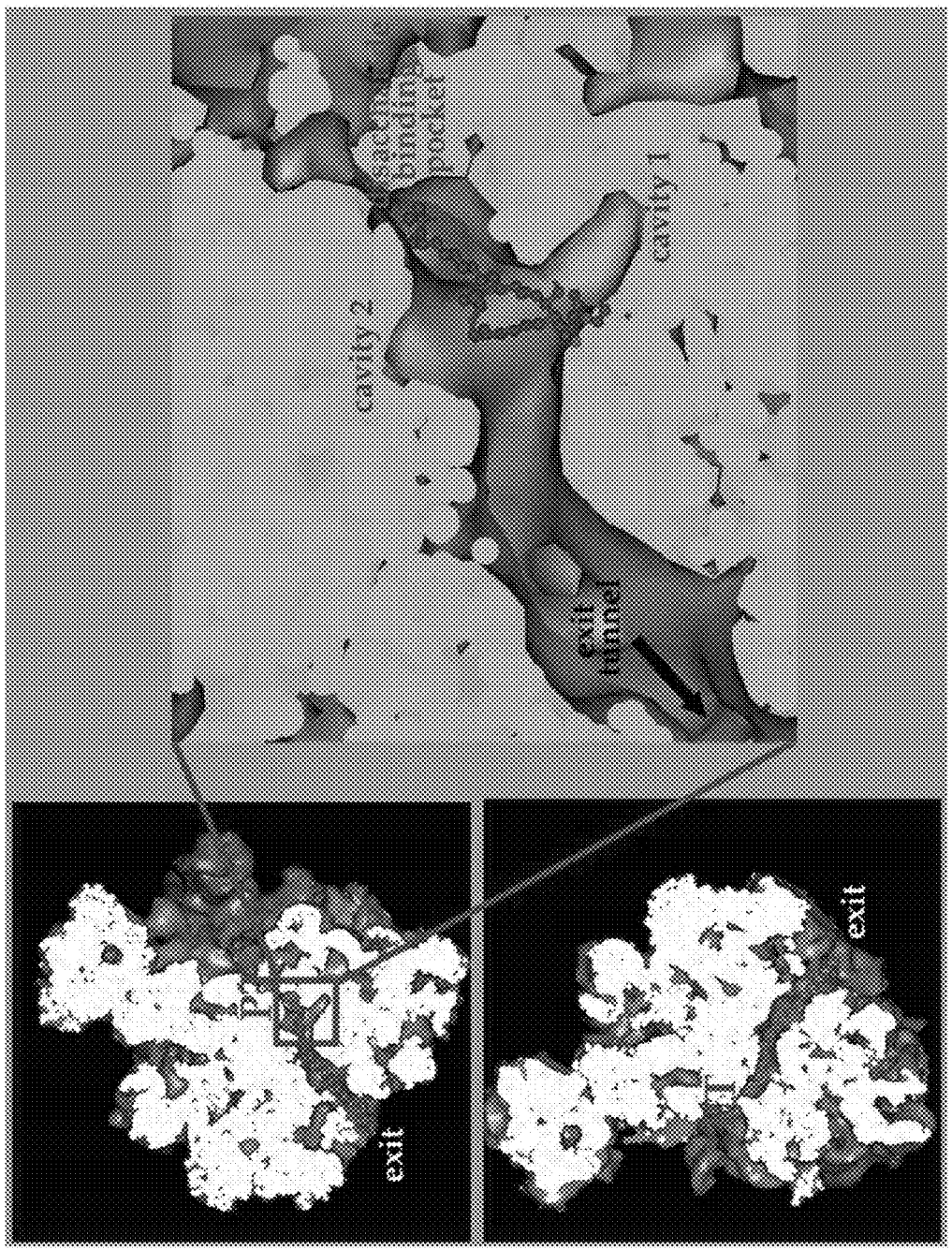

FIGS. 30(A)-(C) are pictorial representations showing a peptidyl transferase site disposed within a large ribosomal subunit. FIG. 30(A) shows a bound tylosin molecule, and identifies a disaccharide binding pocket and two cavities denoted "cavity 1" and "cavity 2." FIGS. 30(B) and (C) are provided on the left hand side to orient the reader to the locations of the peptidyl transferase site (PT) and polypeptide exit tunnel in the large ribosomal subunit.

Figure 31:
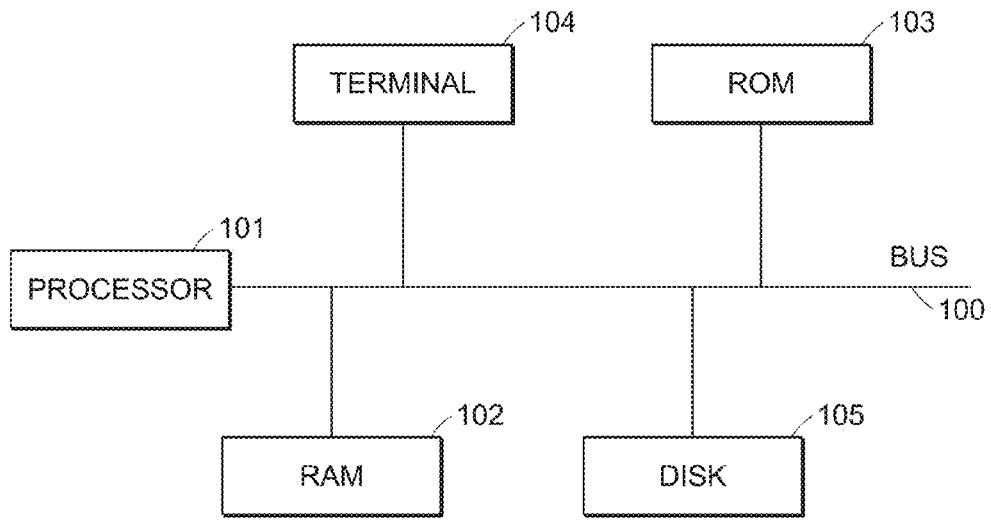

FIG. 31 is a schematic representation of a computer system useful in molecular modeling a ribosomal subunit and/or for performing rational drug design.

Figure 32:
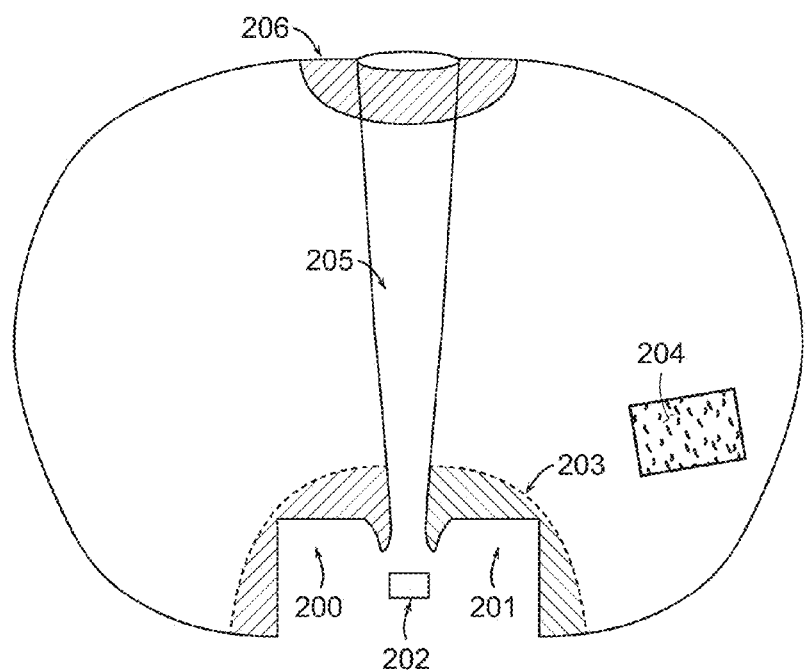

FIG. 32 is a schematic representation of certain potential drug target sites in a large ribosomal subunit.

FIGS. 33(A)-(D) are pictorial representations showing the residues within the wall of the polypeptide exit tunnel that are conserved (red) or non-conserved (blue) between E. coli and rat. The ribosomal subunit has been sliced down the polypeptide exit tunnel with one half of the polypeptide exit tunnel shown in FIG. 33(A), and the other half of the polypeptide exit tunnel is shown in FIG. 33(B). FIG. 33(C) is provided to orient the reader to show the location of the portion of the ribosomal subunit shown in FIG. 33(A) relative to the ribosomal subunit as a whole. FIG. 33(D) is provided to orient the reader to show the location of the portion of the ribosomal subunit shown in FIG. 33(B) relative to the large ribosomal subunit as a whole.

Figure 34:
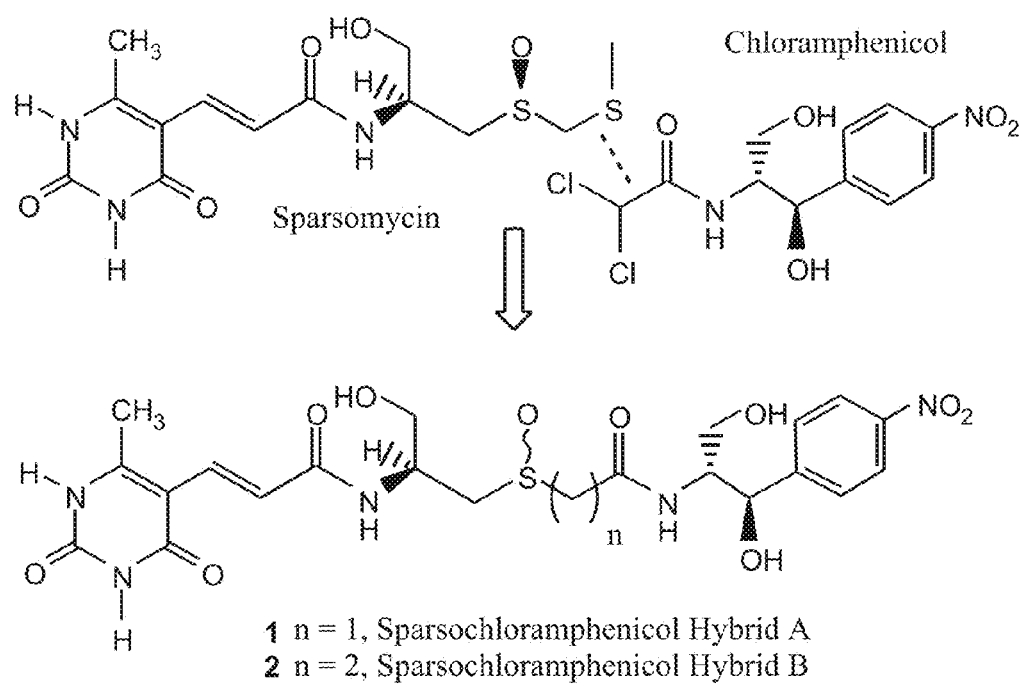

FIG. 34 is a schematic representation showing the synthesis of two hybrid antibiotics, sparsochloramphenicol hybrids A (Compound 1) and B (Compound 2), from the individual antibiotics sparsomycin and chloramphenicol.

Figure 35:
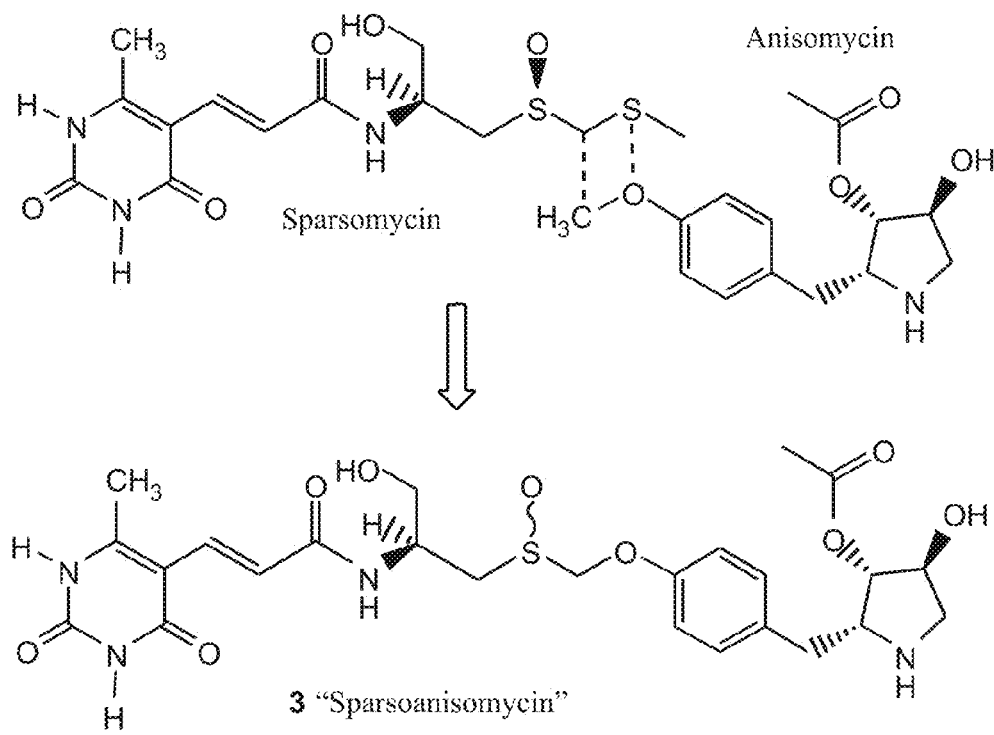

FIG. 35 is a schematic representation showing the synthesis of the hybrid antibiotic sparsoanisomycin (Compound 3) from the individual antibiotics sparsomycin and anisomycin.

Figure 36:
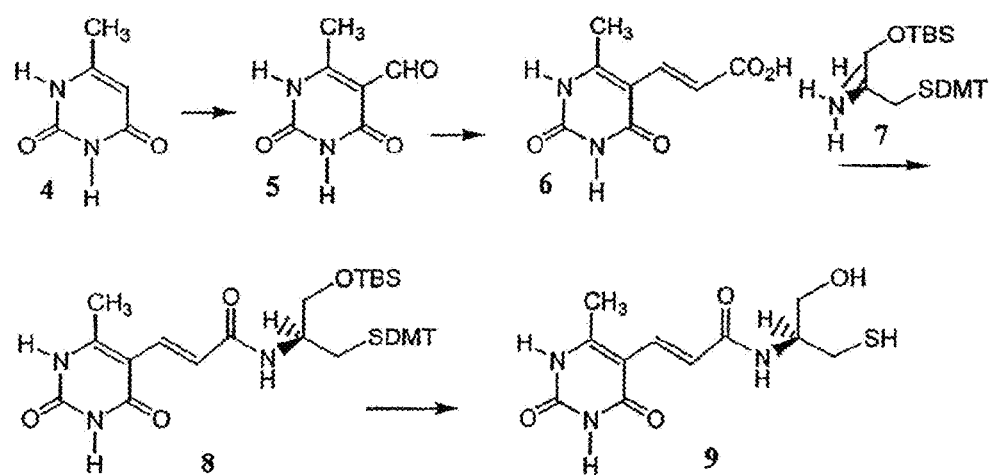

FIG. 36 is a schematic representation showing the synthesis of a sparsomycin fragment (Compound 9).

Figure 37:
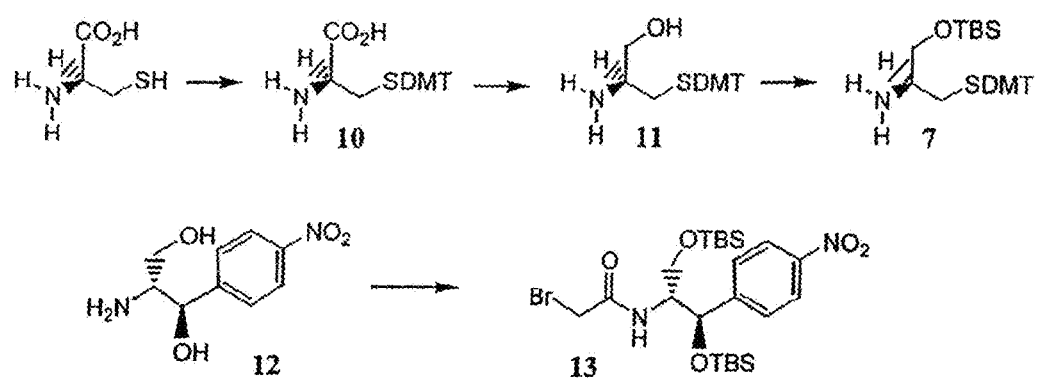

FIG. 37 is a schematic representation showing the synthesis of a cysteine derivative (Compound 7) and a chloramphenicol fragment (Compound 13).

Figure 38:
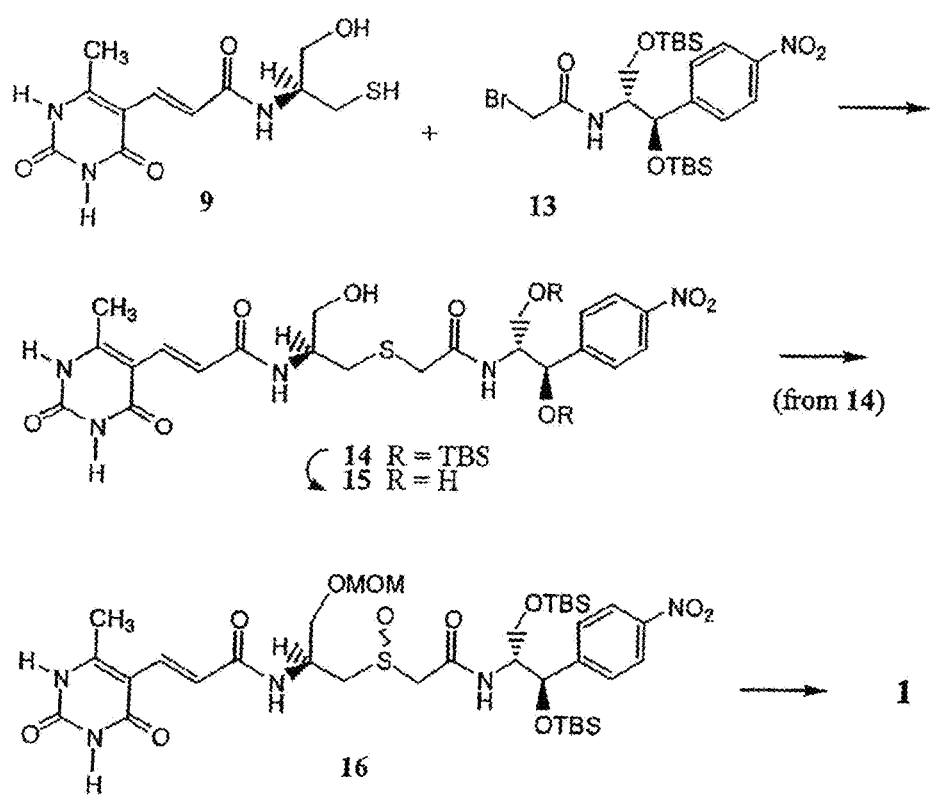

FIG. 38 is a schematic representation showing the synthesis of the sparsochloramphenicol hybrid A (Compound 1).

Figure 39:
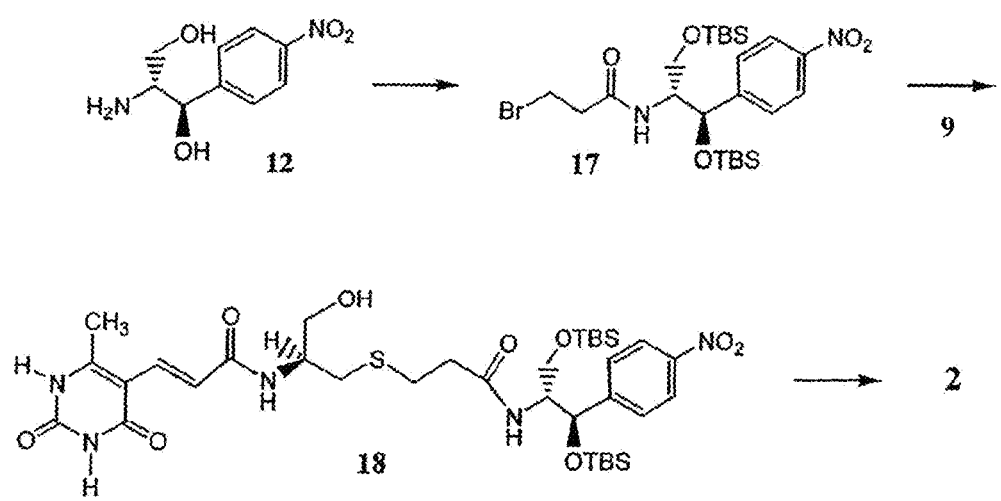

FIG. 39 is a schematic representation showing the synthesis of the sparsochloramphenicol hybrid B (Compound 2).

Figure 40:
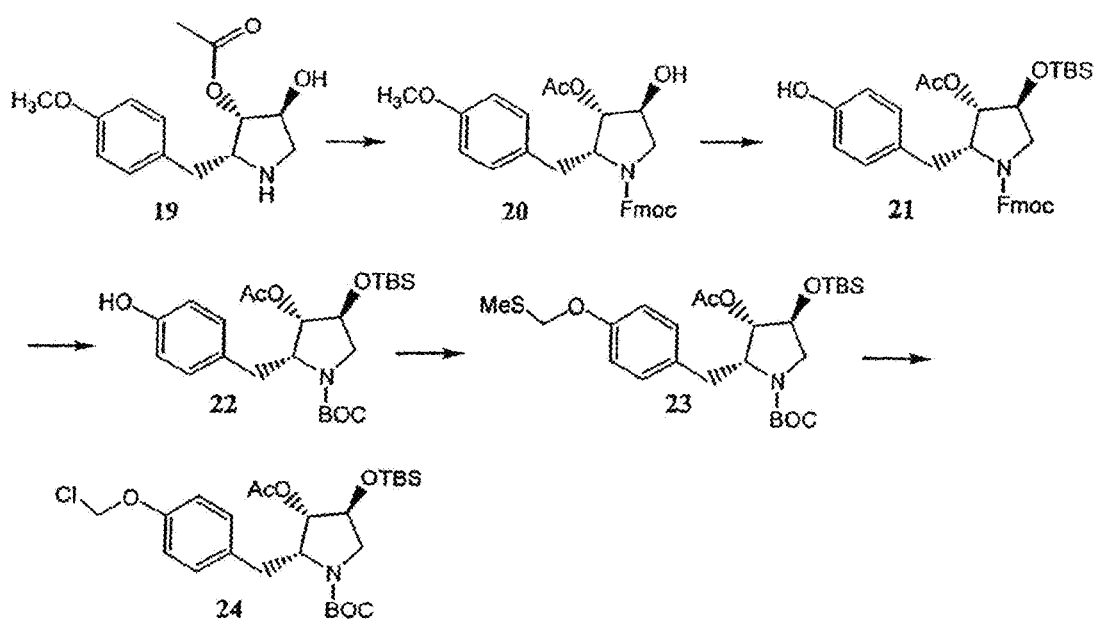

FIG. 40 is a schematic representation showing the synthesis of an anisomycin fragment (Compound 24).

Figure 41:
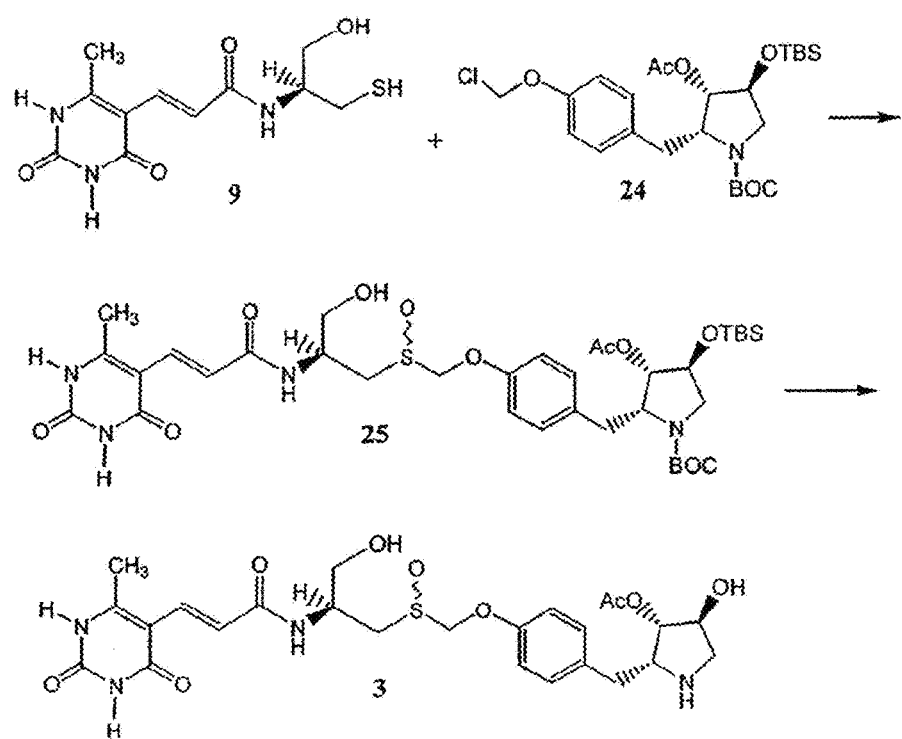

FIG. 41 is a schematic representation showing the synthesis of the sparsoanisomycin hybrid (Compound 3).

DETAILED DESCRIPTION OF THE INVENTION

I. Definitions

As used herein, the term "active site" refers to regions on a ribosome or ribosomal subunit that are directly involved in protein synthesis, e.g., the peptidyl transferase site, the A-site, the P-site, the polypeptide exit tunnel, the elongation factor binding site, and other similar sites.

As used herein, the terms "agent," "ligand" and "lead candidate" are used synonymously and refer to any atom, molecule, or chemical group which binds or interacts with a ribosome, ribosomal subunit or ribosome fragment. Thus, ligands include, but are not limited to, a single heavy atom, an antibiotic or an analogue or derivative thereof, a tRNA, a peptidyl tRNA, an aminoacyl tRNA, or a signal recognition particle ("SRP").

As used herein, "archaebacteria" refers to the kingdom of monerans that includes methane producers, sulfur-dependent species, and many species that tolerate very salty or hot environments.

As used herein, the term "A-site" refers to the locus occupied by an aminoacyl-tRNA molecule immediately prior to its participation in the peptide-bond forming reaction.

As used herein, the term "asymmetric unit" refers to a minimal set of atomic co-ordinates that when operated upon by the symmetry operations of a crystal will regenerate the entire crystal.

As used herein, "at least a portion of" or "at least a portion of the three-dimensional structure of" is understood to mean a portion of the three-dimensional structure of a ribosome or ribosomal subunit, including charge distribution and hydrophilicity/hydrophobicity characteristics, formed by at least three, more preferably at least three to ten, and most preferably at least ten amino acid and/or nucleotide residues of the ribosome or ribosomal subunit. The residues forming such a portion may be, for example, residues which form a contiguous portion of the primary sequence of a ribosomal RNA or ribosomal protein, residues which form a contiguous portion of the three-dimensional structure of the ribosome or ribosomal subunit, or a combination thereof. As used herein, the residues forming "a portion of the three-dimensional structure of" a ribosome or ribosomal subunit, form a three-dimensional shape in which each atom or functional group forming the portion of the shape is separated from the nearest atom or functional group forming the portion of the shape by no more than 40 Å, preferably by no more than 20 Å, more preferably by no more than 5-10 Å, and most preferably by no more than 1-5 Å.

As used herein, the term "atomic co-ordinates" or "structure co-ordinates" refers to mathematical co-ordinates (represented as "X," "Y" and "Z" values) that describe the positions of atoms in a crystal of a ribosome or ribosomal subunit.

The diffraction data obtained from the crystals are used to calculate an electron density map of the repeating unit of the crystal. The electron density maps are used to establish the positions of the individual atoms within a single ribosomal subunit. Those of skill in the art understand that a set of structure co-ordinates determined by X-ray crystallography is not without standard error. For the purpose of this invention, the structures of two ribosomes, ribosomal subunits or portions thereof are considered to be the same if they satisfy one of the following two tests. In a first test, the structures are considered to be the same if a set of structure co-ordinates for a ribosome or ribosomal subunit from any source has a root mean square deviation of non-hydrogen atoms of less than about 2.0 Å, or more preferably less than about 0.75 Å, when superimposed on the non-hydrogen atom positions of the atomic co-ordinates deposited at the Research Collaboratory for Structural Bioinformatics (RCSB) Protein Data Bank (PDB) (Berman et al. (2000) *Nucleic Acids Research* 28, 235-242; http://www.rcsb.org/pdb/) with the accession numbers PDB ID: 1FFK; PDB ID: 1FFZ; PDB ID: 1FG0; PDB ID: 1JJ2; PDB ID: 1K73; PDB ID: 1KC8; PDB ID: 1K8A; PDB ID: 1KD1; or PDB ID: 1K9M, or contained on Disk 1 of 1; the disclosure of each of the foregoing of which is incorporated herein by reference in its entirety. In a second test, the structures are considered to be the same if the r.m.s. deviation between a set of atoms in a test structure and a corresponding set of atoms in a reference structure is less than 2.0 Å. For the purposes of this test, the set of atoms in the reference structure comprises at least five of the series of 23S rRNA residues listed below as 631-633, 835-841, 844-846, 882-885, 1836-1839, 2095-2105, 2474-2478, 2485-2490, 2528-2530, 2532-2543, 2607-2612, 2614-2623, 2642-2648 of the structure deposited in the PDB under accession number PDB ID: 1JJ2 or contained as file name 1jj2.rtf on Disk 1 of 1. The residues in the test structure corresponding to the ones listed above are identified by sequence alignment using the program Lasergene v. 5.0 (DNA Star, Inc., Madison, Wis.) with the default settings. Specifically, the computer program is used to align those residues listed above in the *Haloarcula marismortui* 23S rRNA sequence with those in the test organism's rRNA. Once aligned, the corresponding residues in the test organism's rRNA are identified. The atomic co-ordinates of backbone atoms (P, C5', O5', C4', C3', O3') of atoms in the test structure are superimposed upon the corresponding backbone atoms (P, C5', O5', C4', C3', O3') of the reference structure using the program MIDAS Plus (Ferrin et al. (1988) *J. Mol. Graphics* 6: 13-27 and 36-37). The test and reference structures are considered the same if the r.m.s. deviation between the two sets of atoms after superpositioning is less than 2.0 Å, as determined by MIDAS Plus.

In the list of atomic co-ordinates deposited at the RCSB Protein Data Bank or included herein as files recorded on the compact disks, the term "atomic co-ordinate" or structure co-ordinates refer to the measured position of an atom in the structure in Protein Data Bank (PDB) format, including X, Y, Z and B, for each. The term "atom type" refers to the element whose co-ordinates are measured. The first letter in the column defines the element. The term "X", "Y", "Z" refers to the crystallographically defined atomic position of the element measured with respect to the chosen crystallographic origin. The term "B" refers to a thermal factor that measures the mean variation of an atom's position with respect to its average position.

Reference is made to the sets of atomic co-ordinates and related tables included with this specification and submitted on compact disk (two total compact disks including one original compact disk, and a duplicative copy of original compact disks). Disk No. 1 contains thirty-nine files. Disk No 1 contains the files identified as DB1FFK.DOC and PDB1FFK.ENT which represent files of co-ordinates defining the large ribosomal subunit; PDB1FFZ.DOC and PDB1FFZ.ENT which represent files of the co-ordinates defining the large ribosomal subunit—CCdA-p-Puro complex; and PDB1FGO.DOC and PDB1FGO.ENT which represent files of the co-ordinates defining the large ribosomal subunit—aa-tRNA analogue complex; 1JJ2.RTF and 1JJ2.TXT which represent files of the co-ordinates defining the completely refined large ribosomal subunit; anisomycin.pdb, blasticidin.pdb, carbomycin.pdb, sparsomycin.pdb, spiramycin.pdb, tylosin.pdb and virginiamycin.pdb which represent files of the co-ordinates defining the large ribosomal subunit bound to anisomycin, blasticidin, carbomycin, sparsomycin, spiramycin, tylosin, and virginiamycin, respectively; three folders: FOLDERA contains the file identified as 1 JJ2.PDB (which represents a file of a more highly refined co-ordinates defining the large ribosomal subunit), FOLDERB contains the files identified as ANISOMYC.PDB, BLASTICI.PDB, CARBOMYC.PDB, SPARSOMY.PDB, SPLRAMYC.PDB, TYLOSIN.PDB, and VIRGINIA.PDB (which represent files of the refined co-ordinates defining the large ribosomal subunit bound to anisomycin, blasticidin, carbomycin, sparsomycin, spiramycin, tylosin, and virginiamycin, respectively), FOLDERC contains the files identified as AZITHROM.PDB, and LINEZOLL.PDB (which represent files of the co-ordinates defining the large ribosomal subunit bound to azithromycin and linezolid, respectively); the file identified as erythromycin.pdb (which represents a file of the co-ordinates defining the large ribosomal subunit bound to erythromycin), and azithromycin.pdb and linezolid.pdp (which represent files of the refined co-ordinates defining the large ribosomal subunit bound to azithromycin and linezolid, respectively).

As will be apparent to those of ordinary skill in the art, the atomic structures presented herein are independent of their orientation, and that the atomic co-ordinates identified herein merely represent one possible orientation of a particular large ribosomal subunit. It is apparent, therefore, that the atomic co-ordinates identified herein may be mathematically rotated, translated, scaled, or a combination thereof, without changing the relative positions of atoms or features of the respective structure. Such mathematical manipulations are intended to be embraced herein.

As used herein, the terms "atomic co-ordinates derived from" and "atoms derived from" refers to atomic co-ordinates or atoms derived, either directly or indirectly, from an electron density map. It is understood that atomic co-ordinates or atoms derived "directly" from an electron density map refers to atomic co-ordinates or atoms that are identified from and/or fitted to an electron density map by using conventional crystallographic and/or molecular modeling techniques and thus can be considered to be primary atomic co-ordinates or atoms. It is understood that atomic co-ordinates or atoms derived "indirectly" from an electron density map refers to atomic co-ordinates or atoms that are derived from and thus are derivatives or transforms of the primary atomic co-ordinates or atoms and thus can be considered to be secondary atomic co-ordinates or atoms. The secondary atomic co-ordinates or atoms may be generated from the primary atomic co-ordinates or atoms by using conventional molecular modeling techniques. By way of a non limiting example, the atomic co-ordinates for the *H. marismortui* large ribosomal subunit as described hereinbelow are considered to be primary co-ordinates, whereas the atomic co-ordinates of a mammalian large ribosomal subunit which can be derived from *H. marismortui* atomic co-ordinates by molecular modeling, including, for example, homology modeling and/or molecular replacement, are considered to be secondary co-ordinates. Both types of atomic co-ordinates and atoms are considered to be embraced by the invention.

As used herein the terms "bind," "binding," "bound," "bond," or "bonded," when used in reference to the association of atoms, molecules, or chemical groups, refer to any physical contact or association of two or more atoms, molecules, or chemical groups (e.g., the binding of a ligand with a ribosomal subunit refers to the physical contact between the ligand and the ribosomal subunit). Such contacts and associations include covalent and non-covalent types of interactions.

As used herein, the terms "complex" or "complexed" refer to the assembly of two or more molecules to yield a higher order structure, such as, a 50S ribosomal subunit bound to a ligand.

As used herein, the term "computational chemistry" refers to calculations of the physical and chemical properties of the molecules.

As used herein, the term "conjugated system" refers to more than two double bonds that are positioned spatially so that their electrons are completely delocalized with the entire system. Aromatic residues contain conjugated double bond systems.

As used herein, the terms "covalent bond" or "valence bond" refer to a chemical bond between two atoms in a molecule created by the sharing of electrons, usually in pairs, by the bonded atoms.

As used herein, the term "crystal" refers to any three-dimensional ordered array of molecules that diffracts X-rays.

As used herein, the term "crystallographic origin" refers to a reference point in the unit cell with respect to the crystallographic symmetry operation.

As used herein, the term "elongation factor binding domain" refers to the region of the ribosome that interacts directly with elongation factors, including, for example, the elongation factors, EF-Tu and EF-G.

As used herein, the term "E-site" refers to the locus occupied by a deacylated tRNA molecule as it leaves the ribosome following its participation in peptide-bond formation.

As used herein, the term "heavy atom derivatization" refers to the method of producing a chemically modified form, also known as a "heavy atom derivative", of a crystal of the ribosome and the ribosomal subunit and its complexes. In practice, a crystal is soaked in a solution containing heavy metal atom salts, or organometallic compounds, e.g., mercury chlorides, ethyl-mercury phosphate, osmium pentamine, or iridium pentamine, which can diffuse through the crystal and bind to the ribosome or ribosomal subunit. The location(s) of the bound heavy metal atom(s) can be determined by X-ray diffraction analysis of the soaked crystal. This information, in turn, is used to generate the phase information used to construct three-dimensional structure of the complex (Blundell et al. (1976) supra).

As used herein, the term "homologue" is understood to mean any one or combination of (i) any protein isolated or isolatable from a ribosome or a ribosomal subunit (i.e., a ribosomal protein), (ii) any nucleic acid sequence isolated or isolatable from a ribosome or ribosomal subunit (i.e., a ribosomal RNA), (iii) any protein having at least 25% sequence identity to a ribosomal protein isolated from *E. coli* or *Rattus norvegicus* as determined using the computer program "BLAST" version number 2.1.1 implementing all default parameters, or (iv) any nucleic acid having at least 30% sequence identity to a ribosomal RNA isolated from *E. coli* or

*Rattus norvegicus* as determined using the computer program "BLAST" version number 2.1.1 implementing all default parameters. "BLAST" version number 2.1.1 is available and accessible via the world wide web at http://www/ncbi.nlm-.nih.gov/BLAST/ or can be run locally as a fully executable program on a standalone computer.

As used herein, the term "homology modeling" refers to the practice of deriving models for three-dimensional structures of macromolecules from existing three-dimensional structures for their homologues. Homology models are obtained using computer programs that make it possible to alter the identity of residues at positions where the sequence of the molecule of interest is not the same as that of the molecule of known structure.

As used herein, the term "hydrogen bond" refers to two electronegative atoms (either O or N), which share a hydrogen that is covalently bonded to only one atom, while interacting with the other.

As used herein, the term "hydrophobic interaction" refers to interactions made by two hydrophobic residues.

As used herein, the terms "$IC_{50}$" or "inhibitory concentration$_{50}$" are understood to mean the concentration of a molecule that inhibits 50% of the activity of a biological process of interest, including, without limitation, cell viability and/or protein translation activity.

As referred to herein, ribosomal proteins are designated "LX" or "SX", where L stands for "large subunit; S stands for "small subunit"; and X in either case is an integer.

As used herein, the term "MIR" refers to multiple isomorphous replacement, a technique used for deriving phase information from crystals treated with heavy atom compounds.

As used herein, the term "molecular graphics" refers to three-dimensional representations of atoms, preferably on a computer screen.

As used herein, the terms "molecular model" or "molecular structure" refer to the three-dimensional arrangement of atoms within a particular object (e.g., the three-dimensional structure of the atoms that comprise a ribosome or ribosomal subunit, and the atoms that comprise a ligand that interacts with a ribosome or ribosomal subunit, particularly with a large ribosomal subunit, more particularly with a 50S ribosomal subunit).

As used herein, the term "molecular modeling" refers to a method or procedure that can be performed with or without a computer to make one or more models, and, optionally, to make predictions about structure activity relationships of ligands. The methods used in molecular modeling range from molecular graphics to computational chemistry.

As used herein, the term "molecular replacement" refers to a method that involves generating a model of a ribosome or ribosomal subunit whose atomic co-ordinates are unknown, by orienting and positioning the atomic co-ordinates described in the present invention in the unit cell of the crystals of the unknown ribosome so as best to account for the observed diffraction pattern of the unknown crystal. Phases can then be calculated from this model and combined with the observed amplitudes to give the atomic co-ordinates of the unknown ribosome or ribosomal subunit. This type of method is described, for example, in *The Molecular Replacement Method*, (Rossmann, M. G., ed.), Gordon & Breach, New York, (1972).

As used herein, "noncovalent bond" refers to an interaction between atoms and/or molecules that does not involve the formation of a covalent bond between them.

As used herein, the term "peptidyl transferase site" refers to the locus in the large ribosomal subunit where peptide bonds are synthesized.

As used herein, the term "polypeptide exit tunnel" refers to the channel that passes through the large ribosomal subunit from the peptidyl transferase site to the exterior of the ribosome through which newly synthesized polypeptides pass.

As used herein, the term "protein synthesis inhibitor" refers to any molecule that can reduce, inhibit or otherwise disrupt protein or polypeptide synthesis in a ribosome.

As used herein, the term "P-site" refers to the locus occupied by a peptidyl-tRNA at the time it participates in the peptide-bond forming reaction.

As used herein, the term "ribofunctional locus" refers to a region of the ribosome or ribosomal subunit that participates, either actively or passively, in protein or polypeptide synthesis within the ribosome or ribosomal subunit and/or export or translocation of a protein or polypeptide out of a ribosome. The ribofunctional locus can include, for example, a portion of a peptidyl transferase site, an A-site, a P-site, an E-site, an elongation factor binding domain, a polypeptide exit tunnel, and a signal recognition particle (SRP) binding domain. It is understood that the ribofunctional locus will not only have a certain topology but also a particular surface chemistry defined by atoms that, for example, participate in hydrogen bonding (for example, proton donors and/or acceptors), have specific electrostatic properties and/or hydrophilic or hydrophobic character.

As used herein, the term "ribosomal subunit" refers to one of the two subunits of the ribosome that can function independently during the initiation phase of protein synthesis but which both together constitute a ribosome. For example, a prokaryotic ribosome comprises a 50S subunit (large subunit) and a 30S subunit (small subunit).

As used herein, the term "ribosome" refers to a complex comprising a large ribosomal subunit and a small ribosomal subunit.

As used herein, the term "signal recognition particle binding domain" refers to the portion of the ribosome that interacts directly with the signal recognition particle.

As used herein, the term "space group" refers to the arrangement of symmetry elements of a crystal.

As used herein, the term "symmetry operation" refers to an operation in the given space group that places the atoms in one asymmetric unit on the corresponding atoms in another asymmetric unit.

As used herein, the term "twinned" refers to a single macroscopic crystal that contains microscopic domains of the same symmetry that differ significantly in orientation in such a way that the diffraction patterns of all are superimposed. In a twinned crystal the mosaic blocks, or domains, are orientated so that some point in one direction and others point in a second, distinctly different direction, and the directions are such that the diffraction pattern generated by one group of blocks falls exactly on top of the diffraction pattern of the other group.

As used herein, the term "untwinned" refers to a crystal cell the domains of which are aligned. The domains are also known as the "mosaic blocks." Most crystals diffract as though they were assemblies of mosaic blocks. One can think of them as small, perfectly ordered regions within the larger crystal, which, overall, is not so well ordered. Each block has the same symmetry and unit cell packing as all the others.

As used herein, the term "unit cell" refers to a basic parallelepiped shaped block. The entire volume of crystal may be constructed by regular assembly of such blocks. Each unit cell comprises a complete representation of the unit of pattern, the repetition of which builds up the crystal.

II. Structure and Use of the Large Ribosomal Subunit

A. Atomic Structure of the Large Ribosomal Subunit at 2.4 Å Resolution, Initial Refinement The present invention is based, in part, on the development of a novel method for preparing crystals of ribosomes. The novel method provides crystals of the 50S ribosomal subunit that are much thicker than those available earlier and that can diffract X-rays to a resolution of about 2.4 Å. The method eliminates the twinning of crystals that obstructed progress in determining the crystal structure of the 50S ribosomal subunit from *H. marismortui* for many years. The method of preparing the crystals of the 50S ribosomal subunit is discussed below.

The present invention is also based, in part, on the atomic structure of the crystal of the 50S ribosomal subunit from *H. marismortui* that has been derived from a 2.4 Å resolution electron density map that was experimentally phased using heavy atom derivatives. The atomic co-ordinates defining the large ribosomal unit were deposited on Jul. 10, 2000, at Research Collaboratory for Structural Bioinformatics (RCSB) Protein Data Bank (PDB) (Berman et al. (2000) *Nucleic Acid Research* 28, 235-242; http://www.rcsb.org/pdb/) under accession number PDB ID: 1FFK.

Moreover, the present invention is based, in part, on the derivation from the atomic co-ordinates of the following model which is briefly summarized here and discussed in detail in the following sections of the specification. This model includes 2,811 of the 2,923 nucleotides of 23S rRNA, all 122 nucleotides of its 5S rRNA, and structures for the 27 proteins that are well-ordered in the subunit.

The secondary structures of both 5S and 23S rRNA are remarkably close to those deduced for them by phylogenetic comparison. The secondary structure of the 23S rRNA divides it into 6 large domains, each of which has a highly asymmetric tertiary structure. The irregularities of their shapes notwithstanding, the domains fit together in an interlocking manner to yield a compact mass of RNA that is almost isometric. The proteins are dispersed throughout the structure, concentrated largely on its surface, but they are much less abundant in the regions of the subunit that are of primary functional significance to protein syntheses—the 30S subunit interface, the binding regions for tRNA and the peptidyl transferase active site. The most surprising feature of many of these proteins are the extended, irregular structures of their loops and termini, which penetrate between RNA helices. The primary role of most of the proteins in the subunit appears to be stabilization of the three-dimensional structure of its rRNA.

1. Preparation of the Crystal for the 50S Ribosomal Subunit and Structure Determination.

Several experimental approaches were used to extend the resolution of the electron density maps of the *H. marismortui* 50S ribosomal subunit from 5 Å to 2.4 Å including improvements in the crystals. A back-extraction procedure was developed for reproducibly growing crystals that are much thicker than those available earlier and can diffract to 2.2 Å resolution (see, Example 1). Briefly, the crystals were grown at room temperature in hanging drops by vapor diffusion from seeded solutions back-extracted from precipitated subunits. The crystals that resulted had maximum dimensions of 0.5×0.5× 0.2 mm and were harvested after three weeks. The twinning of crystals that obstructed progress for many years (Ban et al. (1999) supra) was eliminated by adjusting crystal stabilization conditions (see, Example 1). Crystals were stabilized by gradual transfer into a solution containing 12%, PEG 6000, 22% ethylene glycol, 1.7 M NaCl, 0.5 M $NH_4Cl$, 100 mM potassium acetate, 30 mM $MgCl_2$ and 1 mM $CdCl_2$, pH 6.2, and flash frozen in liquid propane. Reducing the salt concentration below 1.7 M NaCl (KCl) increased the tendency of crystals to become twinned. At salt concentrations as low as 1.2 M nearly all of the crystals were twinned.

All the X-ray data used for high resolution phasing were collected at the Brookhaven National Synchrotron Light Source except for two native data sets used, which were collected at the Advanced Photon Source at Argonne (see, Example 2) (Table 1). Osmium pentamine (132 sites) and Iridium hexamine (84 sites) derivatives proved to be the most effective in producing both isomorphous replacement and anomalous scattering phase information to 3.2 Å resolution (see, Example 2). Inter-crystal density averaging which had contributed significantly at lower resolution, was not helpful beyond about 5 Å resolution. Electron density maps were dramatically improved and their resolutions extended, eventually to 2.4 Å, using the solvent flipping procedure in CNS (Abrahams et al. (1996) *Acta Crystollogr. D* 52: 30; Brünger et al. (1998) *Acta Crystallogr. D Biol. Crystallogr.* 54: 905-921).

TABLE 1

Statistics for Data Collection, Phase Determination, and Model Construction

| | Data Statistics | | | | | | |
|---|---|---|---|---|---|---|---|
| | MIRAS1 | | | MIRAS2 | | | |
| | Native1 | $Os(NH_3)_5^{2+}$ | $UO_2F_5^{3-}$ | Native2 | $Ir(NH_3)_6^{3+}$ | $Os(NH_3)_6^{3+}$ | $Ta_6Br_{12}^{2+}$ |
| Heavy atom conc. (mM) | — | 30.0 | 0.5 | — | 20.0 | 4.5 | 3.0 |
| Soaking time (hrs) | — | 1.5 | 4 | — | 24 hrs | 24 hrs | 24 hrs |
| Sites no. | — | 132 | 20 | — | 84 | 38 | 9 |
| Resolution (Å) | 90-2.4 | 40-3.5 | 40-3.8 | 30-2.9 | 30-3.2 | 30-3.5 | 30-3.8 |
| (*) | (2.5-2.4) | (3.6-3.5) | (3.9-3.8) | (3.0-2.9) (3.32-3.22) | (3.27-3.20) | (3.6-3.5) | (3.97-3.80) |
| λ(Å) | 1.00 | 1.14 | 1.30 | 1.00 | 1.075 | 1.14 | 1.255 |
| Observations | 6,089,802 | 1,308,703 | 596,166 | 2,832,360 | 1,823,861 | 1,646,468 | 1,288,524 |
| Unique | 665,928 | 429,761 | 313,863 | 390,770 | 541,488 | 488,275 | 346,745 |
| Redun. (*) | 9.1 (6.5) | 3.0 (2.5) | 1.9 (1.6) | 7.2 | 3.4 | 4.3 (4.2) | 3.7 |
| Completeness (*) | 95.6 (71.0) | 99.4 (96.8) | 92.0 (54.1) | 97.1 | 93.8 | 98.1 (99.0) | 99.5 |
| I/σI (Last bin) | 25.5 (1.9) | 13.5 (3.3) | 8.9 (1.6) | 18.0 (6.4) | 12.0 (2.6) | 10.6 (2.7) | 10.8 (3.2) |
| $R_{merge}$ (*) | 8.6 (69.1) | 7.2 (32.0) | 9.1 (37.9) | 11.2 (36.9) | 8.5 (29.5) | 12.1 (46.0) | 12.1 (40.5) |
| σ2 (ano) (*) | — | 2.8 (1.0) | 1.5 (1.0) | — | 2.63 (1.48) | 1.8 (1.0) | 2.42 (1.18) |
| $R_{merge}$ (ano) | — | 6.2 | 8.0 | — | 6.7 | 6.9 | |
| $R_{iso}$ | — | 14.1 (22.7) | 26.4 (47.0) | — | 12.9 (28.1) | 19.5 (39.4) | |

TABLE 1-continued

Statistics for Data Collection, Phase Determination, and Model Construction

Phasing Statistics

| | Resolution shells (Å): ~73,200 reflections per bin | | | | | |
|---|---|---|---|---|---|---|
| | 30.0 | 5.1 | 4.0 | 3.5 | 3.2 | Total |
| MIRAS1 (FOM) | 0.52 | 0.31 | 0.14 | — | | 0.32 |
| $Os(NH_3)_5^{2+*}$ | | | | | | |
| Phasing power | 0.87 | 0.72 | 0.66 | — | | 0.75 |
| Phasing power (SAD) | 1.40 | 0.58 | 0.26 | — | | 0.75 |
| $R_{cullis}$ (centric) | 0.62 | 0.65 | 0.67 | — | | 0.65 |
| $UO_2F_5^{3-}$ | | | | | | |
| Phasing Power | 0.47 | 0.33 | 0.28 | — | | 0.36 |
| Phasing power (SAD) | 0.46 | 0.25 | — | — | | 0.36 |
| $R_{cullis}$ (centric) | 0.72 | 0.77 | 0.75 | — | | 0.75 |
| MIRAS2 (FOM) | 0.48 | 0.40 | 0.28 | 0.12 | | 0.33 |
| $Ir(NH_3)_6^{3+}$ | | | | | | |
| Phasing power | 1.02 | 0.92 | 0.78 | 0.66 | | 0.89 |
| Phasing power (SAD) | 2.02 | 1.60 | 1.22 | 0.83 | | 1.47 |
| $R_{cullis}$ (centric) | 0.58 | 0.63 | 0.70 | 0.74 | | 0.63 |
| $Os(NH_3)_6^{3+}$ | | | | | | |
| Phasing power | 0.62 | 0.57 | 0.58 | 0.58 | | 0.59 |
| Phasing power (SAD) | 0.47 | 0.39 | — | — | | 0.42 |
| $R_{cullis}$ (centric) | 0.78 | 0.78 | 0.78 | 0.76 | | 0.78 |
| $Ta_6Br_{12}^{2+*}$ (Used for SAD phasing only) | | | | | | |
| Phasing Power (SAD) | 2.77 | 0.35 | 0.13 | — | | 1.19 |
| FOM $_{(MIRAS1+MIRAS2+SAD)}$ | 0.76 | 0.51 | 0.31 | 0.14 | | 0.37 |

Model Statistics

Figure 1:
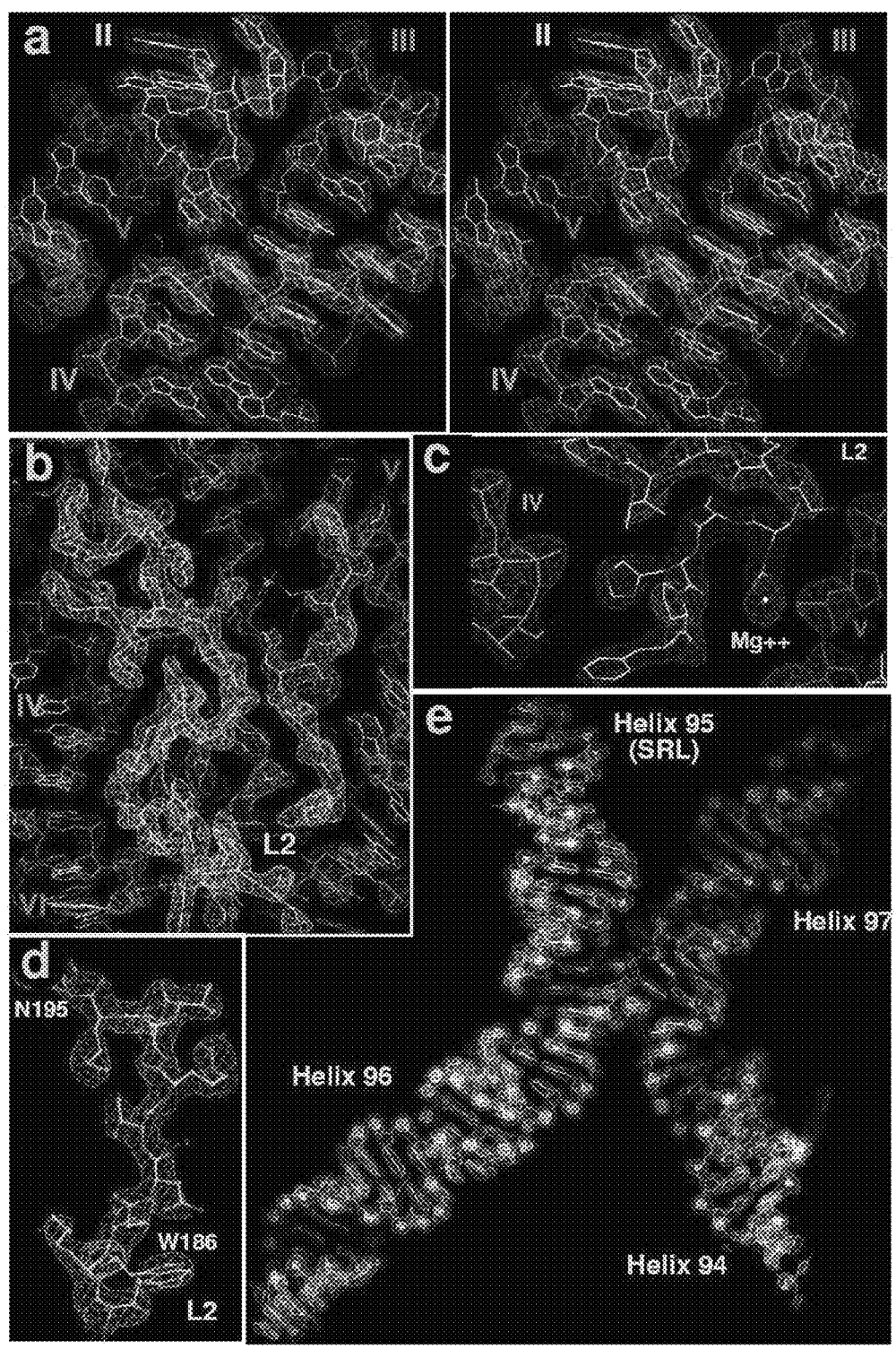

| | | rms deviations | | Average B factors (Å²) | |
|---|---|---|---|---|---|
| Resolution range (Å) | 90.0-2.4 | Bonds (Å) | 0.0064 | All atoms | 37.4 |
| Reflections | 577,304 | Angles (°) | 1.19 | 23S rRNA | 32.3 |
| $R_{syst}$ (%) | 25.2 | Dihedrals (°) | 28.8 | 5S rRNA | 43.2 |
| $R_{free}$ (%) | 26.1 | Impropers (°) | 1.68 | Minimum/Max B factors (Å²) | 70/107.9 |

λ, wavelength; Redun., redundancy; (*) last-resolution shell.
$R_{iso}$: $\Sigma|F_{PH} - F_p|/\Sigma F_{PH}$, where $F_{PH}$ and $F_P$ are the derivative and the native structure factor amplitudes, respectively.
$R_{sym}$: $\Sigma\Sigma_i|I_{(h)i} - I_{(h)i}|/\Sigma\Sigma$: $I_{(h)i}$, where I(h) is the mean intensity after reflections. Phasing power: r.m.s. isomorphous difference divided by the r.m.s. residual lack of closure.
$R_{cullis}$: $\Sigma(||F_{PH} - F_P| - |F_{H(calc)}||)\Sigma|F_{PH} - F_P|$, where $F_{PH}$ is the structure factor of the derivative and $F_P$ is that of the native data. The summation is valid only for centric reflection.
FOM (figure of merit): mean value of the cosine of the error in phase angles.
Abbreviations: MIRAS: multiple isomorphous replacement, anomalous scattering; SAD: single wavelength anomalous diffraction; FOM: figure of merit. Except for regions obscured by disorder, the experimentally-phased, 2.4 Å resolution electron density map was of sufficient quality so that both protein and nucleic acid sequencing errors could be identified and corrected. Each nucleotide could be fitted individually and the difference between A and G was usually clear without reference to the chemical sequence, as was the distinction between purines and pyrimidines (FIG. 1).

Subtraction of the atomic model from the experimental electron density map leaves no significant density except for water and ions, showing that the model accounts for all the macromolecular density. Preliminary refinement of the model was achieved using a mixed target in the program CNS (Brünger et al. (1998) supra). The model was further refined in real space against the 2.4 Å electron density map using the program TNT (Tronrud (1997), *Macromolecular Crystallography, Part B, Methods In Enzymology*), which yielded a model with a free R-factor of 0.33. One additional round of mixed target refinement of both atomic positions and B-factors using CNS led to the structure described below. Its free R-factor is 0.27 (Table 1).

2. Sequence Fitting and Protein Identification.

The sequence of 23S rRNA was fit into the electron density map nucleotide by nucleotide starting from its sarcin/ricin loop sequence (A2691-A2702) (*E. coli* numbers A2654 to A2665), whose position had been determined at 5 Å resolution (Ban et al. (1999) supra). Guided by the information available about the secondary structures of 23S rRNAs (Gutell, R. R. (1996), "Comparative Sequence Analysis and the Structure of 16S and 23S rRNA," *Ribosomal RNA. Structure, Evolution, Processing, and Function in Protein Biosynthesis*, (Dahlberg A. and Zimmerman B., eds.), CRC Press, Boca Raton, Fla. pp. 111-128), the remaining RNA electron density neatly accommodated the sequence of 5S rRNA. The interpretation of protein electron density corresponding to the protein was more complicated because each protein region had to be identified chemically before the appropriate sequence could be fit into it, but about 4,000 amino acid residues were fit into electron density.

The *H. marismortui* 50S subunit appears to contain thirty-one proteins, and there are sequences in the Swiss-Prot data bank for twenty eight of those thirty one proteins, including one, HMS6 or L7ae, that was originally assigned to the small ribosomal subunit (Whittmann-Liebold et al. (1990) supra). The three remaining proteins were identified using the sequences of the ribosomal proteins from eukaryotes and other archeal species as guides. No electron density was found for one of the *H. marismortui* large ribosomal subunit proteins in the sequence database, LX. Either the assignment of LX to the large subunit is in error, or LX is associated with a disordered region of the subunit, or LX is absent from the subunits examined altogether.

The 2.4 Å resolution electron density map lacks clear electron density for proteins L1, L10, L11, and L12, the positions of which are known from earlier low resolution X-ray and/or electron microscopic studies. These proteins are components of the two lateral protuberances of the subunit, which are both poorly ordered in these crystals. L1 is the sole protein component of one of them (Oakes, M. et al. (1986)), *Structure, Function and Genetics of Ribosomes*, (Hardesty, B. and Kramer, G., eds.) Springer-Verlag, New York, N.Y., 47-67) and is evident in 9 Å resolution density maps of the subunit (Ban et al. (1998) supra), but not at higher resolutions. L10, L11 and L12 are components of the other protuberance, which is often referred to as the L7/L12 "stalk" (Oakes et al. (1986) supra). L11 and the RNA to which it binds were located in the 5 Å resolution electron density map of the *H. marismortui* large subunit (Ban et al. (1999) supra) using the independently determined crystal structures of that complex (Conn G L et al. (1999) *Science* 284: 1171-1174; Wimberly et al. (1999) *Cell* 97: 491-502). A protein fragment (about 100 residues) that is associated with the RNA stalk that supports the L11 complex can be seen in the 2.4 Å resolution map. Based on location, it must be part of L10. There is no electron density corresponding to L12 seen at any resolution, but the L12 tetramer is known to be attached to the ribosome through L10, and the L10/L12 assembly is known to be flexible under some circumstances (Moller et al. (1986) *Structure, Function, and Genetics of Ribosomes*, supra, pp. 309-325), which may explain its invisibility here.

The structures of eubacterial homologues of proteins L2, L4, L6, L14, and L22 have previously been determined in whole or in part (see, Table 2). L2, L6 and L14 were initially located in the 5 Å resolution map (Ban et al. (1999) supra). L4 and L22 have now been identified and positioned the same way. Electron density corresponding to most of the remaining proteins was assigned by comparing chain lengths and sequence motifs deduced from the electron density map with known sequence lengths, guided by the information available about relative protein positions (Walleczek et al. (1988) *EMBO J.* 7: 3571-3576) and protein interactions with 23S rRNA and 5S rRNA (Ostergaard et al. (1998) *J. Mol. Biol.* 284: 227-240). Each of the protein electron density regions so identified is well accounted for by its amino acid sequence.

The most interesting of the proteins identified by sequence similarity was L7ae, which first appeared to be L30e. The L30e identification seemed plausible because the structure of yeast L30 superimposes neatly on the electron density of L7ae, and the structure of the RNA to which L7ae binds closely resembles that of the RNA to which yeast L30 binds (Mao, H. et al. (1999) *Nat. Struct. Biol.* 6: 1139-1147). Nevertheless, the sequence of HMS6, which by sequence similarity is a member of the L7ae protein family, fits the electron density better. Four of the other proteins identified by sequence similarity, L24e, L37e, L37ae, and L44e, contain zinc finger motifs. The rat homologues of L37e and L37ae were predicted to be zinc finger proteins on the basis of their sequences (Wool et al. (1995) supra), and this prediction helped identify their homologues in *H. marismortui*.

TABLE 2

Large Subunit Proteins from *Haloarcula marismortui*

| Name[1] | Hmlg[2] | Lgth[3] | Conf[4] | 1 | 2 | 3 | 4 | 5 | 6 | 5S | Proteins |
|---|---|---|---|---|---|---|---|---|---|---|---|
| L1* | | 211 | glb. | | | | | + | | | none |
| L2† | RL8 | 239 | glb + ext | + | + | + | + | | | | (L37ae) |
| L3 | RL3 | 337 | glb + ext | | + | | + | + | + | | L14, L24e, (L13) |
| L4† | RL4 | 246 | glb + ext | + | + | | | Å | | | (L18e), (L24), (L37e) |
| L5 | RL11 | 176 | glb | | | | | + | | + | L18 |
| L6 | RL9 | 177 | glb | Å | | | | Å | + | | (L13) |
| L10* | RP0 | 348 | glb? | + | | | | | | | L12 |
| L11* | RL12 | 161 | glb | + | | | | | | | none |
| L12* | RL1/2 | 115 | glb | | | | | | | | L10 |
| L13 | RL13a | 145 | glb | | + | | | Å | Å | | (L3), (L6) |
| L14 | RL23 | 132 | glb | | | | + | + | + | | L3, L24e |
| L15 | RL27a | 164 | glb + ext | + | + | | | + | | | (L18e), (L32e) |
| L18 | RL5 | 186 | glb + ext | | Å | | | + | | + | L5, L21e |
| L19 | RL19 | 148 | glb + ext | | + | + | + | Å | | | none |
| L22 | RL17 | 154 | glb + ext | + | Å | + | + | + | + | | none |
| L23 | RL23a | 84 | glb | Å | + | | | | | | L29, (L39e) |
| L24 | RL26 | 119 | glb + ext | + | | | | | | | (L4) |
| L29 | RL35 | 70 | glb | + | | | | | | | L23 |
| L30 | RL7 | 154 | glb | | + | | | | + | | none |
| L18e | RL18 | 115 | glb | | + | | | | | | (L4), (L15) |
| L21e | RL21 | 95 | glb | | + | | | + | Å | | L18 |
| L24e | RL24 | 66 | glb | | | | Å | + | | | L3, L14 |
| L31e | RL31 | 91 | glb | | | + | + | + | | | none |
| L32e | RL32 | 240 | glb | Å | + | | | | | | (L15) |
| L37e | RL37 | 56 | glb + ext | + | + | + | Å | | | | (L4) |
| L39e | RL39 | 49 | ext | + | | + | | | | | (L23) |
| L44e | RL36a | 92 | glb + ext | + | | | Å | + | | | (L15e) |
| L7ae | R17a | 110 | glb | Å | | | | | | | L15e |
| L10e | RL10 | 163 | glb | | + | | | + | | Å | none |

TABLE 2-continued

Large Subunit Proteins from *Haloarcula marismortui*

| Name[1] | Hmlg[2] | Lgth[3] | Conf[4] | Interactions | | | | | | Proteins |
| | | | | 1 | 2 | 3 | 4 | 5 | 6 | 5S | |
|---|---|---|---|---|---|---|---|---|---|---|---|
| L15e | RL15 | 184 | glb + ext | + | Å | Å | Å | + | | | (L44e), L7ae |
| L37ae | RL37a | 72 | glb + ext | | + | + | + | | | | L2 |

The top block of proteins include all those known to have eubacterial homologues of the same name. The second block lists proteins found in the *H. marismortui* large ribosomal subunit that have only eukaryotic homologues (Wittmann-Liebold et al. (1990) supra). Their names are all followed by the letter "e" to distinguish them from eubacterial proteins that would otherwise have the same name. The third block are large subunit proteins for which no *H. marismortui* sequence yet exists. They are identified by sequence homology using standard L names.
[1]The structures of all or part of homologues of the following proteins were previously determined: L1 (Nevskaya et al. (2000) Struct. Fold. Des. 8: 363), L2 (Nakagawa, A. et al. (1999) EMBO J. 18: 1459-1467), L4 (Wahl et al. (2000) EMBO J. 19: 807-818), L6 (Golden et al. (1993) EMBO J. 12: 4901-4908), L11 (Conn et al. (1999) supra; Wimberly et al. (1999) supra; Markus et al. (1997) Nature Struct. Biol. 4: 70-77), L12 (Leijonmarck, M. et al. (1980) Nature 286: 824-827), L14 (Davies et al. (1996) Structure 4: 55-66), L22 (Unge et al. (1998) Structure 6: 1577-1586), L30 (Wilson et al. (1986) Proc. Nat. Acad. Sci. USA 83: 7251-7255). All other structures, except 10, have been newly determined in this study.
[2]Rat homologue. Rat equivalents to *H. marismortui* proteins are from (Mao et al. (1999) supra).
[3]Sequence chain length.
[4]Conformation: glb = globular, ext = extension
[5]The protein interactions with the 6 domains of 23S rRNA, 5S rRNA and other proteins are specified. (+) implies that the interaction is substantial. (Å) implies a weak, tangential interaction. Protein names are shown in parentheses implies that the interactions are weak; otherwise, the interaction is substantial.
*All entries so designated describe proteins that are not fully represented in the electron density maps described here. The summary information provided is derived from literature sources and is included here for completeness only.
†The structure available for this protein in isolation does not include the extension(s) reported here.

3. General Appearance of the Subunit.

In its crown view (see FIG. 2), the large ribosomal subunit, which is about 250 Å across, presents its surface that interacts with the small subunit to the viewer with the three projections that radiate from that surface pointed up. Although the protuberance that includes L1 is not visible in the 2.4 Å resolution electron density map, the structure of L1, which has been determined independently (Nikonov et al. (1996) *EMBO J.* 15: 1350-1359), has been positioned approximately in lower resolution maps (Ban et al. (1998) supra) and is included here to orient the reader. It is evident that, except for its two lateral protuberances, the large ribosomal subunit is monolithic. There is no hint of a division of its structure into topologically separate domains. In addition, partly because it lacks obvious domain substructure but also because it is so large, it is impossible to comprehend looking at it as a whole. In order to convey to the reader a sense of how it is put together, the subunit must be dissected into its chemical components.

4. RNA Secondary Structure.

All the base pairs in *H. marismortui* 23S rRNA stabilized by at least two hydrogen bonds were identified using a computer program that searched the structure for hydrogen bond donors and acceptors separated by less than 3.2 Å. Bases linked by at least two such bonds were considered paired if the angle between their normals was less than 45°, and the angle between bonds and base normals was also less than 45°. Based on the results of this analysis, a secondary structure diagram has been prepared in the format standard for 23S/28S rRNAs (see, FIG. 3). The secondary structure predicted for this molecule by phylogenetic comparison was remarkably accurate, but it did not find all of the tertiary pairings and failed to identify interactions involving conserved bases. In addition to base pairs of nearly every type, the RNA contains numerous examples of well-known secondary structure motifs such as base triplets, tetraloops, and cross-strand purine stacks, but no dramatically new secondary structure motifs have been identified so far.

Figure 4:
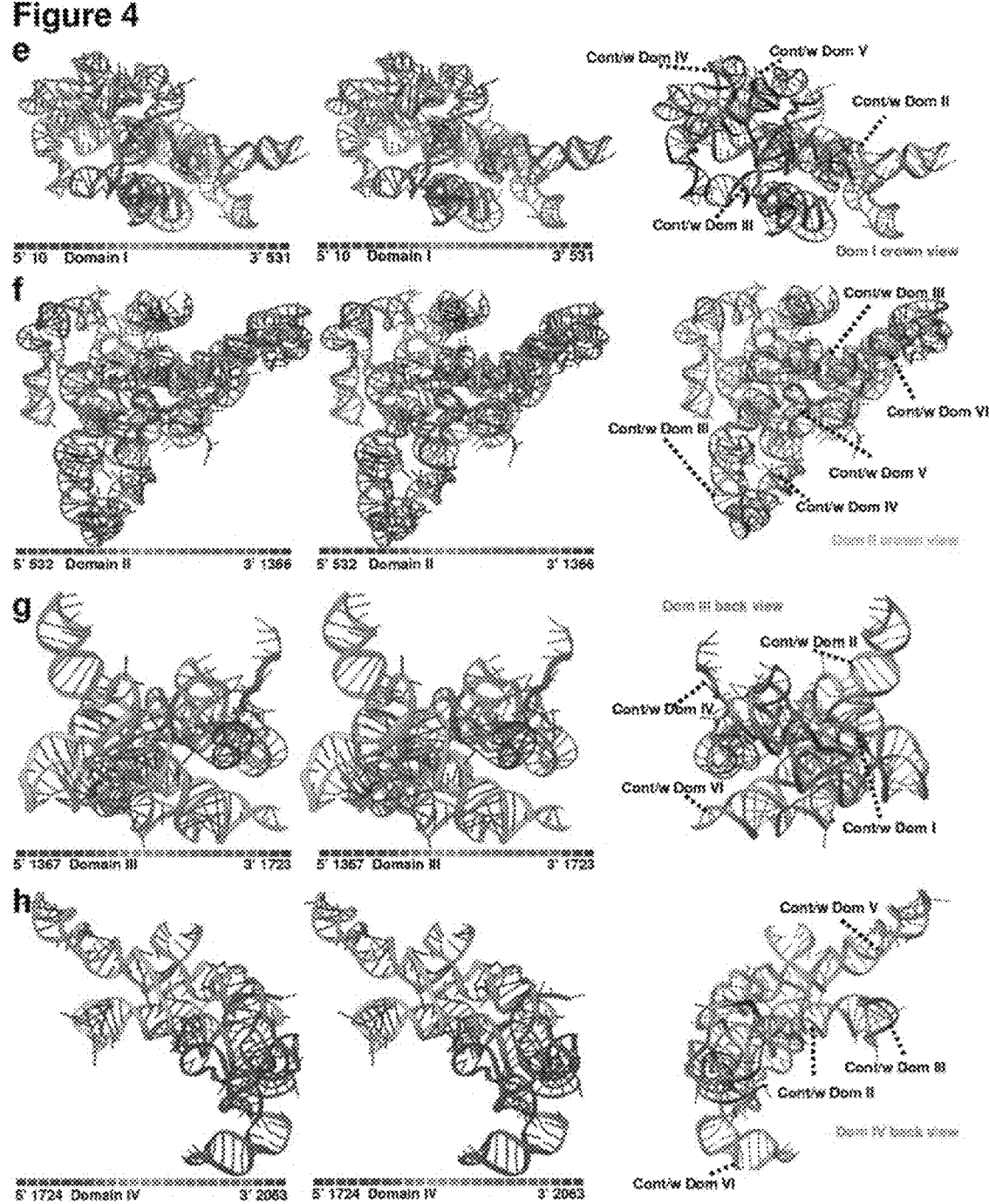
Figure 4:
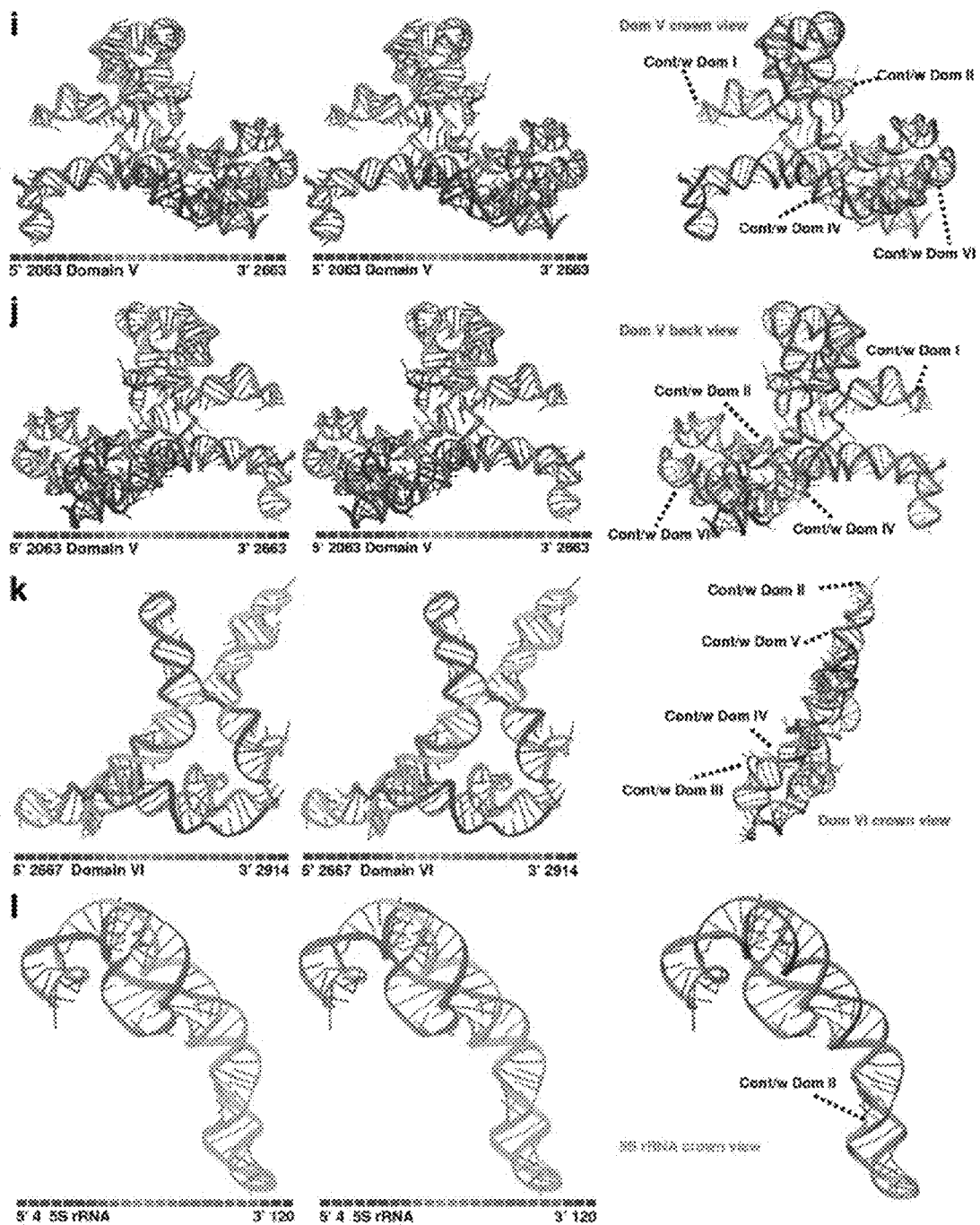

The secondary structure of this 23S rRNA consists of a central loop that is closed by a terminal stem, from which 11 more or less complicated stem/loops radiate. It is customary to describe the molecule as consisting of 6 domains, and to number its helical stems sequentially starting from the 5' end (see, FIG. 4) (Leffers et al. (1987) supra). The division of the molecule into domains shown in FIG. 4 deviates from standard practice with respect to helix 25, which is usually considered to be part of domain I. It is placed in domain II because it interacts more strongly with domain II than it does with the other elements of domain I.

There are five sequences longer than 10 nucleotides in 23S rRNA whose structures cannot be determined from the 2.4 Å resolution map due to disorder. Altogether they account for 207 out of the 232 nucleotides missing from the final model. The disordered regions are: (1) all of helix 1, (2) the distal end of helix 38, (3) helix 43/44 to which ribosomal protein L11 binds, (4) the loop end of stem/loop 69, and (5) helix 76/77/78, which is the RNA structure to which L1 binds. For completeness, these regions are included in FIG. 3 (in gray) with their secondary structures determined phylogenetically.

5. Overall Architecture of rRNA.

The six domains of 23S rRNA and 5S rRNA all have complicated, convoluted shapes that nevertheless fit together to produce a compact, monolithic RNA mass (see FIGS. 4(A) and 4(B)). Thus despite the organization of its RNAs at the secondary structure level, in three-dimensions, the large subunit is a single, gigantic domain. In this respect, it is quite different from the small subunit, which is a flatter object that is not at all monolithic. Even in low resolution electron micrographs the small subunit consists of three structural domains, each of which, it turns out, contains one of the three secondary structure domain of its RNA (Noller et al. (1990) *The Ribosome: Structure, Function, and Evolution*, supra, pp. 73-92). This qualitative difference between the two subunits may reflect a requirement for conformational flexibility that is greater for the small subunit.

Domain I, which looks like a mushroom (see, FIG. 4(E)), lies in the back of the particle, behind and below the L1 region. The thin part of the domain starts in the vicinity of domain VI, which is where its first and last residues are located. Helices 1 and 25 span the particle in the back and then the domain expands into a larger, more globular structure below and behind the L1 region.

The largest of the six 23S rRNA domains, domain II, which accounts for most of the back of the particle, has three protrusions that reach towards the subunit interface side of the particle (see, FIG. 4(F)). One of them (helix 42-44) is the RNA portion of the L7/L12 stalk, which is known to interact with elongation factors, is not well-ordered in these crystals. The second domain II protrusion is helix 38, which is the longest, unbranched stem in the particle. It starts in the back of the particle, bends by about 90 degrees and protrudes towards the small subunit between domains V and 5S rRNA. The third region, helix 32-35.1, points directly towards the small subunit and its terminus, the loop of stem/loop 34, interacts directly with the small ribosomal subunit (Culver et al. (1999) *Science* 285: 2133-2135). This loop emerges at the subunit interface between domains III and IV.

Domain III is a compact globular domain that occupies the bottom left region of the subunit in the crown view (see, FIG. 4(G)). It looks like a four pointed star with the origin of the domain (stem/loop 48) and stem/loops 52, 57, and 58 forming the points. The most extensive contacts of domain III are with domain II, but it also interacts with domains I, IV and VI. Unlike all the other domains, domain III hardly interacts with domain V at all; the sole contact is a single van der Waals contact involving a single base from each domain.

Domain IV accounts for most of the interface surface of the 50S subunit that contacts the 30S subunit (see, FIG. 4(H)). It forms a large diagonal patch of flat surface on that side of the subunit, and connects to domains III and V in the back of the particle. Helices 67-71 are the most prominent feature of domain IV, and form the front rim of the active site cleft, which is clearly visible at low resolution (see, FIG. 2). This is one of the few regions of the 23S rRNA that is not extensively stabilized by ribosomal proteins. Helix 69 in the middle of this ridge interacts with the long penultimate stem of 16S rRNA in the small ribosomal subunit and can be viewed as a divider separating A-site bound tRNAs from P-site bound tRNAs.

Domain V, which is sandwiched between domains IV and II in the middle of the subunit, is known to be intimately involved in the peptidyl transferase activity of the ribosome. Structurally the domain can be divided into three regions (see, FIGS. 4(I) and 4(J)). The first starts with helix 75 and ultimately forms the binding site for protein L1. The second, which consists of helices 80-88, forms the bulk of the central protuberance region, and is supported in the back by the 5S rRNA and domain II. The third region, which includes helices 89-93, extends towards domain VI and helps stabilize the elongation factor binding region of the ribosome.

The smallest domain in 23S rRNA, domain VI, which forms a large part of the surface of the subunit immediately below the L7/L12 stalk, resembles a letter X with a horizontal bar at the bottom (see, FIG. 4(K)). An interesting region of this domain is the sarcin-ricin loop (SRL) (stem/loop 95), the structure of which has been extensively studied in isolation (Szewczak et al. (1995) *J. Mol. Biol.* 247: 81-98). The SRL is essential for factor binding, and ribosomes can be inactivated by the cleavage of single covalent bonds in this loop (Wool et al. (1992) *TIBS* 17: 266-269). As suggested by nucleotide protection data, the major groove of this loop is exposed to solvent (Moazed et al. (1988) *Nature* 334: 362-364), and its conformation is stabilized by proteins and through interaction with domain V that involves two bases on the minor grove side. The nucleotides involved are A 2699 and G 2700 in domain VI, and A 2566 and G 2567 in domain V.

5S ribosomal RNA, which is effectively the seventh RNA domain in the subunit, consists of three stems radiating out from a common junction called loop A (see, FIG. 4(D)). In contrast to what is seen in the crystal structure of fragment 1 from *E. coli* 5S rRNA (Correll et al. (1997) *Cell* 91: 705-712), the helix ⅔ arm of the molecule stacks on its helix ⅘ arm, not helix 1 (see, FIG. 4(L)). This arrangement results from a contorted conformation of loop A residues that involves two stacked base triples. Indeed, from the secondary structure point of view, the loopA-helix 2,3 arm of 5S rRNA is quite remarkable. Nowhere else in the subunit is there a higher concentration of unusual pairings and of convoluted RNA secondary structure.

6. Sequence Conservation and Interactions in 23S rRNA.

Figure 5:
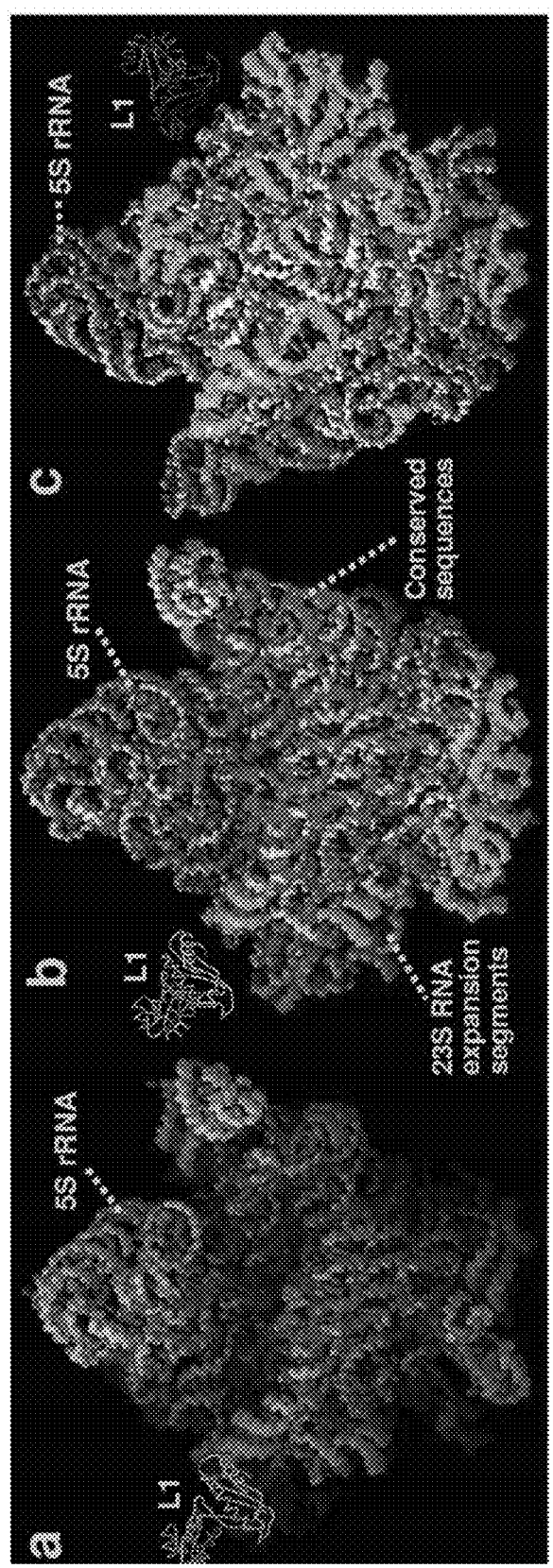

While 23S/28S rRNAs contain many conserved sequences, they also vary substantially in chain length. Shorter 23S/28S rRNAs are distinguished from their longer homologues by the truncation of, or even the elimination of entire stem/loops, and by comparing sequences, one can identify a minimal structure that is shared by all (Gerbi (1995) *Ribosomal RNA: Structure, Evolution, Processing and Function in Protein Biosynthesis*, supra, pp. 77-88). The expansion sequences in the 23S rRNA of *H. marismortui*, i.e., the sequences it contains that are larger than the minimum, are shown in FIG. 5 in green. They are largely absent from the subunit interface surface of the particle, but they are abundant on its back surface, far from its active sites. This is consistent with low resolution electron microscopic observations suggesting that the region of the large subunit whose structure is most conserved is the surface that interacts with the small subunit (Dube et al. (1998) *Structure* 6: 389-399).

There are two classes of conserved sequences in 23S rRNA. One contains residues concentrated in the active site regions of the large subunit. The second class consists of much shorter sequences scattered throughout the particle (FIG. 5: red sequences). The SRL sequence in domain VI and the cluster of conserved residues belonging to domain V that are located at the bottom of the peptidyl transferase cleft are members of the first class. They are conserved because they are essential for substrate binding, factor binding and catalytic activity. Most of the residues in the second class of conserved residues are involved in the inter- and intra-domain interactions that stabilize the tertiary structure of 23S rRNA. Adenosines are disproportionately represented in this class. The predominance of A's among the conserved residues in rRNAs has been pointed out in the past (Ware et al. (1983) *Nucl. Acids. Res.* 22: 7795-7817).

In addition to its reliance on A-dependent motifs, the tertiary structure of the domains of 23S rRNA and their relative positions are stabilized by familiar tertiary structure elements like RNA zippers and tetraloop/tetraloop receptor motifs (Moore, P. B. (1999) *Annu. Rev. Biochem.* 68: 287-300), and in many places, base pairs and triples stabilize the interactions of sequences belonging to different components of the secondary structure of 23S rRNA.

Interestingly, 5S rRNA and 23S rRNA do not interact extensively with each other. The few RNA/RNA interactions there are involve the backbones of the helix ⅘ arm of 5S rRNA and the backbone of helix 38 of 23S rRNA. Most of the free energy and all of the specificity of 5S rRNA binding to the large ribosomal subunit appears to depend on its extensive interactions with proteins that act as modeling clay sticking it to the rest of ribosome.

7. Proteins in the 50S Ribosomal Subunit.

The structures of twenty seven proteins found in the large ribosomal subunit of *H. marismortui* (Table 2) have been determined. Twenty-one of these protein structures have not been previously established for any homologues, and the structures of the six that do have homologues of known structure have been rebuilt into the electron density map using their *H. marismortui* sequences. In addition, there are structures available for homologues of *H. marismortui* L1, L11 and L12, which cannot be visualized in the 2.4 Å resolution electron density map. Only the structure of L10 is still unknown among the thirty one proteins known to be present.

Not every one of these structures is complete. For example, an entire domain of L5 is missing from the electron density, presumably because of disorder. L32e is also noteworthy in this regard. About twenty residues from its N-terminus are not seen in the electron density map, and the electron density map suggests that its C-terminal residue is covalently bound to the most N-terminal of its visible residues.

Of the thirty large subunit ribosomal proteins whose structures are known, 17 are globular proteins, similar in character to thousands whose structures are in the Protein Data Bank (Table 2). The remaining thirteen proteins either have globular bodies with extensions protruding from them ("glb+ext") or are entirely extended ("ext"). Their extensions often lack obvious tertiary structure and in many regions are devoid of secondary structure as well (see FIG. 6). These extensions may explain why many ribosomal proteins have resisted crystallization in isolation. The exceptions that prove the rule are L2 and L4, both of which are proteins belonging to the "glb+ext" class. Protein L2 was crystallized and its structure solved only after its extensions had been removed (Nakagawa et al. (1999) supra), and one of the two regions of L4 that are extended in the ribosome is disordered in the crystal structure of intact L4 (Wahl et al. (2000) supra).

Figure 7:
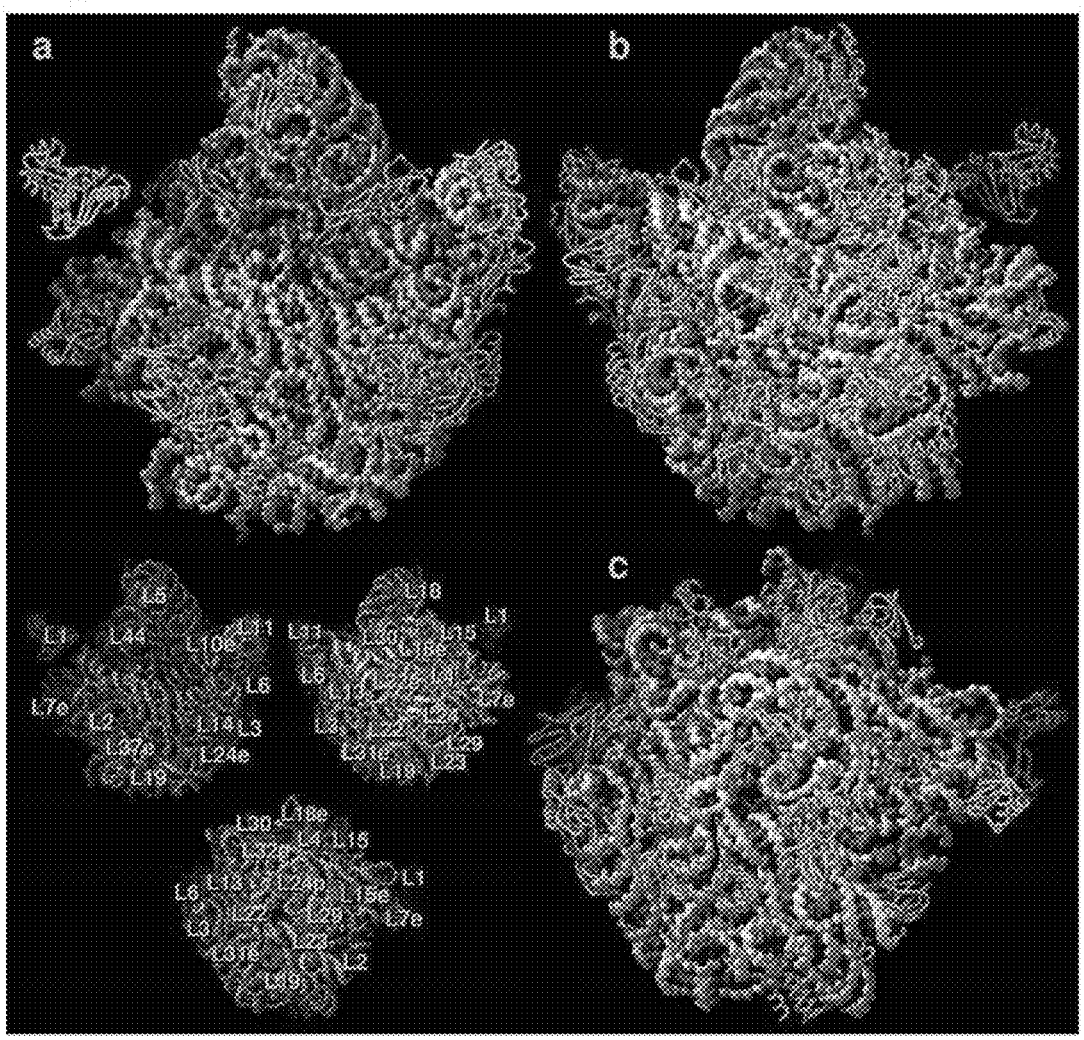

Except for proteins L1, L7, L10 and L11, which form the tips of the two lateral protuberances, the proteins of the 50S subunit do not extend significantly beyond the envelope defined by the RNA (see, FIG. 7). Their globular domains are found largely on the particle's exterior, often nestled in the gaps and crevices formed by the folding of the RNA. Thus, unlike the proteins in spherical viruses, the proteins of the large ribosomal subunit do not form a shell around the nucleic acid with which they associate, and unlike the proteins in nucleosomes, they do not become surrounded by nucleic acid either. Instead, the proteins act like mortar filling the gaps and cracks between "RNA bricks."

The distribution of proteins on the subunit surface is nearly uniform, except for the active site cleft and the flat surface that interacts with the 30S subunit. In the crown view the proteins lie around at the periphery of the subunit (see, FIG. 7(A)), but when viewed from the side opposite the 30S subunit binding site (the "back side"), they appear to form an almost uniform lattice over its entire surface (see, FIG. 7(B)). Similarly, the bottom surface of the subunit, which includes the exit of polypeptide tunnel, is studded with proteins (see, FIG. 7(C)). Indeed, the 5 proteins that surround the tunnel exit may play a role in protein secretion since they are part of the surface that faces the membrane and the translocon when membrane and secreted proteins are being synthesized.

Although FIG. 7 shows protein chains disappearing into the ribosome interior, the degree to which proteins penetrate the body of the particle can only be fully appreciated when the RNA is stripped away. The interior of the particle is not protein-free, but it is protein-poor compared to the surface of the particle. Extended tentacles of polypeptide, many of which emanate from globular domains on the surface, penetrate into the interior, filling the gaps between neighboring elements of RNA secondary structure (see, FIG. 8(E)). The bizarre structures of these extensions are explained by their interactions with RNA.

Although extended, non-globular structures are rare in the protein data base, they are not unknown. Extended protein termini often form inter-protein contacts, e.g., in viral capsids, presumably adopting fixed structures only upon capsid formation. The basic "tails" of histones may behave the same way when nucleosomes form. The N-terminal sequences of capsid proteins are often positively charged, and in virus crystal structures, the electron density for these sequences often disappears into the interior of the virus where these sequences presumably interact with asymmetrically arranged nucleic acid. The interactions observed in the ribosome could be useful models for these viral interactions.

The interactions of extended polypeptides and RNA in the large subunit, which stabilizes its massive nucleic acid structure, result in a tangle of RNA and protein in the center of the subunit (see, FIGS. 8(A) and 8(B)). It is hard to imagine such an object assembling from its components efficiently in anything other than a highly ordered manner. Chaperones may well be required to prevent the aggregation of the extended regions of these proteins, which are likely to be disordered outside the context provided by rRNA, and to manage the folding of rRNA.

8. Protein and RNA Interactions.

Because protein permeates the large subunit to a surprising degree, there are only a few segments of the 23S rRNA that do not interact with protein at all. Of the 2923 nucleotides in 23S rRNA, 1157 nucleotides make at least van der Waals contact with protein (see, FIG. 8(D)), and there are only ten sequences longer than twenty nucleotides in which no nucleotide contacts protein. The longest such sequence contains forty-seven nucleotides, and is the part of domain IV that forms the ridge of the active site cleft.

The extent of the interactions between RNA and protein that occur when the large subunit assembles can estimated quantitatively. Using the Richards algorithm (Lee, B. et al. (1971) *J. Mol. Biol.* 55: 379-400) and a 1.7 Å radius probe to compute accessible surface areas, it can be shown that 180,000 Å$^2$ of surface becomes buried when the subunit forms from its isolated, but fully structured components. This is about half their total surface area. The average is about 6,000 Å$^2$ per protein. While this is an enormous amount compared to the surface buried when most protein oligomers form, it should be recognized that ribosome assembly must be accompanied by a large loss in conformational entropy that does not occur when most proteins oligomerize. The extended protein termini and loops of the ribosomal proteins are almost certainly flexible in isolation, and in the absence of protein, the RNA is probably quite flexible as well. Thus, the burial of a large amount of surface area may be required to provide the energy necessary to fix of the structures of these molecules.

All of the proteins in the particle except L12, interact directly with RNA and all but seven of the remaining thirty proteins interact with two rRNA domains or more (Table 2). The "champion" in this regard is L22, which is the only protein that interacts with RNA sequences belonging to all 6 domains of the 23S rRNA (see, FIG. 8(C)). The protein-mediated interactions between 5S rRNA and 23S rRNA are particularly extensive. Protein L18 attaches helix 1 and helix ⅔ of 5S rRNA to helix 87 of 23S rRNA. Protein L31e mediates an interaction between the same part of 5S rRNA and domains II and V. Loop C is linked to domain V by protein L5 and loop D is attached to domains II and V by protein L10e. Whatever else they may do, it is evident that an important function of these proteins is stabilization of the relative orientations of adjacent RNA domains. Several also help secure the tertiary structures of the domains with which they interact.

Since most ribosomal proteins interact with many RNA sequences and the number of proteins greatly exceeds the number of RNA domains, it can hardly come as a surprise that every rRNA domain interacts with multiple proteins (Table 2). Domain V, for example, interacts with thirteen proteins, some intimately and a few in passing.

It is clear that the oligonucleotide binding experiments long relied on for information about the RNA binding properties of ribosomal proteins have underestimated their potential for interacting with RNA. The high-affinity RNA binding site identified on a protein by such an experiment may indeed be important for ribosome assembly, but its many, weaker interactions with other sequences are likely to be missed, and they too may be vital for ribosome structure. Most ribosomal proteins crosslink RNA and crosslinking is impossible without multiple interactions. Similar considerations may apply to proteins that are components of other ribonucleoproteins such as the sliceosome.

Of the seven proteins that interact with only one domain, three (L1, L10, L11) participate directly in the protein synthesis process. Rather than being included in the ribosome to ensure that the RNA adopts the proper conformation, it seems more appropriate to view the RNA as being structured to ensure their correct placement. Another three (L24, L29, L18e) interact with several secondary structure elements within the domains to which they bind, and presumably function to stabilize the tertiary structures of their domains. The last of the single RNA domain proteins, L7ae, is puzzling. On the one hand, it cannot function as an RNA stabilizing protein because it interacts with only a single, short sequence in domain I, and on the other hand, it is far from the important functional sites in the subunit, the peptidyl transferase site and factor binding site. It is quite close to L1, however, which appears to be important for E-site function (Agrawal et al. (1999) *J. Biol. Chem.* 274: 8723-8729), and maybe it is involved in that activity.

While many ribosomal proteins interact primarily with RNA, a few interact significantly with other proteins. The most striking structure generated by protein-protein interactions is the protein cluster composed of L3, L6, L14, L19 and L24e that is found close to the factor binding site. The protein surface they provide may be important for factor interactions.

The structure presented above illuminates both the strengths and weaknesses of approaches to complex assemblies that depend on determining the structures of components in isolation. The structures of the globular domains of homologues of the proteins in large ribosomal subunit from *H. marismortui* are largely the same as those of the corresponding domains in the intact subunit, though adjustments in domain positions are sometimes required. Consequently, these structures were very useful for locating proteins and interpreting lower resolution electron density maps. However, for obvious reasons, the structures of the extended tails and loops of ribosomal proteins cannot be determined in the absence of the RNAs that give them structure, and the feasibility of strategies that depend on producing low molecular weight RNA-protein complexes that have all the RNA contacts required to fix the structures of such proteins seems remote. RNA is also a problem. While the sarcin/ricin loop has much the same structure in isolation as it does in the ribosome, the structure of 5S rRNA in isolation differs in some respects from what is seen in the ribosome, and the structure of the isolated P-loop (Puglisi et al. (1997) *Nat. Struct. Biol.* 4: 775-778) does not resemble the structure of the P-loop in the ribosome at all. Clearly a "structural genomics" approach to the ribosome, which would have entailed determining the structures of all its proteins and all possible rRNA fragments, would not have worked. It may not be successful for other macromolecular assemblies either.

B. The Structural Basis of Ribosome Activity in Peptide Bond Synthesis

Analysis of the atomic co-ordinates discussed in section IIA above together with additional atomic co-ordinates of a ribosomal subunit complexed with various analogues, similarly refined, permit an analysis of ribosome function. Accordingly, the present invention is also based on the crystals of *Haloarcula marismortui* 50S ribosomal subunit complexed either with the Yarus transition state analogue, CCdA-p-Puro, or with a mini-helix analogue of an aminoacyl-tRNA. The present invention provides the structures of both complexes. The atomic co-ordinates of the structure of both complexes were deposited on Jul. 26, 2000, at Research Collaboratory for Structural Bioinformatics (RCSB) Protein Data Bank (PDB) (Berman et al. (2000) *Nucleic Acid Research* 28: 235-242; hap://www.rcsb.org/pdb/) with accession numbers PDB ID: 1FFZ (50S ribosome/CCdA-p-Puro complex) and PDB ID: 1FG0 (50S ribosome/aa-tRNA analogue).

As discussed below, the complete atomic structures of the large ribosomal subunit and its complexes with two substrate analogues show that the ribosome is a ribozyme. The complete atomic structures also provide information regarding the catalytic properties of its all-RNA active site. Both substrate analogues are contacted exclusively by conserved rRNA residues from domain V of 23S rRNA; there are no protein side-chains closer than about 18 Å to the peptide bond being synthesized. The mechanism of peptide bond synthesis appears to resemble the reverse of the deacylation step in serine proteases, with the base of A2486 (A2451) in *E. coli* playing the same general base role as His57 in chymotrypsin. The unusual pKa that A2486 must possess to perform this function probably derives from its hydrogen bonding to G2482 (G2447) which interacts with a buried phosphate that could stabilize the unusual tautomers of two bases which is required for catalysis. The polypeptide exit tunnel is largely formed by RNA but has significant contributions from proteins L22, L39 and L4 and its exit is encircled by proteins L19, L22, L23a, L24 and L29.

The CCdA from the Yarus analogue binds to the so-called P-loop and hence must be in the P-site. Only the terminal-CCA of the aa-tRNA analogue is visible, but since it interacts appropriately with the A-loop (Kim et al. (1999) *Molec. Cell* 4: 859-864), it must be in the A-site. The puromycin group occupies the same location in both structures, and there are no proteins near that site. Hence, the catalytic activity of the active site must depend entirely on RNA. The N3 of A2486 (*E. coli* A2451) is the titratable group nearest to the peptide bond being synthesized and is likely functioning as a general base to facilitate the nucleophilic attack by the α-amino group of the A-site substrate. In order to function in this capacity, the pKa of this base has to be roughly 5 units higher than normal.

1. Structures of Substrate Analogue Complexes.

In order to establish how substrates interact at the A-site and P-site of the large subunit, two substrate analogues were used. One of the analogues, which was designed to mimic the acceptor stem of an aa-tRNA and bind to the A-site, was a twelve base-pair RNA hairpin with an aminoacylated, four-nucleotide extension on its 3' end (see, FIG. 9). The sequence used was that of the tRNA tyr acceptor stem and it is terminated with puromycin, which itself is an analogue of tyrosyl-A76. The second analogue used was the Yarus transition state analogue, CCdA-p-puromycin. As in the case of the A-site substrate analogue, the puromycin of the Yarus inhibitor is expected to bind at the A-site, while its CCdA moiety should bind at the P-site.

The positions of the Yarus inhibitor and the tRNA acceptor stem analogue were determined by soaking these molecules into crystals of the *H. marismortui* 50S ribosomal subunit, measuring diffraction data to 3.2 Å resolution and calculating difference electron density maps (Welch et al. (1997) *Biochemistry* 36: 6614-6623). Maps of the complexes were also calculated using $2F_o$(complexed)-$F_o$(uncomplexed) as coefficients, to examine the shifts in the positions of ribosome residues that occur when these analogues bind (see, FIG. 10(B) and Table 3).

TABLE 3

Statistics for Data Collection and Scaling.

| Crystal | Native A | Native B | CcdAp-Puro | Mini-helix |
|---|---|---|---|---|
| Soak time (hours) | — | — | 24 | 24 |
| Soak concentration (μM) | — | — | 100 | 100 |
| Wavelength (Å) | 1.0 | 1.0 | 1.0 | 1.0 |
| Observations | 1,571,171 | 1,344,877 | 2,590,726 | 2,712,813 |
| Unique | 284,533 | 369,167 | 367,284 | 447,121 |
| Redundancy | 5.5 | 3.6 | 7.0 | 6.0 |
| Resolution limits (Å) | 70.0-3.2 | 70.0-3.0 | 70.0-3.0 | 70.0-2.8 |
| (High-resolution bin)* | (3.26-3.20) | (3.05-3.00) | (3.23-3.17) | (3.08-3.02) |
| Completeness | 94.1 (96.0) | 98.9 (99.3) | 98.6 (99.9) | 99.6 (100) |
| I/σI | 14.6 (4.0) | 10.8 (3.1) | 11.0 (2.8) | 10.7 (2.9) |
| $R_{merge}$† | 10.2 (40) | 11.5 (38) | 18.8 (84) | 14.3 (72) |
| $R_{iso}$ Native A‡ | — | — | 6.8 (20.8) | 14.4 (25.2) |
| $R_{iso}$ Native B‡ | — | — | 12.6 (27.4) | 17.5 (31.0) |

*Statistics in parenthesis are calculated for the high-resolution bin used in map calculations, which, as indicated was sometimes lower in resolution than the high-resolution bin used in data reduction.
†$R_{merge}$: $\Sigma\Sigma_i |I_{(h)} - I_{(h)i}|/\Sigma\Sigma I_{(h)i}$ where $I_{(h)}$ is the mean intensity after reflection.
‡$R_{iso}$: $\Sigma |F_{PH} - F_P|/\Sigma F_{PH}$ where $F_{PH}$ and $F_P$ are the soaked and the native crystal structure factor amplitudes respectively.

A model for the entire Yarus inhibitor could be fitted into the difference density (see, FIG. 10(A)), and the electron density map of the complex shows the N3 of A2486 (2451) within hydrogen bonding distance of a non-bridging oxygen of the phosphoramide (see, FIG. 10(B)). The inhibitor's two C's, which correspond to C74 and C75 of peptidyl-tRNA, are Watson-Crick base-paired with G2285 (2252) and G2284 (2251) in the P-loop, respectively (see, FIG. 11(A)). The C74-G2285 (2252) interaction was predicted by the results of Noller and coworkers (Noller et al. (1992) *Science* 256: 1416-1419). The dA, which corresponds to A76 of a tRNA in the P-site, is not base-paired, but rather stacks on the ribose of A2486 and hydrogen bonds to the 2'OH of nucleotide A2485 (see, FIG. 12(B)).

Only the CC-puromycin moiety of the mini-helix acceptor stem analogue showed ordered electron density in its difference electron density map (see, FIG. 10(C)). The C75 of the acceptor stem CCA is Watson-Crick base-paired with G2588 (2553) of the A-loop, whereas the C74 is more disordered and not base-paired but appears to stack on a ribosome base. The dimethyl A of the A-site inhibitor puromycin is positioned identically to the dimethyl A of the Yarus inhibitor. Further, the dimethyl A of puromycin, which is the A76 equivalent of an A-site tRNA, interacts with the A-loop in much the same way that the A76 from the P-site CCA interacts with the P-loop (see, FIG. 11(B)).

The most notable of the several conformational changes in the ribosome induced by the binding of the transition state analogue is the ordering of base A2637 (2602), which is disordered in the unliganded enzyme (see, FIG. 11(B)). It becomes positioned between the CCA bound at the A-site and the CCA bound at the P-site. The base of U2620 (2585) also moves so that it can make a hydrogen bond with the 2' hydroxyl of the ribose of A76 in the A-site, and U2619 and G2618 shift to allow the A76 to be positioned. Smaller shifts in positions are observed in the positions of A2486, whose N3 is near to the non-bridging oxygen of the phosphate, and one of the G residues with which it interacts, G2102 (2482).

2. Location and Chemical Composition of the Peptidyl Transferase Site.

The inhibitors are bound to a site made entirely of 23S rRNA with no proteins nearby, proving that the ribosome is a ribozyme. Both the Yarus inhibitor and the A-site analogue of aa-tRNA bind to the large subunit at the bottom of a large and deep cleft at the entrance to the 100 Å long polypeptide exit tunnel that runs through to the back of the subunit (see, FIG. 12). This site is surrounded by nucleotides belonging to the central loop of 23S RNA domain V, the "peptidyl transferase loop." Nucleotides from the single stranded portions of this loop make the closest approach to the phosphate that mimics the tetrahedral carbon intermediate. In general, the helices that extend from the peptidyl transferase loop in 2 secondary structure diagrams of 23S rRNA also extend away from the active site in the tertiary structure (see, FIG. 13). Although there are 13 proteins that interact with domain V (see, FIG. 14(A)), there are no globular proteins in the vicinity of the inhibitor. The closest polypeptides are the non-globular extensions of several proteins (L2, L3, L4, L10e) that penetrate deeply into domain V and approach the active site (see, FIG. 14(B)). These extensions fill many of the voids between the RNA helices of domain V, neutralize phosphate backbone charge, and presumably stabilize the structure of the domain and its association with other RNA regions. However, none of their side chain atoms is closer than about 18 Å to the phosphorus of the inhibitor's phosphate group, which marks the site where peptide bonds form. Furthermore, the substrate analogue is completely enclosed in an rRNA cavity that is so tightly packed that there is no possibility that an unidentified peptide could be lurking nearby (see, FIG. 15). Thus, the catalytic entity in the ribosome must be RNA.

Two of the proteins with long termini or loops penetrating the rRNA scaffold of domain V are proteins that could not previously be excluded from involvement in the peptidyl transferase reaction L2 and L3 (Noller (1991) *Ann. Rev. Biochem.* 60: 191-227). Noller and colleagues (Noller et al. (1992) supra) found that under conditions which prevent RNA denaturation, extensive digestion of *Thermus thermophilus* 50S subunits with proteases followed by extraction with phenol and other agents that disrupt protein-RNA interactions did not remove several peptides from the subunit that were less than 10,000 in molecular weight. The structure makes it clear why these protein fragments were particularly resistant to protease treatments. While protease treatment could digest the globular protein domains on the surface of the large subunit, it could not remove the long termini or loops that penetrate deeply in the 23S rRNA because they are sequestered within the rRNA and thus protected from cleavage, independently of the globular domains.

3. Peptidyl Transferase Active Site.

The RNA that surrounds the substrate analogues is closely packed, much like the active site region of a protein enzyme and the nucleotides in contact with the inhibitor are greater than 95% conserved in all three kingdoms of life (see, FIG. 15). Thus, it is clear that the ribosome is a ribozyme, but what gives the RNA its catalytic power?

Without wishing to be bound by theory, the residue most likely to be involved in catalysis, presumably as a general base, is A2486, whose N3 is about 3 Å from the phosphoramide oxygen of the Yarus inhibitor that is the analogue of the carbonyl oxygen of a nascent peptide bond and about 4 Å from the amide that corresponds to the amide nitrogen of the peptide bond being synthesized. Ordinarily, the pKa of the N1 of adenosine monophosphate is about 3.5 and that of its N3 is perhaps 2 pH units lower (Saenger (1984) *Principles of Nucleic Acid Structure*, (C. R. Cantor, eds.), *Springer Advanced Texts in Chemistry*, Springer-Verlage, New York, N.Y.), and in order for A2486 to function as a general base, its pKa would have to be raised to 7 or higher. The crystal structure itself suggests that its pKa is, in fact, quite unusual. The N3 of A2486 can only hydrogen bond to the phosphate oxygen, as observed, if it (or the phosphate oxygen) is protonated. The distance between these two atoms is about 3 Å indicating that a hydrogen bond does, indeed, exist between them. Since the crystal is at pH 5.8, this implies that the pKa of the N3 is greater than 6. Muth and Strobel have measured the pKa of the corresponding A in *E. coli* 23S RNA by examining its dimethyl sulfate reactivity as a function of pH and have concluded that it is 7.6, though they cannot be sure from their experiments whether it is the N3 or N1 whose pKa they have measured (Muth et al. (2000) *Science* 289: 947-950). Because there is no other available, titratable RNA functional group closer than about 7 Å to the nascent peptide bond, there is not other group available to function as a general base.

There are several features of environment of A2486 (2451) that might affect its pKa. The pKa of the N3 of A2486 (2451) may be increased significantly in part by a charge relay mechanism, analogous to that which occurs in the active site of the serine proteases, with the buried phosphate of A2485 (2450) performing a similar function as the buried carboxylate of Asp102 of chymotrypsin. The experimental 2.4 Å electron density map unambiguously establishes the hydrogen bonding interactions in this most critical region of the active site (see, FIG. 16(A)). The N6 of A2486 interacts with the O6 atoms of G2482 (2447) and G2102 (2061) (see, FIG. 16(B)). The N2 of G2482 is also interacting with a non-bridging oxygen of the phosphate group of A2485 (2450) that is among the total of 3 most solvent inaccessible phosphate groups (826, 1497 and 2485) in the large ribosomal subunit for which we do not see any neutralizing counterion in the 2.4 Å resolution map. Weak density that may correspond to a water molecule is hydrogen bonded to the other non-bridging oxygen. A neutralizing counterion is not apparent in this structure. The buried phosphate of A2485 could abstract the proton from the exocyclic N2 of G2482 in order to neutralize its energetically unfavorable buried negative charge. This, in turn, would stabilize the otherwise rare imino tautomer of that base. The interaction of an imino of G2482 with A2486 likewise can stabilize the imino tautomer of A2486 that would result in a negative charge on its N3 were it unprotonated (see, FIG. 16(C)). In this way, some of the negative electrostatic charge originating on the buried phosphate of A2485 could be relayed to the N3 of A2486, thereby increasing its pKa.

A second feature of the environment of the catalytic site that may affect its stability, tautomeric state and electrostatic charge distribution is a bound monovalent cation. A potassium or a sodium ion interacts with the O6 of G2482 and G2102 as well as with three other bases. Its identity as a potassium ion is established by its observed continuation and by an independent experiment showing that a rubidium ion can bind to this site. The monovalent ion might also stabilize non-standard tautomers, but its expected influence on the pKa of A2486 is less obvious. Early biochemical experiments have shown the importance of potassium for peptidyl transferase activity (Monro (1967) supra; Maden et al. (1968) supra) and this binding site could be responsible for that affect.

It may also be the case that stabilization of an imino tautomer by a buried phosphate explains the expected higher pKa of a catalytic cytosine in the active site of the hepatitis delta virus ribozyme (Ferre-D'Amare et al. (1998) *Nature* 395: 567-574; Naharo et al. (2000) *Science* 287: 1493-1497). In this case, a backbone phosphate, whose solvent accessibility is similar to that of A2485 in the ribosome, is observed to hydrogen bond to the N4 of C, and the protonated form of the imino tautomer of that C would neutralize the phosphate, promoting the function of its N3 as a general acid (Naharo et al. (2000) supra).

4. Catalytic Mechanism of Peptide Bond Formation.

The proximity of the N3 of A2486 (2451) to the peptide bond being synthesized and the nature of the reaction catalyzed suggest a chemical mechanism of peptide synthesis that is analogous to the reverse of the deacylation step seen in serine proteases during peptide hydrolysis (Blow et al. (1969) *Nature* 221: 337-340; Steitz et al. (1982) *Ann. Rev. Biophys. Bioeng.* 11: 419-444). In that mechanism, the basic form of His57 abstracts a proton from the α-amino group of the peptide product as it attacks the acyl-Ser195. Formation of the tetrahedral carbonyl carbon intermediate is stabilized by interaction of the oxyanion formed with backbone amides (the "oxyanion hole"); His57 shuttles the proton acquired from the α-NH₂ to Ser95 as the tetrahedral intermediate breaks down.

The residue A2486 (2451) appears to be the analogous to His57 in chymotrypsin and that the peptidyl-tRNA is analogous to acyl-Ser195. Thus, the N3 of A2486, with its greatly elevated pKa, abstracts a proton from the α-amino group of the A-site bound aminoacyl-tRNA facilitating the nucleophilic attack of that amino group on the carbonyl carbon that acylates the 3' OH of the tRNA in the P-site (see, FIG. 17(A)). In contrast to the serine proteases, however, the oxyanion of the tetrahedral intermediate is near to the protonated N3 of A2486 (A2451) rather than being proximal to a separate oxyanion binding site. Thus, it could be that the protonated N3 of A2486 stabilizes the formation of the oxyanion by hydrogen bonding to it, as we observe in the Yarus inhibitor complex (see, FIG. 17(B)). The N3 of A2486 could then subsequently transfer its proton to the 3' hydroxyl of the P-site bound tRNA, which is liberated as the peptide shifts to the A-site bound tRNA (see, FIG. 17(C)).

An additional question is how is the catalyzed hydrolysis of the peptidyl tRNA in the P-site prevented prior to the delivery of the next appropriate aa-tRNA to the A-site? It appears from this complex that water would not be excluded from access to the peptidyl link to the P-site tRNA if the A-site were vacant. An analogous problem was discussed by Koshland in the 1960s (Koshland, Jr. (1963) *Cold Spring Harbor Symp. Quant. Biol.* 28: 473-489), who theorized why hexokinase does not hydrolyze ATP in the absence of glucose, since water should bind perfectly well to the binding site used by the 6-hydroxyl of glucose. The answer proposed was induced fit, i.e., hexokinase is not catalytically competent until the glucose binds and produces a conformational change that orients substrates and catalytic groups optimally. This indeed appears to be the case (Bennett, Jr. et al. (1978) *Proc. Natl. Acad. Sci. USA* 75: 4848-4852). Similarly, it could be that the catalytic A2486 and/or the peptidyl substrate are not properly oriented or that the binding site for the α-NH₂ group is blocked by a reoriented ribosome base in the absence of aa-tRNA in the A-site. The base of U2620 appears close to A2486 in the ligand free structure, and it may serve as the appropriate plug that prevents spontaneous hydrolysis of peptidyl-tRNA.

Thus, it appears that this RNA enzyme uses the same principles of catalysis as a protein enzyme. First, a large catalytic enhancement is achieved by precisely orienting the two reactants, the αNH₂ from the A-site aminoacyl-tRNA and the carbonyl carbon from the P-site peptidyl-tRNA. This may be accomplished, in part, by the interactions of the CCA ends of the A-site and P-site tRNAs with the A-loop and P-loop, respectively. Secondly, acid-base catalysis and transition state stabilization are achieved by an enzyme functional group (A2486 (2451) in this case) whose chemical properties are altered appropriately by the active site environment. Third, similar chemical principles may be used by RNA and protein enzymes to alter the pKa's of functional groups. A buried carboxylate of Asp102 acting through His57 alters the nucleophilicity of Ser195 in chymotrypsin (Blow et al. (1969) supra). In the ribosome a solvent inaccessible phosphate may act through G2482 (2447) alters the nucleophilicity of the N3 of A2486 (2451). It could be that RNA molecules "learned" how to use the chemical principles of catalysis significantly before protein molecules did.

5. tRNA Binding.

While it is not possible to bind tRNA molecules to either the A- or P-sites in these crystals for steric reasons, it is possible to place the A-, P- and E-site tRNA molecules on the large ribosomal subunit in the same relative orientation that Cate et al. observed in their crystallographic study of the Thermus aquaticus 70S ribosome. The co-ordinates of the three tRNA molecules in the relative positions seen in the 70S ribosome can be docked on the Haloarcula marismortui large ribosomal subunit in a way that avoids steric clashes and places the acceptor stems of the A-site and P-site tRNAs near to the positions of the CCAs we have observed bound to the A-loop and P-loop (see FIG. 18). Although nucleotides C74 and C75 were modeled in a different conformation in the 7.8 Å ribosome map, the C74 residues from the CCAs in both the A- and P-sites can be connected to residue 72 of the docked A-site and P-site tRNAs through a modeled residue 73, and it appears that the tRNA molecules fit well onto the surface of the subunit. Unexpectedly, this modeling places the E-site, P-site and A-site bound tRNA molecules in close proximity to three ribosomal proteins. Proteins L5 and L10e are near tRNAs in the P-site and A-site. Since both of these proteins also interact with 5S rRNA, this observation raises the possibility that 5S rRNA and some of its associated proteins might help stabilize the positioning of ribosome bound tRNAs and is consistent with the fact that 5S rRNA enhances ribosomal activity, but is not absolutely essential for it (Moore, Ribosomal RNA & Structure, Evolution, Processing and Function in Protein Biosynthesis (1996), supra, pp. 199-236). Protein L44e appears to interact with the E-site tRNA and may contribute to E-site activity. According to this docking experiment the A-site tRNA interacts with the highly conserved stem-loop 2502-2518 (2467-2483) which together with L10e forms a large concave surface that contacts the tRNA on the T-stem, utilizing the exact same binding site exploited by EF-Tu (Gutell et al. (2000) supra).

Examination of the relationships between the CCAs bound in the A- and P-sites and the tRNAs to which they are connected as well as their interactions with the ribosome also leads to some insights into translocation. Immediately after formation of the new peptide bond and deacylation of the P-site tRNA, the acceptor end of the P-site tRNA is known to move to the E-side and that of the A-site tRNA moves to the P-site (Blobel et al. (1970) J. Cell. Biol. 45: 130-145). The approximate modeling of the 3 tRNA molecules on the large subunit suggests some possible contributions to this process. First, there are two base-pairs between the P-site tRNA and the P-loop and only one between the A-site and the A-loop. Moving from the A- to the P-site increases base-pairing, though there must be a concomitant attraction of the deacylated P-site tRNA to an E-site. Further, the CCAs bound to the A and P loops are related by 180° rotation, whereas the tRNAs to which they are attached are not. Thus, the relationships of the CCAs to the acceptor stems cannot be the same in both sites and may not be equally stable. If the conformation of the A-site tRNA is less stable, then moving a tRNA from the A- to the P-site might be energetically favored.

6. Polypeptide Exit Tunnel.

It appears very likely from the structure that all nascent polypeptides pass through the polypeptide exit tunnel before emerging from the ribosome, because there appears to be no other way out. We are now able to address two important questions about the functioning of the polypeptide exit tunnel: (1) Why do nascent proteins not stick to its walls? Teflon has the marvelous property of not sticking to denatured egg proteins, so how has the ribosome achieved a similar non-stick surface for the denatured proteins that must pass through the tunnel? (2) Do proteins fold to any degree in the tunnel giving the ribosome a chaperon-like function?

The length of the tunnel from the site of peptide synthesis to its exit is about 100 Å, broadly consistent with the length of nascent polypeptide that is protected from proteolytic cleavage by the ribosome (Moazed et al. (1989) Nature 342:142) and the minimum length required for antibody recognition at the exit (Picking et al. (1992) Biochemistry 31: 2368-2375). The tunnel is largely straight, except for a bend 20 to 35 Å from the peptidyl transferase center (see, FIG. 19). Its diameter varies from about 20 Å at its widest to a narrow point of about 10 Å at the very beginning and at a position 28 Å from the tunnel exit with an average diameter of about 15 Å. Since the smallest orifice through which the polypeptide product must pass only barely accommodates the diameter of an α-helix diameter, it seems unlikely that significant protein folding beyond the formation of α-helix could occur within the ribosome.

The majority of the tunnel surface is formed by domains I-V of 23S rRNA, but significant contributions are also made by the non-globular regions of proteins L22, L4 and L39 which not only fill some of the voids in the RNA scaffold, but also form significant portions of the tunnel wall (see, FIG. 19). The largest protein contributor to the surface of the tunnel is L22 whose long α-hairpin loop lies between RNA segments of domains I through IV and is approximately parallel with the axis of the tunnel. Unlike the other tunnel proteins, protein L39 does not have a globular domain at the surface of the particle and is almost entirely buried in domains I and III underneath protein L23. Interestingly, the nucleotides of 23S rRNA that form the tunnel wall are predominantly from loops in the 23S rRNA secondary structure (see, FIG. 19). As it progresses through the tunnel from the active site, a nascent polypeptide first encounters domain V followed 20 Å further along by domains II and IV and proteins L4 and L22. The last half of the tunnel is formed by domains I and III and the protein L39e.

The narrowest part of the tunnel is formed by proteins L22 and L4 which approach the tunnel from opposite sides forming what appears to be a gated opening (see, FIG. 19C). The function of this constriction, if any, is not obvious. It might be the place where the nature of the nascent chain is sensed and the information transmitted to the surface of the particle, perhaps through L22 or L4. The α-hairpin of L22 at the site of this orifice and the 23S rRNA interacting with it are highly conserved; its globular portion is located adjacent to the tunnel exit on the surface that must face the translocon during protein secretion (see, FIG. 19).

The "non-stick" character of the tunnel wall must reflect a lack of structural and polarity complementarity to any protein sequence or conformation that it encounters. The tunnel surface is largely hydrophilic and includes exposed hydrogen bonding groups from bases, backbone phosphates and polar protein side-chains (see, FIG. 19). While there are many hydrophobic groups (sugars, bases, protein side-chains) facing the tunnel as well, there are no patches of hydrophobic surface large enough to form a significant binding site for hydrophobic sequences in the nascent polypeptide. As the tunnel is some 20 Å in diameter and filled with water and the newly synthesized polypeptide is presumably freely mobile, the binding of a peptide to the tunnel wall would result in a large loss of entropy that would have to be compensated for by a large complementary interaction surface that is larger than 700 Å (Chothia et al. (1975) Nature 256: 705-708). Similarly, while Arg and Lys side-chains from a nascent peptide may indeed interact with the phosphates exposed in the tunnel, the degree of structural complementarity and the net binding energy obtained after displacing bound counterions must be too small to overcome the large unfavorable entropy of immobilization that would result from peptide binding. Thus, although the ribosome tunnel is made primarily of RNA, the nature of its surface is reminiscent of the interior surface of the chaperonin, GroEL (Xu et al. (1998) J. Struct. Biol. 124:129-141) in its non-binding conformation. Only in the conformation that exposes a large hydrophobic surface does GroEL bind a denatured protein.

There are six proteins (L19, L22, L23, L24, L29 and L31e) located at the exit from the tunnel, facing the translocon onto which the ribosome docks during protein secretion. There is evidence that the ribosome binds the translocon even after extensive digestion of its protein by protease implying that interaction between the translocon and the ribosome is mediated by RNA. The proximity of these proteins to the translocon, however, leads us to wonder what role, if any, they might play in the protein secretion process. Recent data from the Dobberstein laboratory shows that the N-terminal domain of SRP54, the G-protein from the signal recognition particle involved in signal peptide binding, can be crosslinked to ribosomal proteins L23 and L29. These two proteins are adjacent to each other and at the tunnel exit (see, FIG. 19).

7. Evolution.

In vitro evolution of RNA oligonucleotides has produced small RNA molecules that can bind molecules like the Yarus inhibitor effectively or catalyze the peptidyl transfer reaction (Zhaug et al. (1998) Chem. Biol. 5: 539-553; Welch et al. (1997) supra). The sequence and secondary structure of one of these selected RNAs is reminiscent of the peptidyl transferase loop in domain V of 23S rRNA (Zhaug et al. (1998) supra). The most striking similarity is a five nucleotide sequence that is identical to a sequence in domain V that includes the catalytic A2486, G2482 and the buried phosphate of A2485. Remarkably, all of the groups involved in the proposed charge relay system for activating A2486 in the ribosome, are present in the in vitro selected ribozyme. Thus, though the surrounding structural context is likely to be different, it seems plausible that this artificially evolved ribozyme uses the same mechanisms as the ribosome for shifting the pKa of an adenine and likewise uses it as a base for peptide synthesis. A second RNA (Welch et al. (1997) supra) contains a 12 nucleotide loop that includes a 9-base sequence identical to that found in the same region of the peptidyl transferase loop.

The striking similarities between the sequences containing the key catalytic elements found in the peptidyl-transferase active site of the ribosome and sequences of in vitro selected RNAs having related activities make it clear that the appearance of a small RNA domain capable of catalyzing peptidyl transferase was a plausible first step in the evolution of protein synthesis on the ribosome. The first peptides synthesized by this primordial peptide synthesizing enzyme might have been random polymers or copolymers, and it may have functioned with substrates as simple as an aminoacylated CCA. Basic peptides of the types observed to form the non-globular extensions that co-fold with the 23S rRNA might have been among the first peptides synthesized that were functionally useful. Such peptides may have enhanced the stability of the protoribosome and other early ribozymes as the more sophisticated peptides of the present day ribosome appear to do.

C. Atomic Structure of the Large Ribosomal Subunit at 2.4 Å Resolution, Complete Refinement The three-dimensional structure of the large ribosomal subunit from Haloarcula marismortui has now been completely refined at 2.4 Å resolution. The model includes 2876 RNA nucleotides, 3701 amino acids from 28 ribosomal proteins, 117 magnesium ions, 88 monovalent cations, and 7898 water molecules. Many of its proteins consist of a surface-exposed globular domain and one or more basic, non-globular extensions that are buried in rRNA. Half of them include motifs common in non-ribosomal proteins including, for example: RRM domains, SH3-like barrels and zinc fingers. Proteins that have significant sequence and structural similarity, such as L15 and L18e, make essentially identical interactions with rRNA.

More particularly, the H. marismortui 50S subunit has been completely rebuilt and refined by successive rounds of gradient energy minimization and B-factor refinement using CNS (Brünger et al. (1998) supra). Ribosomal proteins and rRNA were completely rebuilt using the software program "O" (Jones, T. A. et al. (1991) Acta Crystallogr. A46: 110-119) with $2F_o$-Fc electron density maps prior to the modeling of solvent and metal ions. Modeling errors in the proteins were identified using PROCHECK (Laskowski et al. (1993) J. Appl. Cryst. 26: 283-291) and by inspection of $F_o$-Fc maps. Difference maps also aided in the identification of errors in the rRNA, most often associated with sugar puckers. In the process, some adjustments were made in amino acid conformations, sequence register and in sequences themselves. Sequence changes made were largely limited to L10e, L15e, and L37Ae, the only three proteins from the H. marismortui 50S that have not been sequenced directly. In addition, fifty-one amino acids were added to the model described in section IIA with forty-four of these coming from L10 at the base of the L7/L12 stalk and L39e which lines a portion of the wall of the polypeptide exit tunnel. Fewer adjustments were made to the rRNA structure. Forty-nine new nucleotides were modeled and refined, mainly in helices 43 and 44 in domain II of 23S rRNA. In addition, the sugar pucker or conformation about the glycosidic bond was adjusted for some nucleotides. The refinement process was monitored by the quality of electron density maps calculated using phases derived from the model as well as $R/R_{free}$ values. The completely refined model now includes 2876 RNA nucleotides, 3701 amino acids, 210 metal ions, and 7898 water molecules. The model refines to an $R/R_{free}$ of 18.9%/22.3% and has excellent geometry (Table 4).

Solvent modeling began with the generation of a list of possible magnesium ions obtained by an automatic peak selection using CNS. Peaks greater than 3.5σ in $F_o$-Fc maps positioned within the magnesium inner-sphere coordination distance of 1.9-2.1 Å from N or O atoms were selected. The resulting list was manually inspected and only peaks that displayed clear octahedral coordination geometry were selected as magnesium.

Monovalent cations were identified on the basis of isomorphous differences between rubidium-soaked and native crystals of the *H. marismortui* 50S subunit. Since native crystals were stabilized in the presence of 1.6M NaCl, these sites were initially modeled and refined as $Na^{+1}$. Refinement of these sites as $K^{+1}$ almost always resulted in unusually high temperature factors, with two exceptions where we have modeled $K^{+1}$. Most of the monovalent sites in the 50S subunit appear to occupied by $Na^{+1}$ in our crystals, however, these sites are likely to be occupied by $K^{+1}$ in vivo.

Waters were selected as peaks greater than 3.5a in $F_o$-Fc electron density maps and between 2.5 and 3.3 Å of O or N atoms. Individual B-factor values were used to assess the assignment of water molecules. A number of waters refined to B-factors significantly lower than surrounding RNA and protein atoms. In many cases these peaks were found to be metal or chloride ions. A small number of low B-factor water molecules were retained in the final model because they could not be unambiguously assigned as other species. As a result of adding metal ions and water molecules the final model now contains 98, 547 non-hydrogen atoms. The refinement and model statistics for the large ribosomal subunit are summarized in Table 4.

TABLE 4

Refinement and Model Statistics for the *H. marismortui* 50S Subunit

| | |
|---|---|
| Space Group | $C222_1$ |
| a = 211.66 Å, b = 299.67 Å, c = 573.77 Å | |
| Total non-hydrogen atoms | 98,542 |
| RNA atoms | 61,617 |
| Protein atoms | 28,800 |
| Water molecules | 7,893 |
| Magnesium ions | 117 |
| Potassium ions | 2 |
| Sodium ions | 86 |
| Chloride ions | 22 |
| Cadmium ions | 5 |
| Refinement Statistics: | |
| Resolution Range | 15.0-2.4 Å |
| Number of reflections used in refinement | 623,525 |
| Number of reflections for cross-validation | 6,187 |
| $R_{working}$ | 18.9% |
| $R_{free}$ | 22.3% |
| $\sigma_a$ coordinate error (cross-validated) | 0.35 Å (0.43 Å) |
| luzzati coordinate error (cross-validated) | 0.29 Å (0.35 Å) |
| Deviations from ideality: | |
| r.m.s.d. bond lengths | 0.0052 Å |
| r.m.s.d. bond angles | 1.13° |
| r.m.s.d. dihedrals | 15.7° |
| r.m.s.d. impropers | 2.12° |
| Protein Statistics from Ramachandran Plot: | |
| Residues in most favored regions | 2704 (86.6%) |
| Residues in additional allowed regions | 379 (12.1%) |
| Residues in generously allowed regions | 27 (0.9%) |
| Residues in disallowed regions | 13 (0.4%) |
| Average B-factor Statistics (Å²): | |
| All atoms (high/low) | 44.3 (10.1/133.7) |
| rRNA | 41.2 (11.78/125.0) |
| proteins | 49.7 (13.9/92.5) |
| waters | 41.89 (9.58/115.4) |

Refinement has also permitted additional modeling of L10, L39e, and the L11 binding site in 23S rRNA. Furthermore, it has been discovered that certain motifs, for example, RRM topologies, SH3-like barrels and zinc fingers are common in the 50S proteins and each recognizes rRNA in many different ways. Proteins that have significant three-dimensional homology, however, such as L15 and L18e as well as L18 and S11, make essentially identical interactions with rRNA. Additional structural homologies between 50S proteins and non-ribosomal proteins also are apparent. The solvent exposed surfaces of these globular protein domains are rich in aspartate and glutamate residues, while irregular protein extensions penetrate the RNA core of the ribosome. These extensions are often highly conserved, and their abundance of arginine, lysine, and glycine residues is important for their function. Collectively, the results show evolutionary connections between many ribosomal proteins and illustrate that protein-RNA interactions in the ribosome, although largely idiosyncratic, share some common principles.

D. Antibiotic Binding Sites

In addition to the foregoing structural studies, the structure of the large ribosomal subunit of *H. marismortui* has been determined complexed with each of nine different antibiotics. More specifically, crystals of the *H. marismortui* large ribosomal subunit have been soaked with one of the following antibiotics: anisomycin, blasticidin, carbomycin A, tylosin, sparsomycin, virginiamycin M, spiramycin, azithromycin, linezolid or erythromycin. The structure of the large ribosome subunit complexed with each antibiotic was then resolved based on X-ray diffraction data generated for each crystal.

Briefly, a small amount of a concentrated antibiotic solution was added to a large subunit crystal suspended in stabilization solution and incubated for several hours. Following freezing and the other procedures normally used to prepare such crystals for experimental use, X-ray diffraction data were collected from the antibiotic containing crystals. Because the crystals were isomorphous to those from which the structure described above was derived, the phases obtained for native crystal were combined with the diffraction intensities obtained from the antibiotic-soaked crystal to obtain a structure for the latter. The position of the antibiotic in the crystal to which was bound is revealed most clearly in difference electron density maps, which are electron density maps computed using the phases just referred to and amplitudes obtained by subtracting the amplitudes of crystals that contain no antibiotic from the (suitably scaled) amplitudes of those that contain antibiotic. By using the foregoing methods, it was possible to determine the atomic co-ordinates that show the spatial relationship between particular antibiotics and their binding sites within the large ribosomal subunit. It is contemplated that similar methods can be used to resolve the structure of other antibiotics complexed to the large ribosomal subunit.

The atomic co-ordinates of the large ribosomal subunit complexed with anisomycin are listed in a table on compact disk, Disk No. 1 under the file name anisomycin.pdb, a more refined set of which is represented in a table on compact disk, Disk No. 1 under the file name ANISOMYC.PDB, and deposited at the RCSB Protein Data Bank with the accession number PDB ID: 1K73. In addition, FIG. 20 shows the spatial relationship between the antibiotic anisomycin and the large ribosomal subunit.

The atomic co-ordinates of the large ribosomal subunit complexed with blasticidin are listed in a table on compact Disk No. 1 under the file name blasticidin.pdb, a more refined set of which is represented in a table on compact disk, Disk No. 1 under the file name BLASTICI.PDB, and deposited at the RCSB Protein Data Bank with the accession number PDB ID: 1KC8. FIG. 21 shows the spatial relationship between the antibiotic blasticidin and the large ribosomal subunit. For orientation, FIG. 21 also includes a substrate for the P-site.

The atomic co-ordinates of the large ribosomal subunit complexed with carbomycin A are listed in a table on compact disk, Disk No. 1 under the file name carbomycin.pdb, a more refined set of which is represented in a table on compact disk, Disk No. 1 under the file name CARBOMYC.PDB, and deposited at the RCSB Protein Data Bank with the accession number PDB ID: 1K8A. FIG. 22 shows the spatial relationship between the antibiotic carbomycin A and the large ribosomal subunit. FIG. 22 also shows a portion of the polypeptide exit tunnel.

The atomic co-ordinates of the large ribosomal subunit complexed with tylosin are listed in a table on compact disk, Disk No. 1 under the file name tylosin.pdb, a more refined set of which is represented in a table on compact disk, Disk No. 1 under the file name TYLOSIN.PDB, and deposited at the RCSB Protein Data Bank with the accession number PDB ID: 1K9M. FIG. 22 shows the spatial relationship between the antibiotic tylosin and the large ribosomal subunit. FIG. 22 also shows a portion of the polypeptide exit tunnel.

The atomic co-ordinates of the large ribosomal subunit complexed with sparsomycin are listed in a table on compact disk, Disk No. 1 under the file name sparsomycin.pdb, a more refined set of which is represented in a table on compact disk, Disk No. 1 under the file name SPARSOMY.PDB. FIG. 23 shows the spatial relationship between the antibiotic sparsomycin and the large ribosomal subunit. For orientation, FIG. 23 also shows a substrate for the P-site.

The atomic co-ordinates of the large ribosomal subunit complexed with virginiamycin M are listed in a table on compact disk, Disk No. 1 under the file name virginiamycin.pdb, a more refined set of which is represented in a table on compact disk, Disk No. 1 under the file name VIRGINIA.PDB. FIG. 24 shows the spatial relationship between the antibiotics virginiamycin M as well as carbomycin A, and the large ribosomal subunit.

The atomic co-ordinates of the large ribosomal subunit complexed with spiramycin are listed in a table on compact disk, Disk No. 1 under the file name spiramycin.pdb, a more refined set of which is represented in a table on compact disk, Disk No. 1 under the file name SPIRAMYC.PDB, and deposited at the RCSB Protein Data Bank with the accession number PDB ID: 1 KD1. FIG. 25 shows the spatial relationship between the antibiotic spiramycin and the large ribosomal subunit.

The atomic co-ordinates of the large ribosomal subunit complexed with azithromycin are listed in a table on compact disk, Disk No. 1 under the file name AZITHROM.PDB, a more refined set of which is represented in a table on compact disk, Disk 1 under the file name azithromycin.pdb. FIG. 26 shows the spatial relationship between the antibiotic azithromycin and the large ribosomal subunit.

The atomic co-ordinates of the large ribosomal subunit complexed with linezolid are listed in a table on compact disk, Disk No. 1 under the file name LINEZOLI.PDB, a more refined set of which is represented in a table on compact disk, Disk No. 1 under the file name linezolid.pdb. FIG. 27 shows the spatial relationship between the antibiotic linezolid and the large ribosomal subunit.

The atomic coordinates of the large ribosomal subunit complexed with erythromycin are listed in a table on compact disk, Disk No. 1 under the file name erythromycin.pdb. FIG. 28 shows the spatial relationship between the antibiotic erythromycin and the large ribosomal subunit.

FIG. 29 shows the spatial orientations of several antibiotics, namely, blasticidin, anisomycin, virginiamycin M and carbomycin A, as they bind to their respective antibiotic binding sites within the large ribosomal subunit. For purposes of orienting the reader, the positions of the P-site, A-site and the polypeptide exit tunnel are shown in FIG. 29. As is apparent, these antibiotics bind to or contact specific locations within the large ribosomal subunit to disrupt protein biosynthesis. For example, it appears that blasticidin binds the large ribosomal subunit in the vicinity of the P-site; anisomycin and virginiamycin bind the large ribosomal subunit in the vicinity of the A-site; and carbomycin spiramycin, tylosin, azithromycin and erythromycin (macrolide 5) all binds the large ribosomal subunit in the vicinity of the polypeptide exit tunnel adjacent the peptidyl transferase site.

From FIG. 29, it is apparent that the skilled artisan may identify certain portions of each antibiotic that contact regions in the large ribosomal subunit. By knowing their spatial relationship with respect one another, the skilled artisan may generate a hybrid antibiotic molecule comprising a portion of a first template antibiotic and a portion of a second, different template antibiotic. The two portions may be linked by a chemical linker so as to maintain the spatial orientation of one portion with respect to the other portion. As a result, the hybrid antibiotic may simultaneously bind each of the regions of the ribosomal subunit typically bound by each template antibiotic. The design and testing of such molecules is discussed in more detail below.

FIG. 30(A) shows the tylosin molecule bound within the polypeptide exit tunnel. FIG. 30(A) shows an enlarged portion of the large ribosomal subunit with the antibiotic tylosin bound at the top of the polypeptide exit tunnel adjacent the peptidyl transferase site. FIGS. 30(B) and 30(C) are views showing each half of a large ribosomal subunit cut along the polypeptide exit tunnel and are provided to orient the reader to show the tylosin binding site relative to the large ribosomal unit as a whole. FIG. 30(A) also shows two cavities defined by the wall of the polypeptide exit tunnel and are denoted as "cavity 1" and "cavity 2." In addition, FIG. 30(A) also shows a disaccharide binding pocket. The direction in which the newly synthesized polypeptide chains exits the ribosome through the polypeptide exit tunnel is denoted by an arrow.

E. Experimental Techniques which Exploit X-Ray Diffraction Data

Based on the X-ray diffraction pattern obtained from the assemblage of the molecules or atoms in a crystalline solid, the electron density of that solid may be reconstructed using tools well known to those skilled in the art of crystallography and X-ray diffraction techniques. Additional phase information extracted either from the diffraction data and available in the published literature and/or from supplementing experiments may then be used to complete the reconstruction.

For basic concepts and procedures of collecting, analyzing, and utilizing X-ray diffraction data for the construction of electron densities see, for example, Campbell et al. (1984) *Biological Spectroscopy*, The Benjamin/Cummings Publishing Co., Inc., (Menlo Park, Calif.); Cantor et al. (1980) *Biophysical Chemistry, Part II: Techniques for the study of biological structure and function*, W.H. Freeman and Co., San Francisco, Calif.; A. T. Brünger (1993) X-PLOR Version 3.1: A system for X-ray crystallography and NMR, Yale Univ. Pr., (New Haven, Conn.); M. M. Woolfson (1997) *An Introduction to X-ray Crystallography*, Cambridge Univ. Pr., (Cambridge, UK); J. Drenth (1999) *Principles of Protein X-ray Crystallography* (Springer Advanced Texts in Chemistry), Springer Verlag; Berlin; Tsirelson et al. (1996) *Electron Density and Bonding in Crystals: Principles, Theory and X-ray Diffraction Experiments in Solid State Physics and Chemistry*, Inst. of Physics Pub.; U.S. Pat. No. 5,942,428; U.S. Pat. No. 6,037,117; U.S. Pat. No. 5,200,910 and U.S. Pat. No. 5,365,456 ("Method for Modeling the Electron Density of a Crystal").

A molecular model may then be progressively built using the experimental electron density information and further refined against the X-ray diffraction data resulting in an accurate molecular structure of the solid.

F. Structural Determination of Other Large Ribosomal Subunits

It is understood that the skilled artisan, when provided with the atomic co-ordinates of a first macromolecule may use this information to quickly and easily determine the three-dimensional structure of a different but structurally related macromolecule. For example, the atomic co-ordinates defining the large ribosomal subunit from *H. marismortui* can be used to determine the structure of the large ribosomal subunit from other species either as an isolated subunit, in complex with the small subunit, or either of these complexed with functionally important ligands, for example: aminoacyl tRNA; various protein synthesis factors, such as elongation factor G, elongation factor Tu, termination factor or recycling factor, in both their GTP and GDP conformational states; and protein synthesis inhibitors, for example, antibiotics. In addition, the *H. marismortui* subunit co-ordinates can also be used to solve the structures of ribosomal complexes with components of the protein secretion machinery, for example, the signal recognition particle, and the translocon.

If the crystal being examined contains a macromolecule of unknown structure and no additional information is available, additional experiments sometimes may be required to determine the relevant phases of the macromolecule. These studies can often be time consuming and uncertain of success (Blundell et al. (1976) supra). However, when additional information, for example, structural and/or crystallographic information, is available for molecules related in some way to the macromolecule of interest then the process of resolving the structure of the molecule of interest is a much less challenging and time-consuming task.

Accordingly, the skilled artisan may use information gleaned from the prior resolved structure to develop a three-dimensional model of a new molecule of interest. Furthermore, the skilled artisan may use a variety of approaches to elucidate the three-dimensional structure of the new molecule. The approaches may depend on whether crystals of the molecule of interest are available and/or whether the molecule of interest has a homologue whose structure has already been determined.

In one approach, if the molecule of interest forms crystals that are isomorphous, i.e., that have the same unit cell dimensions and space group as a related molecule whose structure has been determined, then the phases and/or co-ordinates for the related molecule can be combined directly with newly observed amplitudes to obtain electron density maps and, consequently, atomic co-ordinates of the molecule of interest. The resulting maps and/or atomic co-ordinates may then be refined using standard refinement techniques known in the art. In another approach, if the molecule of interest is related to another molecule of known three-dimensional structure, but crystallizes in a different unit cell with different symmetry, the skilled artisan may use a technique known as molecular replacement to obtain useful phases from the co-ordinates of the molecule whose structure is known (Blundell et al. (1976) supra). This approach reportedly was used in the determination of the structure of the 50S subunit of *Deinococcus radiodurans* (Harms J. et al., *Cell* 107(5):679-88; Schlunzen F. et al., (2001) *Nature* 413(6858):814-21). These phases can then be used to generate an electron density map and/or atomic co-ordinates for the molecule of interest. In another approach, if no crystals are available for the molecule of interest but it is homologous to another molecule whose three-dimensional structure is known, the skilled artisan may use a process known as homology modeling to produce a three-dimensional model of the molecule of interest. It is contemplated that other approaches may be useful in deriving a three-dimensional model of a molecule of interest. Accordingly, information concerning the crystals and/or atomic co-ordinates of one molecule can greatly facilitate the determination of the structures of related molecules.

The method of molecular replacement, developed initially by Rossmann and Blow in the 1960s, is now used routinely to establish the crystal structures of macromolecules of unknown structures using the structure of a homologous molecule, or one in a different state of ligation (M. G. Rossmann, ed. "The Molecular Replacement Methods," *Int. Sci. Rev. J.* No. 13, Gordon & Breach, New York, N.Y. (1972); Eaton Lattman, "Use of Rotation and Translation Functions," H. W. Wyckoff C. H. W. Hist. (S. N. Timasheff, ed.) *Methods in Enzymology*, 115: 55-77 (1985)). For an example of the application of molecular replacement, see, for example, Rice, P. A. & Steitz, T. A. (1994) *EMBO J.* 13: 1514-24.

In molecular replacement, the three-dimensional structure of the known molecule is positioned within the unit cell of the new crystal by finding the orientation and position that provides the best agreement between observed diffraction amplitudes and those calculated from the co-ordinates of the positioned subunit. From this modeling, approximate phases for the unknown crystal can be derived. In order to position a known structure in the unit cells of an unknown, but related structure, three rotation angles and three translations relative to the unit cell origin have to be determined. The rotation search is carried out by looking for agreement between the Patterson function of the search and target structures as a function of their relative orientation (the rotation function). X-PLOR (Brünger et al. (1987) *Science* 235:458-460; CNS (Crystallography & NMR System, Brünger et al., (1998) *Acta Cryst. Sect. D* 54: 905-921), and AMORE: an Automatic Package for Molecular Replacement (Navaza, J. (1994) *Acta Cryst. Sect. A*, 50: 157-163) are computer programs that can execute rotation and translation function searches. Once the orientation of a test molecule is known, the position of the molecule must be found using a translational search. Once the known structure has been positioned in the unit cell of the unknown molecules, phases for the observed diffraction data can be calculated from the atomic co-ordinates of the structurally related atoms of the known molecules. By using the calculated phases and X-ray diffraction data for the unknown molecule, the skilled artisan can generate an electron density map and/or atomic co-ordinates of the molecule of interest.

By way of example, it is contemplated that a three-dimensional model of a ribosomal subunit other than that derived from *H. marismortui* can be generated via molecular replacement. In this method, the *H. marismortui* subunit structures are positioned within the unit cell of the new crystal by finding the orientation and position that provides the best agreement between observed diffraction amplitudes and those calculated from the co-ordinates of the positioned subunit. A starting electron density map calculated using $2F_{hkl}$(observed)-$F_{hkl}$(calculated), where F(observed) are the diffraction amplitudes that have been measured from crystals of the unknown structure, and F(calculated) are the diffraction amplitudes calculated from the positioned *H. marismortui* subunit structure. Refinement of the initial model can be done as is standard in the field of macromolecular crystallography.

The *H. marismortui* 50S structure can also be used to establish the structure of a 70S ribosome or 50S ribosome for which an election density map has been calculated, at a resolution that would otherwise be too low to be interpreted, while a 5 Å resolution map could not be interpreted in atomic terms de novo, a plausible atomic model can be constructed by refitting the *H. marismortui* 50S structure to a lower resolution map (e.g., 4.5 Å to 8 Å). This refitting can be combined with homology modeling to obtain a three-dimensional model of a ribosome or ribosomal subunit from a different species. It is contemplated that similar procedures may be used to determine the structure of the eukaryotic 60S subunit and/or a eukaryotic ribosome.

In general, the success of molecular replacement for solving structures depends on the fraction of the structures that are related and their degree of identity. For example, if about 50% or more of the structure shows an r.m.s. difference between corresponding atoms in the range of about 2 Å or less, the known structure can be successfully used to solve the unknown structure.

Homology modeling, also known as comparative modeling or knowledge-based modeling, can be used to generate a three-dimensional model for a molecule based on the known structure of homologues. In general, the procedure may comprise one or more of the following steps: aligning the amino acid or nucleic acid sequence of an unknown molecule against the amino acid or nucleic acid sequence of a molecule whose structure has previously been determined; identifying structurally conserved and structurally variable regions; generating atomic co-ordinates for core (structurally conserved) residues of the unknown structure from those of the known structure(s); generating conformations for the other (structurally variable) residues in the unknown structure; building side chain conformations; and refining and/or evaluating the unknown structure.

By way of example, since the nucleotide sequences of all known 50S subunit rRNAs can be aligned relative to each other and to *H. marismortui* 23S and 5S rRNAs, it is possible to construct models of the structures of other 50S ribosomal rRNAs, particularly in the regions of the tunnel and active sites, using the *H. marismortui* structure. Likewise, homologous proteins can also be modeled using similar methodologies. Methods useful for comparative RNA sequence analysis are known in the art and include visual methods and number pattern methods, as well as methods employing chi-square statistics, phylogenetic algorithms, or empirical algorithms. Descriptions of some of the foregoing methods are available, for example, at http://www.ma.icmb.utexas.edu/; Gutell (1996), "Comparative Sequence Analysis and the Structure of 16S and 23S rRNA," *Ribosomal RNA. Structure, Evolution, Processing, and Function in Protein Biosynthesis*, (Dahlberg A. and Zimmerman B., eds.) CRC Press. Boca Raton, pp. 111-128; Guttell et al. (1993) *Nucl. Acid Res.* 21: 3055-3074; Schnare et al. (1996) *J. Mol. Biol.* 256: 701-719. Particularly useful visual inspection methods include comparison of a particular position in a *H. marismortui* secondary structure diagram with the residues located at the analogous position on an *E. coli* secondary structure diagram. A software program that is particularly useful in homology modeling includes) XALIGN (Wishart, D. et al., (1994) *Cabios* 10: 687-88). See also, U.S. Pat. No. 5,884,230.

To model the rRNA of a new species, bases of the *H. marismortui* rRNA can be replaced, using a computer graphics program such as "O" (Jones et al., (1991) *Acta Cryst. Sect. A,* 47: 110-119), by those of the homologous rRNA, where they differ. In many if not most cases the same orientation of the base will be appropriate. Insertions and deletions may be more difficult and speculative, but the rRNA forming the peptidyl transferase site and the portion of the tunnel closest to it is very highly conserved with essentially no insertions and deletions. Automated web-based homology modeling can be performed using, for example, the computer programs SWISS-MODEL available through Glaxo Welcome Experimental Research in Geneva, Switzerland, and WHATIF available on EMBL servers.

For other descriptions of homology modeling, see, for example, Gutell R. R. (1996), supra; Gutell R. R., et al. (1993) *Nucleic Acids Res.* 21: 3055-3074; Schnare et al. (1996) *J. Mol. Biol.,* 256: 701-719; Blundell et al. (1987) *Nature* 326: 347-352; Fetrow and Bryant (1993) *Bio/Technology* 11:479-484; Greer (1991) *Methods in Enzymology* 202: 239-252; and Johnson et al. (1994) *Crit. Rev. Biochem. Mol. Biol.* 29:1-68. An example of homology modeling can be found, for example, in Szklarz G. D. (1997) *Life Sci.* 61: 2507-2520.

As discussed earlier, the large ribosomal subunit from prokaryotes and eukaryotes and eukaryotic mitochondria are structurally conserved. The amino acid sequences of the large ribosomal subunit from prokaryotes and eukaryotes can be aligned due to the evolutionary conservation of amino acid residues that are important for three-dimensional structure, the nature and shape of the binding sites for substrates and the catalytic site. This similarity in amino acid sequence of the homologous large ribosomal subunit allows the construction of models, via homology modeling, for the molecules whose crystal structures have not been solved.

The new ribosome or large ribosomal subunit structures determined using the *H. marismortui* crystals and/or atomic co-ordinates can then be used for structure-based drug design using one or more of the approaches described hereinbelow. This information can then be used to design molecules that selectively bind and disrupt protein synthesis in the ribosomes of the pathogens while leaving the ribosomes of a host relatively unaffected.

G. Rational Drug Design

1. Introduction

It is contemplated that the atomic co-ordinates defining a large ribosomal subunit of interest, whether derived from one or more of X-ray crystallography; molecular modeling, homology modeling or molecular replacement, may be used in rational drug design (RDD) to design a novel molecule of interest, for example, novel modulators (for example, inducers, mimetics or inhibitors) of ribosome function. Furthermore, it is contemplated that, by using the principles disclosed herein, the skilled artisan can design, make, test, refine and use novel protein synthesis inhibitors specifically engineered to reduce, disrupt, or otherwise or inhibit ribosomal function in an organism or species of interest. For example, by using the principles discussed herein, the skilled artisan can engineer new molecules that specifically target and inhibit ribosomal function in a pathogen, for example, a particular prokaryotic, organism, while preserving ribosomal function in a host, for example, a eukaryotic organism, specifically a mammal, and more specifically, a human. As a result, the atomic co-ordinates provided and discussed herein permit the skilled artisan to design new antibiotics that can kill certain pathogenic organisms while having little or no toxicity in the intended recipient, for example, a human.

It is contemplated that RDD using atomic co-ordinates of the large ribosomal subunit can be facilitated most readily via computer-assisted drug design (CADD) using conventional computer hardware and software known and used in the art. The candidate molecules may be designed de novo or may be designed as a modified version of an already existing molecule, for example, a pre-existing antibiotic, using conventional methodologies. Once designed, candidate molecules can be synthesized using standard methodologies known and used in the art. Following synthesis, the candidate molecules can be screened for bioactivity, for example, by their ability to reduce or inhibit ribosome function, their ability to interact with or bind a ribosome or a ribosomal subunit. Based in part upon these results, the candidate molecules may be refined iteratively using one or more of the foregoing steps to produce a more desirable molecule with a desired biological activity. The resulting molecules can be useful in treating, inhibiting or preventing the biological activities of target organisms, thereby killing the organism or impeding its growth. Alternatively, the resulting molecules can be useful for treating, inhibiting or preventing microbial infections in any organism, particularly animals, more particularly humans.

In summary, the tools and methodologies provided by the present invention may be used to identify and/or design molecules which bind and/or interact in desirable ways with ribosomes and ribosomal subunits. Basically, the procedures utilize an iterative process whereby the molecules are synthesized, tested and characterized. New molecules can be designed based on the information gained in the testing and characterization of the initial molecules and then such newly identified molecules can themselves be tested and characterized. This series of processes may be repeated as many times as necessary to obtain molecules with desirable binding properties and/or biological activities. Methods for identifying candidate molecules are discussed in more detail below.

2. Identification of Candidate Molecules

It is contemplated that the design of candidate molecules of interest can be facilitated by conventional ball and stick-type modeling procedures. However, in view of the size and complexity of the large ribosomal subunit, it is contemplated that the ability to design candidate molecules may be enhanced significantly using computer-based modeling and design protocols.

a. Molecular Modeling.

It is contemplated that the design of candidate molecules, as discussed in detail hereinbelow, can be facilitated using conventional computers or workstations, available commercially from, for example, Silicon Graphics Inc. and Sun Microsystems, running, for example, UNIX based, Windows NT on IBM OS/2 operating systems, and capable of running conventional computer programs for molecular modeling and rational drug design.

It is understood that any computer system having the overall characteristics set forth in FIG. 31 may be useful in the practice of the invention. More specifically, FIG. 31, is a schematic representation of a typical computer work station having in electrical communication (100) with one another via, for example, an internal bus or external network, a central processing unit (101), a random access memory (RAM) (102), a read only memory (ROM) (103), a monitor or terminal (104), and optimally an external storage device, for example, a diskette, CD ROM, or magnetic tape (105).

The computer-based systems of the invention preferably comprise a data storage means having stored therein a ribosome or ribosomal subunit or fragment sequence and/or atomic co-ordinate/X-ray diffraction data of the present invention and the necessary hardware means and software means for supporting and implementing an analysis means. As used herein, "a computer system" or "a computer-based system" refers to the hardware means, software means, and data storage means used to analyze the sequence, X-ray diffraction data, and/or atomic co-ordinates of the invention. As used herein, the term "data storage means" is understood to refer to any memory which can store sequence data, atomic, co-ordinates, and/or X-ray diffraction data, or a memory access means which can access manufactures having recorded thereon the atomic co-ordinates of the present invention.

In one embodiment, a ribosome or ribosomal subunit, or at least a subdomain thereof, amino acid and nucleic acid sequence, X-ray diffraction data and/or atomic co-ordinates of the present invention are recorded on computer readable medium. As used herein, the term "computer readable medium" is understood to mean any medium which can be read and accessed directly by a computer. Such media include, but are not limited to: magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon an amino acid and/or nucleotide sequence, X-ray diffraction data, and/or atomic co-ordinates of the present invention.

As used herein, the term "recorded" is understood to mean any process for storing information on computer readable medium. A skilled artisan can readily adopt any of the presently known methods for recording information on computer readable medium to generate manufactures comprising an amino acid or nucleotide sequence, atomic co-ordinates and/or X-ray diffraction data of the present invention.

A variety of data storage structures are available to a skilled artisan for creating a computer readable medium having recorded thereon amino acid and/or nucleotide sequence, atomic co-ordinates and/or X-ray diffraction data of the present invention. The choice of the data storage structure will generally be based on the means chosen to access the stored information. In addition, a variety of data processor programs and formats can be used to store the sequence information, X-ray data and/or atomic co-ordinates of the present invention on computer readable medium. The foregoing information, data and co-ordinates can be represented in a word processing text file, formatted in commercially-available software such as WordPerfect and MICROSOFT Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the information of the present invention.

By providing a computer readable medium having stored thereon a ribosome or ribosomal subunit sequence, and/or atomic co-ordinates, a skilled artisan can routinely access the sequence, and/or atomic co-ordinates to model a ribosome or ribosomal subunit, a subdomain thereof, mimetic, or a ligand thereof. Computer algorithms are publicly and commercially available which allow a skilled artisan to access this data provided in a computer readable medium and analyze it for molecular modeling and/or RDD. See, e.g., *Biotechnology Software Directory*, MaryAnn Liebert Publ., New York, N.Y. (1995).

Although computers are not required, molecular modeling can be most readily facilitated by using computers to build realistic models of a ribosome, ribosomal subunit, or a portion thereof. Molecular modeling also permits the modeling of new smaller molecules, for example ligands, agents and other molecules, that can bind to a ribosome, ribosomal subunit, or a portion therein. The methods utilized in molecular modeling range from molecular graphics (i.e., three-dimensional representations) to computational chemistry (i.e., calculations of the physical and chemical properties) to make predictions about the binding of the smaller molecules or their activities; to design new molecules; and to predict novel molecules, including ligands such as drugs, for chemical synthesis.

For basic information on molecular modeling, see, for example, M. Schlecht, *Molecular Modeling on the PC* (1998)

John Wiley & Sons; Gans et al., *Fundamental Principals of Molecular Modeling* (1996) Plenum Pub. Corp.; N. C. Cohen, ed., *Guidebook on Molecular Modeling in Drug Design* (1996) Academic Press; and W. B. Smith, *Introduction to Theoretical Organic Chemistry and Molecular Modeling* (1996). U.S. Patents which provide detailed information on molecular modeling include, for example: U.S. Pat. Nos. 6,093,573; 6,080,576; 6,075,014; 6,075,123; 6,071,700; 5,994,503; 5,884,230; 5,612,894; 5,583,973; 5,030,103; 4,906,122; and 4,812,12.

Three-dimensional modeling can include, but is not limited to, making three-dimensional representations of structures, drawing pictures of structures, building physical models of structures, and determining the structures of related ribosomes, ribosomal subunits and ribosome/ligand and ribosomal subunit/ligand complexes using the known co-ordinates. The appropriate co-ordinates are entered into one or more computer programs for molecular modeling, as known in the art. By way of illustration, a list of computer programs useful for viewing or manipulating three-dimensional structures include: Midas (University of California, San Francisco); MidasPlus (University of California, San Francisco); MOIL (University of Illinois); Yummie (Yale University); Sybyl (Tripos, Inc.); Insight/Discover (Biosym Technologies); MacroModel (Columbia University); Quanta (Molecular Simulations, Inc.); Cerius (Molecular Simulations, Inc.); Alchemy (Tripos, Inc.); LabVision (Tripos, Inc.); Rasmol (Glaxo Research and Development); Ribbon (University of Alabama); NAOMI (Oxford University); Explorer Eyechem (Silicon Graphics, Inc.); Univision (Cray Research); Molscript (Uppsala University); Chem-3D (Cambridge Scientific); Chain (Baylor College of Medicine); O (Uppsala University); GRASP (Columbia University); X-Plor (Molecular Simulations, Inc.; Yale University); Spartan (Wavefunction, Inc.); Catalyst (Molecular Simulations, Inc.); Molcadd (Tripos, Inc.); VMD (University of Illinois/Beckman Institute); Sculpt (Interactive Simulations, Inc.); Procheck (Brookhaven National Library); DGEOM (QCPE); RE_VIEW (Brunell University); Modeller (Birbeck College, University of London); Xmol (Minnesota Supercomputing Center); Protein Expert (Cambridge Scientific); HyperChem (Hypercube); MD Display (University of Washington); PKB (National Center for Biotechnology Information, NIH); ChemX (Chemical Design, Ltd.); Cameleon (Oxford Molecular, Inc.); and Iditis (Oxford Molecular, Inc.).

One approach to RDD is to search for known molecular structures that might bind to a site of interest. Using molecular modeling, RDD programs can look at a range of different molecular structures of molecules that may fit into a site of interest, and by moving them on the computer screen or via computation it can be decided which structures actually fit the site well (William Bains (1998) *Biotechnology from A to Z*, second edition, Oxford University Press, p. 259).

An alternative but related approach starts with the known structure of a complex with a small molecule ligand and models modifications of that small molecule in an effort to make additional favorable interactions with a ribosome or ribosomal subunit.

The present invention permits the use of molecular and computer modeling techniques to design and select novel molecules, such as antibiotics or other therapeutic agents, that interact with ribosomes and ribosomal subunits. Such antibiotics and other types of therapeutic agents include, but are not limited to, antifungals, antivirals, antibacterials, insecticides, herbicides, miticides, rodentcides, etc.

In order to facilitate molecular modeling and/or RDD the skilled artisan may use some or all of the atomic co-ordinates deposited at the RCSB Protein Data Bank with the accession number PDB ID: 1FFK, 1JJ2, 1FFZ, IFG0, 1K73, 1KC8, 1K8A, 1 KD1, or 1K9M, and/or those atomic co-ordinates contained on Disk No. 1. Furthermore, the skilled artisan, using the foregoing atomic co-ordinates, the skilled artisan can generate additional atomic co-ordinates via, for example, molecular modeling using, for example, homology modeling and/or molecular replacement techniques, that together define at least a portion of a model of a ribosome from another species of interest. By using the foregoing atomic co-ordinates, the skilled artisan can design inhibitors of protein synthesis that may be tailored to be effective against ribosomes from one or more species but which have little or no effect on ribosomes of other species. Such inhibitors may be competitive inhibitors. As used herein, the term "competitive inhibitor" refers to an inhibitor that binds to the active form of a ribosome or ribosomal subunit at the same sites as its substrate(s) or tRNA(s), thus directly competing with them. The term "active form" of a ribosome or ribosomal subunit refers to a ribosome or ribosomal subunit in a state that renders it capable of protein synthesis. Competitive inhibition can be reversed completely by increasing the substrate or tRNA concentration.

This invention also permits the design of molecules that act as uncompetitive inhibitors of protein synthesis. As used herein, the term "uncompetitive inhibitor" refers to a molecule that inhibits the functional activity of a ribosome or ribosomal subunit by binding to a different site on the ribosome or ribosomal subunit than does its substrates, or tRNA. Such inhibitors can often bind to the ribosome or ribosomal subunit with the substrate or tRNA and not to the ribosome or ribosomal subunit by itself. Uncompetitive inhibition cannot be reversed completely by increasing the substrate concentration. These inhibitors may bind to, all or a portion of, the active sites or other regions of the large ribosomal subunit already bound to its substrate and may be more potent and less non-specific than known competitive inhibitors that compete for large ribosomal subunit active sites or for binding to large ribosomal subunit.

Similarly, non-competitive inhibitors that bind to and inhibit protein synthesis whether or not it is bound to another chemical entity may be designed using the atomic co-ordinates of the large ribosomal subunits or complexes comprising large ribosomal subunit of this invention. As used herein, the term "non-competitive inhibitor" refers to an inhibitor that can bind to either the free or substrate or tRNA bound form of the ribosome or ribosomal subunit.

Those of skill in the art may identify inhibitors as competitive, uncompetitive, or non-competitive by computer fitting enzyme kinetic data using standard equation according to Segel, I. H., (1975) *Enzyme Kinetics: Behaviour and Analysis of Rapid Equilibrium and Steady-State Enzyme Systems*, (Wiley Classics Library). It should also be understood that uncompetitive or non-competitive inhibitors according to the present invention may bind the same or different binding sites.

Alternatively, the atomic co-ordinates provided by the present invention are useful in designing improved analogues of known protein synthesis inhibitors or to design novel classes of inhibitors based on the atomic structures and co-ordinates of the crystals of the 50S ribosomal subunit/CCdA-p-Puro complex and the 50S ribosomal subunit/aa-tRNA analogue complex. This provides a novel route for designing inhibitors of protein synthesis with both high specificity, stability and other drug-like qualities (Lipinski et al. (1997) *Adv. Drug Deliv. Rev.* 23:3).

The atomic co-ordinates of the present invention also permit probing the three-dimensional structure of a ribosome or ribosome subunit or a portion thereof with molecules composed of a variety of different chemical features to determine optimal sites for interaction between candidate inhibitors and/or activators and the ribosome or ribosomal subunit. For example, high resolution atomic co-ordinates based on X-ray diffraction data collected from crystals saturated with solvent allows the determination of where each type of solvent molecule sticks. Small molecules that bind to those sites can then be designed and synthesized and tested for their inhibitory activity (Travis, J. (1993) *Science* 262: 1374). Further, any known antibiotic, inhibitor or other small molecule that binds to the *H. marismortui* large subunit can be soaked into *H. marismortui* large subunit crystals and their exact mode of binding determined from difference electron density maps. These molecules may represent lead compounds from which better drug-like compounds can be synthesized.

b. Identification of Target Sites.

The atomic co-ordinates of the invention permit the skilled artisan to identify target locations in a ribosome or large ribosomal subunit that can serve as a starting point in rational drug design. As a threshold matter, the atomic co-ordinates of the invention permit the skilled artisan to identify specific regions within a ribosome or ribosomal subunit that are involved with protein synthesis and/or protein secretion out of the ribosome. Furthermore, the atomic co-ordinates of the invention permit a skilled artisan to further identify portions of these regions that are conserved or are not conserved between different organisms. For example, by identifying portions of these regions that are conserved among certain pathogens, for example, certain prokaryotes, but are not conserved in a host organism, for example, a eukaryote, more preferably a mammal, the skilled artisan can design molecules that selectively inhibit or disrupt protein synthesis activity of the pathogen's but not the host's ribosomes. Furthermore, by analyzing regions that are either conserved or non-conserved between certain pathogens, it may be possible to design broad or narrow spectrum protein synthesis inhibitors, e.g., antibiotics, as a particular necessity arises.

FIG. 32, is a schematic representation of a large ribosomal subunit that identifies a variety of exemplary target sites that appear to participate in protein synthesis within the ribosome and/or the export or translocation of the newly synthesized protein out of the ribosome. The target sites include, for example, the P-site (200), the A-site (201), the peptidyl transferase center (202), the peptidyl transferase site (203) which includes at least a portion of the P-site and the A-site, a factor binding domain (204) including, for example, the EF-Tu binding domain and the EF-G binding domain, the polypeptide exit tunnel (205) including cavities defined by the wall of the exit tunnel, and the signal recognition particle binding domain (206).

By way of example, inspection of the atomic co-ordinates of the *H. marismortui* 50S ribosomal subunit has identified a variety of target regions that may serve as a basis for the rational drug design of new or modified protein synthesis inhibitors. The target regions include the peptidyl transferase site, A-site, the P-site, the polypeptide exit tunnel, certain cavities disposed in the wall of the polypeptide exit tunnel (for example, cavity 1 and cavity 2), and certain antibiotic binding pockets. The residues that together define at least a portion of each of the foregoing regions are identified in the following tables. However, it is contemplated that the same or similar target sites can be identified in a ribosome or a ribosomal unit of interest using the principles described herein. Furthermore, these principles can be employed using any of the primary sets of atomic co-ordinates provided herein or any additional atomic co-ordinate sets, for example, secondary atomic co-ordinate sets that may be generated by molecular modeling of any ribosome or ribosomal subunit of interest.

Table 5A identifies the residues in the *H. marismortui* 50S ribosomal subunit that together define at least a portion of the ribosomal peptidyl transferase site (5.8 Å shell). In addition, Table 5A identifies the corresponding residues that define at least a portion of the ribosomal peptidyl transferase site in *E. coli*, *Rattus*, human, and human mitochondria large subunit. Table 5B identifies the residues in the *H. marismortui* 50S ribosomal subunit that together define a broader portion of the ribosomal peptidyl transferase site (5.8 Å-12.6 Å shell). The non-conserved residues were identified by comparison of sequences from the structure of *H. marismortui* 23S rRNA or ribosomal protein that form the above-mentioned sites with the corresponding sequences of aligned genomic DNA encoding either the homologous 23S rRNA or ribosomal protein from the other organisms.

TABLE 5A

Residues that Define the Ribosomal Peptidyl-Transferase Site (5.8 Å shell)

| *H. marismortui* Residue 23S rRNA | Corresponding Residue in *E. coli* | Corresponding Residue in *Rattus* | Corresponding Residue in Human | Corresponding Residue in Human Mitochondria |
|---|---|---|---|---|
| G2102 | G2061 | G3632 | G3876 | G1054 |
| A2103 | A2062 | A3633 | A3877 | A1055 |
| C2104 | C2063 | C3634 | C3878 | C1056 |
| C2105 | C2064 | C3635 | C3879 | C1057 |
| C2106 | C2065 | C3636 | C3880 | C1058 |
| G2284 | G2251 | G3917 | G4156 | G1145 |
| G2285 | G2252 | G3918 | G4157 | G1146 |
| G2286 | G2253 | G3919 | G4158 | G1147 |
| A2474 | A2439 | A4106 | A4345 | A1256 |
| G2482 | G2447 | G4114 | G4353 | G1264 |
| A2485 | A2450 | A4117 | A4356 | A1267 |
| A2486 | A2451 | A4118 | A4357 | A1268 |
| C2487 | C2452 | C4119 | C4358 | C1269 |
| A2488 | A2453 | U4120 | U4359 | A1270 |
| U2528 | U2493 | U4160 | U4399 | U1310 |
| G2529 | G2494 | G4161 | G4400 | A1311 |
| C2536 | C2501 | C4168 | C4407 | C1318 |
| A2538 | A2503 | A4170 | A4409 | A1320 |
| G2540 | G2505 | G4172 | G4411 | G1322 |
| U2541 | U2506 | U4173 | U4412 | U1323 |
| C2542 | C2507 | C4174 | C4413 | U1324 |
| G2543 | G2508 | G4175 | G4414 | G1325 |
| G2588 | G2553 | G4220 | G4459 | G1370 |
| U2589 | U2554 | U4221 | U4460 | U1371 |
| U2590 | U2555 | U4222 | U4461 | U1372 |
| C2608 | C2573 | C4240 | C4479 | C1390 |
| G2617 | G2582 | G4249 | G4488 | A1399 |
| G2618 | G2583 | G4250 | G4489 | G1400 |
| U2619 | U2584 | U4251 | U4490 | U1401 |
| U2620 | U2585 | U4252 | U4491 | U1402 |
| C2636 | C2601 | C4268 | C4507 | C1418 |
| A2637 | A2602 | A4269 | A4508 | A1419 |
| G2638 | G2603 | G4270 | G4509 | G1420 |

Residues that together define the peptidyl transferase site (5.8 Å shell) were determined to be those residues in the 50S ribosomal subunit that are within 5.8 angstroms of the atoms of the CC-Puromycin A-site ligand and the atoms of the CCdA-PO₂ moiety of the CCdA-p-Puromycin transition state inhibitor (PDB accession codes: 1fg0 and 1ffz, respectively) using the program MIDAS[a]. Conserved residues in 23S rRNA were determined by comparison of sequences from the *H. marismortui* 23S rRNA[b] with genomic DNA sequences encoding the homologous 23S rRNA (*E. coli*[c], *Rattus norvegicus*[d], Human[e] or Human mitochondria[f]). Sequence alignments were determined with the program MegAlign (DNAS-TAR, Madison, Wisconsin, USA) using default parameters.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683

TABLE 5B

Residues that Define the Ribosomal Peptidyl-Transferase Site (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C1750 | A1672 | C2692 | C2830 | A732 |
| C1982 | C1941 | C3513 | C3757 | A934 |
| C1983 | C1942 | C3514 | C3758 | C935 |
| U1984 | U1943 | U3515 | U3759 | U936 |
| U1985 | U1944 | C3516 | C3760 | U937 |
| U1996 | U1955 | U3527 | U3771 | U948 |
| C2006 | C1965 | C3537 | C3781 | U958 |
| A2007 | A1966 | A3538 | A3782 | A959 |
| G2073 | G2032 | C3603 | C3847 | G1025 |
| A2100 | A2059 | A3630 | A3874 | A1052 |
| A2103 | A2062 | A3633 | A3877 | A1055 |
| U2107 | C2066 | U3637 | U3881 | U1059 |
| U2282 | U2249 | U3915 | U4154 | U1143 |
| G2283 | G2250 | G3916 | G4155 | G1144 |
| C2287 | C2254 | C3920 | C4159 | C1148 |
| C2288 | C2255 | G3921 | G4160 | U1149 |
| C2309 | C2275 | C3942 | C4181 | C1154 |
| C2472 | G2437 | U4104 | U4343 | U1254 |
| U2473 | U2438 | U4105 | U4344 | U1255 |
| C2476 | U2441 | C4108 | C4347 | C1258 |
| A2479 | G2444 | A4111 | A4350 | A1261 |
| G2480 | G2445 | G4112 | G4351 | G1262 |
| G2481 | G2446 | G4113 | G4352 | G1263 |
| G2482 | G2447 | G4114 | G4353 | G1264 |
| U2484 | U2449 | U4116 | U4355 | U1266 |
| G2489 | G2454 | G4121 | G4360 | G1271 |
| A2490 | G2455 | G4122 | G4361 | U1272 |
| C2526 | U2491 | U4158 | U4397 | U1308 |
| U2527 | U2492 | U4159 | U4398 | U1309 |
| G2529 | G2494 | G4161 | G4400 | A1311 |
| C2530 | G2495 | A4162 | A4401 | C1312 |
| U2531 | C2496 | U4163 | U4402 | G1313 |
| A2532 | A2497 | C4164 | C4403 | A1314 |
| C2534 | C2499 | U4166 | U4405 | C1316 |
| U2535 | U2500 | U4167 | U4406 | U1317 |
| G2537 | G2502 | G4169 | G4408 | G1319 |
| A2538 | A2503 | A4170 | A4409 | A1320 |
| U2539 | U2504 | U4171 | U4410 | U1321 |
| G2540 | G2505 | G4172 | G4411 | G1322 |
| G2544 | G2509 | G4176 | G4415 | G1326 |
| U2587 | U2552 | U4219 | U4458 | U1369 |
| C2591 | C2556 | C4223 | C4462 | C1373 |
| G2592 | G2557 | A4224 | A4463 | A1374 |
| A2604 | G2569 | G4236 | G4475 | C1386 |
| G2605 | G2570 | G4237 | G4476 | G1387 |
| U2607 | A2572 | A4239 | A4478 | A1389 |
| G2609 | G2574 | G4241 | G4480 | G1391 |
| U2610 | C2575 | U4242 | U4481 | U1392 |
| G2611 | G2576 | G4243 | G4482 | G1393 |
| G2616 | G2581 | G4248 | G4487 | G1398 |
| G2617 | G2582 | G4249 | G4488 | A1399 |
| U2621 | U2586 | U4253 | U4492 | C1403 |
| A2622 | A2587 | A4254 | A4493 | A1404 |
| G2627 | G2592 | G4259 | G4498 | G1409 |
| U2628 | U2593 | U4260 | U4499 | G1410 |
| G2634 | G2599 | G4266 | G4505 | U1416 |
| A2635 | A2600 | A4267 | A4506 | C1417 |
| G2638 | G2603 | G4270 | G4509 | G1420 |
| G2639 | U2604 | G4271 | G4510 | G1421 |
| U2640 | U2605 | U4272 | U4511 | U1422 |
| G2643 | G2608 | G4275 | G4514 | G1425 |
| U2645 | C2610 | U4277 | U4516 | U1427 |
| Protein L3 | | | | |
| P1 | NP* | S2 | S2 | P2 |

TABLE 5B-continued

Residues that Define the Ribosomal Peptidyl-Transferase Site (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| Protein L10E | | | | |
| D109 | XX** | T113 | T113 | XX |
| G110 | XX | G114 | G114 | XX |
| R112 | XX | R116 | R116 | XX |

Residues that together define the peptidyl transferase site (5.8 Å-12.6 Å shell) were determined to be those residues in the 50S ribosomal subunit that are within 5.8-12.6 angstroms of the atoms of the CC-Puromycin A-site ligand and the atoms of the CCdA-PO₂ moiety of the CCdA-p-Puromycin transition state inhibitor (PDB accession codes: 1fg0 and 1ffz, respectively), using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) using defaul parameters.
*NP means that no homologous residue has been identified.
**XX means that no homologous protein has been identified in that species.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3; GenBank accession 15825950 for protein L10E.
[i]GenBank accession CAA26460 for protein L3.
[j]GenBank accession P21531 for protein L3; GenBank accession NP_112362 for protein L10E.
[k]GenBank accession NP_000958 for protein L3; GenBank accession NP_006004 for protein L10E.
[l]GenBank accession P09001 for protein L3.

Table 6A identifies the residues in the *H. marismortui* 50S ribosomal subunit that together define at least a portion of the ribosomal A-site (5.8 Å shell). In addition, Table 6A identifies the corresponding residues that define at least a portion of the ribosomal A-site in *E. coli*, *Rattus*, human, and human mitochondria large subunit. Table 6B identifies the residues in the *H. marismortui* 50S ribosomal subunit that together define a broader portion of the ribosomal A-site (5.8 Å-12.6 Å shell). The non conserved residues were identified as described previously with respect to Tables 5A and 5B.

TABLE 6A

Residues that Define the Ribosomal A-site (5.8 Å shell)

| H. marismortui Residue 23S rRNA | Corresponding Residue in E. coli | Corresponding Residue in Rattus | Corresponding Residue in Human | Corresponding Residue in Human Mitochondria |
|---|---|---|---|---|
| G2102 | G2061 | G3632 | G3876 | G1054 |
| C2104 | C2063 | C3634 | C3878 | C1056 |
| A2485 | A2450 | A4117 | A4356 | A1267 |
| A2486 | A2451 | A4118 | A4357 | A1268 |
| C2487 | C2452 | C4119 | C4358 | C1269 |
| A2488 | A2453 | U4120 | U4359 | A1270 |
| U2528 | U2493 | U4160 | U4399 | U1310 |
| G2529 | G2494 | G4161 | G4400 | A1311 |
| C2536 | C2501 | C4168 | C4407 | C1318 |
| U2541 | U2506 | U4173 | U4412 | U1323 |
| C2542 | C2507 | C4174 | C4413 | U1324 |
| C2543 | C2508 | G4175 | G4414 | G1325 |
| G2588 | G2553 | G4220 | G4459 | G1370 |
| U2589 | U2554 | U4221 | U4460 | U1371 |
| U2590 | U2555 | U4222 | U4461 | U1372 |
| C2608 | C2573 | C4240 | C4479 | C1390 |
| G2618 | G2583 | G4250 | G4489 | G1400 |

TABLE 6A-continued

Residues that Define the Ribosomal A-site (5.8 Å shell)

| H. marismortui Residue 23S rRNA | Corresponding Residue in E. coli | Corresponding Residue in Rattus | Corresponding Residue in Human | Corresponding Residue in Human Mitochondria |
|---|---|---|---|---|
| U2619 | U2584 | U4251 | U4490 | U1401 |
| U2620 | U2585 | U4252 | U4491 | U1402 |

Residues that together define the A-site (5.8 Å shell) were determined to be those residues in the 50S ribosomal subunit that are within 5.8 angstroms of the atoms of the CC-Puromycin A-site ligand (PDB accession code 1fg0) using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). Sequence alignments were determined with the program MegAlign (DNASTAR, Madison, Wisconsin, USA) using default parameters.

[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683

TABLE 6B

Residues that Define the Ribosomal A-site (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C1750 | A1672 | C2692 | C2830 | A732 |
| C1982 | C1941 | C3513 | C3757 | A934 |
| C1983 | C1942 | C3514 | C3758 | C935 |
| U1984 | U1943 | U3515 | U3759 | U936 |
| U1985 | U1944 | C3516 | C3760 | U937 |
| U1996 | U1955 | U3527 | U3771 | U948 |
| G2073 | G2032 | C3603 | C3847 | G1025 |
| A2100 | A2059 | A3630 | A3874 | A1052 |
| A2103 | A2062 | A3633 | A3877 | A1055 |
| C2105 | C2064 | C3635 | C3879 | C1057 |
| C2106 | C2065 | C3636 | C3880 | C1058 |
| U2107 | U2066 | U3637 | U3881 | U1059 |
| G2284 | G2251 | G3917 | G4156 | G1145 |
| G2285 | G2252 | G3918 | G4157 | G1146 |
| A2474 | A2439 | A4106 | A4345 | A1256 |
| A2479 | G2444 | A4111 | A4350 | A1261 |
| G2480 | G2445 | G4112 | G4351 | G1262 |
| G2481 | G2446 | G4113 | G4352 | G1263 |
| G2482 | G2447 | G4114 | G4353 | G1264 |
| U2484 | U2449 | U4116 | U4355 | U1266 |
| G2489 | G2454 | G4121 | G4360 | G1271 |
| A2490 | G2455 | G4122 | G4361 | C1272 |
| C2526 | U2491 | U4158 | U4397 | U1308 |
| U2527 | U2492 | U4159 | U4398 | U1309 |
| C2530 | G2495 | A4162 | A4401 | C1312 |
| U2531 | C2496 | U4163 | U4402 | G1313 |
| A2532 | A2497 | C4164 | C4403 | A1314 |
| C2534 | C2499 | U4166 | U4405 | C1316 |
| U2535 | U2500 | U4167 | U4406 | U1317 |
| G2537 | G2502 | G4169 | G4408 | G1319 |
| A2538 | A2503 | A4170 | A4409 | A1320 |
| U2539 | U2504 | U4171 | U4410 | U1321 |
| G2540 | G2505 | G4172 | G4411 | G1322 |
| G2544 | G2509 | G4176 | G4415 | G1326 |
| U2587 | U2552 | U4219 | U4458 | U1369 |
| C2591 | C2556 | C4223 | C4462 | C1373 |
| G2592 | G2557 | A4224 | A4463 | A1374 |
| A2604 | G2569 | G4236 | G4475 | C1386 |
| G2605 | G2570 | G4237 | G4476 | C1387 |
| U2607 | A2572 | A4239 | A4478 | A1389 |
| G2609 | C2574 | G4241 | G4480 | G1391 |
| U2610 | C2575 | U4242 | U4481 | U1392 |
| G2611 | C2576 | G4243 | G4482 | G1393 |
| G2616 | G2581 | G4248 | G4487 | G1398 |

TABLE 6B-continued

Residues that Define the Ribosomal A-site (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| G2617 | G2582 | G4249 | G4488 | A1399 |
| U2621 | U2586 | U4253 | U4492 | C1403 |
| C2636 | C2601 | C4268 | C4507 | C1418 |
| A2637 | A2602 | A4269 | A4508 | A1419 |
| G2638 | G2603 | G4270 | G4509 | G1420 |
| G2639 | U2604 | G4271 | G4510 | G1421 |
| U2640 | U2605 | U4272 | U4511 | U1422 |
| U2643 | G2608 | G4275 | G4514 | G1425 |
| U2645 | C2610 | U4277 | U4516 | U1427 |
| Protein L3 | | | | |
| P1 | NP* | S2 | S2 | P2 |

Residues that define the A-site (5.8 Å-12.6 Å shell) were determined to be those residues in the 50S ribosomal subunit that are within 5.8-12.6 angstroms of the atoms of the CC-Puromycin A-site ligand (PDB accession code 1fg0) using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with theprogram MegAlign (DNASTAR, Madison, Wisconsin, USA) with default parameters.
*NP means that no homologous residue has been identified.

[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3.
[i]GenBank accession CAA26460 for protein L3.
[j]GenBank accession P21531 for protein L3.
[k]GenBank accession NP_000958 for protein L3.
[l]GenBank accession P09001 for protein L3.

Table 7A identifies the residues in the H. marismortui 50S ribosomal subunit that together define at least a portion of the ribosomal P-site (5.8 Å shell). In addition, Table 7A identifies the corresponding residues that define at least a portion of the ribosomal P-site in E. coli, Rattus, human, and human mitochondria large subunit. Table 7B identifies the residues in the H. marismortui 50S ribosomal subunit that together define a broader portion of the ribosomal P-site (5.8 Å-12.6 Å shell). The non conserved residues were identified as described previously with respect to Tables 5A and 5B.

TABLE 7A

Residues that Define the Ribosomal P-site (5.8 Å shell)

| H. marisomortui Residue 23S rRNA | Corresponding Residue in E. coli | Corresponding Residue in Rattus | Corresponding Residue in Human | Corresponding Residue in Human Mitochondria |
|---|---|---|---|---|
| C2104 | C2063 | C3634 | C3878 | C1056 |
| C2105 | C2064 | C3635 | C3879 | C1057 |
| C2106 | C2065 | C3636 | C3880 | C1058 |
| G2284 | G2251 | G3917 | G4156 | G1145 |
| G2285 | G2252 | G3918 | G4157 | G1146 |
| G2286 | G2253 | G3919 | G4158 | G1147 |
| A2474 | A2439 | A4106 | A4345 | A1256 |
| A2485 | A2450 | A4117 | A4356 | A1267 |
| A2486 | A2451 | A4118 | A4357 | A1268 |
| U2619 | U2584 | U4251 | U4490 | U1401 |
| U2620 | U2585 | U4252 | U4491 | U1402 |
| C2636 | C2601 | C4268 | C4507 | C1418 |

TABLE 7A-continued

Residues that Define the Ribosomal P-site (5.8 Å shell)

| H. marismortui Residue 23S rRNA | Corresponding Residue in E. coli | Corresponding Residue in Rattus | Corresponding Residue in Human | Corresponding Residue in Human Mitochondria |
|---|---|---|---|---|
| A2637 | A2602 | A4269 | A4508 | A1419 |
| G2638 | G2603 | G4270 | G4509 | G1420 |

Residues that together define the P-site (5.8 Å shell) were determined to be those residues in the 50S ribosomal subunit that are within 5.8 angstroms of the atoms of the CCdA-PO₂ moiety of the CCdA-p-puromycin transition state inhibitor (FIG. 10a) (PDB accession code 1 ffz) using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). Sequence alignments were determined with the program MegAlign (DNASTAR, Madison, Wisconsin, USA) using default parameters.

[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683

TABLE 7B

Residues that Define the Ribosomal P-site (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C1982 | C1941 | C3513 | C3757 | A934 |
| C2006 | C1965 | C3537 | C3781 | U958 |
| A2007 | A1966 | A3538 | A3782 | A959 |
| G2102 | G2061 | G3632 | G3876 | G1054 |
| A2103 | A2062 | A3633 | A3877 | A1055 |
| U2107 | C2066 | U3637 | U3881 | U1059 |
| U2282 | U2249 | U3915 | U4154 | U1143 |
| G2283 | G2250 | G3916 | G4155 | G1144 |
| C2287 | C2254 | C3920 | C4159 | C1148 |
| G2288 | G2255 | G3921 | G4160 | G1149 |
| C2309 | C2275 | C3942 | C4181 | C1154 |
| C2472 | G2437 | U4104 | U4343 | U1254 |
| U2473 | U2438 | U4105 | U4344 | U1255 |
| C2476 | U2441 | C4108 | C4347 | C1258 |
| G2481 | G2446 | G4113 | G4352 | G1263 |
| G2482 | G2447 | G4114 | G4353 | G1264 |
| U2484 | U2449 | U4116 | U4355 | U1266 |
| C2487 | C2452 | C4119 | C4358 | C1269 |
| A2488 | A2453 | U4120 | U4359 | A1270 |
| U2528 | U2493 | U4160 | U4399 | U1310 |
| G2529 | G2494 | G4161 | G4400 | A1311 |
| C2530 | G2495 | A4162 | A4401 | C1312 |
| U2531 | C2496 | U4163 | U4402 | G1313 |
| A2532 | A2497 | C4164 | C4403 | A1314 |
| C2534 | C2499 | U4166 | U4405 | C1316 |
| U2535 | U2500 | U4167 | U4406 | U1317 |
| C2536 | C2501 | C4168 | C4407 | C1318 |
| A2538 | A2503 | A4170 | A4409 | A1320 |
| G2540 | G2505 | G4172 | G4411 | G1322 |
| U2541 | U2506 | U4173 | U4412 | U1323 |
| C2542 | C2507 | C4174 | C4413 | U1324 |
| C2608 | C2573 | C4240 | C4479 | C1390 |
| G2611 | G2576 | G4243 | G4482 | G1393 |
| G2618 | G2583 | G4250 | G4489 | G1400 |
| U2621 | U2586 | U4253 | U4492 | C1403 |
| A2622 | A2587 | A4254 | A4493 | A1404 |
| G2627 | G2592 | G4259 | G4498 | G1409 |
| U2628 | U2593 | U4260 | U4499 | U1410 |
| G2634 | G2599 | G4266 | G4505 | U1416 |
| A2635 | A2600 | A4267 | A4506 | C1417 |
| G2639 | U2604 | G4271 | G4510 | G1421 |
| U2640 | U2605 | U4272 | U4511 | U1422 |
| G2643 | G2608 | G4275 | G4514 | G1425 |
| Protein L10E | | | | |
| D109 | XX** | T113 | T113 | XX |
| G110 | XX | G114 | G114 | XX |
| R112 | XX | R116 | R116 | XX |

Residues that together define the P-site (5.8 Å-12.6 Å shell) were determined to be those residues in the 50S ribosomal subunit that are within the atoms of the CCdA-PO₂ moiety of the CCdA-p-puromycin transition state inhibitor (FIG. 10a) (PDB accession code 1ffz) using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) using default parameters.
**XX means that no homologous protein has been identified in that species.

[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession 15825950 for protein L10E.
[i]No GenBank accession number for protein L10E.
[j]GenBank accession NP_112362 for protein L10E.
[k]GenBank accession NP_006004 for protein L10E.
[l]No GenBank accession number that compares to protein L10E.

Table 8A identifies the residues in the H. marismortui 50S ribosomal subunit that are within 10 Å of a hypothetical, nascent polypeptide within the ribosomal exit tunnel (10 Å shell). In addition, Table 8A identifies the corresponding residues that define at least a portion of the ribosomal polypeptide exit tunnel in E. coli, Rattus, human, and human mitochondria large subunit. Further, Table 8B identifies the residues in the H. marismortui 50S ribosomal subunit that that are between 10-15 Å of a hypothetical, nascent polypeptide within the ribosomal exit tunnel (10 Å-15 Å shell). The non conserved residues were identified as described previously with respect to Tables 5A and 5B.

TABLE 8A

Residues that Define the Ribosomal Peptide Exit Tunnel (10 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| A60 | A64 | C729 | C682 | NP* |
| G88 | G93 | G764 | G713 | NP |
| G89 | A94 | G765 | G714 | NP |
| A90 | A95 | C766 | C715 | NP |
| A462 | C456 | C1112 | C1195 | NP |
| U465 | U459 | U1116 | G1199 | NP |
| A466 | A460 | G1117 | G1200 | NP |
| G467 | C461 | G1118 | G1201 | NP |
| U468 | C462 | G1119 | A1202 | NP |
| A475 | G469 | U1127 | U1208 | NP |
| A476 | A470 | C1128 | C1209 | NP |
| A477 | A471 | A1129 | U1210 | NP |
| C478 | A472 | C1130 | C1211 | NP |
| U488 | U482 | C1140 | C1221 | NP |
| A497 | G491 | G1151 | G1233 | NP |

TABLE 8A-continued

Residues that Define the Ribosomal Peptide Exit Tunnel (10 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| A498 | A492 | G1152 | A1234 | NP |
| A513 | A507 | A1167 | G1249 | NP |
| G514 | A508 | A1168 | A1250 | NP |
| A767 | A676 | A1425 | A1503 | NP |
| U835 | U744 | U1491 | U1570 | NP |
| C839 | U746 | G1495 | G1574 | NP |
| U840 | U747 | U1496 | U1575 | NP |
| A841 | G748 | G1497 | G1576 | NP |
| A844 | A751 | A1500 | A1579 | NP |
| U845 | A752 | A1501 | A1580 | NP |
| U1359 | U1255 | U2191 | U2327 | U351 |
| C1360 | G1256 | C2192 | C2328 | G352 |
| C1361 | C1257 | U2193 | U2329 | U353 |
| U1362 | U1258 | U2194 | U2330 | C354 |
| G1363 | G1259 | G2195 | G2331 | C355 |
| G1364 | A1260 | G2196 | G2332 | A356 |
| A1424 | U1318 | G2255 | G2391 | G412 |
| G1425 | C1319 | C2256 | C2392 | U413 |
| C1426 | C1320 | G2257 | G2393 | A414 |
| A1427 | A1321 | A2258 | A2394 | A415 |
| C1428 | A1322 | A2259 | A2395 | A416 |
| U1429 | C1323 | C2260 | C2396 | U417 |
| G1430 | G1324 | A2261 | A2397 | NP |
| C1439 | G1333 | A2270 | A2406 | U426 |
| U1440 | G1334 | C2271 | C2407 | A427 |
| G1441 | C1335 | A2272 | A2408 | G428 |
| A1442 | A1336 | U2273 | U2409 | U429 |
| A1689 | A1614 | C2635 | C2771 | A680 |
| C1690 | C1615 | A2636 | A2772 | U681 |
| G1837 | U1781 | A3368 | A3612 | C831 |
| U1838 | U1782 | U3369 | U3613 | C832 |
| A2054 | A2013 | A3585 | A3829 | A1006 |
| A2055 | A2014 | A3586 | A3830 | A1007 |
| C2056 | A2015 | A3587 | A3831 | A1008 |
| U2057 | A2016 | C3588 | C3832 | U1009 |
| C2098 | G2057 | A3628 | A3872 | A1050 |
| G2099 | A2058 | G3629 | G3873 | G1051 |
| A2100 | A2059 | A3630 | A3874 | A1052 |
| A2101 | A2060 | A3631 | A3875 | A1053 |
| G2102 | G2061 | G3632 | G3876 | G1054 |
| A2103 | A2062 | A3633 | A3877 | A1055 |
| C2104 | C2063 | C3634 | C3878 | C1056 |
| C2105 | C2064 | C3635 | C3879 | C1057 |
| A2474 | A2439 | A4106 | A4345 | A1256 |
| C2477 | C2442 | C4109 | C4348 | C1259 |
| U2478 | C2443 | C4110 | C4349 | U1260 |
| G2481 | G2446 | G4113 | G4352 | G1263 |
| G2482 | G2447 | G4114 | G4353 | G1264 |
| A2485 | A2450 | A4117 | A4356 | A1267 |
| A2486 | A2451 | A4118 | A4357 | A1268 |
| C2487 | C2452 | C4119 | C4358 | C1269 |
| A2488 | A2453 | U4120 | U4359 | A1270 |
| C2536 | C2501 | C4168 | C4407 | C1318 |
| G2537 | G2502 | G4169 | G4408 | G1319 |
| A2538 | A2503 | A4170 | A4409 | A1320 |
| U2539 | U2504 | U4171 | U4410 | U1321 |
| G2540 | G2505 | G4172 | G4411 | G1322 |
| U2541 | U2506 | U4173 | U4412 | U1323 |
| C2542 | C2507 | C4174 | C4413 | U1324 |
| C2608 | C2573 | C4240 | C4479 | C1390 |
| G2611 | G2576 | G4243 | G4482 | G1393 |
| G2616 | G2581 | G4248 | G4487 | G1398 |
| G2618 | G2583 | G4250 | G4489 | G1400 |
| U2619 | U2584 | U4251 | U4490 | U1401 |
| U2620 | U2585 | U4252 | U4491 | U1402 |
| U2621 | U2586 | U4253 | U4492 | C1403 |
| A2637 | A2602 | A4269 | A4508 | A1419 |
| C2644 | U2609 | U4276 | U4515 | U1426 |
| U2645 | C2610 | U4277 | U4516 | U1427 |
| G2646 | C2611 | U4278 | U4517 | U1428 |
| C2647 | C2612 | U4279 | U4518 | C1429 |

| H. marismortui Residue | Corresponding Residue in E. coli | Corresponding Residue in Rattus | Corresponding Residue in Human | Corresponding Residue in Human Mitochondria |
|---|---|---|---|---|
| Protein L4 | | | | |
| E59 | E51 | E65 | E65 | R70 |
| S60 | V52 | S66 | S66 | G71 |
| F61 | T53 | W67 | W67 | F72 |
| G62 | G54 | G68 | G68 | E73 |
| S63 | S55 | T69 | T69 | Q74 |
| G64 | G56 | G70 | G70 | E75 |
| R65 | K57 | R71 | R71 | R76 |
| G66 | NP* | A72 | A72 | G78 |
| Q67 | NP | V73 | V73 | L79 |
| A68 | NP | A74 | A74 | A80 |
| H69 | K58 | R75 | R75 | D81 |
| V70 | P59 | I76 | I76 | L82 |
| P71 | W60 | P77 | P77 | H83 |
| K72 | R61 | R78 | R78 | P84 |
| L73 | Q62 | V79 | V79 | D85 |
| D74 | G64 | G81 | G81 | F87 |
| G75 | T65 | G82 | G82 | A88 |
| R76 | G66 | G83 | G83 | T89 |
| A77 | R67 | T84 | T84 | A90 |
| Protein L22 | | | | |
| E20 | H9 | N21 | N21 | Q73 |
| E121 | S81 | K124 | K124 | P177 |
| Q122 | M82 | M125 | M125 | P178 |
| Q123 | K83 | R126 | R126 | P179 |
| G124 | R84 | R127 | R127 | P180 |
| R125 | I85 | R128 | R128 | E181 |
| K126 | M86 | T129 | T129 | P182 |
| P127 | P87 | Y130 | Y130 | P183 |
| R128 | R88 | R131 | R131 | K184 |
| A129 | A89 | A132 | A132 | A186 |
| M130 | K90 | H133 | H133 | V187 |
| G131 | G91 | G134 | G134 | A188 |
| R132 | R92 | R135 | R135 | H189 |
| A133 | A93 | I136 | I136 | A190 |
| S134 | D94 | N137 | N137 | K191 |
| A135 | R95 | P138 | P138 | E192 |
| W136 | I96 | Y139 | Y139 | Y193 |
| N137 | L97 | M140 | M140 | I194 |
| Q140 | T100 | P143 | P143 | F197 |
| Protein L39E | | | | |
| N18 | XX** | N20 | N20 | N98 |
| S19 | XX | R21 | R21 | H106 |
| R20 | XX | P22 | P22 | R107 |
| V21 | XX | I23 | I23 | I108 |
| P22 | XX | P24 | P24 | G109 |
| A23 | XX | Q25 | Q25 | D110 |
| Y24 | XX | W26 | W26 | F111 |
| V25 | XX | I27 | I27 | I112 |
| M26 | XX | R28 | R28 | D113 |
| L27 | XX | M29 | M29 | V114 |
| K28 | XX | K30 | K30 | S115 |
| T29 | XX | T31 | T31 | E116 |
| D30 | XX | G32 | G32 | G117 |
| E31 | XX | N33 | N33 | P118 |
| R35 | XX | Y37 | Y37 | H135 |
| N36 | XX | N38 | N38 | N136 |
| H37 | XX | S39 | S39 | L137 |
| K38 | XX | K40 | K40 | Q138 |
| R39 | XX | R41 | R41 | R146 |
| R40 | XX | R42 | R42 | R147 |
| H41 | XX | H43 | H43 | H156 |

TABLE 8A-continued

Residues that Define the Ribosomal Peptide Exit Tunnel (10 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| R44 | XX | R46 | R46 | R170 |
| N45 | XX | T47 | T47 | S171 |

The residues in the 10 Å shell were determined to be those residues in the 50S ribosomal subunit that are within 10 angstroms of the atoms of a model of a newly synthesized peptide positioned in the center of the exit tunnel using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) using default parameters.
*NP means, that no homologous residue has been identified.
**XX means that no homologous protein has been identified in that species.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession P12735 for protein L4; GenBank accession R5HS22 for protein L22; GenBank accession P22452 for protein L39E.
[i]GenBank accession CAA26461 for protein L4; GenBank accession CAA26465 for protein L22; no GenBank accession for protein L39E.
[j]GenBank accession JC4277 for protein L4; GenBank accession P24049 for protein L22; GenBank accession CAA57900 for protein L39E.
[k]GenBank accessions P36578, NP_00959, S39803, and T09551 for protein L4; GenBank accession XP_057521 for protein L22; GenBank accession NP_000991 for protein L39E.
[l]GenBank accession XP_049502 for protein L4; GenBank accession XP_051279 for protein L22; GenBank accession NP_059142 and NP_542984 for protein L39E.

TABLE 8B

Residues that Define the Ribosomal Peptide Exit Tunnel (10 Å-15 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| U22 | U25 | G686 | G637 | NP* |
| G23 | G26 | G687 | G638 | NP |
| G24 | G27 | G688 | G639 | NP |
| C57 | C61 | C726 | U679 | NP |
| C58 | U62 | U727 | U680 | NP |
| A59 | A63 | U728 | U681 | NP |
| G61 | U65 | C730 | C683 | NP |
| A86 | A91 | A762 | A711 | NP |
| C87 | U92 | C763 | C712 | NP |
| G91 | C96 | U767 | U716 | NP |
| U454 | U448 | C1104 | C1187 | NP |
| C461 | C455 | C1111 | C1194 | NP |
| A463 | A457 | G1114 | G1197 | NP |
| G469 | G463 | G1120 | G1203 | NP |
| U470 | U464 | C1122 | NP | NP |
| A473 | U467 | C1125 | U1206 | NP |
| C474 | C468 | G1126 | G1207 | NP |
| G479 | G473 | G1131 | G1212 | NP |
| C480 | C474 | C1132 | G1213 | NP |
| A485 | A479 | U1137 | A1218 | NP |
| A486 | A480 | C1138 | C1219 | NP |
| G487 | G481 | C1139 | G1220 | NP |
| A489 | A483 | U1141 | G1222 | NP |
| C490 | C484 | G1142 | C1223 | NP |
| C491 | C485 | C1143 | C1224 | NP |
| A495 | G489 | U1147 | C1228 | NP |
| G496 | C490 | C1148 | C1229 | NP |
| G499 | G493 | G1153 | A1235 | NP |
| G512 | G506 | G1166 | G1248 | NP |
| C515 | C509 | G1169 | G1251 | NP |
| C633 | U576 | C1284 | G1365 | NP |
| G634 | G577 | C1285 | C1366 | NP |
| A635 | G578 | A1286 | A1367 | NP |
| G636 | G579 | A1287 | A1368 | NP |
| C637 | U580 | U1288 | U1369 | NP |
| C638 | C581 | C1289 | G1370 | NP |
| C764 | C673 | C1422 | C1500 | NP |
| G765 | G674 | G1423 | G1501 | NP |
| A766 | A675 | A1424 | A1502 | NP |
| G836 | G745 | G1492 | G1571 | NP |
| U837 | NP* | A1493 | A1572 | NP |
| C838 | NP | C1494 | C1573 | NP |
| C842 | A749 | C1498 | C1577 | NP |
| A843 | A750 | A1499 | A1578 | NP |
| A846 | A753 | U1502 | U1581 | NP |
| A882 | A789 | A1538 | A1617 | NP |
| U883 | U790 | U1539 | U1618 | NP |
| C884 | C791 | C1540 | C1619 | NP |
| G885 | A792 | G1541 | G1620 | NP |
| C889 | C796 | C1545 | C1624 | NP |
| C890 | G797 | A1546 | A1625 | NP |
| A1358 | A1254 | A2190 | A2326 | U350 |
| C1365 | C1261 | U2197 | U2333 | A357 |
| C1366 | A1262 | G2198 | G2334 | G358 |
| A1367 | U1263 | G2199 | G2335 | A359 |
| U1368 | A1264 | U2200 | U2336 | U360 |
| A1369 | A1265 | A2201 | A2337 | A361 |
| U1419 | U1313 | U2250 | U2386 | C407 |
| C1423 | G1317 | U2254 | U2390 | U411 |
| U1432 | U1326 | C2263 | C2399 | U419 |
| C1436 | C1330 | U2267 | U2403 | U423 |
| A1437 | G1331 | U2268 | G2404 | G424 |
| G1438 | G1332 | A2269 | A2405 | U425 |
| G1443 | G1337 | G2274 | G2410 | C430 |
| G1688 | G1613 | G2634 | G2770 | G679 |
| A1691 | A1616 | G2637 | G2773 | U682 |
| C1692 | C1617 | C2638 | C2774 | A683 |
| A1836 | A1780 | A3367 | A3611 | A830 |
| A1839 | A1783 | U3370 | U3614 | A833 |
| U2052 | U2011 | C3583 | C3827 | U1004 |
| G2053 | G2012 | G3584 | G3828 | G1005 |
| G2058 | U2017 | G3589 | C3833 | U1010 |
| U2059 | U2018 | NP | NP | U1011 |
| G2073 | G2032 | C3603 | C3847 | G1025 |
| G2097 | G2056 | A3627 | A3871 | G1049 |
| C2106 | C2065 | C3636 | C3880 | C1058 |
| U2107 | U2066 | U3637 | U3881 | U1059 |
| G2284 | G2251 | G3917 | G4156 | G1145 |
| G2285 | G2252 | G3918 | G4157 | G1146 |
| U2473 | U2438 | U4105 | U4344 | U1255 |
| C2475 | C2440 | C4107 | C4346 | C1257 |
| C2476 | U2441 | C4108 | C4347 | C1258 |
| A2479 | G2444 | A4111 | A4350 | A1261 |
| G2480 | G2445 | G4112 | G4351 | G1262 |
| U2484 | U2449 | U4116 | U4355 | U1266 |
| G2489 | G2454 | G4121 | G4360 | G1271 |
| U2528 | U2493 | U4160 | U4399 | U1310 |
| G2529 | G2494 | G4161 | G4400 | A1311 |
| U2531 | C2496 | U4163 | U4402 | G1313 |
| A2532 | A2497 | C4164 | C4403 | A1314 |
| C2534 | C2499 | U4166 | U4405 | C1316 |
| U2535 | U2500 | U4167 | U4406 | U1317 |
| G2543 | G2508 | G4175 | G4414 | G1325 |
| G2588 | G2553 | G4220 | G4459 | G1370 |

TABLE 8B-continued

Residues that Define the Ribosomal Peptide Exit Tunnel (10 Å-15 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| U2607 | A2572 | A4239 | A4478 | A1389 |
| U2610 | C2575 | U4242 | U4481 | U1392 |
| A2612 | A2577 | A4244 | A4483 | A1394 |
| G2613 | G2578 | G4245 | G4484 | U1395 |
| C2614 | C2579 | C4246 | C4485 | C1396 |
| U2615 | U2580 | U4247 | U4486 | U1397 |
| G2617 | G2582 | G4249 | G4488 | A1399 |
| A2622 | A2587 | A4254 | A4493 | A1404 |
| C2636 | C2601 | C4268 | C4507 | C1418 |
| G2639 | U2604 | G4271 | G4510 | G1421 |
| G2642 | G2607 | A4274 | A4513 | G1424 |
| G2643 | G2608 | G4275 | G4514 | G1425 |
| U2648 | U2613 | A4280 | A4519 | U1430 |
| Protein L4 | | | | |
| T56 | T48 | T62 | T62 | E67 |
| P57 | R49 | S63 | R63/S63" | S68 |
| A58 | A50 | A64 | A64 | L69 |
| R78 | A68 | H85 | H85 | P91 |
| R79 | R69 | R86 | R86 | R92 |
| V80 | S70 | S87 | S87 | L96 |
| Q82 | NP | Q89 | Q89 | Q98 |
| A83 | S72 | G90 | G90 | V99 |
| V84 | I73 | A91 | A91 | A100 |
| K85 | K74 | F92 | F92 | M101 |
| Protein L22 | | | | |
| R19 | NP | S20 | S20 | R72 |
| R21 | A10 | L22 | L22 | I74 |
| Q22 | R11 | R23 | R23 | K75 |
| V119 | G79 | A122 | A122 | G175 |
| G120 | P80 | P123 | P123 | P176 |
| S138 | K98 | S141 | S141 | Q195 |
| P139 | R99 | S142 | S142 | Q196 |
| Protein L24 | | | | |
| K81 | N74 | K89 | K89 | Y95 |
| R83 | A76 | N91 | N91 | Y97 |
| G84 | T77 | G92 | G92 | I98 |
| E85 | G78 | T93 | T93 | G99 |
| Protein L29 | | | | |
| G37 | G35 | G38 | G38 | XX** |
| G38 | NP | G39 | G39 | XX |
| A39 | Q36 | A40 | A40 | XX |
| P40 | L37 | A41 | A41 | XX |
| E41 | Q38 | S42 | S42 | XX |
| P43 | S40 | L44 | L44 | XX |
| Protein L37E | | | | |
| G4 | XX | G4 | G4 | XX |
| T5 | XX | T5 | T5 | XX |
| Protein L39E | | | | |
| L14 | XX | K16 | K16 | K94 |
| D15 | XX | Q17 | Q17 | A95 |
| N16 | XX | K18 | K18 | S96 |
| Q17 | XX | Q19 | Q19 | Q97 |
| W24 | XX | W26 | W26 | F111 |
| W42 | XX | W44 | W44 | L157 |
| R43 | XX | R45 | R45 | R158 |
| D46 | XX | K48 | K48 | R172 |

The residues in the 10-15 Å shell were determined to be those residues in the 50S ribosomal subunit that are within 10-15 angstroms of the atoms of a model of a newly synthesized peptide positioned in the center of the exit tunnel using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) with default parameters.
*NP means that no homologous residue has been identified.
**XX means that no homologous protein has been identified in that species.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession P12735 for protein L4; GenBank accession R5HS22 for protein L22; GenBank accession R5HS22 for protein L24; GenBank accession R5HS29 for protein L29; GenBank accession P32410 for protein L37E; GenBank accession P22452 for protein L39E.
[i]GenBank accession CAA26461 for protein L4; GenBank accession CAA26465 for protein L22; GenBank accession R5EC24 for protein L24; GenBank accession R5EC29 for protein L29; no GenBank accession for protein L37E; no GenBank accession for protein L39E.
[j]GenBank accession JC4277 for protein L4; GenBank accession P24049 for protein L22; GenBank accession P12749 for protein L24; GenBank accession R5RT35 for protein L29; GenBank accession CAA47012 for protein L37E; GenBank accession CAA57900 for protein L39E.
[k]GenBank accessions P36578, NP_00959, S39803, and T09551 for protein L4; GenBank accession XP_057521 for protein L22; GenBank accession AAA60279 and NP_000978 for protein L24; GenBank accession AAA51648 for protein L29; GenBank accession NP_000988 for protein L37E; GenBank accession NP_000991 for protein L39E.
[l]GenBank accession XP_049502 for protein L4; GenBank accession XP_051279 for protein L22; GenBank accession XP_056380 for protein L24; no GenBank accession for protein L29; no GenBank accession for protein L37E; GenBank accessions NP_059142 and NP_542984 for protein L39E.
["]R63 is present in GenBank sequences T09551 and S39803 whereas S63 is present in GenBank sequences P36578 and NP_000959.

FIG. 30 shows a region of the large ribosomal subunit in which an antibiotic binds. FIG. 30(A) shows an enlarged portion of the large ribosomal subunit with the antibiotic tylosin bound at the top of the polypeptide exit tunnel adjacent the peptidyl transferase site. FIGS. 30(B) and 30(C) are views showing each half of a large ribosomal subunit cut along the polypeptide exit tunnel and are provided to orient the reader to show the tylosin binding site relative to the large ribosomal unit as a whole. FIG. 30(A) also shows two cavities defined by the wall of the polypeptide exit tunnel and are denoted as "cavity 1" and "cavity 2." In addition, FIG. 30(A) also shows a disaccharide binding pocket. The direction in which the newly synthesized polypeptide chains exits the ribosome through the polypeptide exit tunnel is denoted by an arrow.

Table 9 identifies the residues in the H. marismortui 50S ribosomal subunit that together define a first cavity within the wall of polypeptide exit tunnel (cavity 1). In addition, Table 9 identifies which of those residues that define corresponding residues from cavity 1 in E. coli, Rattus, human, and human mitochondria. The non-conserved residues were identified as described previously with respect to Tables 5A and 5B.

TABLE 9

Residues that Define Cavity 1 in the Ribosomal Peptide Exit Tunnel

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C474 | G468 | G1126 | C1207 | NP* |
| A766 | A675 | A1424 | A1502 | NP |
| A767 | A676 | A1425 | A1503 | NP |
| U768 | A677 | A1426 | A1504 | NP |
| U883 | U790 | U1539 | U1618 | NP |
| C884 | C791 | C1540 | C1619 | NP |
| G885 | A792 | G1541 | G1620 | NP |
| A886 | A793 | A1542 | A1621 | NP |
| U888 | C795 | C1544 | C1623 | NP |
| C889 | C796 | C1545 | C1624 | NP |
| C890 | G797 | A1546 | A1625 | NP |
| U1359 | U1255 | U2191 | U2327 | U351 |
| G1837 | U1781 | A3368 | A3612 | C831 |
| A2100 | A2059 | A3630 | A3874 | A1052 |
| A2101 | A2060 | A3631 | A3875 | A1053 |
| G2102 | G2061 | G3632 | G3876 | G1054 |
| A2103 | A2062 | A3633 | A3877 | A1055 |
| C2475 | C2440 | C4107 | C4346 | C1257 |
| C2476 | U2441 | C4108 | C4347 | C1258 |
| C2477 | C2442 | A4109 | A4348 | C1259 |
| U2478 | C2443 | C4110 | C4349 | U1260 |
| A2479 | G2444 | A4111 | A4350 | A1261 |
| A2538 | A2503 | A4170 | A4409 | A1320 |
| Protein L4 | | | | |
| P57 | R49 | S63 | R63/S63[n] | S68 |
| A58 | A50 | A64 | A64 | L69 |
| E59 | E51 | E65 | E65 | R70 |
| S60 | V52 | S66 | S66 | G71 |
| F61 | T53 | W67 | W67 | F72 |
| G62 | G54 | G68 | G68 | E73 |
| S63 | S55 | T69 | T69 | Q74 |
| G64 | G56 | G70 | G70 | E75 |
| R65 | K57 | R71 | R71 | R76 |
| Q67 | NP* | V73 | V73 | L79 |
| V70 | P59 | I76 | I76 | L82 |
| P71 | W60 | P77 | P77 | H83 |
| K72 | R61 | R78 | R78 | P84 |
| L73 | Q62 | V79 | V79 | D85 |
| D74 | G64 | G81 | G81 | F87 |
| G75 | T65 | G82 | G82 | A88 |
| R76 | G66 | G83 | G83 | T89 |

Cavity residues were identified using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA).
*NP means that no homologous residue has been identified.
[a]T. E. Ferrin, C. C. Huang, L. E. Jarvis, and R. Langridge. (1988). "The MIDAS Display System," J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession P12735 for protein L4.
[i]GenBank accession CAA26461 for protein L4.
[j]GenBank accession JC4277 for protein L4.
[k]GenBank accessions P36578, NP_00959, S39803, and T09551 for protein L4.
[l]GenBank accession XP_049502 for protein L4.
[n]R63 is present in GenBank sequences T09551 and S39803 whereas S63 is present in GenBank sequences P36578 and NP_000959.

Table 10 identifies the residues in the H. marismortui 50S ribosomal subunit that together define a second cavity in the wall of polypeptide exit tunnel (cavity 2). In addition, Table 10 identifies which of those residues that define corresponding residues from cavity 2 in E. coli, Rattus, human, and human mitochondria. The non-conserved residues were identified as described previously with respect to Tables 5A and 5B.

TABLE 10

Residues that Define Cavity 2 in the Ribosomal Peptide Exit Tunnel

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| U831 | C740 | U1488 | U1567 | NP* |
| U832 | U741 | C1489 | C1568 | NP |
| G833 | A742 | C1490 | C1569 | NP |
| G834 | A743 | NP | NP | NP |
| U835 | U744 | U1491 | U1570 | NP |
| G836 | G745 | G1492 | G1571 | NP |
| U837 | NP | A1493 | A1572 | NP |
| C838 | NP | C1494 | C1573 | NP |
| C839 | U746 | G1495 | G1574 | NP |
| U840 | U747 | U1496 | U1575 | NP |
| A841 | G748 | G1497 | G1576 | NP |
| A843 | A750 | A1499 | A1578 | NP |
| A844 | A751 | A1500 | A1579 | NP |
| U845 | A752 | A1501 | A1580 | NP |
| A846 | A753 | U1502 | U1581 | NP |
| C847 | U754 | C1503 | C1582 | NP |
| C848 | U755 | G1504 | G1583 | NP |
| C849 | A756 | G1505 | G1584 | NP |
| C1753 | C1675 | C2695 | C2833 | NP |
| A1754 | A1676 | A2696 | A2834 | U734 |
| G1837 | U1781 | A3368 | A3612 | C831 |
| U1838 | U1782 | U3369 | U3613 | C832 |
| A1839 | A1783 | U3370 | U3614 | A833 |
| G2099 | A2058 | G3629 | G3873 | G1051 |
| A2100 | A2059 | A3630 | A3874 | A1052 |
| A2103 | A2062 | A3633 | A3877 | A1055 |
| U2615 | U2580 | U4247 | U4486 | U1397 |
| G2616 | G2581 | G4248 | G4487 | G1398 |
| U2621 | U2586 | U4253 | U4492 | C1403 |
| A2622 | A2587 | A4254 | A4493 | A1404 |
| G2643 | G2608 | G4275 | G4514 | G1425 |
| C2644 | U2609 | U4276 | U4515 | U1426 |
| U2645 | C2610 | U4277 | U4516 | U1427 |
| G2646 | C2611 | U4278 | U4517 | U1428 |
| C2647 | C2612 | U4279 | U4518 | C1429 |

Cavity residues were determined using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). Sequence alignments were determined with the program MegAlign (DNASTAR, Madison, Wisconsin, USA) using default parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683

Tables 9 and 10, however, define only two of many cavities disposed within the wall of the polypeptide exit tunnel. However, by using the atomic co-ordinates and molecular modeling methodologies described herein, the skilled artisan may identify the residues (contributed by amino acids, nucleotides or a combination of both) that together define other cavities within the wall of the polypeptide exit tunnel.

In addition, by using the atomic co-ordinates described herein, the skilled artisan can identify the antibiotic binding site of any antibiotic of interest. This information also provides contact sites between an antibiotic and the residues in a ribosome or ribosomal subunit, which can be used to advantage in the design of novel or modified protein synthesis inhibitors. The binding or contact sites for a variety of antibiotics are discussed in more detail below.

Table 11A identifies the residues in the *H. marismortui* 50S ribosomal subunit that together define at least a portion of an anisomycin binding pocket (5.8 Å shell). In addition, Table 11A identifies the corresponding residues that define at least a portion of the anisomycin binding pocket in *E. coli*, *Rattus*, human, and human mitochondria large subunit. Table 11B identifies the residues in the *H. marismortui* 50S ribosomal subunit that together define a broader portion of an anisomycin binding pocket (5.8 Å-12.6 Å shell). The non-conserved residues were identified as described previously with respect to Tables 5A and 5B.

TABLE 11A

Residues that Define the Anisomycin Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| A2100[v] | A2059 | A3630 | A3874 | A1052 |
| G2102[v] | G2061 | G3632 | G3876 | G1054 |
| A2103[v] | A2062 | A3633 | A3877 | A1055 |
| G2482[v] | G2447 | G4114 | G4353 | G1264 |
| A2486[v] | A2451 | A4118 | A4357 | A1268 |
| C2487[h,v] | C2452 | C4119 | C4358 | C1269 |
| A2488[v] | A2453 | C4120 | U4359 | U1270 |
| U2535[h,v] | U2500 | U4167 | U4406 | U1317 |
| C2536 | C2501 | C4168 | C4407 | C1318 |
| A2538[v] | A2503 | A4170 | A4409 | A1320 |
| U2539[h,v] | U2504 | U4171 | U4410 | U1321 |
| G2540[v] | G2505 | G4172 | G4411 | G1322 |
| U2541[v] | U2506 | U4173 | U4412 | U1323 |
| U2620[v] | U2585 | U4252 | U4991 | U1402 |

The residues that define the binding pocket (5.8 Å shell) were determined as those residues in the 50S ribosomal subunit that are located within 5.8 angstroms of the atoms of anisomysin using the program MIDAS[a]. Conserved residues in 23S rRNA were determined by comparison of sequences from the structure of *H. marismortui* 23S rRNA[b] with the corresponding genomic DNA encoding the homologous 23S rRNA (*E. coli*[c],*Rattus norvegicus*[d], Human[e] or Human mitochondria[f]). Sequence alignments were determined with the program MegAlign (DNASTAR, Madison, Wisconsin, USA) with default parameters.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[h]Indicates residue that is within hydrogen-bonding distance (3.5 Å) of the ligand; for example, see Jorgensen, WL, Nguyen, TB. J. Comput. Chem. (1993) 14: 195-205.
[v]Residues in van der Waals contact with the antibiotic are defined as those residues within rmin of any atom in the antibiotic, where rmin = 21/6 s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

TABLE 11B

Residues that Define the Anisomycin Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| A631 | A574 | G1282 | G1363 | NP* |
| A632 | A575 | C1283 | C1364 | NP |
| C633 | U576 | G1284 | G1365 | NP |
| G2073 | G2032 | C3603 | C3847 | G1025 |
| A2095 | A2054 | G3625 | G3869 | A1047 |
| A2096 | C2055 | A3626 | A3870 | C1048 |
| G2097 | G2056 | A3627 | A3871 | G1049 |
| C2098 | G2057 | A3628 | A3872 | A1050 |
| G2099 | A2058 | G3629 | G3873 | G1051 |
| G2102 | G2061 | G3632 | G3876 | G1054 |
| C2104 | C2063 | C3634 | C3878 | C1056 |
| C2105 | C2064 | C3635 | C3879 | C1057 |
| A2474 | A2439 | A4106 | A4345 | A1256 |
| G2481 | G2446 | G4113 | G4352 | G1263 |
| U2484 | U2449 | U4116 | U4355 | U1266 |
| A2485 | A2450 | A4117 | A4356 | A1267 |
| G2489 | G2454 | G4121 | G4360 | G1271 |
| A2490 | G2455 | G4122 | G4361 | C1272 |
| A2532 | A2497 | C4164 | C4403 | A1314 |
| C2533 | C2498 | C4165 | C4404 | C1315 |
| C2534 | C2499 | U4166 | U4405 | C1316 |
| G2537 | G2502 | G4169 | G4408 | G1319 |
| C2542 | C2507 | C4174 | C4413 | U1324 |
| G2543 | G2508 | G4175 | G4414 | G1325 |
| G2588 | G2553 | G4220 | G4459 | G1370 |
| U2607 | A2572 | A4239 | A4478 | A1389 |
| C2608 | C2573 | C4240 | C4479 | C1390 |
| G2609 | G2574 | G4241 | G4480 | G1391 |
| U2610 | C2575 | U4242 | U4481 | U1392 |
| C2611 | G2576 | G4243 | G4482 | G1393 |
| A2612 | A2577 | A4244 | A4483 | A1394 |
| G2618 | G2583 | G4250 | G4489 | G1400 |
| U2619 | U2584 | U4251 | U4490 | U1401 |
| A2637 | A2602 | A4269 | A4508 | A1419 |
| G2646 | C2611 | U4278 | U4517 | U1428 |
| L3 | | | | |
| W242 | Q150 | W257 | W257 | G246 |

The residues that define the binding pocket (5.8 Å-12.6 Å shell) were determined as those residues in the 50S ribosomal subunit that are located within 5.8-12.6 angstroms of the atoms of anisomysin using the program MIDAS[a]. Conserved residues were determined by comparison between the proposed secondary structures of *H. marismortui*[b], *E. coli*[b], and *Rattus norvegicus*[c], Human[d], and Human Mitochondria[e]. Sequencealignments were determined with the program MegAlign (DNASTAR, Madison, Wisconsin, USA) using defaul parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3.
[i]GenBank accession CAA26460 for protein L3.
[j]GenBank accession P21531 for protein L3.
[k]GenBank accession NP_000964 for protein L3.
[l]GenBank accession P09001 for protein L3.

Table 12A identifies the residues in the *H. marismortui* 50S ribosomal subunit that together define at least a portion of a blasticidin binding pocket (5.8 Å shell). In addition, Table 12A identifies the corresponding residues that define at least a portion of the blasticidin binding pocket in *E. coli*, *Rattus*, human, and human mitochondria large subunit. Table 12B identifies the residues in the *H. marismortui* 50S ribosomal subunit that together define a broader portion of a blasticidin binding pocket (5.8 Å-12.6 Å shell). The non-conserved residues were identified as described previously with respect to Tables 5A and 5B.

TABLE 12A

Residues that Define the Blasticidin Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| A2007[v] | A1966 | A3538 | A3782 | A959 |
| C2104[v] | C2063 | C3634 | C3878 | C1056 |
| C2105[h,v] | C2064 | C3635 | C3879 | C1057 |
| C2106[v] | C2065 | C3636 | C3880 | C1058 |
| G2284[h,v] | G2251 | G3917 | G4156 | G1145 |
| G2285[h,v] | G2252 | G3918 | G4157 | G1146 |
| G2286[h,v] | G2253 | G3919 | G4158 | G1147 |
| C2287[v] | C2254 | C3920 | C4159 | C1148 |
| U2473[v] | U2438 | U4105 | U4344 | U1255 |
| A2474[h,v] | A2439 | A4106 | A4345 | A1256 |
| A2485[v] | A2450 | A4117 | A4356 | A1267 |
| A2486[v] | A2451 | A4118 | A4357 | A1268 |
| U2620[v] | U2585 | U4252 | U4491 | U1402 |
| G2627[v] | G2592 | G4259 | G4498 | G1409 |
| U2628[v] | U2593 | U4260 | U4499 | G1410 |
| C2629[v] | C2594 | C4261 | C4500 | C1411 |
| G2634[v] | G2599 | G4266 | G4505 | U1416 |
| A2635[h,v] | A2600 | A4267 | A4506 | C1417 |
| C2636[h,v] | C2601 | C4268 | C4507 | C1418 |
| A2637[v] | A2602 | A4269 | A4508 | A1419 |

The residues that define the binding pocket (5.8 Å shell) were determined as those residues in the 50S ribosomal subunit that are located within 5.8 angstroms of the atoms of Blasticidin using the program MIDAS[a]. Conserved residues in 23S rRNA were determined by comparison of sequences from the structure of H. marismortui 23S rRNA[b] with the corresponding aligned sequences of aligned genomic DNA encoding the homologous 23S rRNA (E. coli[c], Rattus norvegicus[d], Human[e] or Human mitochondria[f]). Sequence alignments were determined with the program MegAlign (DNASTAR, Madison, Wisconsin, USA) using default parameters.

[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[h]Indicates residue that is within hydrogen-bonding distance (3.5 Å) of the ligand; for example, see Jorgensen, WL, Nguyen, TB. (1993) J. Comput. Chem. 14: 195-205.
[v]Residues in van der Waals contact with the antibiotic are defined as those residues within rmin of any atom in the antibiotic, where rmin = 21/6 s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem.Soc., 1996, 118, 11225-11236 and Jorgensen, W. L. BOSS, Version 4.3; Yale University: New Haven, CT, 2002).

TABLE 12B

Residues that Define the Blasticidin Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| G885 | A792 | G1541 | G1620 | NP* |
| U1980 | U1939 | U3511 | U3755 | U932 |
| A1981 | U1940 | G3512 | G3756 | C933 |
| C1982 | C1941 | C3513 | C3757 | A934 |
| C2006 | C1965 | C3537 | C3781 | U958 |
| U2008 | C1967 | U3539 | U3783 | U960 |
| G2102 | G2061 | G3632 | G3876 | G1054 |
| A2103 | A2062 | A3633 | A3877 | A1055 |
| U2107 | C2066 | U3637 | U3881 | U1059 |
| G2110 | G2069 | U3640 | U3884 | G1062 |
| G2111 | A2070 | G3641 | G3885 | NP |
| A2112 | A2071 | A3642 | A3886 | NP |
| G2113 | G2072 | G3643 | G3887 | NP |
| C2114 | C2073 | C3644 | C3888 | NP |
| U2282 | U2249 | U3915 | U4154 | U1143 |
| G2283 | G2250 | G3916 | G4155 | G1144 |
| G2288 | G2255 | G3921 | G4160 | G1149 |
| G2289 | G2256 | G3922 | G4161 | A1150 |
| G2471 | G2436 | G4103 | G4342 | G1253 |
| C2472 | G2437 | U4104 | U4343 | U1254 |
| C2475 | C2440 | C4107 | C4346 | C1257 |
| C2476 | U2441 | C4108 | C4347 | C1258 |
| C2477 | C2442 | A4109 | A4348 | C1259 |
| U2478 | U2443 | C4110 | C4349 | U1260 |
| G2481 | G2446 | G4113 | G4352 | G1263 |
| G2482 | G2447 | G4114 | G4353 | G1264 |
| U2484 | U2449 | U4116 | U4355 | U1266 |
| C2487 | C2452 | C4119 | C4358 | C1269 |
| G2529 | G2494 | G4161 | G4400 | A1311 |
| C2530 | G2495 | A4162 | A4401 | C1312 |
| U2531 | C2496 | U4163 | U4402 | G1313 |
| A2532 | A2497 | C4164 | C4403 | A1314 |
| C2536 | C2501 | C4168 | C4407 | C1318 |
| U2619 | U2584 | U4251 | U4490 | U1401 |
| U2621 | U2586 | U4253 | U4492 | U1403 |
| A2622 | A2587 | A4254 | A4493 | A1404 |
| G2623 | G2588 | G4255 | G4494 | G1405 |
| A2624 | A2589 | A4256 | A4495 | A1406 |
| C2625 | A2590 | C4257 | C4496 | C1407 |
| G2630 | G2595 | G4262 | G4501 | G1412 |
| A2633 | A2598 | A4265 | A4504 | A1415 |
| G2638 | G2603 | G4270 | G4509 | G1420 |
| G2639 | U2604 | G4271 | G4510 | G1421 |
| U2640 | U2605 | U4272 | U4511 | U1422 |
| G2642 | G2607 | A4274 | A4513 | G1424 |
| G2643 | G2608 | G4275 | G4514 | G1425 |
| Protein L2 | | | | |
| G204 | G235 | G214 | G214 | W281 |
| G205 | E236 | N215 | N215 | A282 |
| R206 | G237 | H216 | H216 | G283 |
| Protein L10E | | | | |
| D109 | XX** | T113 | T113 | XX |
| G110 | XX | G114 | G114 | XX |
| M111 | XX | M115 | M115 | XX |
| R112 | XX | R116 | R116 | XX |

The residues that define the binding pocket (5.8 Å-12.6 Å shell) were determined as those residues in the 50S ribosomal subunit that are located within 5.8-12.6 angstroms of the atoms of blasticidin using the program MIDAS[a]. Conserved residues in 23S rRNA were determined by comparison of sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin,USA) using default parameters.

*NP means that no homologous residue has been identified.
**XX means that no homologous protein has been identified in that species.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession R5HS2L for protein L2; GenBank accession 15825950 for protein L10E.
[i]GenBank accession CAA26463 for protein L2; NO GenBank accession for protein L10E.
[j]GenBank accession R5RTL8 for protein L2; GenBank accession NP_112362 for protein L10E.
[k]GenBank accession NP_000964 for protein L2; GenBank accession NP_006004 for protein L10E.
[l]GenBank accession XP_004140 for protein L2; no GenBank accession for protein L10E.

Table 13A identifies the residues in the *H. marismortui* 50S ribosomal subunit that together define at least a portion of a carbomycin A binding pocket (5.8 Å shell). In addition, Table 13A identifies the corresponding residues that define at least a portion of the carbomycin A binding pocket in *E. coli*, *Rattus*, human, and human mitochondria large subunit. Further, Table 13B identifies the residues in the *H. marismortui* 50S ribosomal subunit that together define a broader portion of a carbomycin A binding pocket (5.8 Å-12.6 Å shell). The non-conserved residues were identified as described previously with respect to Tables 5A and 5B.

TABLE 13A

Residues that Define the Carbomycin A Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C839[v] | U746 | G1495 | G1574 | NP* |
| C2098[v] | G2057 | A3628 | A3872 | A1050 |
| G2099[h,v] | A2058 | G3629 | G3873 | G1051 |
| A2100[v] | A2059 | A3630 | A3874 | A1052 |
| G2102[h,v] | G2061 | G3632 | G3876 | G1054 |
| A2103[h,v] | A2062 | A3633 | A3877 | A1055 |
| C2104 | C2063 | C3634 | C3878 | C1056 |
| A2486[v] | A2451 | A4118 | A4357 | A1268 |
| C2487[v] | C2452 | C4119 | C4358 | C1269 |
| A2538[h,v] | A2503 | A4170 | A4409 | A1320 |
| U2539[m,v] | U2504 | U4171 | U4410 | U1321 |
| G2540[h,v] | G2505 | G4172 | G4411 | G1322 |
| U2541[v] | U2506 | U4173 | U4412 | U1323 |
| U2620[v] | U2585 | U4252 | U4491 | U1402 |
| C2644[v] | U2609 | U4276 | U4515 | A1426 |
| G2646[v] | C2611 | U4278 | U4517 | U1428 |
| Protein L22 | | | | |
| M130[v] | K90 | H133 | H133 | V187 |

The residues that define the binding pocket (5.8 Å shell) were determined as those residues in the 50S ribosomal subunit that are located within 5.8 angstroms of the atoms of carbomycin A using the program MIDAS[a]. Conserved residues in 23S rRNA were determined by comparison of sequences from the structure of *H. marismortui* 23S rRNA[b] with the corresponding sequences of aligned genomic DNA encoding the homologous 23S rRNA (*E. coli*[c], *Rattus norvegicus*[d], Human[e] or Human mitochondria[f]). In cases of ribosomal proteins, comparisons were also made between the *H. marismortui* structural protein sequence[g] and the corresponding sequences of aligned protein sequences encoding homologous proteins in *E. coli*[i], *Rattus norvegicus*[j], Human[k] or Human mitochondria[l]. Sequence alignments were determined with the program MegAlign (DNASTAR,Madison, Wisconsin, USA) with default parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession R5HS22 for protein L22.
[h]Indicates residue that is within hydrogen-bonding distance (3.5 Å) of the ligand; for example, see Jorgensen, WL, Nguyen, TB. (1993) J. Comput. Chem. 14: 195-205.
[i]GenBank accession CAA26465 for protein L22.
[j]GenBank accession P24049 for protein L22.
[k]GenBank accession XP_057521 for protein L22.
[l]GenBank accession XP_051279 for protein L22.
[m]This residue is actually at 5.85 Å.
[v]Residues in van der Waals contact with the antibiotic are defined as those residues within rmin of any atom in the antibiotic, where rmin = 21/6 s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem.Soc., 1996, 118, 11225-11236 and Jorgensen, W. L. BOSS, Version 4.3; Yale University: New Haven, CT, 2002).

TABLE 13B

Residues that Further Define the Carbomycin A Binding Pocket

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C633 | U576 | G1284 | G1365 | NP* |
| U835 | U744 | U1491 | U1570 | NP |
| G836 | G745 | G1492 | G1571 | NP |
| U837 | NP | A1493 | A1572 | NP |
| C838 | NP | C1494 | C1573 | NP |
| U840 | U747 | U1496 | U1575 | NP |
| A841 | G748 | G1497 | G1576 | NP |
| A843 | A750 | A1499 | A1578 | NP |
| A844 | A751 | A1500 | A1579 | NP |
| U845 | A752 | A1501 | A1580 | NP |
| A846 | A753 | U1502 | U1581 | NP |
| A882 | A789 | A1538 | A1617 | NP |
| U883 | U790 | U1539 | U1618 | NP |
| U1359 | U1255 | U2192 | U2327 | U351 |
| G1837 | U1781 | A3368 | A3612 | C831 |
| U1838 | U1782 | U3369 | U3613 | C832 |
| C2056 | A2015 | A3587 | A3831 | A1008 |
| U2057 | U2016 | C3588 | C3832 | U1009 |
| G2073 | G2032 | C3603 | C3847 | G1025 |
| A2095 | A2054 | G3625 | G3869 | A1047 |
| A2096 | C2055 | A3626 | A3870 | C1048 |
| G2097 | G2056 | A3627 | A3871 | G1049 |
| A2101 | A2060 | A3631 | A3875 | A1053 |
| C2105 | C2064 | C3635 | C3879 | C1057 |
| A2474 | A2439 | A4106 | A4345 | A1256 |
| C2476 | U2441 | C4108 | C4347 | C1258 |
| C2477 | C2442 | A4109 | A4348 | C1259 |
| U2478 | C2443 | C4110 | C4349 | U1260 |
| G2481 | G2446 | G4113 | G4352 | G1263 |
| G2482 | G2447 | G4114 | G4353 | G1264 |
| A2485 | A2450 | A4117 | A4356 | A1267 |
| A2488 | A2453 | U4120 | U4359 | A1270 |
| G2489 | G2454 | G4121 | G4360 | G1271 |
| U2534 | C2499 | U4166 | U4405 | C1316 |
| U2535 | U2500 | U4167 | U4406 | U1317 |
| C2536 | C2501 | C4168 | C4407 | C1318 |
| G2537 | G2502 | G4169 | G4408 | G1319 |
| C2542 | C2507 | C4174 | C4413 | U1324 |
| G2543 | G2508 | G4175 | G4414 | G1325 |
| U2607 | A2572 | A4239 | A4478 | A1389 |
| C2608 | C2573 | C4240 | C4479 | C1390 |
| U2610 | C2575 | U4242 | U4481 | U1392 |
| G2611 | G2576 | G4243 | G4482 | G1393 |
| A2612 | A2577 | A4244 | A4483 | A1394 |
| C2614 | C2579 | C4246 | C4485 | C1396 |
| U2615 | U2580 | U4247 | U4486 | U1397 |
| G2616 | G2581 | G4248 | G4487 | G1398 |
| G2618 | G2583 | G4250 | G4489 | G1400 |
| U2619 | U2584 | U4251 | U4490 | U1401 |
| U2621 | U2586 | U4253 | U4492 | C1403 |
| A2622 | A2587 | A4254 | A4493 | A1404 |
| A2637 | A2602 | A4269 | A4508 | A1419 |
| G2643 | G2608 | G4275 | G4514 | G1425 |
| U2645 | C2610 | U4277 | U4516 | U1427 |
| C2647 | C2612 | U4279 | U4518 | U1429 |
| L3 | | | | |
| W242 | Q150 | W257 | W257 | G246 |
| L4 | | | | |
| F61 | T53 | W67 | W67 | F72 |
| G62 | G54 | G68 | G68 | E73 |
| S63 | S55 | T69 | T69 | Q74 |
| G64 | G56 | G70 | G70 | E75 |
| R65 | K57 | R71 | R71 | R76 |
| G66 | NP | A72 | A72 | G78 |
| Q67 | NP | V73 | V73 | L79 |
| A129 | A89 | A132 | A132 | A186 |

TABLE 13B-continued

Residues that Further Define the Carbomycin A Binding Pocket

| H. marismortui Residue | Corresponding Residue in E. coli | Corresponding Residue in Rattus | Corresponding Residue in Human | Corresponding Residue in Human Mitochondria |
|---|---|---|---|---|
| G131 | G91 | G134 | G134 | A188 |
| R132 | R92 | R135 | R135 | H189 |

The residues that define the binding pocket (5.8 Å-12.6 Å shell) were determined as those residues in the 50S ribosomal subunit that are located within 5.8-12.6 angstroms of the atoms of carbomycin A using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA(E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) using default parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3; GenBank accession P12735 for protein L4.
[i]GenBank accession CAA26460 for protein L3; GenBank accession CAA26461 for protein L4.
[j]GenBank accession P21531 for protein L3; GenBank accession JC4277 for protein L4.
[k]GenBank accession NP_000958 for protein L3; GenBank accessions P36578, NP_000959, S39803, and T09551 for protein L4.
[l]GenBank accession P09001 for protein L3; GenBank accession XP_049502 for protein L4.

Table 14A identifies the residues in the H. marismortui 50S ribosomal subunit that together define at least a portion of a tylosin binding pocket (5.8 Å shell). In addition, Table 14A identifies the corresponding residues that define at least a portion of the tylosin binding pocket in E. coli, Rattus, human, and human mitochondria large subunit. Further, Table 14B identifies the residues in the H. marismortui 50S ribosomal subunit that together define a broader portion of a tylosin binding pocket (5.8 Å-12.6 Å shell). The non-conserved residues were identified as described previously with respect to Tables 5A and 5B.

TABLE 14A

Residues that Define the Tylosin Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C839[v] | U746 | G1495 | G1574 | NP* |
| A841[h,v] | G748 | G1497 | G1576 | NP |
| A843[v] | A750 | A1499 | A1578 | NP |
| A844[h,v] | A751 | A1500 | A1579 | NP |
| U845[v] | A752 | A1501 | A1580 | NP |
| A846[v] | A753 | U1502 | U1581 | NP |
| G1837 | U1781 | A3368 | A3612 | C831 |
| C2098[v] | G2057 | A3628 | A3872 | A1050 |
| G2099[h,v] | A2058 | G3629 | G3873 | G1051 |
| A2100[v] | A2059 | A3630 | A3874 | A1052 |
| G2102[v] | G2061 | G3632 | G3876 | G1054 |
| A2103[h,v] | A2062 | A3633 | A3877 | A1055 |
| A2486[v] | A2451 | A4118 | A4357 | A1268 |
| A2538[h,v] | A2503 | A4170 | A4409 | A1320 |
| U2539[v] | U2504 | U4171 | U4410 | U1321 |
| G2540[v] | G2505 | G4172 | G4411 | G1322 |
| U2541 | U2506 | U4173 | U4412 | U1323 |
| U2620[m,v] | U2585 | U4252 | U4491 | U1402 |
| C2644[v] | U2609 | U4276 | U4515 | U1426 |
| U2645[v] | C2610 | U4277 | U4516 | U1427 |
| G2646[v] | C2611 | U4278 | U4517 | U1428 |
| Protein L22 | | | | |
| M130[v] | K90 | H133 | H133 | V187 |

The residues that define the binding pocket (5.8 Å shell) were determined as those residues in the 50S ribosomal subunit that are located within 5.8 angstroms of the atoms of tylosin using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR,Madison, Wisconsin, USA) using default parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession R5HS22 for protein L22.
[h]Indicates residue that is within hydrogen-bonding distance (3.5 Å) of the ligand; for example, see Jorgensen, WL, Nguyen, TB. (1993) J. Comput. Chem. 14: 195-205.
[i]GenBank accession CAA26465 for protein L22.
[j]GenBank accession P24049 for protein L22.
[k]GenBank accession XP_057521 for protein L22.
[l]GenBank accession XP_051279 for protein L22.
[m]This residue is actually at 5.87 Å.
[v]Residues in van der Waals contact with the antibiotic are defined as those residues within rmin of any atom in the antibiotic, where rmin = 21/6 s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996,118, 11225-11236 and Jorgensen, W. L. BOSS, Version 4.3; Yale University: New Haven, CT, 2002).

TABLE 14B

Residues that Define the Tylosin Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C633 | U576 | G1284 | G1365 | NP* |
| U835 | U744 | U1491 | U1570 | NP |
| G836 | G745 | G1492 | G1571 | NP |
| U837 | NP | A1493 | A1572 | NP |
| C838 | NP | C1494 | C1573 | NP |
| U840 | U747 | U1496 | U1575 | NP |
| C842 | A749 | C1498 | C1577 | NP |
| C847 | U754 | C1503 | C1582 | NP |
| A882 | A789 | A1538 | A1617 | NP |
| U883 | U790 | U1539 | U1618 | NP |
| U1359 | U1255 | U2191 | U2327 | U351 |
| G1688 | G1613 | G2634 | G2770 | G679 |
| A1689 | A1614 | A2635 | C2771 | A680 |
| C1690 | C1615 | A2636 | A2772 | U681 |
| C1692 | C1617 | C2638 | C2774 | A683 |
| G1694 | G1619 | G2640 | G2776 | A685 |
| A1836 | A1780 | A3367 | A3611 | A830 |
| C2056 | A2015 | A3587 | A3831 | A1008 |
| U2057 | U2016 | C3588 | C3832 | U1009 |
| G2073 | G2032 | C3603 | C3847 | G1025 |
| A2095 | A2054 | G3625 | G3869 | A1047 |
| A2096 | C2055 | A3626 | A3870 | C1048 |
| G2097 | G2056 | A3627 | A3871 | G1049 |
| A2101 | A2060 | A3631 | A3875 | A1053 |
| C2104 | C2063 | C3634 | C3878 | C1056 |
| C2105 | C2064 | C3635 | C3879 | C1057 |

TABLE 14B-continued

Residues that Define the Tylosin Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| A2474 | A2439 | A4106 | A4345 | A1256 |
| C2476 | U2441 | C4108 | C4347 | C1258 |
| C2477 | C2442 | A4109 | A4348 | C1259 |
| U2478 | C2443 | C4110 | C4349 | U1260 |
| G2481 | G2446 | G4113 | G4352 | G1263 |
| G2482 | G2447 | G4114 | G4353 | G1264 |
| A2485 | A2450 | A4117 | A4356 | A1267 |
| C2487 | C2452 | C4119 | C4358 | C1269 |
| A2488 | A2453 | U4120 | U4359 | A1270 |
| U2535 | U2500 | U4167 | U4406 | U1317 |
| C2536 | C2501 | C4168 | C4407 | C1318 |
| G2537 | G2502 | G4169 | G4408 | G1319 |
| C2542 | C2507 | C4174 | C4413 | U1324 |
| U2607 | A2572 | A4239 | A4478 | A1389 |
| C2608 | C2573 | C4240 | C4479 | C1390 |
| U2610 | C2575 | U4242 | U4481 | U1392 |
| G2611 | G2576 | G4243 | G4482 | G1393 |
| A2612 | A2577 | A4244 | A4483 | A1394 |
| C2614 | C2579 | C4246 | C4485 | C1396 |
| U2615 | U2580 | U4247 | U4486 | U1397 |
| G2616 | G2581 | G4248 | G4487 | G1398 |
| G2618 | G2583 | G4250 | G4489 | G1400 |
| U2619 | U2584 | U4251 | U4490 | U1401 |
| U2621 | U2586 | U4253 | U4492 | C1403 |
| A2622 | A2587 | A4254 | A4493 | A1404 |
| G2643 | G2608 | G4275 | G4514 | G1425 |
| C2647 | C2612 | U4279 | U4518 | C1429 |
| U2648 | U2613 | A4280 | A4519 | U1430 |
| Protein L3 | | | | |
| W242 | Q150 | W257 | W257 | G246 |
| Protein L4 | | | | |
| G62 | G54 | G68 | G68 | E73 |
| S63 | S55 | T69 | T69 | Q74 |
| G64 | G56 | G70 | G70 | E75 |
| R65 | K57 | R71 | R71 | R76 |
| G66 | NP | A72 | A72 | G78 |
| Q67 | NP | V73 | V73 | L79 |
| Protein L22 | | | | |
| R128 | R88 | R131 | R131 | K184 |
| A129 | A89 | A132 | A132 | A186 |
| G131 | G91 | G134 | G134 | A188 |
| R132 | R92 | R135 | R135 | H189 |
| Protein L37E | | | | |
| T1 | XX** | M1 | M1 | XX |
| G2 | XX | T2 | T2 | XX |
| A3 | XX | K3 | K3 | XX |
| G4 | XX | G4 | G4 | XX |
| T5 | XX | T5 | T5 | XX |
| P6 | XX | S6 | S6 | XX |
| S7 | XX | S7 | S7 | XX |
| Q8 | XX | F8 | F8 | XX |

The residues that define the binding pocket (5.8 Å-12.6 Å shell) were determined as those residues in the 50S ribosomal subunit that are located within 5.8-12.6 angstroms of the atoms of tylosin using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) with default parameters.

*NP means that no homologous residue has been identified.
**XX means that no homologous protein has been identified in that species.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3; GenBank accession P12735 for protein L4; GenBank accession R5HS24 for protein L22; GenBank accession P32410 for protein L37E.
[i]GenBank accession CAA26460 for protein L3; GenBank accession CAA26461 for protein L4; GenBank accession CAA26465 for protein L22; no GenBank accession for protein L37E.
[j]GenBank accession P21531 for protein L3; GenBank accession JC4277 for protein L4; GenBank accession P24049 for protein L22; GenBank accession CAA47102 for protein L37E.
[k]GenBank accession NP_000958 for protein L3; GenBank accessions P36578, NP_000959, S39803, and T09551 for protein L4; GenBank accession XP_051279 for protein L22; GenBank accession NP_000988 for protein L37E.
[l]GenBank accession P09001 for protein L3; GenBank accession XP_049502 for protein L4; GenBank accession XP_051279 for protein L22; NO GenBank accession for protein L37E.

Table 15A identifies the residues in the H. marismortui 50S ribosomal subunit that together define at least a portion of a sparsomycin binding pocket (5.8 Å shell). In addition, Table 15A identifies the corresponding residues that define at least a portion of the sparsomycin binding pocket in E. coli, Rattus, human, and human mitochondria large subunit. Further, Table 15B identifies the residues in the H. marismortui 50S ribosomal subunit that together define a broader portion of a sparsomycin binding pocket (5.8 Å-12.6 Å shell). The non-conserved residues were identified as described previously with respect to Tables 5A and 5B.

TABLE 15A

Residues that Define the Sparsomycin Binding Pocket (5.8 Å shell)

| H. marisomortui Residue 23S rRNA | Corresponding Residue in E. coli | Corresponding Residue in Rattus | Corresponding Residue in Human | Corresponding Residue in Human Mitochondria |
|---|---|---|---|---|
| A2486[h,v] | A2451 | A4118 | A4357 | A1268 |
| C2487[v] | C2452 | C4119 | C4358 | C1269 |
| A2488[m,v] | A2453 | U4120 | U4359 | A1270 |
| G2540[m,v] | G2505 | G4172 | G4411 | G1322 |
| U2541[v] | U2506 | U4173 | U4412 | U1323 |
| C2542 | C2507 | C4174 | C4413 | U1324 |
| C2608[v] | C2573 | C4240 | C4479 | C1390 |
| U2619[h,v] | U2584 | U4251 | U4490 | U1401 |
| U2620[h,v] | U2585 | U4252 | U4491 | U1402 |

TABLE 15A-continued

Residues that Define the Sparsomycin Binding Pocket (5.8 Å shell)

| H. marisomortui Residue 23S rRNA | Corresponding Residue in E. coli | Corresponding Residue in Rattus | Corresponding Residue in Human | Corresponding Residue in Human Mitochondria |
|---|---|---|---|---|
| C2636 | C2601 | C4268 | C4507 | C1418 |
| A2637[h,v] | A2602 | A4269 | A4508 | A1419 |

The residues that define the binding pocket (5.8 Å shell) were determined as those residues in the 50S ribosomal subunit that are located within 5.8 angstroms of the atoms of sparsomycin using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). Sequence alignments were determined with the program MegAlign (DNASTAR, Madison, Wisconsin, USA) using default parameters.

[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[h]Indicates residue that is within hydrogen-bonding distance (3.5 Å) of the ligand; for example, see Jorgensen, W L, Nguyen, T B. (1993) J. Comput. Chem. 14: 195-205.
[m]Residue A2488 is actually 6.0 Å; residue G2540 is actually 5.85 Å
[v]Residues in van der Waals contact with the antibiotic are defined as those residues within rmin of any atom in the antibiotic, where rmin = 21/6s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

TABLE 15B

Residues that Define the Sparsomycin Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| G2073 | G2032 | C3603 | C3847 | G1025 |
| G2102 | G2061 | G3632 | G3876 | G1054 |
| A2103 | A2062 | A3633 | A3877 | A1055 |
| C2104 | C2063 | C3634 | C3878 | C1056 |
| C2105 | C2064 | C3635 | C3879 | C1057 |
| C2106 | C2065 | C3636 | C3880 | G1058 |
| G2284 | G2251 | G3917 | G4156 | G1145 |
| G2285 | G2252 | G3918 | G4157 | G1146 |
| G2286 | G2253 | G3919 | G4158 | G1147 |
| U2473 | U2438 | U4105 | U4344 | U1255 |
| A2474 | A2439 | A4106 | A4345 | A1256 |
| G2482 | G2447 | G4114 | G4353 | G1264 |
| A2485 | A2450 | A4117 | A4356 | A1267 |
| G2498 | C2463 | C4130 | C4369 | U1280 |
| U2527 | U2492 | U4159 | U4398 | U1309 |
| U2528 | U2493 | U4160 | U4399 | U1310 |
| G2529 | G2494 | G4161 | G4400 | A1311 |
| C2530 | G2495 | A4162 | A4401 | C1312 |
| A2532 | A2497 | C4164 | C4403 | A1314 |
| C2534 | C2499 | U4166 | U4405 | C1316 |
| U2535 | U2500 | U4167 | U4406 | U1317 |
| C2536 | C2501 | C4168 | C4407 | C1318 |
| A2538 | A2503 | A4170 | A4409 | A1320 |
| U2539 | U2504 | U4171 | U4410 | U1321 |
| G2543 | G2508 | G4175 | G4414 | G1325 |
| G2588 | G2553 | G4220 | G4459 | G1370 |
| U2589 | U2554 | U4221 | U4460 | U1371 |
| U2590 | U2555 | U4222 | U4461 | U1372 |
| U2607 | A2572 | A4239 | A4478 | A1389 |
| G2609 | G2574 | G4241 | G4480 | G1391 |
| U2610 | C2575 | U4242 | U4481 | U1392 |
| G2611 | G2576 | G4243 | G4482 | G1393 |
| G2617 | G2582 | G4249 | G4488 | A1399 |
| G2618 | G2583 | G4250 | G4489 | G1400 |
| U2621 | U2586 | U4253 | U4492 | C1403 |
| A2622 | A2587 | A4254 | A4493 | A1404 |
| G2627 | G2592 | G4259 | G4498 | G1409 |
| A2635 | A2600 | A4267 | A4506 | C1417 |
| G2638 | G2603 | G4270 | G4509 | G1420 |
| G2639 | U2604 | G4271 | G4510 | G1421 |
| U2640 | U2605 | U4272 | U4511 | U1422 |
| G2643 | G2608 | G4275 | G4514 | G1425 |
| Protein L3 | | | | |
| W242 | Q150 | W257 | W257 | G246 |

The residues that define the binding pocket (5.8 Å-12.6 Å shell) were determined as those residues in the 50S ribosomal subunit that are located within 5.8-12.6 angstroms of the atoms of sparsomycin using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) with default parameters.

[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3.
[i]GenBank accession CAA26460 for protein L3.
[j]GenBank accession P21531 for protein L3.
[k]GenBank accession NP_000958 for protein L3.
[l]GenBank accession P09001 for protein L3.

Table 16A identifies the residues in the H. marismortui 50S ribosomal subunit that together define at least a portion of a virginiamycin M binding pocket (5.8 Å shell). In addition, Table 16A identifies the corresponding residues that define at least a portion of the virginiamycin M binding pocket in E. coli, Rattus, human, and human mitochondria large subunit. Further, Table 16B identifies the residues in the H. marismortui 50S ribosomal subunit that together define a broader portion of a virginiamycin M binding pocket (5.8 Å-12.6 Å shell). The non-conserved residues were identified as described previously with respect to Tables 5A and 5B.

TABLE 16A

Residues that Define the Virginiamycin M Binding Pocket (5.8 Å shell)

| H. marismortui Residue 23S rRNA | Corresponding Residue in E. coli | Corresponding Residue in Rattus | Corresponding Residue in Human | Corresponding Residue in Human Mitochondria |
|---|---|---|---|---|
| A2100[v] | A2059 | A3630 | A3874 | A1052 |
| G2102[h,v] | G2061 | G3632 | G3876 | G1054 |
| A2103[h,v] | A2062 | A3633 | A3877 | A1055 |
| C2104[h,v] | C2063 | C3634 | C3878 | C1056 |
| C2105 | C2064 | C3635 | C3879 | C1057 |
| A2474 | A2439 | A4106 | A4345 | A1256 |
| G2482[v] | G2447 | G4114 | G4353 | G1264 |
| A2486[v] | A2451 | A4118 | A4357 | A1268 |
| C2487[v] | C2452 | C4119 | C4358 | C1269 |
| U2535[v] | U2500 | U4167 | U4406 | U1317 |
| A2538[h,v] | A2503 | A4170 | A4409 | A1320 |
| U2539[v] | U2504 | U4171 | U4410 | U1321 |
| G2540[v] | G2505 | G4172 | G4411 | G1322 |

TABLE 16A-continued

Residues that Define the Virginiamycin M Binding Pocket (5.8 Å shell)

| H. marismortui Residue 23S rRNA | Corresponding Residue in E. coli | Corresponding Residue in Rattus | Corresponding Residue in Human | Corresponding Residue in Human Mitochondria |
|---|---|---|---|---|
| U2541[v] | U2506 | U4173 | U4412 | U1323 |
| U2620[v] | U2585 | U4252 | U4491 | U1402 |

The residues that define the binding pocket (5.8 Å shell) were determined as those residues in the 50S ribosomal subunit that are located within 5.8 angstroms of the atoms of virginiamycin M using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). Sequence alignments were determined with the program MegAlign (DNASTAR, Madison, Wisconsin, USA) using default parameters.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[h]Indicates residue that is within hydrogen-bonding distance (3.5 Å) of the ligand; for example, see Jorgensen, WL, Nguyen, TB. J. Comput. Chem. (1993) 14: 195-205.
[v]Residues in van der Waals contact with the antibiotic are defined as those residues within rmin of any atom in the antibiotic, where rmin = 21/6 s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

TABLE 16B

Residues that Define the Virginiamycin M Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| A631 | A574 | G1282 | G1363 | NP* |
| A632 | A575 | C1283 | C1364 | NP |
| C633 | U576 | G1284 | G1365 | NP |
| U1838 | U1782 | U3369 | U3613 | C832 |
| G2073 | G2032 | C3603 | C3847 | G1025 |
| A2095 | A2054 | G3625 | G3869 | A1047 |
| A2096 | C2055 | A3626 | A3870 | C1048 |
| G2097 | G2056 | A3627 | A3871 | G1049 |
| C2098 | G2057 | A3628 | A3872 | A1050 |
| G2099 | A2058 | G3629 | G3873 | G1051 |
| A2101 | A2060 | A3631 | A3875 | A1053 |
| C2106 | C2065 | C3636 | C3880 | C1058 |
| U2107 | C2066 | U3637 | U3881 | U1059 |
| G2284 | G2251 | G3917 | G4156 | G1145 |
| U2473 | U2438 | U4105 | U4344 | U1255 |
| C2475 | C2440 | C4107 | C4346 | C1257 |
| C2476 | U2441 | C4108 | C4347 | C1258 |
| C2477 | C2442 | A4109 | A4348 | C1259 |
| U2478 | C2443 | C4110 | C4349 | U1260 |
| A2479 | G2444 | A4111 | A4350 | A1261 |
| G2480 | G2445 | G4112 | G4351 | G1262 |
| G2481 | G2446 | G4113 | G4352 | G1263 |
| U2484 | U2449 | U4116 | U4355 | U1266 |
| A2485 | A2450 | A4117 | A4356 | A1267 |
| A2488 | A2453 | U4120 | U4359 | A1270 |
| G2489 | G2454 | G4121 | G4360 | G1271 |
| A2532 | A2497 | C4164 | C4403 | A1314 |
| C2534 | C2499 | U4166 | U4405 | C1316 |
| C2536 | C2501 | C4168 | C4407 | C1318 |
| G2537 | C2502 | G4169 | G4408 | G1319 |
| C2542 | C2507 | C4174 | C4413 | U1324 |
| U2607 | A2572 | A4239 | A4478 | A1389 |
| C2608 | C2573 | C4240 | C4479 | C1390 |
| U2610 | C2575 | U4242 | U4481 | U1392 |
| G2611 | G2576 | G4243 | G4482 | G1393 |
| A2612 | A2577 | A4244 | A4483 | A1394 |
| G2618 | G2583 | G4250 | G4489 | G1400 |
| U2619 | U2584 | U4251 | U4490 | U1401 |
| U2621 | U2586 | U4253 | U4492 | C1403 |
| A2622 | A2587 | A4254 | A4493 | A1404 |
| C2636 | C2601 | C4268 | C4507 | C1418 |
| A2637 | A2602 | A4269 | A4508 | A1419 |
| G2643 | G2608 | G4275 | G4514 | G1425 |
| C2644 | U2609 | U4276 | U4515 | U1426 |
| U2645 | C2610 | U4277 | U4516 | U1427 |
| G2646 | C2611 | U4278 | U4517 | U1428 |
| L3 | | | | |
| W242 | Q150 | W257 | W257 | G246 |

The residues that define the binding pocket (5.8 Å-12.6 Å shell) were determined as those residues in the 50S ribosomal subunit that are located within 5.8-12.6 angstroms of the atoms of virginiamycin M using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) with default parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3.
[i]GenBank accession CAA26460 for protein L3.
[j]GenBank accession P21531 for protein L3.
[k]GenBank accession NP_000958 for protein L3.
[l]GenBank accession P09001 for protein L3.

Table 17A identifies the residues in the H. marismortui 50S ribosomal subunit that together define at least a portion of a spiramycin binding pocket (5.8 Å shell). In addition, Table 17A identifies the corresponding residues that define at least a portion of the spiramycin binding pocket in E. coli, Rattus, human, and human mitochondria large subunit. Further, Table 17B identifies the residues in the H. marismortui 50S ribosomal subunit that together define a broader portion of a spiramycin binding pocket (5.8 Å-12.6 Å shell). The non-conserved residues were identified as described previously with respect to Tables 5A and 5B.

TABLE 17A

Residues that Define the Spiramycin Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C839[v] | U746 | G1495 | G1574 | NP* |
| C2098 | G2057 | A3628 | A3872 | A1050 |
| G2099[h,v] | A2058 | G3629 | G3873 | G1051 |
| A2100[v] | A2059 | A3630 | A3874 | A1052 |
| G2102[v] | G2061 | G3632 | G3876 | G1054 |
| A2103[h,v] | A2062 | A3633 | A3877 | A1055 |
| A2538[v] | A2503 | A4170 | A4409 | A1320 |
| U2539[v] | U2504 | U4171 | U4410 | U1321 |

TABLE 17A-continued

Residues that Define the Spiramycin Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| G2540[h,v] | G2505 | G4172 | G4411 | G1322 |
| U2541[v] | U2506 | U4173 | U4412 | U1323 |
| U2620[m,v] | U2585 | U4252 | U4491 | U1402 |
| C2644 | U2609 | U4276 | U4515 | U1426 |
| G2646[v] | C2611 | U4278 | U4517 | U1428 |
| L4 | | | | |
| S63[v] | S55 | T69 | T69 | Q74 |
| G64[v] | G56 | G70 | G70 | E75 |
| R65[v] | K57 | R71 | R71 | R76 |
| L22 | | | | |
| M130[m,v] | K90 | H133 | H133 | V187 |

The residues that define the binding pocket (5.8 Å shell) were determined as those residues in the 50S ribosomal subunit that are located within 5.8 angstroms of the atoms of spiramycin using the program MIDAS[a]. Conserved residues were determined by comparison between the proposed secondary structures of H. marismortui[b], E. coli[b], and Rattus norvegicus[c], Human[d], and Human Mitochondria[e]. Sequence alignments were determined with the program MegAlign (DNASTAR, Madison, Wisconsin, USA) using defaul parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession P12735 for protein L4; GenBank accession R5HS24 for protein L22.
[h]Indicates residue that is within hydrogen-bonding distance (3.5 Å) of the ligand; for example, see Jorgensen, WL, Nguyen, TB. (1993) J. Comput. Chem. 14: 195-205.
[i]GenBank accession CAA26461 for protein L4; GenBank accession CAA26465 for protein L22.
[j]GenBank accession JC4277 for protein L4; GenBank accession P24049 for protein L22
[k]GenBank accessions P36578, NP_000959, S39803, and T09551 for protein L4; GenBank accession XP_051279 for protein L22.
[l]GenBank accession XP_049502 for protein L4; GenBank accession XP_051279 for protein L22.
[m]Residue U2620 is actually at 5.83 Å; M130 is actually at 5.87 Å.
[v]Residues in van der Waals contact with the antibiotic are defined as those residues within rmin of any atom in the antibiotic, where rmin = 21/6s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

TABLE 17B

Residues that Define the Spiramycin Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| A766 | A675 | A1424 | A1502 | NP* |
| A767 | A676 | A1425 | A1503 | NP |
| U835 | U744 | U1491 | U1570 | NP |
| G836 | G745 | G1492 | G1571 | NP |
| U837 | NP | A1493 | A1572 | NP |
| C838 | NP | C1494 | C1573 | NP |
| U840 | U747 | U1496 | U1575 | NP |
| A841 | G748 | G1497 | G1576 | NP |
| A843 | A750 | A1499 | A1578 | NP |
| A844 | A751 | A1500 | A1579 | NP |
| U845 | A752 | A1501 | A1580 | NP |
| A846 | A753 | U1502 | U1581 | NP |
| A882 | A789 | A1538 | A1617 | NP |
| U883 | U790 | U1539 | U1618 | NP |
| C884 | C791 | C1540 | C1619 | NP |
| U1359 | U1255 | U2192 | U2327 | U351 |
| G1837 | U1781 | A3368 | A3612 | C831 |
| U1838 | U1782 | U3369 | U3612 | C832 |
| C2056 | A2015 | A3587 | A3831 | A1008 |
| U2057 | U2016 | C3588 | C3832 | U1009 |
| G2073 | G2032 | C3603 | C3847 | G1025 |
| A2095 | A2054 | G3625 | G3869 | A1047 |
| G2097 | G2056 | A3627 | A3871 | G1049 |
| A2101 | A2060 | A3631 | A3875 | A1053 |
| C2104 | C2063 | C3634 | C3878 | C1056 |
| C2105 | C2064 | C3625 | C3879 | C1057 |
| A2474 | A2439 | A4106 | A4345 | A1256 |
| C2476 | U2441 | C4108 | C4347 | C1258 |
| C2477 | C2442 | A4109 | A4348 | C1259 |
| U2478 | C2443 | C4110 | C4349 | U1260 |
| A2479 | G2444 | A4111 | A4350 | A1261 |
| G2481 | G2446 | G4113 | G4352 | G1263 |
| G2482 | G2447 | G4114 | G4353 | G1264 |
| A2485 | A2450 | A4117 | A4356 | A1267 |
| A2486 | A2451 | A4118 | A4357 | A1268 |
| C2487 | C2452 | C4119 | C4358 | C1269 |
| A2488 | A2453 | U4120 | U4359 | A1270 |
| U2535 | U2500 | U4167 | U4406 | U1317 |
| C2536 | C2501 | C4168 | C4407 | C1318 |
| G2537 | G2502 | G4169 | G4408 | G1319 |
| C2542 | C2507 | C4174 | C4413 | U1324 |
| U2607 | A2572 | A4239 | A4478 | A1389 |
| C2608 | C2573 | C4240 | C4479 | C1390 |
| U2610 | C2575 | U4242 | U4481 | U1392 |
| G2611 | G2576 | G4243 | G4482 | G1393 |
| A2612 | A2577 | A4244 | A4483 | A1394 |
| C2614 | C2579 | C4246 | C4485 | C1396 |
| U2615 | U2580 | U4247 | U4486 | U1397 |
| G2616 | G2581 | G4248 | G4487 | G1398 |
| G2618 | G2583 | G4250 | G4489 | G1400 |
| U2619 | U2584 | U4251 | U4490 | U1401 |
| U2621 | U2586 | U4253 | U4492 | C1403 |
| G2643 | G2608 | G4275 | G4514 | G1425 |
| U2645 | C2610 | U4277 | U4516 | U1427 |
| C2647 | C2612 | U4279 | U4518 | C1429 |
| U2648 | U2613 | A4280 | A4519 | U1430 |
| Protein L3 | | | | |
| W242 | Q150 | W257 | W257 | G246 |
| Protein L4 | | | | |
| S60 | V52 | S66 | S66 | G71 |
| F61 | T53 | W67 | W67 | F72 |
| G62 | G54 | G68 | G68 | E73 |
| G66 | NP | A72 | A72 | G78 |
| Q67 | NP | V73 | V73 | L79 |
| A68 | NP | A74 | A74 | A80 |
| H69 | K58 | R75 | R75 | D81 |

TABLE 17B-continued

Residues that Define the Spiramycin Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| Protein L22 | | | | |
| A129 | A89 | A132 | A132 | A186 |
| G131 | G91 | G134 | G134 | A188 |
| R132 | R92 | R135 | R135 | H189 |

The residues that define the binding pocket (5.8 Å-12.6 Å shell) were determined as those residues in the 50S ribosomal subunit that are located within 5.8-12.6 angstroms of the atoms of spiramycin using the program MIDAS$^a$. Conserved residues in 23S rRNA were determined by comparison of sequences from the structure of H. marismortui 23S rRNA$^b$ with the corresponding sequences of aligned genomic DNA encoding the homologous 23S rRNA (E. coli$^c$, Rattus norvegicus$^d$, Human$^e$ or Human mitochondria$^f$). In cases of ribosomal proteins, comparisons were also made between the H. marismortui structural protein sequence$^g$ and the corresponding sequences of aligned protein sequences encoding homologous proteins in E. coli$^i$, Rattus norvegicus$^j$, Human$^k$ or Human mitochondria$^l$. Sequence alignments were determined with the program MegAlign (DNASTAR, Madison, Wisconsin, USA) using default parameters.

*NP means that no homologous residue has been identified.

$^a$T. E. Ferrin, C. C. Huang, L. E. Jarvis, and R. Langridge (1988) "The MIDAS Display System" J. Mol. Graphics, 6(1): 13-27, 36-37.
$^b$GenBank accession AF034619
$^c$GenBank accession J01695
$^d$GenBank accession 2624399
$^e$GenBank accession M11167
$^f$GenBank accession 13683
$^g$GenBank accession AAA86859 for protein L3; GenBank accession P12735 for protein L4; GenBank accession R5HS24 for protein L22.
$^h$Indicates residue that is within hydrogen-bonding distance (3.5 Å) of the ligand; for example, see Jorgensen, WL, Nguyen, TB. (1993) J. Comput. Chem. 14: 195-205.
$^i$GenBank accession CAA26460 for protein L3; GenBank accession CAA26461 for protein L4; GenBank accession CAA26465 for protein L22.
$^j$GenBank accession P21531 for protein L3; GenBank accession JC4277 for protein L4; GenBank accession P24049 for protein L22.
$^k$GenBank accession NP_000958 for protein L3; GenBank accessions P36578, NP_000959, S39803, and T09551 for protein L4; GenBank accession XP_051279 for protein L22.
$^l$GenBank accession P09001 for protein L3; GenBank accession XP_049502 for protein L4; GenBank accession XP_051279 for protein L22.
$^v$Residues in van der Waals contact with the antibiotic are defined as those residues within rmin of any atom in the antibiotic, where rmin = 21/6s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

Table 18A identifies the residues in the H. marismortui 50S ribosomal subunit that together define at least a portion of an erythromycin binding pocket (5.8 Å shell). In addition, Table 18A identifies the corresponding residues that define at least a portion of the erythromycin binding pocket in E. coli, Rattus, human, and human mitochondria large subunit. Further, Table 18B identifies the residues in the H. marismortui 50S ribosomal subunit that together define a broader portion of a erythromycin binding pocket (5.8 Å-12.6 Å shell). The non-conserved residues were identified as described previously with respect to Tables 5A and 5B.

TABLE 18A

Residues that Define the Erythromycin Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| C839$^v$ | U746 | G1495 | G1574 | NP* |
| A841$^v$ | G748 | G1497 | G1576 | NP |
| C2098$^{m,v}$ | G2057 | A3628 | A3872 | A1050 |
| G2099$^{h,v}$ | A2058 | G3629 | G3873 | G1051 |
| A2100$^v$ | A2059 | A3630 | A3874 | A1052 |
| A2103$^v$ | A2062 | A3633 | A3877 | A1055 |
| A2538$^v$ | A2503 | A4170 | A4409 | A1320 |
| G2540$^v$ | G2505 | G4172 | G4411 | G1322 |
| C2644$^v$ | U2609 | U4276 | U4515 | U1426 |
| U2645$^v$ | C2610 | U4277 | U4516 | U1427 |
| G2646$^v$ | C2611 | U4278 | U4517 | U1428 |
| L4 | | | | |
| G64$^v$ | G56 | G70 | G70 | E75 |
| L22 | | | | |
| M130$^{m,v}$ | K90 | H133 | H133 | V187 |

The residues that define the binding pocket (5.8 Å shell) were determined as those residues in the 50S ribosomal subunit that are located within 5.8 angstroms of the atoms of erythromycin using the program MIDAS$^a$. Conserved residues in 23S rRNA were determined by comparison of sequences from the structure of H. marismortui 23S rRNA$^b$ with the corresponding sequences of aligned genomic DNA encoding the homologous 23S rRNA (E. coli$^c$, Rattus norvegicus$^d$, Human$^e$ or Human mitochondria$^f$). In cases of ribosomal proteins, comparisons were also made between the H. marismortui structural protein sequence$^g$ and the corresponding sequences of aligned protein sequences encoding homologous proteins in E. coli$^i$, Rattus norvegicus$^j$, Human$^k$ or Human mitochondria$^l$. Sequence alignments were determined with the program MegAlign (DNASTAR, Madison, Wisconsin, USA) using default parameters.

*NP means that no homologous residue has been identified.

$^a$T. E. Ferrin, C. C. Huang, L. E. Jarvis, and R. Langridge (1988) "The MIDAS Display System" J. Mol. Graphics, 6(1): 13-27, 36-37.
$^b$GenBank accession AF034619
$^c$GenBank accession J01695
$^d$GenBank accession 2624399
$^e$GenBank accession M11167
$^f$GenBank accession 13683
$^g$GenBank accession P12735 for protein L4; GenBank accession R5HS24 for protein L22.
$^h$Indicates residue that is within hydrogen-bonding distance (3.5 Å) of the ligand; for example, see Jorgensen, WL, Nguyen, TB. (1993) J. Comput. Chem. 14: 195-205.
$^i$GenBank accession CAA26461 for protein L4; GenBank accession CAA26465 for protein L22.
$^j$GenBank accession JC4277 for protein L4; GenBank accession P24049 for protein L22
$^k$GenBank accessions P36578, NP_000959, S39803, and T09551 for protein L4; GenBank accession XP_051279 for protein L22.
$^l$GenBank accession XP_049502 for protein L4; GenBank accession XP_051279 for protein L22.
$^m$Residue C2098 is actually at 5.99 Å; M130 is at 5.90 Å.
$^v$Residues in van der Waals contact with the antibiotic are defined as those residues within rmin of any atom in the antibiotic, where rmin = 21/6s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

TABLE 18B

Residues that Further Define the Erythromycin Binding Pocket

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C633 | U576 | G1284 | G1365 | NP* |
| U835 | U744 | U1491 | U1570 | NP |
| G836 | G745 | G1492 | G1571 | NP |
| U837 | NP | A1493 | A1572 | NP |
| C838 | NP | C1494 | C1573 | NP |
| U840 | U747 | U1496 | U1575 | NP |
| A843 | A750 | A1499 | A1578 | NP |
| A844 | A751 | A1500 | A1579 | NP |
| U845 | A752 | A1501 | A1580 | NP |
| A846 | A753 | U1502 | U1581 | NP |
| C847 | U754 | C1503 | C1582 | NP |
| U1359 | U1255 | U2191 | U2327 | U351 |
| G1837 | U1781 | A3368 | A3612 | C831 |
| U1838 | U1782 | U3369 | U3613 | C832 |

TABLE 18B-continued

Residues that Further Define the Erythromycin Binding Pocket

| H. marismortui Residue | Corresponding Residue in E. coli | Corresponding Residue in Rattus | Corresponding Residue in Human | Corresponding Residue in Human Mitochondria |
|---|---|---|---|---|
| C2056 | A2015 | A3587 | A3831 | A1008 |
| U2057 | U2016 | C3588 | C3832 | U1009 |
| A2096 | C2055 | A3626 | A3870 | C1048 |
| G2097 | G2056 | A3627 | A3871 | G1049 |
| A2101 | A2060 | A3631 | A3875 | A1053 |
| G2102 | G2061 | G3632 | G3876 | G1054 |
| C2104 | C2063 | C3634 | C3878 | C1056 |
| C2105 | C2064 | C3635 | C3879 | C1057 |
| A2474 | A2439 | A4106 | A4345 | A1256 |
| C2476 | U2441 | C4108 | C4347 | C1258 |
| C2477 | C2442 | A4109 | A4348 | C1259 |
| U2478 | C2443 | C4110 | C4349 | U1260 |
| G2482 | G2447 | G4114 | G4353 | G1264 |
| A2486 | A2451 | A4118 | A4357 | A1268 |
| C2487 | C2452 | C4119 | C4358 | C1269 |
| U2535 | U2500 | U4167 | U4406 | U1317 |
| C2536 | C2501 | C4168 | C4407 | C1318 |
| G2537 | G2502 | G4169 | G4408 | G1319 |
| U2539 | U2504 | U4171 | U4410 | U1321 |
| U2541 | U2506 | U4173 | U4412 | U1323 |
| C2542 | C2507 | C4174 | C4413 | U1324 |
| G2543 | G2508 | G4175 | G4414 | G1325 |
| G2611 | G2576 | G4243 | G4482 | G1393 |
| A2612 | A2577 | A4244 | A4483 | A1394 |
| G2613 | G2578 | G4245 | G4484 | U1395 |
| C2614 | C2579 | C4246 | C4485 | C1396 |
| U2615 | U2580 | U4247 | U4486 | U1397 |
| G2616 | G2581 | G4248 | G4487 | G1398 |
| G2617 | G2582 | G4249 | G4488 | A1399 |
| G2618 | G2583 | G4250 | G4489 | G1400 |
| U2619 | U2584 | U4251 | U4490 | U1401 |
| U2620 | U2585 | U4252 | U4491 | U1402 |
| U2621 | U2586 | U4253 | U4492 | C1403 |
| A2622 | A2587 | A4254 | A4493 | A1404 |
| G2643 | G2608 | G4275 | G4514 | G1425 |
| C2647 | C2612 | U4279 | U4518 | C1429 |
| U2648 | U2613 | A4280 | A4519 | U1430 |
| Protein L3 | | | | |
| W242 | Q150 | W257 | W257 | G246 |
| Protein L4 | | | | |
| G62 | G54 | G68 | G68 | E73 |
| S63 | S55 | T69 | T69 | Q74 |
| R65 | K57 | R71 | R71 | R76 |
| Q67 | NP* | A72 | A72 | D78 |
| Protein L22 | | | | |
| A129 | A89 | A132 | A132 | A186 |
| G131 | G91 | G134 | G134 | A188 |
| R132 | R92 | R135 | R135 | H189 |

The residues that define the binding pocket (5.8 Å-12.6 Å shell) were determined as those residues in the 50S ribosomal subunit that are located within 5.8-12.6 angstroms of the atoms of erythromycin using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) using default parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3; GenBank accession P12735 for protein L4; GenBank accession R5HS24 for protein L22.
[h]Indicates residue that is within hydrogen-bonding distance (3.5 Å) of the ligand; for example, see Jorgensen, WL, Nguyen, TB. (1993) J. Comput. Chem. 14: 195-205.
[i]GenBank accession CAA26460 for protein L3; GenBank accession CAA26461 for protein L4; GenBank accession CAA26465 for protein L22.
[j]GenBank accession P21531 for protein L3; GenBank accession JC4277 for protein L4; GenBank accession P24049 for protein L22.
[k]GenBank accession NP_000958 for protein L3; GenBank accessions P36578 NP_000959, S39803, and T09551 for protein L4; GenBank accession XP_051279 for protein L22.
[l]GenBank accession P09001 for protein L3; GenBank accession XP_049502 for protein L4; GenBank accession XP_051279 for protein L22.
[v]Residues in van der Waals contact with the antibiotic are defined as those residues within rmin of any atom in the antibiotic, where rmin = 21/6 s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

Table 19A identifies the residues in the H. marismortui 50S ribosomal subunit that together define at least a portion of an azithromycin binding pocket (5.8 Å shell). In addition, Table 19A identifies the corresponding residues that define at least a portion of the azithromycin binding pocket in E. coli, Rattus, human, and human mitochondria large subunit. Table 19B identifies the residues in the H. marismortui 50S ribosomal subunit that together define a broader portion of a azithromycin binding pocket (5.8 Å-12.6 Å shell). The non-conserved residues were identified as described previously with respect to Tables 5A and 5B.

TABLE 19A

Residues that Define the Azithromycin Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23SrRNA | | | | |
| C839[v] | U746 | G1495 | G1574 | NP* |
| G2099[h,v] | A2058 | G3629 | G3873 | G1051 |

TABLE 19A-continued

Residues that Define the Azithromycin Binding Pocket (5.8 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| A2100[v] | A2059 | A3630 | A3874 | A1052 |
| A2103[v] | A2062 | A3633 | A3877 | A1055 |
| A2538[v] | A2503 | A4170 | A4409 | A1320 |
| G2540[v] | G2505 | G4172 | G4411 | G1322 |
| U2541[m,v] | U2506 | U4173 | U4412 | U1323 |
| C2644[v] | U2609 | U4276 | U4515 | U1426 |
| U2645[v] | C2610 | U4277 | U4516 | U1427 |
| G2646[v] | C2611 | U4278 | U4517 | U1428 |
| Protein L22 | | | | |
| M130[m,v] | K90 | H133 | H133 | V187 |

The residues that define the binding pocket (5.8 Å shell) were determined as those residues in the 50S ribosomal subunit that are located within 5.8 angstroms of the atoms of azithromycin using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) using default parameters.

*NP means that no homologous residue has been identified.

[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession R5HS24 for protein L22.
[h]Indicates residue that is within hydrogen-bonding distance (3.5 Å) of the ligand; for example, see Jorgensen, WL, Nguyen, TB. (1993) J. Comput. Chem. 14: 195-205.
[i]GenBank accession CAA26465 for protein L22.
[j]GenBank accession P24049 for protein L22.
[k]GenBank accession XP_051279 for protein L22.
[l]GenBank accession XP_051279 for protein L22.
[m]Residue U2541 is actually at 5.93 Å; M130 is at 5.95 Å.
[v]Residues in van der Waals contact with the antibiotic are defined as those residues within rmin of any atom in the antibiotic, where rmin = 21/6s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

TABLE 19B

Residues that Further Define the Azithromycin Binding Pocket

| H. marismortui Residue | Corresponding Residue in E. coli | Corresponding Residue in Rattus | Corresponding Residue in Human | Corresponding Residue in Human Mitochondria |
|---|---|---|---|---|
| 23S rRNA | | | | |
| C633 | U576 | G1284 | G1365 | NP* |
| U835 | U744 | U1491 | U1570 | NP |
| G836 | G745 | G1492 | G1571 | NP |
| U837 | NP | A1493 | A1572 | NP |
| C838 | NP | C1494 | C1573 | NP |
| U840 | U747 | U1496 | U1575 | NP |
| A841 | G748 | G1497 | G1576 | NP |
| A843 | A750 | A1499 | A1578 | NP |
| A844 | A751 | A1500 | A1579 | NP |
| U845 | A752 | A1501 | A1580 | NP |
| A846 | A753 | U1502 | U1581 | NP |
| C847 | U754 | C1503 | C1582 | NP |
| U1359 | U1255 | U2191 | U2327 | U351 |
| G1837 | U1781 | A3368 | A3612 | C831 |
| U1838 | U1782 | U3369 | U3613 | C832 |
| C2056 | A2015 | A3587 | A3831 | A1008 |
| U2057 | U2016 | C3588 | C3832 | U1009 |
| A2096 | C2055 | A3626 | A3870 | C1048 |
| G2097 | G2056 | A3627 | A3871 | G1049 |
| C2098 | G2057 | A3628 | A3872 | A1050 |
| A2101 | A2060 | A3631 | A3875 | A1053 |
| G2102 | G2061 | G3632 | G3876 | G1054 |
| C2104 | C2063 | C3634 | C3878 | C1056 |
| C2105 | C2064 | C3635 | C3879 | C1057 |
| A2474 | A2439 | A4106 | A4345 | A1256 |
| C2476 | U2441 | C4108 | C4347 | C1258 |
| C2477 | C2442 | A4109 | A4348 | C1259 |
| U2478 | C2443 | C4110 | C4349 | U1260 |
| G2481 | G2446 | G4113 | G4352 | G1263 |
| G2482 | G2447 | G4114 | G4353 | G1264 |
| A2486 | A2451 | A4118 | A4357 | A1268 |
| C2487 | C2452 | C4119 | C4358 | C1269 |
| U2535 | U2500 | U4167 | U4406 | U1317 |
| C2536 | C2501 | C4168 | C4407 | C1318 |
| G2537 | G2502 | G4169 | G4408 | G1319 |
| U2539 | U2504 | U4171 | U4410 | U1321 |
| C2542 | C2507 | C4174 | C4413 | U1324 |
| G2543 | G2508 | G4175 | G4414 | G1325 |
| U2607 | A2572 | A4239 | A4478 | A1389 |
| G2611 | G2576 | G4243 | G4482 | G1393 |
| A2612 | A2577 | A4244 | A4483 | A1394 |
| G2613 | G2578 | G4245 | G4484 | U1395 |
| C2614 | C2579 | C4246 | C4485 | C1396 |
| U2615 | U2580 | U4247 | U4486 | U1397 |
| G2616 | G2581 | G4248 | G4487 | G1398 |
| G2617 | G2582 | G4249 | G4488 | A1399 |
| G2618 | G2583 | G4250 | G4489 | G1400 |
| U2619 | U2584 | U4251 | U4490 | U1401 |
| U2620 | U2585 | U4252 | U4491 | U1402 |
| U2621 | U2586 | U4253 | U4492 | C1403 |
| A2622 | A2587 | A4254 | A4493 | A1404 |
| G2643 | G2608 | G4275 | G4514 | G1425 |
| C2647 | C2612 | U4279 | U4518 | C1429 |
| U2648 | U2613 | A4280 | A4519 | U1430 |
| Protein L3 | | | | |
| W232 | S139 | NP | NP | T236 |
| W242 | Q150 | W257 | W257 | G246 |
| Protein L4 | | | | |
| G62 | G54 | G68 | G68 | E73 |
| S63 | S55 | T69 | T69 | Q74 |
| G64 | G56 | G70 | G70 | E75 |
| R65 | K57 | R71 | R71 | R76 |
| G66 | NP | A72 | A72 | G78 |
| Q67 | NP | V73 | V73 | L79 |

TABLE 19B-continued

Residues that Further Define the Azithromycin Binding Pocket

| H. marismortui Residue | Corresponding Residue in E. coli | Corresponding Residue in Rattus | Corresponding Residue in Human | Corresponding Residue in Human Mitochondria |
|---|---|---|---|---|
| Protein L22 | | | | |
| A129 | A89 | A132 | A132 | A186 |
| G131 | G91 | G134 | G134 | A188 |
| R132 | R92 | R135 | R135 | H189 |

The residues that define the binding pocket (5.8 Å-12.6 Å shell) were determined as those residues in the 50S ribosomal subunit that are located within 5.8-12.6 angstroms of the atoms of azithromycin using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) with default parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3; GenBank accession P12735 for protein L4; GenBank accession R5HS24 for protein L22.
[h]Indicates residue that is within hydrogen-bonding distance (3.5 Å) of the ligand; for example, see Jorgensen, WL, Nguyen, TB. (1993) J. Comput. Chem. 14: 195-205.
[i]GenBank accession CAA26460 for protein L3; GenBank accession CAA26461 for protein L4; GenBank accession CAA26465 for protein L22.
[j]GenBank accession P21531 for protein L3; GenBank accession JC4277 for protein L4; GenBank accession P24049 for protein L22.
[k]GenBank accession NP_000958 for protein L3; GenBank accessions P36578, NP_000959, S39803, and T09551 for protein L4; GenBank accession XP_051279 for protein L22.
[l]GenBank accession P09001 for protein L3; GenBank accession XP_049502 for protein L4; GenBank accession XP_051279 for protein L22.
[v]Residues in van der Waals contact with the antibiotic are defined as those residues within rmin of any atom in the antibiotic, where rmin = 21/6s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

Table 20A identifies the residues in the H. marismortui 50S ribosomal subunit that together define at least a portion of a linezolid binding pocket (5.8 Å shell). In addition, Table 20A identifies the corresponding residues that define at least a portion of the linezolid binding pocket in E. coli, Rattus, human, and human mitochondria large subunit. Table 20B identifies the residues in the H. marismortui 50S ribosomal subunit that together define a broader portion of a linezolid binding pocket (5.8 Å-12.6 Å shell). The non-conserved residues were identified as described previously with respect to Tables 5A and 5B.

TABLE 20A

Residues that Define the Linezolid Binding Pocket (5.8 Å shell)

| H. marismortui Residue 23S rRNA | Corresponding Residue in E. coli | Corresponding Residue in Rattus | Corresponding Residue in Human | Corresponding Residue in Human Mitochondria |
|---|---|---|---|---|
| A2100[v] | A2059 | A3630 | A3874 | A1052 |
| G2102[v] | G2061 | G3632 | G3876 | G1054 |
| A2103[v] | A2062 | A3633 | A3877 | A1055 |
| G2482[v] | G2447 | G4114 | G4353 | G1264 |
| A2486[v] | A2451 | A4118 | A4357 | A1268 |
| C2487[h,v] | C2452 | C4119 | C4358 | C1269 |
| A2488[v] | A2453 | U4120 | U4359 | A1270 |
| U2535[v] | U2500 | U4167 | U4406 | U1317 |
| A2538[v] | A2503 | A4170 | A4409 | A1320 |
| U2539[h,v] | U2504 | U4171 | U4410 | U1321 |
| G2540[h,v] | G2505 | G4172 | G4411 | G1322 |
| U2541[h,v] | U2506 | U4173 | U4412 | U1323 |
| C2542[v] | C2507 | C4174 | C4413 | U1324 |
| U2619[v] | U2584 | U4251 | U4490 | U1401 |
| U2620[v] | U2585 | U4252 | U4491 | U1402 |

The residues that define the binding pocket (5.8 Å shell) were determined as those residues in the 50S ribosomal subunit that are located within 5.8 angstroms of the atoms of linezolid using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). Sequence alignments were determined with the program MegAlign (DNASTAR, Madison, Wisconsin, USA) with default parameters.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[h]Indicates residue that is within hydrogen-bonding distance (3.5 Å) of the ligand; for example, see Jorgensen, WL, Nguyen, TB. (1993) J. Comput. Chem. 14: 195-205.
[v]Residues in van der Waals contact with the antibiotic are defined as those residues within rmin of any atom in the antibiotic, where rmin = 21/6s and is the minimum in the Lennard-Jones pair potential (see Computer Simulation of Liquids; Allen, M. P. and Tildesley, D. J.; Oxford University Press: New York, 1992, 11.). The Lennard-Jones ss are taken from the OPLS-AA force field (see, Jorgensen, W. L.; Maxwell, D. S. and Tirado-Rives, J. J. Am. Chem. Soc., 1996, 118, 11225-11236 and Jorgensen, W. L. BOSS, Version 4.3; Yale University: New Haven, CT, 2002).

TABLE 20B

Residues that Further Define the Linezolid Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| 23s rRNA | | | | |
| A631 | A574 | G1282 | G1363 | NP* |
| A632 | A575 | C1283 | C1364 | NP |
| C633 | U576 | G1284 | G1365 | NP |
| G2073 | G2032 | C3603 | C3847 | G1025 |
| G2094 | G2053 | G3624 | G3868 | G1046 |
| A2095 | A2054 | G3625 | G3869 | A1047 |
| A2096 | C2055 | A3626 | A3870 | C1048 |
| G2097 | G2056 | A3627 | A3871 | G1049 |
| C2098 | C2057 | A3628 | A3872 | A1050 |
| G2099 | A2058 | G3629 | G3873 | G1051 |
| A2101 | A2060 | A3631 | A3875 | A1053 |
| C2104 | C2063 | C3634 | C3878 | C1056 |
| C2105 | C2064 | C3635 | C3879 | C1057 |
| A2474 | A2439 | A4106 | A4345 | A1256 |
| G2480 | G2445 | G4112 | G4351 | G1262 |
| G2481 | G2446 | G4113 | G4352 | G1263 |
| A2485 | A2450 | A4117 | A4356 | A1267 |
| G2489 | G2454 | G4121 | G4360 | G1271 |
| U2528 | U2493 | U4160 | U4399 | U1310 |
| G2529 | G2494 | G4161 | G4400 | A1311 |
| C2534 | C2499 | U4166 | U4405 | C1316 |
| C2536 | C2501 | C4168 | C4407 | C1318 |
| G2537 | G2502 | G4169 | G4408 | G1319 |
| G2543 | G2508 | G4175 | G4414 | G1325 |
| G2588 | G2553 | G4220 | G4459 | G1370 |
| U2607 | A2572 | A4239 | A4478 | A1389 |
| C2608 | C2573 | C4240 | C4479 | C1390 |
| G2609 | G2574 | G4241 | G4480 | G1391 |
| U2610 | G2575 | U4242 | U4481 | U1392 |
| G2611 | G2576 | G4243 | G4482 | G1393 |
| A2612 | A2577 | A4244 | A4483 | A1394 |
| G2616 | G2581 | G4248 | G4487 | G1398 |
| G2617 | G2582 | G4249 | G4488 | A1399 |
| G2618 | G2583 | G4250 | G4489 | G1400 |

TABLE 20B-continued

Residues that Further Define the Linezolid Binding Pocket
(5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| U2621 | U2586 | U4253 | U4492 | C1403 |
| A2637 | A2602 | A4269 | A4508 | A1419 |
| U2645 | C2610 | U4277 | U4516 | U1427 |
| G2646 | C2611 | U4278 | U4517 | U1428 |
| Protein L3 | | | | |
| W242 | Q150 | W257 | W257 | G246 |

The residues that define the binding pocket (5.8 Å-12.6 Å shell) were determined as those residues in the 50S ribosomal subunit that are located within 5.8-12.6 angstroms of the atoms of linezolid using the program MIDAS[a]. Conserved residues in 23S rRNA were determined by comparison of sequences from the structure of H. marismortui 23S rRNA[b] with the corresponding sequences of aligned genomic DNA encoding the homologous 23S rRNA (E. coli[c], Rattus norvegicus[d], Human[e] or Human mitochondria[f]). In cases of ribosomal proteins, comparisons were also made between the H. marismortui structural protein sequence[g] and the corresponding sequences of aligned protein sequences encoding homologous proteins in E. coli[i], Rattus norvegicus[j], Human[k] or Human mitochondria[l]. Sequence alignments were determined with the program MegAlign (DNASTAR, Madison, Wisconsin, USA) with default parameters.
*NP means that no homologous residue has been identified.
[a]T. E. Ferrin, C. C. Huang, L. E. Jarvis, and R. Langridge (1988) "The MIDAS Display System" J. Mol. Graphics, 6(1): 13-27, 36-37.
[b]GenBank accession AF034619
[c]GenBank accession J01695
[d]GenBank accession 2624399
[e]GenBank accession M11167
[f]GenBank accession 13683
[g]GenBank accession AAA86859 for protein L3.
[i]GenBank accession CAA26460 for protein L3.
[j]GenBank accession P21531 for protein L3.
[k]GenBank accession NP_000958 for protein L3.
[l]GenBank accession P09001 for protein L3.

The skilled artisan, when in possession of the foregoing or other exemplary target sites, may use the process of rational drug design to identify molecules that potentially bind to one or more of the target sites and/or inhibit ribosomal activity. Furthermore, by taking into account which of the residues that define the target site are conserved between pathogens but not conserved between host species, the skilled artisan can design new species-specific protein synthesis inhibitors. It is apparent that the skilled artisan can take advantage of the regions that are not conserved between E. coli and rat or human to provide target regions for rational drug design. By way of example, FIG. 33 shows certain regions of the polypeptide exit tunnel that are conserved between E. coli and rat or human (denoted in red) and regions of the polypeptide exit tunnel that are not conserved between E. coli and rat or human (denoted in blue). FIGS. 33(A) and 33(B) provide enlarged views of a large ribosomal subunit when cut in half along the polypeptide exit tunnel. FIG. 33(C) is provided to orient the reader to the view in FIG. 33(A) relative to the large ribosomal subunit. FIG. 33(D) is provided to orient the reader to the view in FIG. 33B relative to the large ribosomal subunit. In addition, the skilled artisan when in possession of mutations that prevent or reduce antibiotic activity (i.e., are related to antibiotic resistance) can use this information to model the relevant antibiotic binding product which can then be used as a basis for rational drug design to identify small molecules that overcome drug resistance. It is contemplated that a variety of computer modeling procedures, for example, homology modeling protocols, can be used to provide a model of a drug resistance target site by implementing site directed mutagenesis of nucleotides and/or amino acids and then using the appropriate energy minimization and refinement protocols.

c. Identification of Candidate Molecules.

It is contemplated that candidate molecules that inhibit protein biosynthesis can be designed entirely de novo or may be based upon a pre-existing protein biosynthesis inhibitor. Either of these approaches can be facilitated by computationally screening databases and libraries of small molecules for chemical entities, agents, ligands, or compounds that can bind in whole, or in part, to ribosomes and ribosomal subunits, more preferably to large ribosomal subunits, and even more preferably to 50S ribosomal subunits. In this screening, the quality of fit of such entities or compounds to the binding site or sites may be judged either by shape complementarity or by estimated interaction energy (Meng et al. (1992) J. Comp. Chem. 13: 505-524).

The design of molecules that bind to or inhibit the functional activity of ribosomes or ribosomal subunits according to this invention generally involves consideration of two factors. First, the molecule must be capable of physically and structurally associating with the large ribosomal subunit. Non-covalent molecular interactions important in the association of ribosomes and ribosomal subunits with the molecule, include hydrogen bonding, van der Waals and hydrophobic interactions. Second, the molecule must be able to assume a conformation that allows it to associate with the ribosomes or ribosomal subunits, more preferably with the large ribosomal subunits, and even more preferably with the 50S ribosomal subunit. Although certain portions of the molecule may not directly participate in this association with a ribosome or ribosomal subunits those portions may still influence the overall conformation of the molecule. This, in turn, may have a significant impact on binding affinities, therapeutic efficacy, drug-like qualities, and potency. Such conformational requirements include the overall three-dimensional structure and orientation of the chemical entity or molecule in relation to all or a portion of the active site or other region of the ribosomes or ribosomal subunits, or the spacing between functional groups of a molecule comprising several chemical entities that directly interact with the ribosomes or ribosomal subunits, more preferably with the large ribosomal subunits, and even more preferably with the 50S ribosomal subunit.

The potential, predicted, inhibitory or binding effect of a molecule on ribosomes and ribosomal subunits may be analyzed prior to its actual synthesis and testing by the use of computer modeling techniques. If the theoretical structure of the given molecule suggests insufficient interaction and association between it and ribosomes or ribosomal subunits, synthesis and testing of the molecule is obviated. However, if computer modeling indicates a strong interaction, the molecule may then be synthesized and tested for its ability to interact with the ribosomes or ribosomal subunits and inhibit protein synthesis. In this manner, synthesis of inoperative molecules may be avoided. In some cases, inactive molecules are synthesized predicted on modeling and then tested to develop a SAR (structure-activity relationship) for molecules interacting with a specific region of the ribosome or ribosomal subunit, more preferably of the large ribosomal subunit, and even more preferably of the 50S ribosomal subunit. As used herein, the term "SAR", shall collectively refer to the structure-activity/structure property relationships pertaining to the relationship(s) between a compound's activity/properties and its chemical structure.

d. De Novo Design.

One skilled in the art may use one of several methods to identify chemical moieties or entities, compounds, or other agents for their ability to associate with a preselected target site within a ribosomes or ribosomal subunit. This process may begin by visual inspection or computer assisted modeling of, for example, the target site on the computer screen based on the atomic co-ordinates of the 50S ribosomal subunit and/or its complexes with other analogues and antibiotics, deposited in the RCSB Protein Data Bank with accession numbers PDB ID: 1FFK, 1JJ2, 1FFZ, 1FG0, 1K73, 1KC8, 1K8A, 1 KD1, or 1K9M, and/or contained on Disk No. 1. In one embodiment, compound design uses computer modeling programs which calculate how different molecules interact with the various sites of the ribosome, ribosomal subunit, or a fragment thereof. Selected chemical moieties or entities, compounds, or agents may then be positioned in a variety of orientations, or docked, within at least a portion of the target site of a ribosome or ribosomal subunit, more preferably of a large ribosomal subunit, and even more preferably of a 50S ribosomal subunit. Databases of chemical structures are available from, for example, Cambridge Crystallographic Data Center (Cambridge, U.K.) and Chemical Abstracts Service (Columbus, Ohio). Docking may be accomplished using software such as Cerius, Quanta or Sybyl, followed by energy minimization and molecular dynamics with standard molecular mechanics forcefields, such as OPLS-AA, CHARMM or AMBER.

Specialized computer programs may also assist in the process of selecting chemical entities. These include, but are not limited to:

(1) GRID (Goodford, P. J., "A Computational Procedure for Determining Energetically Favorable Binding Sites on Biologically Important Macromolecules" (1985) *J. Med. Chem.* 28, 849-857). Software such as GRID, a program that determines probable interaction sites between probes with various functional group characteristics and the macromolecular surface, can be used to analyze the surface sites to determine structures of similar inhibiting proteins or molecules. The GRID calculations, with suitable inhibiting groups on molecules (e.g., protonated primary amines) as the probe, are used to identify potential hotspots around accessible positions at suitable energy contour levels. GRID is available from Oxford University, Oxford, UK.

(2) MCSS (Miranker, A. and M. Karplus (1991) "Functionality Maps of Binding Sites: A Multiple Copy Simultaneous Search Method." *Proteins: Structure, Function and Genetics* 11: 29-34). MCSS is available from Molecular Simulations, Burlington, Mass.

(3) AUTODOCK (Goodsell, D. S. and A. J. Olsen (1990) "Automated Docking of Substrates to Proteins by Simulated Annealing" *Proteins: Structure, Function, and Genetics* 8: 195-202). AUTODOCK is available from Scripps Research Institute, La Jolla, Calif.

(4) DOCK (Kuntz, I. D. et al. (1982) "A Geometric Approach to Macromolecule-Ligand Interactions" *J. Mol. Biol.* 161: 269-288). The program DOCK may be used to analyze an active site or ligand binding site and suggest ligands with complementary steric properties. DOCK is available from University of California, San Francisco, Calif.

(5) ALADDIN (Van Drie et al. (1989) "ALADDIN: An Integrated Tool of Computer Assisted Molecular Design and Pharmacophore Recognition From Geometric, Steric and Substructure Searching of Three-Dimensional Structures" *J. Comp-Aided Mol. Des.* 3: 225).

(6) CLIX (Davie and Lawrence (1992) "CLIX: A Search Algorithm for Funding Novel Ligands Capable of Binding Proteins of Known Three-Dimensional Structure" *Proteins* 12: 31-41).

(7) GROUPBUILD (Rotstein and Murcko (1993) "GroupBuild: A Fragment-Based Method for De Novo Drug Design" *J. Med. Chem* 36: 1700).

(8) GROW (Moon and Howe (1991) "Computer Design of Bioactive Molecules: A Method for Receptor-Based De Novo Ligand Design" *Proteins* 11: 314).

Once suitable chemical moieties or entities, compounds, or agents have been selected, they can be assembled into a single molecule. Assembly may proceed by visual inspection and/or computer modeling and computational analysis of the spatial relationship of the chemical moieties or entities, compounds or agents with respect to one another in three-dimensional space. This could then be followed by model building using software such as Quanta or Sybyl.

Useful programs to aid one of skill in the art in connecting the individual chemical entities, compounds, or agents include but are not limited to:

(1) CAVEAT (Bartlett, P. A. et al. (1989) "CAVEAT: A Program to Facilitate the Structure-Derived Design of Biologically Active Molecules". In molecular Recognition in Chemical and Biological Problems", Special Pub., *Royal Chem. Soc.* 78: 82-196) and (Bacon et al. (1992) *J. Mol. Biol.* 225: 849-858). CAVEAT uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding. CAVEAT is available from the University of California, Berkeley, Calif.

(2) 3D Database systems such as MACCS-3D (MDL Information Systems, San Leandro, (Calif.). This area is reviewed in Martin, Y. C., (1992) "3D Database Searching in Drug Design", *J. Med. Chem.* 35: 2145-2154.

(3) HOOK (available from Molecular Simulations, Burlington, Mass.).

Instead of proceeding to build a molecule of interest in a step-wise fashion one chemical entity at a time as described above, the molecule of interest may be designed as a whole using either an empty active site or optionally including some portion or portions of a known inhibitor or inhibitors. Software that implements these methods include:

(1) LUDI (Bohm, H.-J. (1992) "The Computer Program LUDI: A New Method for the De Novo Design of Enzyme Inhibitors" *J. Comp. Aid. Molec. Design* 6: 61-78). The program LUDI can determine a list of interaction sites into which to place both hydrogen bonding and hydrophobic fragments. LUDI then uses a library of approximately 600 linkers to connect up to four different interaction sites into fragments. Then smaller "bridging" groups such as —$CH_2$— and —COO— are used to connect these fragments. For example, for the enzyme DHFR, the placements of key functional groups in the well-known inhibitor methotrexate were reproduced by LUDI. See also, Rotstein and Murcko, (1992) *J. Med. Chem.* 36:1700-1710. LUDI is available from Biosym Technologies, San Diego, Calif.

(2) LEGEND (Nishibata, Y. and A. Itai (1991) *Tetrahedron* 47, 8985). LEGEND is available from Molecular Simulations, Burlington, Mass.

(3) LeapFrog (available from Tripos Associates, St. Louis, Mo.).

(4) Aladdin (available from Daylight Chemical Information Systems, Irvine, Calif.)

Other molecular modeling techniques may also be employed in accordance with this invention. See, e.g., Cohen, N. C. et al. (1990) "Molecular Modeling Software and Methods for Medicinal Chemistry, *J. Med. Chem.* 33: 883-894. See also, Navia, M. A. and M. A. Murcko (1992) "The Use of Structural Information in Drug Design", *Current Opinions in Structural Biology* 2: 202-210; and Jorgensen (1998) "BOSS—Biochemical and Organic Simulation System" in the *Encyclopedia of Computational Chemistry* (P. V. R. Schleyer, ed.) Wiley & Sonstra., Athens, U.S.A. 5: 3281-3285).

It is contemplated that during modeling, it may be possible to introduce into the molecule of interest, chemical moieties that may be beneficial for a molecule that is to be administered as a pharmaceutical. For example, it may be possible to introduce into or omit from the molecule of interest, chemical moieties that may not directly affect binding of the molecule to the target area but which contribute, for example, to the overall solubility of the molecule in a pharmaceutically acceptable carrier, the bioavailability of the molecule and/or the toxicity of the molecule. Considerations and methods for optimizing the pharmacology of the molecules of interest can be found, for example, in "Goodman and Gilman's The Pharmacological Basis of Therapeutics" Eighth Edition (Goodman, Gilman, Rall, Nies, & Taylor (eds.)). Pergaman Press (1985); Jorgensen & Duffy (2000) *Bioorg. Med. Chem. Lett.* 10: 1155-1158.

Furthermore, the computer program "Qik Prop" can be used to provide rapid predictions for physically significant descriptions and pharmaceutically-relevant properties of an organic molecule of interest. A 'Rule of Five' probability scheme can be used to estimate oral absorption of the newly synthesized compounds (Lipinski et al. (1997) *Adv. Drug Deliv. Rev.* 23:3).

Programs suitable for pharmacophore selection and design include:

(1) DISCO (Abbot Laboratories, Abbot Park, Ill.).
(2) Catalyst (Bio-CAD Corp., Mountain View, Calif.).
(3) Chem DBS-3D (Chemical Design Ltd., Oxford, U.K.)

Furthermore, the skilled artisan may use the information available on how to design suitable therapeutically active and pharmaceutically useful compounds, and use this information in the design of new protein synthesis inhibitors of the invention. See, for example, Lipinski et al. (1997) *Ad. Drug Deliv. Reviews* 23: 3-25; Van de Waterbeemd et al. (1996) *Quantitative Structure-Activity Relationships* 15: 480-490; and Cruciani et al. (2000), *Theochem-J. Mol. Struct.* 503: 17-30.

The entry of the co-ordinates of the ribosome's or ribosomal subunit's proteins and RNAs into the computer programs discussed above results in the calculation of most probable structure of the macromolecule, including overall atomic co-ordinates of a ribosome, ribosomal subunit or a fragment thereof. These structures can be combined and refined by additional calculations using such programs to determine the probable or actual three-dimensional structure of the ribosome, ribosomal subunit or a fragment thereof, including potential or actual active or binding sites of ligands.

e. Modification of Existing Molecules.

Instead of designing molecules of interest entirely de novo it is contemplated that pre-existing molecules or proteins thereof may be used as a starting point for the design of a new candidate. It is contemplated that many of the approaches useful for designing molecules de novo may also be useful for modifying existing molecules.

It is contemplated that knowledge of the spatial relationship between a protein biosynthesis inhibitor, for example, an antibiotic, and its respective binding site within a ribosome permits the design of modified inhibitors that may have better binding properties, for example, higher binding affinity and/ or specificity, relative to the molecule from which it was derived. Alternatively, knowledge of inhibitor contact sites within a ribosome permits the synthesis of a new molecule that contains, for example, a portion of a first molecule (for example, an antibiotic or an analogue or derivative thereof) that binds to the contact site and another portion that contributes additional functionality.

It is contemplated that a variety of modified molecules (for example, modified antibiotics) may be designed using the atomic co-ordinates provided herein. For example, it is contemplated that by knowing the spatial relationship of one or more of antibiotics relative to the large ribosomal subunit it is possible to generate new antibiotic-based molecules. The atomic co-ordinates of each antibiotic relative to the large ribosomal subunit provides information on what portions of the ribosome or ribosomal subunit and the antibiotic contact one another. Accordingly, from this information the skilled artisan may not only identify contact locations within the ribosome that can be used for de novo drug design, as discussed above, but also may identify portions of an antibiotic that can act as a ribosome binding domain.

Based on the information provided herein, the skilled artisan may readily identify and produce hybrid antibiotics that comprise a ribosome binding domain of a first antibiotic or an analogue or a derivative thereof and a ribosome binding domain of a second, different antibiotic or an analogue or a derivative thereof. The resulting hybrid antibiotics preferably bind to each of respective contact locations within the ribosomal subunit simultaneously. The atomic co-ordinates provided herein permit the skilled artisan to identify candidate antibiotics that may be used as templates in the synthesis of a hybrid, and also provide steric information necessary to produce linking chemistries such that each ribosome binding domain is properly orientated relative to its respective contact site. As a result, it is contemplated that the skilled artisan may produce a hybrid antibiotic that binds to a ribosome or ribosomal subunit with a higher affinity and/or have higher protein synthesis inhibitory activity than either of the individual template antibiotics used to generate the hybrid. Alternatively, the hybrid antibiotic may overcome resistance phenotypes that may have developed against either of the template antibiotics. For example, the proximity of the site occupied by the disaccharide moiety of carbomycin to the site filled by anisomycin suggests that a hybrid compound including portions of both carbomycin and anisomycin may be an effective inhibitor of protein synthesis.

Furthermore, the atomic co-ordinates provided herein permit the skilled artisan to use the information pertaining to identify a ribosome binding domain and to design other types of protein synthesis inhibitors. For example, with an understanding of the ribosome contact region and the surrounding environment, the skilled artisan can provide novel molecules, a portion of which is based upon the antibiotic binding region (binding domain) and another portion of which (effector domain) can be designed as a novel space filling domain that sterically inhibits or disrupts protein biosynthesis within the ribosome or secretion through the polypeptide exit tunnel. For example, the skilled artisan may combine the ribosome binding region of the antibiotic, tylosin or an analogue or derivative thereof, which binds to one side of the polypeptide exit tunnel close to the peptidyl transferase site, with, for example, a novel chemical moiety not present in antibiotics identified to date that is bulky enough to block the polypeptide exit tunnel. However, it is contemplated that the skilled artisan may take advantage of one or more of the many of the antibiotic contact regions disclosed herein to design entirely new binding and effector domains.

The resulting protein synthesis inhibitors preferably have a molecular weight no greater than about 1,500, more preferably no greater than about 1,000, more preferably no greater than 750 and, most preferably no greater than about 500. The protein synthesis inhibitors preferably have a molecular weight in the range from about 250 to about 1500, and more preferably in the range from about 500 to about 1200. In addition, the protein synthesis inhibitors have a minimal inhibitor concentration preferably no greater than 50 µM, more preferably no greater than 10 µM, and more preferably no greater than 1 µM to inhibit 50% activity ($IC_{50}$) in a biological assay, for example, an in vitro translation assay, for example, an E. coli translation assay. The protein synthesis inhibitors preferably have an $IC_{50}$ in the range from about 0.001 µM to about 50 µM, or in the range from about 0.01 µM to about 10 µM, or in the range from about 0.1 µM to about 1 µM.

Furthermore, the present invention permits the skilled artisan to design molecules, for example, selective protein synthesis inhibitors that are tailored to be more potent with respect to ribosomes of a target organism, for example, a pathogen such a microbe, and less potent, i.e., less toxic, to ribosomes of a non target organism, for example, host organism such as a human. Also, the invention permits the skilled artisan to use the atomic co-ordinates and structures of the large ribosomal subunit and its complexes with protein synthesis inhibitors to design modifications to starting compounds, such as an antibiotic, that will bind more tightly to a target ribosome (e.g., the 50S ribosomal subunit of bacteria) and less tightly to a non-targeted ribosome (e.g., human 60S ribosomal subunit or a human mitochondrial ribosome).

The structure of a complex between the large ribosomal subunit and the starting compound (e.g., tylosin or another protein synthesis inhibitor) can also be used to guide the modification of that compound to produce new compounds that have other desirable properties for the applicable industrial and other uses (e.g., as pharmaceuticals, herbicides or insecticides), such as chemical stability, solubility or membrane permeability.

A variety of antibiotics bind the large ribosomal subunit and disrupt protein synthesis and include members of antibiotic families which include, but are not limited to: chloramphenicols, macrolides, lincosamides, streptogramins, althiomycins, oxazolidinones, nucleotide analogs, thiostreptons (including micrococcin family), peptides, glutarimides, trichothecenes, TAN-1057, pleuromutilins, hygromycins, betacins, eveminomicins, boxazomycins, and fusidanes.

Members of the chloramphenicol family include, for example, Chloramphenicol and Iodoamphenicol. Members of the macrolide family include, for example, Biaxin (Clarithromycin), Zithromax (Azithromycin; azalide), Ketek (Telithromycin; ketolide), ABT-773, Tylosin, Spiramycin I, Spiramycin II, Spiramycin III, Erythromycin A, Carbomycin A, Telithromycin, Methymycin, Narbomycin, Lankamycin, Oleandomycin, Megalomycin, Chalcomycin, Niddamycin, Leucomycin, Angolamycin, Picromycin, and Relomycin. Members of the licosamide family include, for example, Clindamycin and Lincomycin. Members of the streptogramin family include, for example, Streptogramin A, Streptogramin B, Ostreogrycin G, Synercid, Virginiamycin S1, Virginiamycin S2, Virginiamycin S3, Virginiamycin S4, Vernamycin B, Vernamycin C, Patricin A, and Patricin B. A member of the althiomycin family, includes, for example, Althiomycin. Members of the oxazolidinone family, include, for example, Linezolid, Eperezolid, and DuP721. Members of the family of nucleotide analogs include, for example, Sparsomycin, Puromycin, Anisomycin, and Blasticidin S. Members of the thiostrepton family include, for example, Thiostrepton, Siomycin, Sporangiomycin, Micrococcin M1, Micrococcin P, and Thiopeptin. Members of the peptide family include, for example, Viomycin, Capreomycin IA, Capreomycin IB, Capreomycin IIA, and Capreomycin IIB. Members of the glutarimide family include, for example, Cycloheximide, Streptovitacins, Streptimidone, Inactone, Actiphenol. Members of the trichothecene family include, for example, Trichodermin, Trichodermol, Trichodermone, Vomitoxin, T-2 toxin, Trichothecin, Nivalenol, and Verrucarin A. Tan-1057 includes Tan-1057A, Tan-1057B, Tan-1057C, and Tan-1057D. Pleuromutilins include, for example, Pleuromutilin, Tiamulin, Azamilin, and Valnemulin. Hygromycins includes the Hygromycin A antibiotics. Betacins include, for example, the family of betacin natural products and VCR4219. Everninomicins include, for example, Ziracin, Avilamycin, Evernimicin, and Curamicin. Boxazomycins include, for example, Boxazomycin A and B. Fusidanes include, for example, fusidic acid and 17S, 20S-dihydrofusidic acid diethylene glycol hydrate Inhibitors can be diffused into or soaked with the stabilized crystals of the large ribosomal subunit as described in Examples 4 and 5 to form a complex with the large ribosomal subunit for collecting X-ray diffraction data. Alternatively, the inhibitors can be co-crystallized with the large ribosomal subunit by mixing the inhibitor with the large ribosomal subunit before precipitation with high salt.

Starting with the structure of the ribosome from H. marismortui, the structure of the ribosome from a non-targeted organism (for example, the human 60S ribosomal subunit) can be constructed by homology modeling, i.e., by changing the structure of residues at a target site of interest for the residues at the same positions in of the non-target ribosome. This can be achieved by removing computationally the side chains from the ribosome of known structure and replacing them with the side chains of the unknown structure put in sterically plausible positions. In this way, it can be understood how the shapes of the target sites within the targeted and non-targeted ribosomes differ. This process, therefore, provides information concerning how a molecule that binds the target site can be chemically altered in order to produce molecules that will bind tightly and specifically to the targeted ribosome but will simultaneously be prevented from binding to the non-targeted ribosome. Likewise, knowledge of portions of the bound molecules that face the solvent permit introduction of other functional groups for additional pharmaceutical purposes. The process of homology structure modeling can also be used to understand the mechanisms whereby mutant ribosomes become resistant to the effects of pharmaceuticals or pesticides, such as herbicides or insecticides. Furthermore, with knowledge of the portions of the ribosomal subunit that participates in drug resistance, the skilled artisan may design new molecules that overcome the problem of drug resistance.

The use of homology structure modeling to design molecules that bind more tightly to the target ribosome than to the non-target ribosome has wide-spread applicability. The methods outlined herein can be used to control any targeted organism, for example, a pathogen, by designing molecules that inhibit large ribosomal subunits of the targeted organisms while failing to inhibit the 50S or 60S ribosomal subunit of the non-targeted organism, for example, a host, to the same extent or not at all. The molecules identified or prepared by the methods of the present invention can be used to control the targeted organisms while causing the non-targeted organism little or no adverse effects. Thus, the molecules identified or developed using the methods of the present invention can be designed so that their administration kills the target organisms or inhibits some aspect of the biological functions of the target organisms while failing to have a similar effect on the non-targeted organism. The adverse effects of the agent on the targeted organisms may include, but are not limited to, death of the target organism; slowing growth rates; slowing or eliminating passage from one growth phase to another (e.g., extending the larval growth stage); slowing or eliminating reproduction, decreasing or preventing mating, decreasing or eliminating offspring production, limiting or eliminating target organism weight gains; decreasing or eliminating feeding ability and behaviors; and disrupting cellular, tissue and/or organ functions.

The novel agents contemplated by the present invention can be useful as herbicides, pesticides (e.g., insecticides, nematocides, rodenticides, etc.), miticides, or antimicrobial agents (e.g., antifungals, antibacterials, antiprotozoals, etc.) to target specific organisms. For example, the novel agents can target animal and plant parasitic nematodes, prokaryotic organisms (disease causing microbes), and eukaryotic multi-cellular pests. Specific examples of multicellular pests include, but are not limited to, insects, fungi, bacteria, nematodes, mites and ticks, protozoan pathogens, animal-parasitic liver flukes, and the like.

Herbicides, pesticides, miticides, and antimicrobial agents that inhibit protein synthesis by interacting with ribosomes are known to the skilled artisan. A few examples are discussed below. These known agents can be modified to obtain novel agents by using computer modeling techniques and knowledge of the structure of ribosomes and ribosomal subunits and the structure of ribosome/agent and ribosomal subunit/agent complexes.

The ketolide ABT-773 binds ribosomes tighter than erythromycin in *S. pneumoniae* and is able to defeat macrolide resistance in bacteria (Capobianco et al. (2000) *Antimicrob. Agents Chemother.* 44(6): 1562-1567). The tools and methodologies of the present invention can be used to obtain erythromycin derivatives that bind the ribosomes or ribosomal subunits of target bacteria more tightly than they bind the ribosomes and ribosomal subunits of non-target animals. The target bacteria can be any infectious bacteria, particularly *S. pneumoniae*, and even more particularly erythromycin-resistant *S. pneumoniae*. The non-target animals can be any animal, particularly mammals, and even more particularly humans.

Examples of antibiotics that are inhibitors of protein synthesis include, but are not limited to, puromycin, cycloheximide, chloramphenicol, tetracycline, and streptomycin (Heldt (1996) *Plant Biochemistry and Molecular Biology* 21.2: 458-464). Puromycin, as discussed earlier, binds as an analogue of an aminoacyl-tRNA to the A-site and is added to nascent peptide chains, and, prevents further elongation steps in prokaryotes and eukaryotes. Cycloheximide inhibits peptidyl transferase in eukaryotic ribosomes. Chloramphenicol inhibits peptidyl transferase in prokaryotic ribosomes. Tetracycline binds to the 30S subunit and inhibits the binding of aminoacyl-tRNA to prokaryotic ribosomes much more than to eukaryotic ones. Streptomycin interacts with 30S ribosomes which results in an incorrect recognition of mRNA sequences and thus inhibits initiation in prokaryotic ribosomes. U.S. Pat. No. 5,801,153 discloses antibiotics against pathogens. Aminoglycosides are examples of antibacterial antibiotics that appear to inhibit protein synthesis. However, there is a limitation to their use because of their ototoxic and nephrotoxic properties. Amikacin sulfate, Framycetin sulfate, Gentamycin sulfate, Kanamycin sulfate, Neomycin sulfate, Netilmicin sulfate, Paromomycin sulfate, Sissomycin sulfate, Tobramycin, Vancomycin hydrochloride, and Viomycin sulfate are the members of the aminoglycoside family. The tools and methodologies of the present invention can be used to obtain derivatives of any antibiotic of choice so that they inhibit the protein synthesis of target organisms to a greater degree than they inhibit the protein synthesis of non-target organisms, such as humans.

Examples of targeted and non-targeted organisms include, but are not limited to, those provided in Table 21.

TABLE 21

Examples of Classes of Molecules which can be Identified and/or Developed by the Methods of the Invention and Applicable Target/Non-Target Organisms.

| Type of Molecule | Target Organisms | Non-Target Organisms |
|---|---|---|
| Herbicides | Dicotyledonous plants | Monocotyledonous plants |
| Herbicides | Grasses | Soybeans, potatoes, coffee |
| Insecticides | Flies, Mites | Honey bees |
| Pesticides | Ticks | Deer |
| Pesticides | Lice | Birds |
| Miticides | Parasitic mites (mange) | Dogs |
| Antimicrobial Agents (Antibacterials) | *Streptococcus pneumoniae* | Humans |
| Antimicrobial Agents (Antibacterials) | *Clostridium difficile* | *Escherichia coli* |
| Antimicrobial Agents (Antifungals) | *Erysiphe graminis* | Barley |
| Antimicrobial Agents (Antiprotozoals) | *Toxoplasma gondii* | Animals |
| Poisons (Rodentcides) | Rats | Dogs, cats, humans |

It is contemplated that the tools and methodologies of the present invention can be used to obtain inhibitors of protein synthesis of target insects, such as bollworms and mosquitoes, more than they inhibit the protein synthesis of non-target insects, such as beetles of the family Coccinellidae (e.g., ladybugs) and *Apis mellifera* (honey bees). Other possible target insects include, but are not limited to, insects selected from the orders Coleoptera (beetles), Diptera (flies, mosquitoes), Hymenoptera (wasps, ants, sawflies), Lepidoptera (butterflies and moths), (lice), Homoptera (whiteflies, aphids), Hemiptera (bugs), Orthroptera (locusts, cockroaches), Thysanoptera (drips), Dermaptera (earwigs), Isoptera, Anoplura, Siphonaptera, and Trichoptera (caddis flies).

Furthermore, it is contemplated that the tools and methodologies of the present invention can be used to obtain inhibitors of protein synthesis of target plants which inhibit protein synthesis of the target plants more than they inhibit the protein synthesis of non-target plants and animals. The target plants can be any unwanted plant species, particular weeds, and even more particularly noxious weeds. Whether or not a particular plant is considered a weed will depend upon the context in which it is growing. For example, unwanted *Zea mays* (corn) plants growing in a *Glycine max* (soybean) field could be considered unwanted weeds. Examples of weeds which are likely target plants include, but are not limited to, *Allium vineale* (wild garlic), *Bromus tectorum* (downy brome), *Triticum cylindricum* (jointed goatgrass), *Amaranthus* spp. (pigsweed), *Chenopodium album* (lambsquarters), *Avena fatua* (wild oats), *B. secalinus* (cheat), *Echinochloa crus-galli* (barnyardgrass), *Alopecurus myosuroides* (blackgrass), *Setaria faberii* (giant foxtail), *Xanthium strumarium* (common cocklebur), *Ambrosia artemisiifolia* (common ragweed), and *Ipomoea* spp. (morning glories). The non-target organisms can be any plant, particularly any desirable plant, and even more particularly any crop plant. The non-target organisms can also be any animals, particularly mammals, and even more particularly humans. In one preferred embodiment, the tools and methodologies of the present invention can be used to produce protein synthesis inhibitors which kill or injure one or more noxious weed species but fail to harm non-target plants and animals.

Target bacteria of interest include, but are not limited to, *Staphylococcus aureus, Streptococcus pyogenes, Streptococcus agalactiae, Streptococcus bovis, Streptococcus pneumoniae, Moraxella catarrhalis, Neisseria gonorrhoeae, Neisseria meningitides, Bacillus anthracis, Corynebacterium diphtheriae, Listeria monocytogenes, Erysipelothrix rhusiopathiae, Clostridium perfringens, Clostridium tetani, Clostridium difficile, Eschericia coli, Proteus mirabilis, Psuedomonas aeruginosa, Klebsiella pneumoniae, Haemophilus influenzae, Haemophilus ducreyi, Yersinia pestis, Yersinia enterocolitica, Francisella tularensis, Pasteurella multocida, Vibrio cholerae, Flavobacterium meningosepticum, Pseudomonas mallei, Pseudomonas pseudomallei, Campylobacter jejuni, Campylobacter fetus, Fusobacterium nucleatum, Calymmatobacterium granulomatis, Streptobacillus moniliformis, Legionella pneumophila, Mycobacterium avium-intracellulare, Mycobacterium tuberculosis, Mycobacterium leprae, Treponema pallidum, Treponema pertenue, Borrelia burgdorferi, Borrelia recurrentis, Actinomyces isrealii, Nocardia asteroides, Ureaplasma urealyticum, Mycoplasma pneumoniae, Chlamydia psittaci, Chlamydia trachomatis, Chlamydia pnemoniae, Pneumocystis carinii, Coccidioides immitis, Histoplasma capsulatum, Blastomyces dermatitidis, Paracoccidioides brasiliensis, Sporothrix schenckii, Cryptococcus neoformans.*

Once a candidate molecule has been designed or selected by the above methods, the affinity with which that molecule may bind to the ribosome or ribosomal subunit may be tested and optimized by computational evaluation and/or by testing biological activity after synthesizing the compound. Candidate molecules may interact with the ribosomes or ribosomal subunits in more than one conformation each of which has a similar overall binding energy. In those cases, the deformation energy of binding may be considered to be the difference between the energy of the free molecule and the average energy of the conformations observed when the molecule binds to the ribosomes or ribosomal subunits, more preferably to the large ribosomal subunits, and even more preferably to the 50S ribosomal subunits.

A molecule designed or selected as binding to a ribosome or ribosomal subunit may be further computationally optimized so that in its bound state it preferably lacks repulsive electrostatic interaction with the target region. Such non-complementary (e.g., electrostatic) interactions include repulsive charge-charge, dipole-dipole and charge-dipole interactions. Specifically, the sum of all electrostatic interactions between the inhibitor and the enzyme when the inhibitor is bound to the ribosome or the ribosomal subunit, preferably make a neutral or favorable contribution to the enthalpy of binding. Weak binding compounds can also be designed by these methods so as to determine SAR.

Specific computer programs that can evaluate a compound deformation energy and electrostatic interaction are available in the art. Examples of suitable programs include: Gaussian 92, revision C (M. J. Frisch, Gaussian, Inc., Pittsburgh, Pa.); AMBER, version 4.0 (P. A. Kollman, University of California at San Francisco, Calif.); QUANTA/CHARMM (Molecular Simulations, Inc., Burlington, Mass.); OPLS-AA ("OPLS Force Fields." W. L. Jorgensen. Encyclopedia of Computational Chemistry, Schleyer, Ed.; Wiley: New York, 1998; Vol. 3, pp 1986-1989.) and Insight II/Discover (Biosysm Technologies Inc., San Diego, Calif.). These programs may be implemented, for instance, using a Silicon Graphics workstation, IRIS 4D/35 or IBM RISC/6000 workstation model 550. Other hardware systems and software packages are known to those skilled in the art.

Once a molecule of interest has been selected or designed, as described above, substitutions may then be made in some of its atoms or side groups in order to improve or modify its binding properties. Generally, initial substitutions are conservative, i.e., the replacement group will approximate the same size, shape, hydrophobicity and charge as the original group. It should, of course, be understood that components known in the art to alter conformation should be avoided. Such substituted chemical compounds may then be analyzed for efficiency of fit to the ribosome or ribosomal subunit by the same computer methods described in detail, above.

In addition, the actual ribosome-related ligands, complexes or mimetics may be crystallized and analyzed using X-ray diffraction. The diffraction pattern co-ordinates are similarly used to calculate the three-dimensional interaction of a ligand and the ribosome, ribosomal subunit, or a mimetic, in order to confirm that the ligand binds to, or changes the conformation of, a particular site on the ribosome or ribosomal subunit, or where the mimetic has a similar three-dimensional structure to that of a ribosome, ribosomal subunit or a fragment thereof.

3. Synthesis of Lead Molecules

A lead molecule of the present invention can be, but is not limited to, at least one selected from a lipid, nucleic acid, peptide, small organic or inorganic molecule, chemical compound, element, saccharide, isotope, carbohydrate, imaging agent, lipoprotein, glycoprotein, enzyme, analytical probe, and an antibody or fragment thereof, any combination of any of the foregoing, and any chemical modification or variant of any of the foregoing. In addition, a lead molecule may optionally comprise a detectable label. Such labels include, but are not limited to, enzymatic labels, radioisotope or radioactive compounds or elements, fluorescent compounds or metals, chemiluminescent compounds and bioluminescent compounds. Well known methods may be used for attaching such a detectable label to a lead molecule.

Methods useful for synthesizing lead molecules such as lipids, nucleic acids, peptides, small organic or inorganic molecules, chemical compounds, elements, saccharides, isotopes, carbohydrates, imaging agents, lipoproteins, glycoproteins, enzymes, analytical probes, antibodies, and antibody fragments are well known in the art. Such methods include the traditional approach of synthesizing one such lead molecule, such as a single defined peptide, at a time, as well as combined synthesis of multiple lead molecules in a one or more containers. Such multiple lead molecules may include one or more variants of a previously identified lead molecule. Methods for combined synthesis of multiple lead molecules are particularly useful in preparing combinatorial libraries, which may be used in screening techniques known in the art.

By way of example, it is well known in the art that multiple peptides and oligonucleotides may be simultaneously synthesized. Lead molecules that are small peptides up to 50 amino acids in length, may be synthesized using standard solid-phase peptide synthesis procedures, for example, procedures similar to those described in Merrifield (1963) *J. Am. Chem. Soc.*, 85: 2149. For example, during synthesis, N-α-protected amino acids having protected side chains are added stepwise to a growing polypeptide chain linked by its C-terminal end to an insoluble polymeric support, e.g., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile.

Briefly, the C-terminal N-α-protected amino acid is first attached to the polystyrene beads. Then, the N-α-protecting group is removed. The deprotected α-amino group is coupled to the activated α-carboxylate group of the next N-α-protected amino acid. The process is repeated until the desired peptide is synthesized. The resulting peptides are cleaved from the insoluble polymer support and the amino acid side chains deprotected. Longer peptides, for example greater than about 50 amino acids in length, typically are derived by condensation of protected peptide fragments. Details of appropriate chemistries, resins, protecting groups, protected amino acids and reagents are well known in the art and so are not discussed in detail herein. See for example, Atherton et al. (1963) *Solid Phase Peptide Synthesis: A Practical Approach* (IRL Press), and Bodanszky (1993) *Peptide Chemistry, A Practical Textbook, 2nd Ed*. Springer-Verlag, and Fields et al. (1990) *Int. J. Peptide Protein Res*. 35:161-214.

Purification of the resulting peptide is accomplished using conventional procedures, such as preparative HPLC, e.g., gel permeation, partition and/or ion exchange chromatography. The choice of appropriate matrices and buffers are well known in the art and so are not described in detail herein.

It is contemplated that a synthetic peptide in accordance with the invention may comprise naturally occurring amino acids, unnatural amino acids, and/or amino acids having specific characteristics, such as, for example, amino acids that are positively charged, negatively charged, hydrophobic, hydrophilic, or aromatic. As used herein, the term "naturally occurring amino acids" refers to the L-isomers of amino acids normally found in proteins. The predominant naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specifically indicated, all amino acids are referred to in this application are in the L-form. Furthermore, as used herein, the term "unnatural amino acids" refers to amino acids that are not naturally found in proteins. For example, selenomethionine.

Amino acids that are "positively charged" include any amino acid having a positively charged side chain under normal physiological conditions. Examples of positively charged naturally occurring amino acids include, for example, arginine, lysine, and histidine. Conversely, amino acids that are "negatively charged" include any amino acid having a negatively charged side chains under normal physiological conditions. Examples of negatively charged naturally occurring amino acids include, for example, aspartic acid and glutamic acid.

As used herein, the term "hydrophobic amino acid" includes any amino acids having an uncharged, nonpolar side chain that is relatively insoluble in water. Examples of naturally occurring hydrophobic amino acids include, for example, alanine, leucine, isoleucine, valine, proline, phenylalanine, tryptophan, and methionine. In addition, as used herein, the term "hydrophilic amino acid" refers to any amino acids having an uncharged, polar side chain that is relatively soluble in water. Examples of naturally occurring hydrophilic amino acids include, for example, serine, threonine, tyrosine, asparagine, glutamine and cysteine.

Finally, as used herein, the term "aromatic" refers to amino acid residues which side chains have delocalized conjugated system. Examples of aromatic residues include, for example, phenylalanine, tryptophan, and tyrosine.

With regard to the production of non-peptide small organic molecules which act as a ligand in the present invention, these molecules can be synthesized using standard organic chemistries well known and thoroughly documented in the patent and other literatures.

Many of the known methods useful in synthesizing lead of the present invention may be automated, or may otherwise be practiced on a commercial scale. As such, once a lead molecule has been identified as having commercial potential, mass quantities of that molecule may easily be produced.

4. Characterization of Molecules

Molecules designed, selected and/or optimized by methods described above, once produced, may be characterized using a variety of assays known to those skilled in the art to determine whether the compounds have biological activity. For example, the molecules may be characterized by conventional assays, including but not limited to those assays described below, to determine whether they have a predicted activity, binding activity and/or binding specificity.

Furthermore, high-throughput screening may be used to speed up analysis using such assays. As a result, it may be possible to rapidly screen new molecules for their ability to interact with a ribosome or ribosomal subunit using the tools and methods of the present invention. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies. A variety of binding assays may be useful in screening new molecules for their binding activity. One approach includes surface plasmon resonance (SPR) which can be used to evaluate the binding properties molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscatawy, N.J.) provides a focused beam of polychromatic light to the interface between a gold film (provided as a disposable biosensor "chip") and a buffer compartment that can be regulated by the user. A 100 nm thick "hydrogel" composed of carboxylated dextran which provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies which are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Immunodiagnostics and Immunoassays. These are a group of techniques that can be used for the measurement of specific biochemical substances, commonly at low concentrations in complex mixtures such as biological fluids, that depend upon the specificity and high affinity shown by suitably prepared and selected antibodies for their complementary antigens. A substance to be measured must, of necessity, be antigenic—either an immunogenic macromolecule or a haptenic small molecule. To each sample a known, limited amount of specific antibody is added and the fraction of the antigen combining with it, often expressed as the bound:free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including: enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

Common assay formats include the sandwich assay, competitive or competition assay, latex agglutination assay, homogeneous assay, microtitre plate format and the microparticle-based assay.

(3) Enzyme-linked immunosorbent assay (ELISA). ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to "capture" the relevant antigen (or antibody) in the test solution. The antigen-antibody complex is then detected by measuring the activity of an appropriate enzyme that had previously been covalently attached to the antigen (or antibody).

General methods and compositions for practicing ELISA are described, for example, in Crowther (1995) *ELISA—Theory and Practice* (*Methods in Molecular Biology*), Humana Press; Challacombe and Kemeny, (1998) *ELISA and Other Solid Phase Immunoassays—Theoretical and Practical Aspects*, John Wiley; Kemeny, (1991) *A Practical Guide to ELISA*, Pergamon Press; Ishikawa, (1991) *Ultrasensitive and Rapid Enzyme Immunoassay* (Laboratory Techniques in Biochemistry and Molecular Biology) Elsevier.

(4) Colorimetric Assays. Colorimetry is any method of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically.

Standard colorimetric assays of beta-galactosidase enzymatic activity are well known to those skilled in the art (see, for example, Norton et al. (1985) *Mol. Cell. Biol.* 5: 281-290). A colorimetric assay can be performed on whole cell lysates using O-nitrophenyl-β-D-galactopyranoside (ONPG, Sigma) as the substrate in a standard colorimetric beta-galactosidase assay (Sambrook et al. (1989) *Molecular Cloning—A Laboratory Manual*, Cold Spring Harbor Laboratory Press). Automated colorimetric assays are also available for the detection of β-galactosidase activity, as described in U.S. Pat. No. 5,733,720.

(5) Immunofluorescence Assays. Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

A general description of immunofluorescent techniques appears for example, in Knapp et al. (1978) *Immunofluorescence and Related Staining Techniques*, Elsevier; Allan, (1999) *Protein Localization by Fluorescent Microscopy—A Practical Approach* (The Practical Approach Series) Oxford University Press; Caul, (1993) *Immunofluorescence Antigen Detection Techniques in Diagnostic Microbiology*, Cambridge University Press. For detailed explanations of immunofluorescent techniques applicable to the present invention, see, for example, U.S. Pat. No. 5,912,176; U.S. Pat. No. 5,869,264; U.S. Pat. No. 5,866,319; and U.S. Pat. No. 5,861,259.

(6) Fluorescence Polarization. Fluorescence polarization (FP) is a measurement technique that can readily be applied to protein-protein and protein-ligand interactions in order to derive $IC_{50}$s and Kds of the association reaction between two molecules. In this technique one of the molecules of interest is conjugated with a fluorophore. This is generally the smaller molecule in the system (in this case, the molecule of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(7) Protein Synthesis. It is contemplated that, in addition to characterization by the foregoing biochemical assays, the molecule of interest may also be characterized as a modulator (for example, an inducer of protein synthesis or an inhibitor of protein synthesis) of the functional activity of the ribosome or ribosomal subunit.

Inhibitors of protein synthesis may be assayed on the cellular level. For example, molecules of interest can be assayed for inhibitory action against organisms, for example, microorganism, by growing the micro-organism of interest in media either containing or lacking the molecule of interest. Growth inhibition may be indicative that the molecule may be acting as a protein synthesis inhibitor.

Furthermore, more specific protein synthesis inhibition assays may be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3$H leucine or $^{35}$S methionine, or similar experiments can be performed to investigate protein synthesis activity.

A change in the amount or the rate of protein synthesis in the cell in the presence of a molecule of interest indicates that the molecule is an inducer of protein synthesis. A decrease in the rate or the amount of protein synthesis indicates that the molecule is a inhibitor of protein synthesis.

In addition, the antibacterial activity of the compounds of the present invention against bacterial pathogens can be demonstrated by the compound's ability to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays may be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition. NCCLS Document M100-S12/M7 (ISBN 1-56238-394-9).

H. Drug Formulation and Administration

It is contemplated that once identified, the active molecules of the invention may be incorporated into any suitable carrier prior to use. More specifically, the dose of active molecule, mode of administration and use of suitable carrier will depend upon the target and non-target organism of interest.

It is contemplated that with regard to mammalian recipients, the compounds of interest may be administered by any conventional approach known and/or used in the art. Thus, as appropriate, administration can be oral or parenteral, including intravenous and intraperitoneal routes of administration. In addition, administration can be by periodic injections of a bolus, or can be made more continuous by intravenous or intraperitoneal administration from a reservoir which is external (e.g., an intravenous bag). In certain embodiments, the compounds of the invention can be therapeutic-grade. That is, certain embodiments comply with standards of purity and quality control required for administration to humans. Veterinary applications are also within the intended meaning as used herein.

The formulations, both for veterinary and for human medical use, of the drugs according to the present invention typically include such drugs in association with a pharmaceutically acceptable carrier therefore and optionally other therapeutic ingredient(s). The carrier(s) should be "acceptable" in the sense of being compatible with the other ingredients of the formulations and not deleterious to the recipient thereof. Pharmaceutically acceptable carriers, in this regard, are intended to include any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations may conveniently be presented in dosage unit form and may be prepared by any of the methods well known in the art of pharmacy/microbiology. In general, some formulations are prepared by bringing the drug into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, e.g., intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's *Pharmaceutical Sciences*, (Gennaro, A., ed.), Mack Pub., (1990). Formulations for parenteral administration can also include glycocholate for buccal administration, methoxysalicylate for rectal administration, or cutric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, hydrogenated naphthalenes, and the like. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration may be in the form of discrete units such as capsules, gelatin capsules, sachets, tablets, troches, or lozenges, each containing a predetermined amount of the drug; in the form of a powder or granules; in the form of a solution or a suspension in an aqueous liquid or non-aqueous liquid; or in the form of an oil-in-water emulsion or a water-in-oil emulsion. The drug may also be administered in the form of a bolus, electuary or paste. A tablet may be made by compressing or moulding the drug optionally with one or more accessory ingredients. Compressed tablets may be prepared by compressing, in a suitable machine, the drug in a free-flowing form such as a powder or granules, optionally mixed by a binder, lubricant, inert diluent, surface active or dispersing agent. Moulded tablets may be made by moulding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration may be in the form of a sterile aqueous preparation of the drug which may be in microcrystalline form, for example, in the form of an aqueous microcrystalline suspension. Liposomal formulations or biodegradable polymer systems may also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pasts; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect may be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents, bile salts, and filsidic acid derivatives. Transmucosal administration can be accomplished through the use of nasal sprays or suppositories. For transdermal administration, the active compounds typically are formulated into ointments, salves, gels, or creams as generally known in the art.

The active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials also can be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. Microsomes and microparticles also can be used.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

As noted above, drugs identified or designed according to the invention can be formulated into pharmaceutical compositions by admixture with pharmaceutically acceptable non-toxic excipients and carriers. Such compositions can be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition can include the drug dispersed in a fibrinogen-thrombin composition or other bioadhesive. The drug then can be painted, sprayed or otherwise applied to the desired tissue surface. Alternatively, the drugs can be formulated for parenteral or oral administration to humans or other mammals, for example, in therapeutically effective amounts, e.g., amounts which provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The drug can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art.

Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

The effective concentration of the compounds to be delivered in a therapeutic composition will vary depending upon a number of factors, including the final desired dosage of the compound to be administered and the route of administration. The preferred dosage to be administered also is likely to depend on such variables as the type and extent of disease or indication to be treated, the overall health status of the particular patient, the relative biological efficacy of the compound delivered, the formulation of the drug, the presence and types of excipients in the formulation, and the route of administration. In general terms, the drugs of this invention can be provided to an individual using typical dose units deduced from the earlier-described mammalian studies using non-human primates and rodents.

When the active compounds are nucleic acid molecules, the nucleic acid may be inserted into vectors and used as gene therapy vectors. Gene therapy vectors can be delivered to a subject by, for example, intravenous injection, local administration (see, U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

When an active compound of the invention is intended for administration to a plant host, the invention may be applied directly to the plant environment, for example, to the surface of leaves, buds, roots or floral parts. Alternatively, the present invention can be used as a seed coating. The determination of an effective amount of the present invention as required for a particular plant is within the skill of the art and will depend on such factors as the plant species, method of planting, and soil type. It is contemplated that compositions containing drugs of the invention can be prepared by formulating such drugs with adjuvants, diluents, carriers, etc., to provide compositions in the form of filings/divided particulate solids, granules, pellets, wettable powders, dust, aqueous suspensions or dispersions, and emulsions. It is further contemplated to use such drugs in capsulated form, for example, the drugs can be encapsulated within polymer, gelatin, lipids or other formulation aids such as emulsifiers, surfactants wetting agents, antifoam agents and anti-freeze agents, may be incorporated into such compositions especially if such compositions will be stored for any period of time prior to use. Application of compositions containing drugs of the invention as the active agent can be carried out by conventional techniques. When an active compound is intended for administration to an insect host, standard methods such as, but not limited to, aerial dispersal are contemplated.

Active compound identified or designed by a method of the invention also include precursors of the active compounds. The term precursors refers to a pharmacologically inactive (or partially inactive) derivative of a parent molecule that requires biotransformation, either spontaneous or enzymatic, within the organism to release the active compounds. Precursors are variations or derivatives of the compounds of the invention which have groups cleavable under metabolic conditions. Precursors become the active compounds of the invention which are pharmaceutically active in vivo, when they undergo solvolysis under physiological conditions or undergo enzymatic degradation. Precursor forms often offer advantages of solubility, tissue compatibility, or delayed release in the mammalian organism (see Bundgard, *Design of Prodrugs*, pp. 7-9, 21-24, Elsevier, Amsterdam (1985); and Silverman, *The Organic Chemistry of Drug Design and Drug Action*, pp. 352-401, Academic Press, San Diego, Calif. (1992).

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a drug as well as tailoring the dosage and/or therapeutic regimen of treatment with the drug.

With regard to mammals, it is contemplated that the effective dose of a protein synthesis inducer or inhibitor will be in the range of about 0.01 to about 50 mg/kg, preferably about 0.1 to about 10 mg/kg of body weight, administered in single or multiple doses. Typically, the inducer or inhibitor may be administered to a human recipient in need of treatment at a daily dose range of about 1 to about 2000 mg per patient.

In light of the foregoing general discussion, the specific examples presented below are illustrative only and are not intended to limit the scope of the invention. Other generic and specific configurations will be apparent to those persons skilled in the art.

III. Examples

A. Example 1

Preparation of 50S Ribosomal Subunit Crystals

*H. marismortui* (ATCC 43049) was grown as described previously (Ban et al. (1998) supra) on a slightly modified version of ATCC culture medium 1230, which was supplemented with 4.3 g of yeast extract, 5.1 g of Tris, and 3.4 g of glucose per liter. Bacteria were grown at 37° C. to an $OD_{550nm}$ between 1.0 and 2.2. They were harvested by centrifugation, and stored at −80° C. until use. Cells were ruptured using a French press. Ribosomes were prepared from lysates by centrifugation, and subunits were isolated on sucrose gradients as previously described (Shevack et al. (1985) *FEBS Lett.* 184: 68-71).

The crystals were prepared and stabilized as follows:

1. Reverse Extraction (1) Mix 1 mg of subunits in a concentrated 50S ribosomal subunit stock (30 mg/ml in 1.2 M KCl, 0.5 M $NH_4Cl$, 20 mM $MgCl_2$, 10 mM Tris, 1 mM $CdCl_2$, 5 mM Tris, pH 7.5) with ½ volume of 30% PEG6000 (300 g PEG, 700 ml $H_2O$ to make 1 liter of 30% PEG; filter through 0.2 µm filter). Leave on ice for 1 to 2 hours.

(2) Spin down the precipitate in an eppendorf tube for about 30 seconds using a desktop centrifuge.

(3) Remove the supernatant and add 100 µl of RE-buffer (7% PEG6000, 1.2 M KCl, 0.5 M $NH_4Cl$, 100 mM KAc, 30 mM $MgCl_2$, 10 mM Tris, 10 mM MES (pH 7.5), and 1 mM $CdCl_2$).

(4) Resuspend the pellet at room temperature by mixing with a P200 pipette set at 50 µl. The resuspended material should appear a little cloudy.

(5) Wrap the eppendorf tube in aluminum foil and leave for equilibration at room temperature for 30-60 minutes The solution will be saturated with 50S ribosomal subunits.

(6) Spin down the precipitate for 2 minutes in desk-top centrifuge at room temperature, and transfer the supernatant to new eppendorf tube. A little pellet should be found in the tube used for centrifugation. Store the supernatant at room temperature.

(7) Place 8-10 µl of the supernatant in the sample well of a sitting drop tray (Charles-Supper). Streak seed one hour later from a seed stock. Seed stock is prepared by putting previously grown crystals in stabilizing solution buffer A (see below), and then vortexing them violently. To streak seed, a human hair cleaned with water and ethanol and then dried is passed through the vortexed solution and then touched on the new crystallization drop. Drops should look cloudy. The reservoirs in the sitting drop trays contain 1000 µl of a solution containing 8% PEG6000, 1.2 M KCl, 0.5 M $NH_4Cl$, 100 mM KAc, 6.5 mM HAc (yields pH 5.8), 30 mM $MgCl_2$, and 1 mM $CdCl_2$.

(8) After one day, see if the seeding is successful and, if so, let the crystals grow for three weeks.

2. Stabilization Protocol

When the crystals have finished growing (after approximately 3 weeks), open each sitting drop chamber by making just a single cut (slit) going from the middle to the edge of the well. Through this narrow slit, add to each drop in each reservoir 10 µl of buffer A (1.2 M KCl, 0.5 M $NH_4Cl$, 30 mM $MgCl_2$, 10% PEG6000, 1 mM $CdCl_2$, 100 mM KAc, 10 mM Tris (titrated to final pH 6.1), 30 mM MES) at room temperature and 45 µl of Buffer C (0.667 M MES, 0.333 M Tris).

Place trays in a plastic box with a lid, and place in a 16° C. incubator for approximately one day, and then lower the temperature of the incubator to 12° C. for another day. Then place the plastic box in a polystyrene container with a lid, and put in a cold room for yet another day. Crystals can be stored like this for a long time, but need to undergo a further buffer change prior to use.

Make the following transition series using buffer A (see above) and buffer B (1.7 M NaCl, 0.5 M $NH_4Cl$, 30 mM $MgCl_2$, 1 mM $CdCl_2$, 12% PEG6000, 20% EG, 100 mM KAC (titrated to final pH 5.8 with HAC) to give final ratios of buffer B to buffer A of: 1/16, 1/8, 1/4, 1/2, 3/4. All solutions should be kept at cold room temperature. All of the following manipulations of the drops will take place through the narrow slit (1) Add 40 µl "1/16" to the drop, and leave for 15 minutes.

(2) Add 40 µl "1/8" to the drop, and leave for 30-60 minutes.

(3) Take out 40 µl from the drop (and discard it in the reservoir), add 40 µl "1/4", and leave for 30-60 minutes.

(4). Take out 40 µl from the drop (and discard it in the reservoir), add 40 µl "1/2", and leave for 15 minutes.

(5) Take out 40 µl from the drop (and discard it in the reservoir), add 40 µl "3/4", and leave for 15 minutes.

(6) Take out 40 µl from the drop (and discard it in the reservoir), add 40 µl buffer B, and leave for 15 minutes.

(7) Take out 60-80 µl from the drop (and discard it in the reservoir), add 60-80 µl Buffer B, and replace reservoirs with 500 µl buffer B.

B. Example 2

Determination of the Crystal Structure of the 50S Ribosomal Subunit, with the Initial Refinement All data, except the two native data sets, were collected at the National Synchrotron Light Source (Brookhaven) from crystals frozen at 100 K, using beamlines X12b and X25 and recorded using a 345 mm MAR imaging plate. For each heavy atom derivative, anomalous diffraction data were collected at the wavelength corresponding to the peak anomalous scattering. The beam size was 100×100 µm for most data collections at X25 and 200×200 µm at beamline X12b. The crystals were aligned along the long axis of the unit cell (570 Å) so that 1.0° oscillations could be used to collect reflections out to a maximum of 2.7 Å resolution at the edge of the MAR detector. At beamline X12b the crystal to detector distances varied between 450.0 mm and 550.0 mm depending on wavelength, crystal quality, and beam divergence, and it was chosen so that maximum resolution data could be collected while avoiding overlapping of spots. At beamline X25 the detector was positioned on a rigid platform at 480 mm which allowed data collection to 3.2 Å for iridium and osmium derivatives with the wavelength set at the anomalous edge. Native data to 2.4 Å resolution were collected at the structural biology beamline ID19 of the Advanced Photon Source (Argonne) using a CCD detector. Data sets were processed by using DENZO and SCALEPACK (Otwinowski, (1993) *Data Collection and Processing*).

Heavy atom based phasing was extended to 3.2 Å resolution by combining MIR phases calculated for two different isomorphous groups of data (MIR1 and MIR2, Table 1) with single derivative anomalous dispersion (SAD) phases. The best two derivatives were osmium pentamine and iridium hexamine, each of which contained a large number of binding sites (Table 1). Several other derivatives with smaller number of sites further improved map quality. All phasing was done by maximum likelihood method implemented in CNS (Brünger et al. (1998) supra) with the exception of the $Ta_6Br_{12}$ derivative, which was refined in SHARP (de La Fortelle, (1997) *Meth. Enzymol.* 276: 472-494) represented as spherically averaged electron density (Table 1). Phases were improved and extended from 3.3 Å to 2.4 Å by solvent flipping (Abrahams et al. (1996) supra), and models were built from the data set.

C. Example 3

Preparation of Crystals of 50S Ribosomal Subunit/Puromycin Complex and Collection of X-Ray Diffraction Data Crystals of 50S ribosomal subunits were grown and stabilized as described earlier. CCdA-p-puromycin (see, FIG. 9A)

was a generous gift from Michael Yarus (Welch et al. (1995) supra). Oligonucleotides from amino-N-acylated minihelices (see, FIG. 9B) were synthesized by Dharmacon. Following deprotection, the oligonucleotides were heated briefly to 100° C. and snap-cooled on ice to reanneal. Ribosomal 50S subunit crystals were stabilized and then soaked for 24 hours in stabilization buffer plus 100 μM CCdA-p-puromycin or amino-N-acylated mini-helices prior to cryovitrification in liquid propane and collection of X-ray diffraction data. Phases were calculated by density modification (CNS) beginning with the best experimental phases using $2F_o(\text{analogue})-F_o(\text{native})$ for amplitudes, from 60.0 to 3.2 Å. (Native amplitudes were from the most isomorphous native 1 data set, except for those amplitudes which were present only in the more complete native 2 data set. Calculated $2F_o-F_o$ amplitudes which were less than twice the corresponding calculated and were replaced by $F_o(\text{analogue})$). Maps then were calculated using phases from density modified and $2F_o(\text{analogue})-F_o(\text{native})$ or $F_o(\text{analogue})-F_o(\text{native})$ amplitudes.

D. Example 4

Antibiotic Binding Sites Located in the Polypeptide Exit Tunnel Near the Peptidyl Transferase Center Electron density maps derived from crystalline complexes of the *H. marismortui* large subunit complexed with the three antibiotics tylosin, carbomycin A and anisomycin at about 3.0 Å resolution. All these antibiotics bind to the ribosome in the region that lies between the peptidyl transferase center as defined by the Yarus inhibitor, CCdA-p-puromycin, and the tips of the proteins L22 and L4 at the point that they form a small orifice in the polypeptide exit tunnel. The general location of this major antibiotic binding site is shown in FIG. 19. Tylosin and carbomycin A appear to function by blocking the exit of newly synthesized polypeptides. Anisomycin appears to block the A-site.

The vast majority of the interactions between these antibiotics and the ribosome are through rRNA that defines the A-site, and the surface of the tunnel between the peptidyl transferase center and protein L22. Since these antibiotics do not bind identically, there will be many additional ways that small molecule compounds can be designed to bind in this region using the tools and methodologies of the present invention. For example, by connecting together components of each of the different antibiotics which bind to non-overlapping sites it will be possible to create new hybrid antibiotics (see, Example 6). In addition, based on new principles of small molecule RNA interaction shown by these antibiotic complexes it is possible to design entirely novel small molecules that will bind to the same sites on the ribosome, as well as other potential RNA targets.

E. Example 5

Design and Testing of Hybrid Antibiotics

Many antibiotics that target ribosomes, more particularly large ribosomal subunits, and disrupt protein synthesis are complex molecules that are effectively concatenations of simpler substructures, at least one of which interacts with a discrete part of the ribosome. When the compound in question includes several interactive substructures, its binding site is effectively the sum of the subsites that contact and engage each such substructure. It has been found that many antibiotics that target the large ribosomal subunit bind the ribosomal subunit at sites that are close to one another. Thus the possibility exists of synthesizing new antibiotics in which one ribosome-binding moiety of a first known antibiotic is linked chemically to a ribosome-binding moiety of a second known antibiotic that interacts with an adjacent subsite. The new compound that results is thus a chimera or hybrid of the two antibiotics from which it derives.

Chimeric antibiotics can be designed using the information about the structures of antibiotic/ribosome complexes discussed hereinabove. These structures permit the identification of antibiotic binding subsites in the ribosome, and the specification of the chemical entities that interact with them. Equipped with such knowledge, those skilled in the art of organic synthesis can synthesize compounds that link the substructures of interest together in ways that should enable them to interact with their respective subsites at the same time. Any compound devised this way that functions in the manner intended is likely to inhibit cell growth and if it does, protein synthesis in vivo. At the very least, it should block protein synthesis in in vitro assay systems. Further information about the ribosomal interactions of such a compound can be obtained by determining the structure of the complex it forms with the ribosome using the methods described in Section D, hereinabove.

For example, as a result of the work described herein, it has been discovered that the disaccharide moiety of carbomycin binds the large ribosomal subunit at a site in close proximity to the binding site for a portion of the anisomycin. Using this information and the software packages described hereinabove, the skilled artisan can design a hybrid antibiotic comprising the relevant ribosome binding portions of carbomycin and anisomycin linked by a suitable chemical linker.

FIG. 34 shows the design of exemplary hybrid antibiotics. In this figure, a portion of the sparsomycin antibiotic is linked to a portion of the chloramphenicol antibiotic to produce a sparsochloramphenicol hybrid antibiotic. In a first sparsochloramphenicol hybrid antibiotic, Hybrid A, n=1 in the linking region (1). In a second sparsochloramphenicol hybrid antibiotic, Hybrid B, n=2 in the linking region (2). The portion of the chloramphenicol molecule was chosen as a result of the structural studies described in Schlünzen et al. (2001) *Nature* 413: 814-821. The hybrid antibiotic again was designed to permit each component of the hybrid antibiotic to bind its respective binding site in the large ribosomal subunit.

FIG. 35 shows the design of another exemplary hybrid antibiotic. In this figure, a portion of the sparsomycin antibiotic is linked to a portion of the anisomycin antibiotic to produce a sparsoanisomycin hybrid antibiotic. The portions of each antibiotic were chosen as a result of the structural studies herein which showed how each of the antibiotics bind the large ribosomal subunit. The hybrid antibiotic was designed to permit each component of the hybrid antibiotic to simultaneously bind its respective binding site in the large ribosomal subunit.

These hybrid molecules, once designed, can be synthesized and purified using conventional synthetic organic chemistries and conventional purification schemes. Once synthesized and purified, the hybrid molecule of interest can be screened for bioactivity and to determine, for example, the $IC_{50}$ value for each molecule of interest. These screens can include, for example, growing micro-organisms on or in media either supplemented or lacking the hybrid molecule. Any reduction in the number of micro-organisms or the size of colonies in the presence of the hybrid molecule would be indicative of bioactivity. Furthermore, the hybrid molecule could be tested in a cell-free coupled transcription/translation assay or in translation system in the presence of one or more labeled amino acids or using a nonradioactive reporter system. Any reduction in the level of labeled amino acids incorporated into proteins in cell-free systems that include the hybrid molecule relative to cell-free systems lacking the hybrid molecule would be indicative that the hybrid molecule acts as a functional protein synthesis inhibitor. It is contemplated that the hybrid molecule could then be iteratively refined as discussed hereinabove to enhance its bioactivity and bioavailability.

F. Example 6

Synthesis of Sparsochloramphenicol Hybrids

The synthesis of the sparsochloramphenicol hybrids (1 and 2) are shown in FIGS. 36 to 39, and described stepwise as follows.

i. Synthesis of Acid 6

Acid 6 in FIG. 36 was obtained by the procedures described in Ottenheijm et al., *J. Org. Chem.* 1981, 46, 3273-3283, starting with compound 4 and through intermediate aldehyde 5.

ii. Synthesis of Amine 7

Amine 7 in FIG. 36 was synthesized as shown in FIG. 37. L-cysteine (1.00 g, 5.41 mmol), dimethoxytrityl (DMT) chloride (2.12 g, 5.95 mmol), and triethylamine (1.20 mL, 8.56 mmol) were combined in 25 mL 80% aqueous acetic acid and allowed to react at room temperature for 2 hours. The solvents were evaporated in vacuo, and the residue taken up in 60 mL ethyl acetate (EtOAc). The solution was washed with saturated aqueous sodium bicarbonate ($NaHCO_3$) (3×50 mL), and brine (2×50 mL). The organic layer was dried with sodium sulfate ($Na_2SO_4$), and evaporated to provide the DMT thioether of L-cysteine 10 (2.13 g, 5.03 mmol, 93%) of suitable purity for use in the next reaction.

The protected amino acid 10 (5.41 mmol) was dissolved in 20 mL anhydrous tetrahydro-furan (THF), and sodium borohydride (0.70 g, 18.2 mmol) was added in portions. Boron trifluoride etherate (3.03 mL, 23.9 mmol) was added dropwise, and the mixture was allowed to stir overnight at room temperature. Excess boron trifluoride etherate was destroyed with ethanol, and the mixture filtered. The filtrate was evaporated, and the residue dissolved in chloroform (60 mL) and washed with saturated aqueous $NaHCO_3$ (40 mL). The aqueous layer was extracted with chloroform (20 mL), and the combined organic phase washed with brine, and dried over $Na_2SO_4$. The solvent was evaporated to provide the expected amino alcohol 11 (1.75 g, 85%) as a white solid of suitable purity for use in the next step.

Amino alcohol 11 (1.70 g, 4.15 mmol) was dissolved in 5 mL acetonitrile and 5 mL methylene chloride, and the solution cooled to 0° C. Tert-butyldimethylsilyl chloride (1M, 5.00 mL, 5.00 mmol) was added, followed by 1,8-diazabicyclo [5.4.0]undec-7-ene (DBU) (0.67 mL, 4.40 mmol), and the mixture allowed to stir overnight at room temperature. The reaction was quenched by stirring with saturated aqueous $NaHCO_3$ for 20 minutes. Additional methylene chloride was added and the layers were separated. The organic layer was washed with $NaHCO_3$, water and then brine. The organic phase was dried ($Na_2SO_4$) and evaporated. The residue was chromatographed on silica gel using 0-2% methanol/chloroform to provide amine 7 (0.100 g, 5%), $^1$H-NMR (500 MHz, $CDCl_3$) δ 7.41 (d, J=2 Hz, 2H), 7.41-7.19 (m, 8H), 6.82-6.79 (m, 4H), 3.79 (s, 6H), 3.44-3.41 (m, 1H), 3.35-3.32 (m, 1H), 2.69-2.67 (m, 1H), 2.36-2.33 (m, 1H), 2.19-2.15 (m, 1H), 0.85 (s, 9H), 0.05-0.00 (m, 6H).

iii. Synthesis of Amide 8

Amide 8 in FIG. 36 was synthesized as follows. Acid 6 (0.044 g, 0.221 mmol), amine 7 (0.070 g, 0.134 mmol), and 1-hydroxybenzotriazole (HOBt) (0.030 g, 0.21 mmol) were dissolved in 2 mL dimethyl formamide (DMF). 1,3-dicyclohexylcarbodiimide (DCC) (0.056 g, 0.272 mmol) was added, and the mixture was stirred for 24 hours at room temperature. The mixture was evaporated and chromatographed on silica gel using 0-4% methanol/chloroform to provide amide 8 (0.070 grams, 75%), $^1$H-NMR (500 MHz, $CDCl_3$) δ 7.50-7.15 (m, 12H), 6.80 (d, J=2 Hz, 4H), 5.91 (br d, J=5 Hz, 1H), 4.20-4.11 (m, 1H), 3.74 (s, 6H), 3.66-3.63 (m, 1H), 3.52-3.49 (m, 1H), 2.49-2.44 (m, 2H), 2.36 (s, 3H), 0.84 (s, 9H), 0.01 (s, 3H), −0.01 (s, 3H).

iv. Synthesis of Thiol 9

Thiol 9 in FIG. 36 was synthesized as follows. Amide 8 (0.060 g, 0.086 mmol) was dissolved in THF at 0° C. Boron trifluoride etherate (0.30 mL, 2.37 mmol) was added dropwise, and stirring was continued for 20 minutes. The reaction mixture was quenched with ethanol (5 mL, stirred for 5 min), and the solvents were evaporated. The residue was triturated with chloroform, and the solids collected by centrifugation were washed with chloroform. The solids were dried to provide thiol 9 (0.015 g, 63%), $^1$H-NMR (500 MHz, $CDCl_3$) δ 7.31 (d, J=9 Hz, 1H), 7.11 (d, J=9 Hz, 1H), 3.93-3.90 (m, 1H), 3.59-3.50 (m, 3H), 3.22-3.20 (m, 1H), 2.68-2.64 (m, 1H), 2.56-2.53 (m, 1H), 2.23 (s, 3H).

v. Synthesis of Bromoacetamide 13

Bromoacetamide 13 in FIG. 37 was synthesized as follows. The free base of (1R,2R)-chloramphenicol 12 was converted to the bis t-butyldimethylsilylether derivative as described in Orsini et al., *Organic Preparations and Procedures International* 1989, 21, 505-508. The resulting bis-silyl ether of (1R,2R)-chloramphenicol (0.56 g, 1.30 mmol), bromoacetic acid (0.146 g, 1.00 mmol) and HOBt (0.163 g, 1.20 mmol) were dissolved in 6 mL THF. DCC (0.330 g 1.6 mmol) was added and the mixture was stirred overnight at room temperature. The precipitate was filtered, and the filtrate evaporated. The residue was taken up in 60 mL EtOAc and extracted with 5% aqueous $NaHCO_3$ (30 mL) and brine (2×40 mL). The organic layer was dried over $Na_2SO_4$, and evaporated. The residue was chromatographed on silica using 1:7 EtOAc/hexane to 1:5 EtOAc/hexane as eluants to provide bromoacetamide 13 (0.480 g, 86%) as an oil, $^1$H-NMR (500 MHz, $CDCl_3$) δ 8.32 (d, J=5 Hz, 2H), 7.62 (d, J=5 Hz, 2H), 7.21 (br d, J=5 Hz, 1H), 5.36 (s, 1H), 4.11-4.06 (m, 1H), 4.01-3.85 (m, 4H), 3.75-3.68 (m, 2H), 3.39-3.31 (m, 1H), 1.10 (s, 9H), 1.05 (s, 9H), 0.24 (s, 3H), 0.22 (s, 3H), 0.21 (s, 3H), 0.00 (s, 3H).

vi. Synthesis of Sulfide 14.

Sulfide 14 in FIG. 38 was synthesized as follows. Thiol 9 (0.090 g, 0.315 mmol) was suspended in 3 mL THF/0.5 mL DMF and DBU (49 μL, 0.315 mmol) was added. A solution of bromoacetamide 13 (0.16 g, 0.284 mmol) in 2 mL THF was added at 0° C., and the mixture was warmed to room temperature and then stirred at room temperature for 12 hours. The reaction was poured into saturated brine (20 mL) and chloroform ($CHCl_3$) (40 mL), and the layers were separated. The organic layer was washed with saturated brine (2×20 mL) and dried over $Na_2SO_4$. The solvents were evaporated, and the residue chromatographed on silica (pipet column) using a gradient elution from 1:20 methanol/chloroform to 1:10 methanol/chloroform to produce sulfide 14 (0.093 g, 43%) as a white solid, $^1$H-NMR (500 MHz, 1:1 chloroform-d/methanol-$d_4$ ($CDCl_3/CD_3OD$)) δ 8.15 (d, J=6 Hz, 2H), 7.55 (d, J=5 Hz, 1H), 7.53 (s, 1H), 7.47 (d, J=6 Hz, 2H), 7.37 (d, J=9 Hz, 1H), 7.14 (d, J=9 Hz, 1H), 5.20 (br s, 1H), 4.09-4.02 (m, 1H), 3.98-3.92 (m, 1H), 3.70-3.53 (m, 5H), 3.33-3.12 (m, 4H), 2.67-2.61 (m, 2H), 2.31 (s, 3H), 0.91 (s, 9H), 0.90 (s, 9H), 0.08 (s, 3H), 0.06 (s, 3H), −0.06 (s, 3H), −0.14 (s, 3H).

vii. Synthesis of Sulfoxide 16

Sulfoxide 16 in FIG. 38 was synthesized as follows. Sulfide 14 (0.060 g, 0.078 mmol) was dissolved in 2 mL THF, and the mixture was cooled to 0° C. Diisopropylethylamine (i-Pr$_2$Net) (18 µL, 0.10 mmol) was added, followed by chloromethyl methyl ether (33.2 µL, 0.39 mmol), and stirring was continued for 1 hour at 0° C. The cooling bath was removed and the reaction allowed to stir for 12 hours at room temperature. The reaction was quenched with saturated aqueous NaHCO$_3$, and partitioned with chloroform (40 mL). The aqueous layer was extracted with chloroform (20 mL), and the combined organic phase was dried over Na$_2$SO$_4$, and evaporated. The crude material was chromatographed on silica using 0-4% methanol/chloroform as eluant. Two fractions were obtained. Fraction 1 (10.8 mg) contained a minor impurity at $R_f$=0.63 (12% methanol/chloroform) and a major component at $R_f$=0.58. Fraction 2 (16 mg) contained only one compound at $R_f$=0.50. (The starting alcohol had an $R_f$=0.36.) These fractions appeared to contain compounds that were protected fully on the hydroxyl group of interest, and partially over protected (MOM ethers on the uracil portion of the molecules).

Material from Fraction 2 above (0.016 g, 0.020 mmol) was dissolved in 1 mL carbon tetrachloride (CCl$_4$). To this solution was added a mixture containing Titanium (IV) isopropoxide (Ti(Oi-Pr)$_4$) (0.6 µL, 0.002 mmol), BINAP (0.001 g, 0.004 mmol), water (0.72 uL, 0.02 mmol) in CCl$_4$ (1 mL), and the resulting mixture stirred at 20° C. (see Komatsu et al., *J. Org. Chem.* 1993, 58, 4529-4533 for a detailed description of this oxidation protocol). Tert-butyl hydroperoxide in toluene (1M, 60 µL, 0.06 mmol) was added to the mixture and stirring continued for 72 hours. At this time, TLC analysis indicated ~75% conversion to a new lower $R_f$ product ($R_f$=0.39, CHCl$_3$/MeOH 8:1). The reaction was partitioned between saturated NaHCO$_3$ (10 mL) and CHCl$_3$ (20 mL). The aqueous layer was washed with CHCl$_3$ (2×10 mL) and the combined organic phase was dried over Na$_2$SO$_4$ and the solvent was evaporated. The crude material was chromatographed on silica gel eluting with 0-5% methanol (MeOH) in CHCl$_3$. Two fractions were obtained: fraction 1 contained unreacted starting material (4.1 mg), while fraction 2 contained sulfoxide 16 (7.7 mg, 0.036 mmol).

viii. Synthesis of Sparsochloramphenicol Hybrid A 1

Sparsochloramaphenicol hybrid A 1 in FIG. 38 (full structure in FIG. 34) was synthesized as follows. Sulfoxide 16 (0.0075 g 0.0091 mmol) was dissolved in 0.1% hydrochloric acid (HCl) in MeOH (2 mL) and Dowex® 50 (H$^+$ form) (0.2 g) was added. The mixture was stirred at 50° C. for 3 hours and TLC analysis showed a complete conversion to a single lower $R_f$ product ($R_f$=0.25, CHCl$_3$/MeOH 25:3). The Dowex® 50 was removed by filtration and the solvent evaporated in vacuo. The crude product was dissolved in THF (0.5 mL) and MeOH (0.5 mL), a solution of H$_2$SiF$_6$ (20 wt/vol. in H$_2$O) (120 µL, 0.15 mmol) was added and the mixture was stirred for 3 hours at room temperature. TLC analysis showed ~50% conversion to a baseline product within 3 hours, hence stirring continued overnight (~20 hours) during which almost a quantitative formation of the baseline product was observed. The reaction was partitioned between CHCl$_3$ (1 mL) and water (H$_2$O) (1.5 mL), the layers were separated and the aqueous layer was extracted once with CHCl$_3$/MeOH 2:1 (1.5 mL). TLC analysis (CHCl$_3$/MeOH 7:1) showed that the baseline product was exclusively in the aqueous layer, while TLC (CHCl$_3$/MeOH/H$_2$O 2:1:0.1) showed the presence of closely associated compounds ($R_f$s 0.71 and 0.67). The aqueous layer was concentrated and chromatographed on silica (pipet column) using CHCl$_3$/MeOH/H$_2$O 2:1:0.1 to yield a diastereomeric mixture of 1 (0.0017 g, 34%) as a white solid, $^1$H-NMR, partial (500 MHz, deuterium oxide (D$_2$O)/CD$_3$OD) δ 8.15 (app d, J=8.5 Hz, 2H), 7.57 (app d, J=8.5 Hz, 2H), {7.42 (app d, J=15.5 Hz, major diastereomer), 7.39 (app d, J=15.5 Hz, minor diastereomer); 1H}, {6.99 (app d, J=16 Hz, minor diastereomer), 6.96 (app d, J=15.5 Hz, major diastereomer); 1H}, {2.53 (s, major diastereomer), 2.51 (s, minor diastereomer); 3H). HRMS calcd for C$_{22}$H$_{27}$N$_5$O$_{10}$S (M, monodeuterated)$^+$: 555.15. Found: 555.15.

ix. Synthesis of Sulfide 15

Sulfide 15 in FIG. 38 was synthesized as follows. Sulfide 14 (0.02 g, 0.026 mmol) was dissolved in THF (0.3 mL) and MeOH (0.3 mL), a solution of H$_2$SiF$_6$ (20 wt/vol. in H$_2$O) (200 µL, 0.25 mmol) was added and the mixture was stirred for 20 hours at 20° C. The reaction was partitioned between CHCl$_3$ (1 mL) and H$_2$O (0.5 mL), and the layers were separated. The aqueous layer was concentrated and chromatographed on silica (pipet column) using CHCl$_3$/MeOH/H$_2$O 2.5:1:0.1 to provide compound 15 (0.0097 g, 70%) as a white solid, $^1$H-NMR (500 MHz, D$_2$O/CD$_3$OD) δ 8.21 (d, J=9 Hz, 2H), 7.67 (d, J=9 Hz, 2H), 7.44 (d, J=15.5 Hz, 1H), 7.15 (d, J=15.5 Hz, 1H), 5.17 (d, J=3 Hz, 1H), 4.27 (m, 1H), 4.12 (m, 1H), 3.85 (m, 2H), 3.65 (m, 3H), 3.20-3.39 (m, 4H), 2.60 (m, 2H), 2.43 (s, 3H). HRMS calcd for C$_{22}$H$_{27}$N$_5$O$_9$S (M+H)$^+$: 538.16. Found: 538.12.

x. Synthesis of Bromopropionamide 17

Bromopropionamide 17 in FIG. 39 was made using the same protocol described for the synthesis of bromoacetamide 13, except 3-bromopropionic acid was used in place of bromoacetic acid. Bromopropionamide 17 was purified on silica gel column using 1:8 EtOAc/hexane to 1:4 EtOAc/hexane as eluants to provide bromopropionamide 17 (45%) as an oily foam, $^1$H-NMR (500 MHz, CDCl$_3$) (contaminated by ~30% acrylamide impurity) δ 8.18 (app d, J=9 Hz, 2H), 7.47 (app d, J=9, 2H), 5.24 (app d, J=4.5 Hz, 1H), 4.04 (m, 1H), 3.52-3.67 (m, 4H), 2.69 (m, 2H), 0.95 (s, 9H), 0.92 (s, 9H), 0.08 (s, 3H), 0.06 (s, 3H), −0.05 (s, 3H), −0.10 (s, 3H).

xi. Synthesis of Sulfide 18

Sulfide 18 in FIG. 39 was made from thiol 9 and bromopropionamide 17 using the protocol described for the synthesis of sulfide 14. The resulting product was purified on silica gel column eluting with 10:1 CHCl$_3$/MeOH to 8:1 CHCl$_3$/MeOH to provide sulfide 18 (7%) as a white solid.

xii. Synthesis of Sparsochloramphenicol Hybrid B 2

Sparsochloramphenicol Hybrid B 2 in FIG. 39 (full structure in FIG. 34) was synthesized as follows. Sulfide 18 (0.02 g, 0.026 mmol) was dissolved in CCl$_4$ (1.28 mL) containing Ti(Oi-Pr)$_4$ (0.77 µL, 0.0026 mmol), BINAP (0.0015 g, 0.0052 mmol), water (0.92 µL, 0.026 mmol) and the solution was stirred at 20° C. Tert-butyl hydroperoxide in toluene (1M, 71.3 µL, 0.07 mmol) was added and stirring continued at 20° C. for 72 hours. The reaction was partitioned between saturated NaHCO$_3$ (10 mL) and CHCl$_3$ (20 mL). The aqueous layer was washed with CHCl$_3$ (2×10 mL), the combined organic layer was dried over Na$_2$SO$_4$ and the solvent evaporated. The crude material was chromatographed on silica eluting with 0-10% MeOH in CHCl$_3$. Two fractions were obtained: fraction 1 contained unreacted sulfide 18 (0.0055 g) and fraction 2 contained the desired sulfoxide (0.008 g, 38%).

The sulfoxide product in fraction 2 above (0.008 g 0.01 mmol) was dissolved in THF (0.5 mL) and MeOH (0.5 mL), a solution of H$_2$SiF$_6$ (20 wt/vol. in H$_2$O) (120 µL, 0.15 mmol) was added and the mixture was stirred at room temperature overnight (~20 hours) during which almost a quantitative formation of a baseline product was noticed. The reaction was partitioned between CHCl$_3$ (1 mL) and H$_2$O (1.5 mL), the layers separated and the aqueous layer extracted once with CHCl$_3$/MeOH 2:1 (1.5 mL). TLC analysis (CHCl$_3$/MeOH 7:1) showed that the baseline product was exclusively in the aqueous layer, while TLC using CHCl$_3$/MeOH/H$_2$O 2:1:0.1 showed the presence of closely associated compounds (R$_f$s 0.52 and 0.47). The aqueous layer was concentrated and chromatographed on silica (pipet column) using CHCl$_3$/MeOH/H$_2$O 2:1:0.1 to yield a diastereomeric mixture of 2 (0.0036 g 69%) as a white solid, $^1$H-NMR, partial (500 MHz, D$_2$O/CD$_3$OD) δ {8.20 (app d, J=8.8 Hz), 8.13 (app d, J=8.8 Hz); 2H}, {7.58 (app d, J=9 Hz), 7.54 (app d, J=9 Hz); 2H}, {7.34 (app d, J=15 Hz), 7.24 (app d, J=15 Hz); 1H}, {7.01 (app d, J=15 Hz), 7.00 (app d, J=15 Hz); 1H}, 2.76 (m, 2H), 2.34 (bs, 3H). HRMS calcd for C$_{23}$H$_{29}$N$_5$O$_{10}$S (M+H)$^+$: 568.17. Found: 568.14.

G. Example 7

Synthesis of Sparsoanisomycin Hybrid

The synthesis of the sparsoanisomycin hybrid 3 is shown in FIGS. 40 and 41, and is described stepwise as follows:
i. Synthesis of Phenol 21

Phenol 21 in FIG. 40 was synthesized as follows. Anisomycin 19 (0.5 g 1.88 mmol) was suspended in 15 mL of acetonitrile. 9-Fluorenylmethyl succinimide (0.762 g 2.26 mmol) was added to the suspension. Upon addition, all solid dissolved. After stirring for 16 hours at room temperature, water was added to the reaction solution, and it was extracted with ethyl acetate. The organics were combined and dried over sodium sulfate. After filtration and concentration, purification was accomplished by column chromatography using 3:1 hexanes:ethyl acetate as the mobile phase. This gave 9-fluorenylmethyl carbamate 20 as foam in quantitative yields (0.916 g).

Compound 20 (0.929 g 1.90 mmol) was dissolved in 1.5 mL of dry 1-methyl-2-pyrrolidinone. Imidazole (0.776 g 11.4 mmol) and then tert-butyldimethylsilyl chloride (0.859 g 5.70 mmol) was added to the solution. After stirring at room temperature for 1.5 hours, the reaction solution was applied directly to a silica column. The column was eluted with a 6:1 hexanes:ethyl acetate solution to give the desired silylated product (1.04 g 91%) as white foam.

The silylated product above (1.04 g 1.73 mmol) was dissolved in 15 mL of dry methylene chloride. The solution was cooled to −10° C. A −10° C. 1.0 M solution of boron tribromide (17.3 mL) was added. After 2 hours, 4 mL of the boron tribromide solution was added. After an additional 2 hours at −10° C., the reaction solution was poured into a 0° C. saturated aqueous solution of sodium bicarbonate. The mixture was stirred vigorously for 30 minutes. It was then separated and extracted with methylene chloride. The organic layers were combined and dried over sodium sulfate. Purification was accomplished using column chromatography eluting with 4:1 hexanes/ethyl acetate and then 2:1 hexanes/ethyl acetate after the starting material was off the column to provide phenol 21 (0.748 g 74%) as a white foam, $^1$H-NMR (300 MHz, CDCl$_3$) δ 7.80 (d, J=7.4 Hz, 1H), 7.74 (d, J=7.4 Hz, 1H), 7.63 (m, 2H), 7.36 (m, 4H), 7.06 (d, J=8.0 Hz, 1H), 6.79 (d, J=8.3 Hz, 1H), 6.74 (s, 2H), 4.84 (m, 1H), 4.69 (d, J=4.9 Hz, 1H), 4.50 (m, 2H), 4.34 (m, 2H), 4.02 (m, 1H), 3.90 (m, 1H), 3.35 (m, 3H), 2.84 (m, 1H), 2.51 (m, 1H), 2.01 (s, 3H), 0.87 and 0.83 (two s, 9H), 0.06 and −0.01 (two s, 6H).
ii. Synthesis of Methlythiomethylphenyl Ether 23

Methylthiomethyl phenyl ether 23 in FIG. 40 was prepared as follows. Phenol 21 (0.748 mg 1.27 mmol) was dissolved in 10 mL of THF and 0.2 mL of piperidine was added. After stirring at room temperature for 2 hours, water was added and the mixture was extracted with ethyl acetate. The organic layers were combined and dried over sodium sulfate and filtered. The filtrate was concentrated and dried on a vacuum pump for several hours. The yellowish crude foam was then dissolved in 10 mL dry THF and triethylamine (0.35 mL, 2.54 mmol) was added. After stirring a few minutes, di-tert-butylcarbonate (1.11 g 5.08 mmol) was added. The reaction was stirred at room temperature for 20 hours. Water was added and the mixture was extracted with ethyl acetate and the organic layers were combined and dried over sodium sulfate. Purification was achieved by column chromatography using 4:1 hexanes/ethyl acetate. The desired N—BOC protected compound 22 was isolated as white foam (0.348 g 59%, two steps).

N—BOC protected compound 22 (0.202 g 0.434 mmol) was dissolved in 2.0 mL of dry THF under argon and cooled to 0° C. Sodium hydride (0.018 g of a 60% dispersion, 0.46 mmol) was added and the reaction continued to stir at 0° C. for fifteen minutes. Sodium iodide (0.071 g 0.48 mmol), hexamethylphosphoramide (0.45 mL, 2.6 mmol), and chloromethylthiomethyl ether (36 µL, 0.48 mmol) were added in that order. After stirring for five minutes, the ice bath was removed and the reaction was warmed to room temperature. After stirring for another 45 minutes, water was added to the reaction mixture and it was extracted with ethyl acetate. The organics were combined and dried over sodium sulfate. Purification was accomplished using column chromatography eluting with 6:1 hexanes/ethyl acetate to provide methylthiomethylphenyl ether 23 (0.203 g 89%) as an oil, $^1$H-NMR (300 MHz, CDCl$_3$) δ 7.07 (m, 2H), 6.86 (d, J=8.5 Hz, 2H), 5.11 (s, 2H), 4.84 (m, 1H), 4.33 (m, 1H), 3.91 (m, 1H), 3.35 (m, 3H), 2.83 (m, 1H), 2.24 (s, 3H), 2.06 (s, 3H), 1.48 (s, 9H), 0.81 (s, 9H), −0.02 (s, 6H).
iii. Synthesis of Chloromethylphenyl Ether 24

Chloromethylphenyl ether 24 in FIG. 40 was synthesized as follows. Methylthiomethylphenyl ether 23 (0.032 g 0.061 mmol) was dissolved in 1 mL of dry methylene chloride that contained 0.050 g of 3 Å molecular sieves and then cooled to 0° C. Diisopropylethylamine (15 µL, 0.085 mmol) and sulfuryl chloride (6.5 µL, 0.079 mmol) was added to the reaction mixture. After the reaction mixture was stirred two minutes, cyclohexene (12 μL, 0.12 mmol) was added. Five minutes after the addition of the cyclohexene, the reaction mixture was allowed to warm to room temperature and was stirred for another twenty minutes. The reaction was then quenched with water, extracted with methylene chloride, and dried over sodium sulfate. Purification was accomplished using column chromatography eluting with 6:1 hexanes:ethyl acetate to provide chloromethylphenyl ether 24 (0.021 g 67%) as an oil, $^1$H NMR (300 MHz, CDCl$_3$) δ 7.26 (m, 2H), 7.00 (d, J=8.5 Hz, 2H), 5.87 (s, 2H), 4.84 (m, 1H), 4.35 (m, 1H), 3.92 (m, 1H), 3.33 (m, 3H), 2.85 (m, 1H), 2.06 (s, 3H), 1.48 (s, 9H), 0.81 (s, 9H), −0.01 (s, 6H).

iv. Synthesis of Sulfoxide 25

Sulfoxide 25 in FIG. 41 was synthesized as follows. Thiol 9 (0.022 g 0.078 mmol) was dissolved in THF (0.5 mL), DMF (0.2 mL) and DBU (10.3 μL, 0.066 mmol). A solution in THF (0.5 mL) of a 3:2 mixture of methylthiomethylphenol ether 23 and chloromethylphenyl ether 24 (0.03 grams 0.023 mmol based on 24) was added and the resulting mixture stirred at room temperature overnight. The reaction was poured into saturated brine (10 mL) and CHCl$_3$ (20 mL) and the two layers were separated. The organic layer was washed with saturated brine and dried over Na$_2$SO$_4$. TLC analysis (CHCl$_3$/MeOH 7:1) showed a quantitative removal of the unreacted thiol 9. The solvent was evaporated, and $^1$H NMR of the residue in CD$_3$OD/CDCl$_3$ revealed a complete disappearance of the chloromethylphenoxy methylene peak at 5.9 ppm.

The crude material above was dissolved in CCl$_4$ (3.5 mL) containing Ti(Oi-Pr)$_4$ (1.81 μL, 0.006 mmol), BINAP (0.0035 g 0.012 mmol), water (2.17 μL, 0.06 mmol) and the solution was stirred at 20° C. Tert-butyl hydroperoxide in toluene (1M, 200 μL, 0.2 mmol) was added and stirring continued at 20° C. for 72 hours. The reaction was partitioned between saturated NaHCO$_3$ (10 mL) and CHCl$_3$ (20 mL). The aqueous layer was washed with CHCl$_3$ (2×10 mL), the combined organic layers were dried over Na$_2$SO$_4$ and the solvent evaporated off. The crude product was chromatographed on silica eluting with 0-7% MeOH in CHCl$_3$ to yield sulfoxide 25 (0.0054 g 30% two steps) as a yellow-white solid.

v. Synthesis of Sparsoanisomycin 3

Sparsoanisomycin 3 in FIG. 41 was synthesized as follows. Sulfoxide 25 (0.0035 g 0.0045 mmol) was dissolved in anhydrous methylene chloride (CH$_2$Cl$_2$) (0.25 mL) at 0° C. To this solution was added trifluoroacetic acid (TFA) (0.25 mL) and the mixture was stirred at room temperature for 30 minutes during which a quantitative consumption of 25 was noticed. The solvent was evaporated to give a brown residue.

The brown residue above was dissolved in anhydrous THF (0.4 mL) and pyridine (0.2 mL) in a falcon tube, and kept stirring at 0° C. Pyridine hydrofluoride (HF.pyr) (0.1 mL) was added to the reaction; the mixture was warmed to 20° C. and stirred overnight. The reaction was quenched by adding aqueous triethylammonium bicarbonate (1M, 50 μL) and chromatographed on silica (pipet column), first eluting with CHCl$_3$/MeOH 3:1 to 2:1, then CHCl$_3$/MeOH/H$_2$O 2:1:0.1 to yield sparsoanisomycin 3 (0.0012 g 47%) as a white solid, $^1$H-NMR, partial (500 MHz, D$_2$O/CD$_3$OD) δ {7.36 (app d, J=15.5 Hz), 7.35 (app d, J=15.5 Hz); 1H}, 7.25 (app d, J=8.6 Hz, 2H), {7.10 (app d, J=8.6 Hz), 7.09 (app d, J=8.6 Hz); 2H}, {7.04 (app d, J=15 Hz), 7.02 (app d, J=15 Hz); 1H}, {2.36 (s), 2.35 (s); 3H}, {2.18, (s), 2.17 (s); 3H}. HRMS calcd for C$_{25}$H$_{32}$N$_4$O$_9$S (M+H)$^+$: 565.19. Found: 565.16.

G. Example 8

Assay for Translational Inhibitory Activity

The translational inhibitory activity of the antibiotic hybrids produced in Examples 6 and 7 were tested in *E. coli* 30 S extracts and rabbit reticulocyte lysate assays as follows.

The *E. coli* S30 extract system for circular DNA (Promega part number: L1020) was used to assess translation inhibition following a variation of the protocol in Promega's Technical Bulletin No. 092. 5 μL S30 extract was incubated with 0.4 μg BestLuc plasmid DNA, 16 units ribonuclease inhibitor (Promega part number: N2115), 1 mM nucleotide triphosphates (NTPs), 10 mM MgCl$_2$, 40 mM Tris pH 7.5, for 30 minutes at 37° C. After allowing for transcription, the antibiotic (in a final concentration of 0.1% DMSO), 7 μL Promega's premix and amino acids at a final concentration of 0.1 mM were added in final volume of 20 μL. Reactions were incubated for 20 minutes at 37° C. and 50 μL of Luciferase assay reagent (Promega part number: E1483) was added to stop the reaction. Luminescence of the sample was measured using a Victor$^2$V spectrophotometer (Perkin Elmer).

The rabbit reticulocyte lysate (nuclease treated) system (Promega part number L4960) was used as the source of eukaryotic translation and the protocol in Promega's Technical Manual 232 was followed. For example, 10 μL of lysate was added to 2 μL of 1 mM amino acids and 3 μL of water. 2 μL of antibiotic in 1% DMSO was added followed by the addition of 0.6 μg Luciferase mRNA (Promega part number L4561) and 16 units ribonuclease inhibitor (Promega part number: N2115) in a final volume of 20 μL. The reaction was incubated at 24.5° C. for 45 minutes and 40 μL of Luciferase assay reagent (Promega part number: E1483) was added to stop the reaction. Luminescence of the sample was read by a Victor$^2$V spectrophotometer (Perkin Elmer).

The resulting IC$_{50}$ data for each hybrid antibiotic versus anisomycin, sparsomycin and chloramphenicol is summarized in Table 22.

TABLE 22

| | IC$_{50}$ (uM) | |
|---|---|---|
| Compound | E. coli | Rabbit Reticulocyte |
| Sparsochloramphenicol Hybrid A 1 | 29.9 | 0.82 |
| Sparsochloramphenicol Hybrid B 2 | 4.1 | 0.36 |
| Deoxysparsochloramphenicol 15 | 14 | 6.4 |
| Sparsoanisomycin 3 | 26.7 | 0.07 |
| Anisomycin | >100 | 0.19 |
| Sparsomycin | 0.21 | 0.14 |
| Chloramphenicol | 12.3 | >100 |

The data in Table 22 indicate that all of the hybrid antibiotics produced in Examples 6 and 7 are capable of inhibiting translation in two different translation assays. Furthermore, under certain assay conditions, at least one of the hybrid antibiotics (Sparsoanisomycin) was a more potent protein synthesis inhibitor than either of the antibiotics on which it was based.

H. Example 9

Binding of Macrolide Antibiotics to the Large Ribosomal Subunit

Crystal structures of the *H. marismortui* large ribosomal subunit complexed with five macrolides, carbomycin A, spiramycin, tylosin, azithromycin, and erythromycin show that these antibiotics bind in the polypeptide exit tunnel immediately adjacent to the peptidyl transferase center. Tylosin, carbomycin A and spiramycin are 16-membered macrolides. Azithothromycin is a 15-membered macrolide. Erythromycin is a 14-membered macrolide.

Their respective binding locations and bulk suggest that they inhibit protein synthesis by blocking the passage of nascent polypeptides through peptide exit tunnel. The saccharide at the C5 position of each of the lactone rings extends up the exit tunnel towards the peptidyl transferase site. The isobutyrate extension of the carbomycin A disaccharide overlaps the A-site substrate binding site. A reversible covalent bond appears to form between the ethylaldehyde substituent at the C6 of the lactone ring and the N6 of A2103 (A2602, *E. coli*) in 23 rRNA.

Crystals containing *H. marismortui* large ribosomal subunits with carbomycin A, spiramycin, tylosin, azithromycin, and erythromycin bound were obtained adding stabilizing buffers containing these antibiotics to pre-formed, large ribosomal subunit crystals. The structures of these antibiotics complexed with these crystals were determined at 3.0 Å resolution (3.5 Å for erythromycin) from difference Fourier maps calculated initially using observed diffraction amplitudes from the native and complex crystals [$F_o$ (complex)-$F_o$ (native)], and then the co-ordinates of the entire complex were refined.

Ribosomes were purified and crystallized as described previously (Ban et al., (2000). Antibiotics were selected for testing based on their known activity against *H. marismortui* (Sanz et al., (1993) *Can. J. Microbiol.* 39: 311-317) and their availability. Carbomycin A was obtained from Pfizer. Tylosin was purchased from Sigma. A mixture of spiramycins I, II and II which differ only in the size of the moiety attached to C3, also were purchased from Sigma. Azithromycin was generously provided by Dale L. Boger, Department of Chemistry, the Scripps Research Institute, La Jolla, Calif. Erythromycin was obtained from Sigma.

Crystals containing *H. marismortui* large ribosomal subunits complexed with carbomycin A, spiramycin, tylosin, azithromycin and erythromycin were obtained by soaking pre-formed, large-subunit crystals in stabilizing buffers containing the antibiotics. Antibiotics were solubilized in dimethylsulfoxide (DMSO), then added to the standard stabilization buffer (Ban et al., (2000) supra) to a final concentration of 1.0 mM (and final DMSO of 1 to 4%), and then incubated at 4° C. for 24 hours prior to cryo-vitrification of crystals in liquid propane. Initial x-ray diffraction data for the carbomycin A, spiramycin and tylosin antibiotics were collected at beamlines X25, X12b or X12c at Brookhaven National Laboratory. Data were reduced using denzo or HKL2000 software and scaled with scalepack (Otwinowski (1997) "Processing of X-ray Diffraction Data Collected In Oscillation Mode," *Methods in Enzymology* 276(A):307-326). Electron density corresponding to these macrolides was first seen in $F_o$(antibiotic)-$F_o$(native) difference Fourier maps at 4.0 A resolution. Higher resolution data were collected at beamline ID19 at the Advanced Photon Source, Argonne National Laboratory. Beginning macrolide models and their topology and parameter files were constructed by connecting and modifying the lactone rings and sugars from various related small molecule structures (Woo et al. (1996) *Tetrahedron* 52(11): 3857-3872; Jones et al. (1982) *Journal of Antibiotics* 35(4): 420-5; Stephenson et al. (1997) *Pharmaceutical Sci.*, 86:1239) using standard stereochemical geometry and software xplo-2d (Kleywegt et al. (1998) *Acta Cryst*, D54: 1119-1131) and O (Jones et al. (1991) *Acta Cryst.* A47: 110-119). For the mixture of spiramycins, only spiramycin I was used in structure determination. The antibiotic models initially were fit into $F_o$-$F_o$ difference electron density maps. The structures of the antibiotics complexed with these crystals were determined at 3.0 Å resolution from difference Fourier maps calculated initially using observed diffraction amplitudes from the native and complex crystals, [$F_o$(complex)-$F_o$(native)], and then the co-ordinates of the entire complex were refined. The structures of these complexes were refined using CNS (Brünger et al., (1998) *Acta Cryst.* D54: 905-921) for rigid body refinement, energy minimization, and B-factor refinement of the entire native ribosome structure including the antibiotic, and by manual modifications of only the immediate area surrounding the bound antibiotic. Nonisomorphous differences distant from the antibiotic were ignored. The refinement process then was repeated iteratively on the antibiotic-containing model. The covalent structures of the macrolides and a conformational change involving A2103 accounted for the principal features in the difference electron density maps.

Based on these studies, the ethylaldehyde group at the C6 position of the lactone ring of each of the 16-membered macrolides appears to form a covalent bond with the N6 of A2103. Not only are the N6 of A2103 and the ethylaldehyde at C6 of the macrolides juxtaposed, they are joined by continuous electron density, which, at 3.0 Å resolution, is indicative of chemical bonding. In contrast, for both the 15-membered and 14-membered macrolides (both of which lack aldehyde groups) no such continuous electron density was observed. The only models for the macrolide-ribosome complex that fit the observed electron density satisfactorily are those in which the N6 of A2103 is covalently bonded to the carbon of the aldehyde group of the macrolide. Aldehydes react reversibly with primary amines, and if the resulting carbinolamines dehydrate, Schiff's bases are produced. However, when the exocyclic amine of a nucleotide base is involved, the expected product is a carbinolamine, not a Schiff's base (McGhee et al. (1977) *Biochem.* 14(6): 1281-1303). Therefore, the model that best fits the out of plane electron density in this region links them via a carbinolamine, not a Schiff's base.

Based upon these studies, it has been found that carbomycin A, spiramycin, tylosin, azithromycin, and erthyromycin all bind in the peptide exit tunnel of the large ribosomal subunit, immediately adjacent to the peptidyl transferase center. The five co-crystal structures were superimposed based only on the phosphates of the ribosomal RNA in order to objectively compare their relative binding. The three 16-membered macrolides superimpose on almost an atom by atom basis. Furthermore, all five lactone rings occupy a very similar position, share a common conformation and orientation, and form similar interactions with the ribosome. In addition, shared moieties such as the mycaminose of the 16-membered rings (and the corresponding desosamine of the other macrolides) superimpose on almost an atom by atom basis. All the sugar moieties assume the same relaxed extended conformations with respect to the lactone ring that are observed in small molecule macrolide structures.

Based on the resolved structures, it appears that hydrophobic interactions are important in macrolide binding. One face of the lactone rings of these antibiotics is quite hydrophobic, while the opposite face is more hydrophilic in character. All five of these macrolides bind to the ribosome with the hydrophobic faces of their lactone rings facing the wall of the exit tunnel and the hydrophilic faces of their lactone rings exposed to solution. The tunnel wall binding site includes the aromatic face of G2646, which is exposed because the C2098-G2646 base pair is helix terminating.

In addition, these structures shed light on why the lengths of the oligopeptides synthesized by macrolide-poisoned ribosomes vary the way they do. The length of the oligopeptides synthesized in the presence of macrolide inhibitors is determined by the extent to which the substituents at the C5 position of the lactone ring penetrate the peptidyl transferase center. Erythromycin and azithromycin, which have only a monosaccharide at this position, should permit the synthesis of longer peptides than tylosin or spiramycin, which have a disaccharide. These observations are consistent with those derived from biochemical studies which indicate that erythromycin does permit the formation of tetrapeptides, tylosin and spiramycin allow formation of only dipeptides, and carbomycin A strongly inhibits the formation of even the first peptide bond.

INCORPORATION BY REFERENCE

The disclosure of each of the patent documents, scientific articles, atomic-co-ordinates (including, without limitation, those sets deposited at the Research Collaboratory for Structural Bioinformatics Protein Data Bank (PDB) with the accession numbers PDB ID: 1FFK; PDB ID: 1FF2; PDB ID: 1FG0; PDB ID: 1JJ2; PDB ID: 1K73; PDB ID: 1KC8; PDB ID: 1K8A; PDB ID: 1KD1; and PDB ID: 1K9M, and/or contained on Disk No. 1) referred to herein is incorporated by reference herein.

All materials submitted on compact disk, Disk No. 1 in U.S. patent application Ser. No. 10/211,931, filed Aug. 2, 2002, which issued as U.S. Pat. No. 6,947,845 on Sep. 20, 2005, are incorporated by reference herein. Disk No. 1 was created on Feb. 6, 2002 and is identified as containing the following thirty-nine files:

| Disk No. 1: | |
|---|---|
| File: | Size (in bytes) |
| <DIR> | |
| <DIR> | |
| 1JJ2.RTF | 12,742,023 |
| 1JJ2.TXT | 8,372,780 |
| ANISOMYCIN.PDB | 7,593,128 |
| azithromycin.pdb | 8,088,411 |
| BLASTICIDIN.PDB | 7,594,206 |

| Disk No. 1: | |
|---|---|
| File: | Size (in bytes) |
| CARBOMYCIN.PDB | 7,592,552 |
| erythromycin.pdb | 7,690,337 |
| FOLDERA <DIR> | |
| FOLDERB <DIR> | |
| FOLDERC <DIR> | |
| linezolid.pdb | 8,086,197 |
| PDB1FFK.DOC | 7,046,656 |
| PDB1FFK.ENT | 5,484,652 |
| PDB1FFZ.DOC | 1,219,072 |
| PDB1FFZ.ENT | 937,342 |
| PDB1FG0.DOC | 1,225,728 |
| PDB1FG0.ENT | 942,344 |
| SPARSOMYCIN.PDB | 7,541,230 |
| SPIRAMYCIN.PDB | 7,592,549 |
| TYLOSIN.PDB | 7,595,512 |
| VIRGINIAMYCIN.PDB | 7,591,745 |
| FOLDERA: | |
| <DIR> | |
| <DIR> | |
| 1JJ2.PDB | 8,270,586 |
| FOLDERB: | |
| <DIR> | |
| <DIR> | |
| ANISOMYC.PDB | 8,383,598 |
| BLASTICI.PDB | 8,393,766 |
| CARBOMYC.PDB | 8,387,042 |
| SPARSOMY.PDB | 7,593,360 |
| SPIRAMYC.PDB | 8,402,048 |
| TYLOSIN.PDB | 8,339,400 |
| VIRGINIA.PDB | 7,590,514 |
| FOLDERC: | |
| <DIR> | |
| <DIR> | |
| AZITHROM.PDB | 7,989,198 |
| LINEZOLI.PDB | 7,987,583 |

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A protein synthesis inhibitor comprising:
a first binding domain having a surface that mimics or duplicates a surface of sparsomycin that binds with a first contact site in a large ribosomal subunit; and
a second binding domain having a surface that mimics or duplicates a surface of anisomycin that binds with a second contact site in the ribosomal subunit,
wherein the first domain is attached to the second domain so as to permit both the first domain and the second domain to bind with its respective contact site thereby to disrupt protein synthesis in a ribosomal subunit, and wherein the protein synthesis inhibitor has a molecular weight of less than about 1,500 and an $IC_{50}$ lower than about 50 μM.

2. The inhibitor of claim 1, wherein the inhibitor has a molecular weight in the range from about 250 to about 1500.

3. The inhibitor of claim 1, wherein the inhibitor has an $IC_{50}$ in the range from about 0.001 μM to about 50 μM.

* * * * *

SEQUENCE LISTING

```
<160> NUMBER OF SEQ ID NOS: 1

<210> SEQ ID NO 1
<211> LENGTH: 33
<212> TYPE: RNA
<213> ORGANISM: Artificial
<220> FEATURE:
<223> OTHER INFORMATION: oligonucleotide sequence that should form 12
      base pairs

<400> SEQUENCE: 1
ccggcgggcu gguucaaacc ggcccgccgg acc                                       33
```